US011262326B2

(12) United States Patent
Wang et al.

(10) Patent No.: US 11,262,326 B2
(45) Date of Patent: Mar. 1, 2022

(54) MEMBRANE LAYERS FOR ANALYTE SENSORS

(71) Applicant: DexCom, Inc., San Diego, CA (US)

(72) Inventors: Shanger Wang, Castro Valley, CA (US); Robert J. Boock, Carlsbad, CA (US); Andrew Trinin Dennis, La Jolla, CA (US); Ted Tang Lee, San Diego, CA (US); Jeff T. Suri, Fallbrook, CA (US); David Sze, San Diego, CA (US); Mark A Tapsak, Bloomsburg, PA (US); Huashi Zhang, San Diego, CA (US); Jiong Zou, San Diego, CA (US)

(73) Assignee: DEXCOM, INC., San Diego, CA (US)

( * ) Notice: Subject to any disclaimer, the term of this patent is extended or adjusted under 35 U.S.C. 154(b) by 138 days.

(21) Appl. No.: 15/395,892

(22) Filed: Dec. 30, 2016

(65) Prior Publication Data

US 2017/0188916 A1 Jul. 6, 2017

Related U.S. Application Data

(60) Provisional application No. 62/273,155, filed on Dec. 30, 2015, provisional application No. 62/273,142, (Continued)

(51) Int. Cl.
*A61B 5/145* (2006.01)
*G01N 27/327* (2006.01)
(Continued)

(52) U.S. Cl.
CPC ....... *G01N 27/3273* (2013.01); *A61B 5/0004* (2013.01); *A61B 5/1473* (2013.01); (Continued)

(58) Field of Classification Search
CPC .................. A61B 5/14532; A61B 5/14546
See application file for complete search history.

(56) References Cited

U.S. PATENT DOCUMENTS

| 4,861,830 | A | | 8/1989 | Ward | |
|---|---|---|---|---|---|
| 4,939,007 | A | * | 7/1990 | Hu | A61L 33/068 428/34.1 |

(Continued)

FOREIGN PATENT DOCUMENTS

| CA | 2998398 | 7/2017 |
|---|---|---|
| CA | 3002099 | 7/2017 |

(Continued)

OTHER PUBLICATIONS

ASTM International, Designation D03418-12 Standard Test Method for Transition Temperatures and Enthalpies of Fusion and Crystallization of Polymers by Differential Scanning Calorimetry, Sep. 2012 (Year: 2012).*

(Continued)

*Primary Examiner* — Puya Agahi
(74) *Attorney, Agent, or Firm* — Moore & Van Allen PLLC

(57) ABSTRACT

Disclosed are devices for determining an analyte concentration (e.g., glucose). The devices comprise a sensor configured to generate a signal associated with a concentration of an analyte and a sensing membrane located over the sensor. The sensing membrane comprises a biointerface layer which interfaces with a biological fluid containing the analyte to be measured. The biointerface layer can comprises a biointerface polymer, wherein the biointerface polymer comprises polyurethane and/or polyurea segments and one or more zwitterionic repeating units. The sensing membrane can also comprise an enzyme layer, wherein the enzyme layer comprises an enzyme and a polymer comprising polyurethane and/or polyurea segments and one or more (Continued)

zwitterionic repeating units. The sensing membrane can also comprise a diffusion-resistance layer, which can comprise a base polymer having a lowest Tg of greater than −50 C.

23 Claims, 62 Drawing Sheets

Related U.S. Application Data filed on Dec. 30, 2015, provisional application No. 62/273,219, filed on Dec. 30, 2015.

(51) Int. Cl.

| | | |
|---|---|---|
| *C08G 18/08* | (2006.01) | |
| *C08G 18/48* | (2006.01) | |
| *C08G 18/40* | (2006.01) | |
| *C08G 18/38* | (2006.01) | |
| *C08G 18/12* | (2006.01) | |
| *C08G 18/44* | (2006.01) | |
| *C08G 18/75* | (2006.01) | |
| *C12N 11/089* | (2020.01) | |
| *C12N 11/093* | (2020.01) | |
| *C08L 39/06* | (2006.01) | |
| *C08L 69/00* | (2006.01) | |
| *C08L 75/04* | (2006.01) | |
| *C12Q 1/00* | (2006.01) | |
| *A61B 5/00* | (2006.01) | |
| *A61B 5/1486* | (2006.01) | |
| *G01N 33/66* | (2006.01) | |
| *A61K 31/045* | (2006.01) | |
| *A61K 31/137* | (2006.01) | |
| *A61K 31/46* | (2006.01) | |
| *A61K 31/465* | (2006.01) | |
| *A61K 31/485* | (2006.01) | |
| *A61K 31/515* | (2006.01) | |
| *A61K 31/56* | (2006.01) | |
| *A61K 33/00* | (2006.01) | |
| *A61K 36/185* | (2006.01) | |
| *A61K 38/28* | (2006.01) | |
| *A61B 5/1473* | (2006.01) | |

(52) U.S. Cl.
CPC ........ *A61B 5/1486* (2013.01); *A61B 5/14532* (2013.01); *A61B 5/14546* (2013.01); *A61B 5/14865* (2013.01); *A61K 31/045* (2013.01); *A61K 31/137* (2013.01); *A61K 31/46* (2013.01); *A61K 31/465* (2013.01); *A61K 31/485* (2013.01); *A61K 31/515* (2013.01); *A61K 31/56* (2013.01); *A61K 33/00* (2013.01); *A61K 36/185* (2013.01); *A61K 38/28* (2013.01); *C08G 18/0828* (2013.01); *C08G 18/12* (2013.01); *C08G 18/3857* (2013.01); *C08G 18/4018* (2013.01); *C08G 18/44* (2013.01); *C08G 18/4833* (2013.01); *C08G 18/755* (2013.01); *C08L 39/06* (2013.01); *C08L 69/00* (2013.01); *C08L 75/04* (2013.01); *C12N 11/089* (2020.01); *C12N 11/093* (2020.01); *C12Q 1/002* (2013.01); *C12Q 1/006* (2013.01); *G01N 33/66* (2013.01); *A61B 5/002* (2013.01); *A61B 2562/12* (2013.01); *G01N 27/3275* (2013.01)

(56) References Cited

U.S. PATENT DOCUMENTS

| | | | |
|---|---|---|---|
| 5,030,252 A * | 7/1991 | Sanders, Jr. | C08G 65/4025 |
| | | | 95/47 |
| 5,124,430 A * | 6/1992 | Parker | C08G 64/183 |
| | | | 528/176 |
| 5,250,066 A * | 10/1993 | Lambert | A61B 5/150404 |
| | | | 606/181 |
| 5,428,123 A | 6/1995 | Ward et al. | |
| 5,846,558 A | 12/1998 | Nielsen et al. | |
| 5,976,529 A | 11/1999 | Navia et al. | |
| 6,432,362 B1 | 8/2002 | Shinar et al. | |
| 6,932,894 B2 | 8/2005 | Mao et al. | |
| 7,034,061 B1 | 4/2006 | Luthra et al. | |
| 7,445,792 B2 | 11/2008 | Toner et al. | |
| 7,670,470 B2 | 3/2010 | Mao et al. | |
| 7,699,964 B2 | 4/2010 | Feldman et al. | |
| 7,871,456 B2 | 1/2011 | Gough et al. | |
| 7,879,444 B2 | 2/2011 | Jiang et al. | |
| 8,101,156 B2 | 1/2012 | Pacetti | |
| 8,103,456 B2 | 1/2012 | Doniger et al. | |
| 8,147,666 B2 | 4/2012 | Mao et al. | |
| 8,155,722 B2 | 4/2012 | Feldman et al. | |
| 8,224,415 B2 | 7/2012 | Budiman | |
| 8,255,030 B2 | 8/2012 | Petisce et al. | |
| 8,380,274 B2 | 2/2013 | Mao et al. | |
| 8,574,660 B2 | 11/2013 | Weaver et al. | |
| 8,583,204 B2 | 11/2013 | Boock et al. | |
| 8,632,838 B2 | 1/2014 | Roth et al. | |
| 8,682,408 B2 | 3/2014 | Boock et al. | |
| 9,394,435 B2 | 7/2016 | Jiang et al. | |
| 9,737,250 B2 | 8/2017 | Hughes et al. | |
| 2003/0042137 A1 | 3/2003 | Mao et al. | |
| 2005/0054909 A1 | 3/2005 | Petisce et al. | |
| 2005/0090607 A1 | 4/2005 | Tapsak et al. | |
| 2005/0095174 A1 | 5/2005 | Wolfe et al. | |
| 2005/0173245 A1 | 8/2005 | Feldman et al. | |
| 2006/0004272 A1 | 1/2006 | Shah et al. | |
| 2006/0257995 A1 | 11/2006 | Simpson et al. | |
| 2006/0275860 A1 | 12/2006 | Kjaer et al. | |
| 2007/0034512 A1 | 2/2007 | Yamaoka et al. | |
| 2007/0197890 A1 | 8/2007 | Boock et al. | |
| 2008/0034972 A1 | 2/2008 | Gough et al. | |
| 2008/0176271 A1 | 7/2008 | Silver et al. | |
| 2008/0181861 A1 | 7/2008 | Jiang et al. | |
| 2008/0214910 A1 | 9/2008 | Buck et al. | |
| 2009/0099433 A1 | 4/2009 | Staib et al. | |
| 2009/0247855 A1 | 10/2009 | Boock et al. | |
| 2010/0041971 A1 | 2/2010 | Goode et al. | |
| 2010/0168381 A1 | 7/2010 | O'Mahony et al. | |
| 2010/0209301 A1 | 8/2010 | Hartmann-Thompson | |
| 2010/0234793 A1 | 9/2010 | Dacey, Jr. et al. | |
| 2010/0279377 A1 | 11/2010 | Shah et al. | |
| 2010/0280341 A1* | 11/2010 | Boock | A61B 5/14532 |
| | | | 600/309 |
| 2011/0077490 A1* | 3/2011 | Simpson | A61B 5/14532 |
| | | | 600/345 |
| 2011/0180404 A1 | 7/2011 | Miyazaki et al. | |
| 2011/0305872 A1 | 12/2011 | Li et al. | |
| 2011/0305881 A1 | 12/2011 | Schultz et al. | |
| 2011/0305895 A1 | 12/2011 | Roth et al. | |
| 2011/0305909 A1 | 12/2011 | Weaver et al. | |
| 2012/0197576 A1 | 8/2012 | Feldman et al. | |
| 2012/0296186 A1 | 11/2012 | Ouyang et al. | |
| 2013/0098775 A1 | 4/2013 | Pei et al. | |
| 2013/0132416 A1 | 5/2013 | Hayter et al. | |
| 2013/0178726 A1 | 7/2013 | Wang et al. | |
| 2014/0018653 A1 | 1/2014 | Staib et al. | |
| 2014/0024060 A1 | 1/2014 | Muller et al. | |
| 2014/0094671 A1* | 4/2014 | Boock | A61B 5/14865 |
| | | | 600/345 |
| 2014/0094673 A1 | 4/2014 | Johnson et al. | |
| 2014/0114156 A1 | 4/2014 | Bohm et al. | |
| 2014/0275896 A1 | 9/2014 | Hughes et al. | |
| 2014/0278189 A1 | 9/2014 | Vanslyke et al. | |
| 2015/0034230 A1 | 2/2015 | Abad et al. | |

(56) References Cited

U.S. PATENT DOCUMENTS

| | | | |
|---|---|---|---|
| 2015/0037598 | A1 | 2/2015 | Jiang et al. |
| 2015/0080691 | A1 | 3/2015 | Boock et al. |
| 2015/0289788 | A1 | 10/2015 | Simpson et al. |
| 2015/0366491 | A1 | 12/2015 | Boock et al. |
| 2016/0251470 | A1 | 9/2016 | Cheng et al. |
| 2017/0188902 | A1 | 7/2017 | Wang et al. |
| 2017/0188905 | A1 | 7/2017 | Lee et al. |
| 2017/0188921 | A1 | 7/2017 | Wang et al. |
| 2017/0188922 | A1 | 7/2017 | Lee et al. |
| 2017/0188923 | A1 | 7/2017 | Zou et al. |
| 2017/0191955 | A1 | 7/2017 | Zou et al. |

FOREIGN PATENT DOCUMENTS

| | | |
|---|---|---|
| CA | 3003533 | 7/2017 |
| JP | 03070751 A | 3/1991 |
| JP | 2005-520172 A | 7/2005 |
| JP | 2009-540889 A | 11/2009 |
| WO | WO 2003-085372 | 10/2003 |
| WO | WO 2007-147475 | 12/2007 |
| WO | WO 2011-057219 | 5/2011 |
| WO | WO 2014-052080 | 4/2014 |

OTHER PUBLICATIONS

ASTM International, Designation D1708-13 Standard Test Method for Tensile Properties of Plastics by Use of Microtensile Specimens, Sep. 2013 (Year: 2013).*

ASTM Intl, Sep. 2012. Designation D3418-12 Standard Test Method for Transition Temperatures and enthalpies of Fusion and Crystallization of polymers by differential scanning c.

Chen et al. 2010. Polymer 51:5283-5293: Surface hydration: Principles and applications toward low-fouling/nonfouling biomaterials.

Jiang and Cao, 2010. Adv. Mater. 22:920-932. Ultralow-Fouling, Functonalizable, adn Hydrolyzable Zwitterionic Materials and Their Derivatives for Biological Applications.

Lin el al. 2013. Biosensors & Bloelectronics 47:451-460: Improving biocompatibility by surface modification techniques on implantable bioelectronics.

U.S. Appl. No. 14/841,446, filed Aug. 31, 2015: U.S. PTO Office Action dated Apr. 28, 2017.

Yang et al. 2011. Biosensors & Bioelectronics 26(5):2454-2459: Zwitterionic poly(carboxybetaine) hydrogels for glucose biosensors in complex media.

Extended European Search Report for Application No. 16882775.6 dated May 24, 2019, 12 pages.

International Preliminary Report on Patentability for Application No. PCT/US2016/069576 dated Jul. 12, 2018, 12 pages.

International Search Report and Written opinion for Application No. PCT/US2016/069576 dated May 15, 2017, 14 pages.

Office Action from European Patent Application No. 16882775.6, dated Jul. 21, 2020, 4 pages.

Cao et al., "Polyurethanes containing zwitterionic sulfobetaines and their molecular chain rearrangement in water", J Biomed Mater Res Part A (2013) 101A:909-918.

CarboSil® Thermoplastic Silicone Polycarbonate Polyurethane (TSPCU) <URL: https://www.dsm.com/content/dam/dsm/medical/en_US/documents/carbosil(r)-tspcu-product-sheet.pdf?download=0d8ab528-9415-45b9-b7ef-f1422d915fa91558401937562>; first published 2012; 2 pages.

Huang et al., Zwitterionic monomer graft copolymerization onto polyurethane surface through a PEG spacer. Appl Surface Science (2010) 256:3921-3927.

Laschewsky A., "Structures and Synthesis of Zwitterionic Polymers," Polymers 2014, doi:10.3390/polym6051544, pp. 1544-1601.

Office Action for Canadian Application No. 2,994,318, dated Feb. 5, 2021, 5 pages.

Office Action from Canadian Patent Application No. 3,003,533, dated Mar. 18, 2021, 4 pages.

Office Action from Australian Patent Application No. 2020204319, dated Oct. 29, 2020, 6 pages.

* cited by examiner

MEMBRANE LAYERS FOR ANALYTE SENSORS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 62/273,155, filed Dec. 30, 2015; U.S. Provisional Application No. 62/273,142, filed Dec. 30, 2015; and U.S. Provisional Application No. 62/273,219, filed Dec. 30, 2015. Each of the aforementioned applications is incorporated by reference herein in its entirety, and each is hereby expressly made a part of this specification.

FIELD

The subject matter disclosed herein relates to devices for measuring a biological analyte in a host and to components of such devices.

BACKGROUND

Electrochemical sensors are useful for determining the presence or concentration of a biological analyte, such as blood glucose. Such sensors are effective, for example, at monitoring glucose in diabetic patients and lactate during critical care events. A variety of intravascular, transcutaneous and implantable sensors have been developed for continuously detecting and quantifying blood analytes, such as blood glucose levels.

A challenge associated with long-term use of continuous sensors and other medical devices is biomaterial-associated inflammation, which is the inflammation caused by implantation of foreign materials into the body. Biomaterial-associated inflammation is the result of a dynamic microenvironment around an implanted device, which includes the initial injury, neutrophil and macrophage recruitment, foreign body giant cell (FBGC) response, neovascularization, fibroblast recruitment, and downstream fibrosis. The formation of a barrier cell layer around the implanted device can result in impaired tissue integration.

In the case of a continuous sensor, biomaterial-associated inflammation can impair analyte transport from tissues to the sensor surface, whether by creating a diffusion barrier or active consumption of analytes. The FBGC response to implantable materials results in fibrous capsule formation that impedes sensor function through the modulation of glucose diffusion through dense fibrotic "scar-tissue" layers. Other constituents of the biomaterial-associated inflammatory cascade, such as inflammatory cytokines and other small molecules, sometimes act as interferents to sensor performance. These interferents can cause sensor inaccuracy due to the constant change in transport properties at the sensor/tissue interface. Aside from diffusion limitations, there exists an active cellular component of the biomaterial-associated inflammatory cascade, involving inflammatory and wound healing cells; these cells that can be activated by implanted materials can actively consume glucose and produce $H_2O_2$, which can also lead to sensor inaccuracy. Reduction in biomaterial-associated inflammation is thus important in creating long-term, stable, implantable sensors and devices. Thus what are needed are methods and compositions that can reduce inaccuracies in an implanted sensor that can be caused by biomaterial-associated inflammation.

What are also needed are methods and compositions that can increase the longevity of an implanted device. The methods and compositions disclosed herein address these and other needs.

Also, in such analyte sensors there is a membrane layer or domain that contains an enzyme responsible for converting the analyte into agent that can be registered as a measurable signal. For example, glucose sensors contain enzymes that convert glucose into hydroperoxide, which is further converted into a sensor signal. So the performance of enzymatic glucose sensors, like other sensors that rely on enzymatic conversions, can be affected by the amount of active enzyme incorporated in the sensor's membrane layer.

It is often a challenge to have sufficient active enzyme incorporated and maintained in the membrane to efficiently catalyze analyte reactions (e.g., glucose to hydrogen peroxide). Enzyme can leach out of the membrane in hydrated conditions. Leached enzyme can also result in a severe Foreign Body Response (FBR). These events change sensor sensitivity and degrade the resistance layer, which will finally decrease the accuracy and longevity of the sensor. Furthermore, enzyme degradation can occur by many different mechanisms leading to irreversible or reversible inactivation of enzyme. Enzymes can be sensitive to environment conditions including, for example, temperature changes, pH changes, and exposure to the reactive chemicals including crosslinkers often employed in immobilization the enzyme such as glutaraldehyde and carbodiimide, as well as bi-products from the redox reaction such as hydrogen peroxide and gluconic acid and endogenous bi-products. Enzyme degradation severely limits the functional life of analyte sensors in vivo and can result in gradual sensor sensitivity decline and early onset of sensor end-of-life.

The incorporation and immobilization of enzymes into various carriers or binders including polymers, sol gel, particles, and mixtures thereof to create an enzyme layer has been tried to prevent the leaching of enzymes in analyte sensors. These layers can, however, swell and degrade in aqueous environments and suffer from poor adhesion to adjacent layers in the membrane system. As a result, these by-products can also leach out of the membrane and also contribute to the FBR and affect sensor sensitivity and accuracy. Poor adhesion can further result in reduced mechanical stability and delamination of the membrane layers in vivo.

There is thus a desire for engineered enzyme layers in which enzymes are immobilized in the membrane via strong molecular level interactions between enzymes and base polymeric materials. Such layers can reduce (or prevent) leaching of enzymes, which will lessen the FBR, and improve the longevity, sensitivity, and accuracy of the sensor. What are also needed are enzyme layers engineered with physiochemical stability and catalytic performance stability in aqueous environment and have good adhesion to other layers in the sensor's membrane system. The compositions, methods, and devices disclosed herein address these and other needs.

Further, in such analyte sensors there is a membrane layer or domain that is primarily responsible for limiting the diffusion of the analyte to the sensor. The function of this so-called diffusion-resistance layer can be important when the analyte of interest is present in the patient in amounts that can exceed the sensor's sensitivity. For example, there exists a molar excess of glucose relative to the amount of oxygen in the body. So for every free oxygen molecule in extracellular fluid, there are typically more than 100 glucose molecules present (see Updike et al., Diabetes Care 5:207-

21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

Some diffusion-resistance layers suffer from changes in permeability to analyte due to changes in microstructure, phase separation, degradation, and interferants from external molecules. These changes can affect sensor sensitivity and therefore result in changes in sensor output for the same analyte concentration over time—a phenomenon known as "drift." This also confounds the development of robust algorithms due to the need for sensor "drift" correction. There is thus a desire for an engineered semipermeable diffusion-resistance layer that contains polymers capable of providing a structurally stable matrix wherein an analyte permeable phase resides throughout, and electrochemical sensors equipped with such membrane. The compositions, methods, and devices disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions, and devices containing compounds and compositions.

In a first aspect, a device is provided for determining an analyte concentration (e.g., glucose), the device comprising: a sensor configured to generate a signal associated with a concentration of an analyte and a sensing membrane located over the sensor. The sensing membrane comprises a biointerface layer which interfaces with a biological fluid containing the analyte to be measured. In devices of this aspect, the biointerface layer comprises a biointerface polymer, wherein the biointerface polymer comprises polyurethane and/or polyurea segments and one or more zwitterionic repeating units.

A biointerface layer increases sensor longevity and decrease sensor inaccuracy by inhibiting accumulation of cells, proteins, and other biological species on the outermost layers of the sensor. Early attenuation of these events in the biomaterial-associated inflammation cascade can lessen the overall severity of the response, and therefore the sensor inaccuracy in vivo can be reduced.

In further embodiments of the disclosed devices the sensing membrane further comprises an enzyme domain comprising an enzyme selected from the group consisting of glucose oxidase, glucose dehydrogenase, galactose oxidase, cholesterol oxidase, amino acid oxidase, alcohol oxidase, lactate oxidase, and uricase. In certain embodiments, the enzyme is glucose oxidase.

In embodiments of devices of this aspect, the one or more zwitterionic repeating units comprise a betaine compound or derivative thereof. In examples of devices of this aspect, the one or more zwitterionic repeating units comprise a betaine compound or precursor thereof.

In embodiments of devices of this aspect, the one or more zwitterionic repeating units comprise at least one moiety selected from the group consisting of a carboxyl betaine, a sulfo betaine, a phosphor betaine, and derivatives thereof.

In embodiments of devices of this aspect, the one or more zwitterionic repeating units are derived from a monomer selected from the group consisting of:

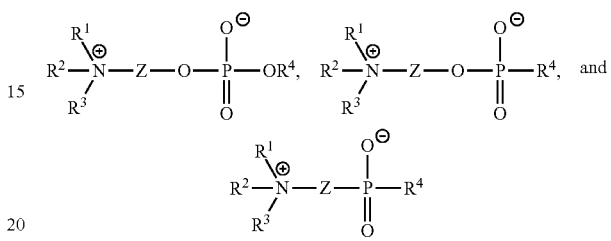

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$, $R^3$, and $R^4$ are independently chosen from alkyl, heteroalkyl, cycloalkyl, heterocycloalkyl, aryl, or heteroaryl; and wherein one or more of $R^1$, $R^2$, $R^3$, $R^4$, and Z are substituted with a polymerization group.

In embodiments of devices of this aspect, the one or more zwitterionic repeating units are derived from a monomer selected from the group consisting of:

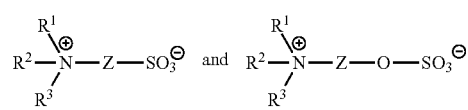

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$, are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

In embodiments of devices of this aspect, the one or more zwitterionic repeating units are derived from a monomer selected from the group consisting of:

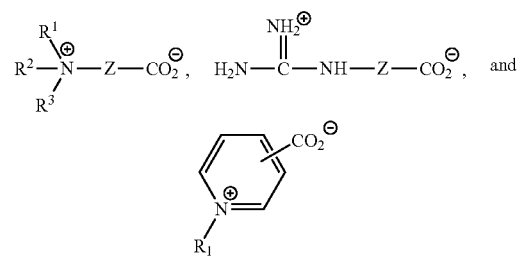

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and R² and R³ are independently chosen from alkyl, heteroalkyl, cycloalkyl, heterocycloalkyl, aryl, or heteroaryl; wherein one or more of R¹, R², R³, and Z are substituted with a polymerization group.

In embodiments of devices of this aspect, wherein the polymerization group is selected from alkene, alkyne, epoxide, lactone, amine, hydroxyl, isocyanate, carboxylic acid, anhydride, silane, halide, aldehyde, and carbodiimide.

In embodiments of devices of this aspect, the one or more zwitterionic repeating units is at least about 1 wt. % based on the total weight of the polymer.

In embodiments of devices of this aspect, the polyurethane and/or polyurea segments are from about 15 wt. % to about 75 wt. %, based on the total weight of the polymer.

In embodiments of devices of this aspect, the biointerface polymer further comprises at least one segment selected from the group consisting of epoxides, polyolefins, polysiloxanes, polyamide, polystylene, polyacrylate, polyethers, polyesters, and polycarbonates.

In embodiments of devices of this aspect, the biointerface polymer further comprises a polyethylene oxide segment, which in some examples is from about 5 wt. % to about 60 wt. %, based on the total weight of the biointerface polymer.

In embodiments of devices of this aspect, the biointerface polymer has a molecular weight of from about 10 kDa to about 500,000 kDa, a polydispersity index of from about 1.4 to about 3.5, and/or a contact angle of from about 20° to about 90°.

In a second aspect, a device is provided where the biointerface layer further comprises one or more zwitterions selected from the group consisting of cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine), poly(sulfobetaine), and derivatives thereof.

In an embodiment of the second aspect, a device is provided where the biointerface layer further comprises a pharmaceutical or bioactive agent.

In a third aspect, a device is provided for determining an analyte concentration, the device comprising: a sensor configured to generate a signal associated with a concentration of an analyte and a sensing membrane located over the sensor. The sensing membrane comprises a biointerface layer which interfaces with a biological fluid containing the analyte to be measured. In devices of this aspect, the biointerface domain comprises a biointerface polymer, wherein the biointerface polymer comprises a polymer chain having both hydrophilic and hydrophobic regions and wherein the hydrophilic regions comprise a liner polymer chain having hydrophilic oligomers bound thereto and where the linear polymer is grafted to the biointerface polymer.

In a fourth aspect, a device is provided for determining an analyte concentration, the device comprising: a sensor configured to generate a signal associated with a concentration of an analyte and a sensing membrane located over the sensor. The sensing membrane comprises a biointerface layer which interfaces with a biological fluid containing the analyte to be measured. In devices of this aspect, the biointerface layer comprises a biointerface polymer, wherein the biointerface polymer comprises a fluorescent moiety covalently bonded to the biointerface polymer.

In a fifth aspect, a device is provided for determining an analyte concentration, the device comprising: a sensor configured to generate a signal associated with a concentration of an analyte and a sensing membrane located over the sensor. The sensing membrane comprises a biointerface layer which interfaces with a biological fluid containing the analyte to be measured. In devices of this aspect, the biointerface layer comprises a base polymer and a surface modifying polymer, wherein the surface modifying polymer comprises a polymer chain having both hydrophilic and hydrophobic regions and wherein one or more zwitterionic compounds; and wherein the base polymer is selected from silicone, epoxide, polyolefin, polystylene, polyoxymethylene, polysiloxane, polyether, polyacrylic, polymethacrylic, polyester, polycarbonate, polyamide, poly(ether ketone), poly(ether imide), polyurethane, and polyurethane urea.

In a sixth aspect, a device is provided for determining an analyte concentration (e.g., glucose), the device comprising: a sensor configured to generate a signal associated with a concentration of an analyte and a sensing membrane located over the sensor. The sensing membrane comprises an enzyme layer, wherein the enzyme layer comprises an enzyme and a polymer comprising polyurethane and/or polyurea segments and one or more zwitterionic repeating units. The enzyme layer protects the enzyme and prevents it from leaching from the sensing membrane into a host, without adversely affecting the enzyme's activity. The enzyme layer can be from 0.01 μm to about 250 μm thick.

In a seventh aspect, a device is provided for determining an analyte concentration (e.g., glucose), the device comprising: a sensor configured to generate a signal associated with a concentration of an analyte and a sensing membrane located over the sensor. The sensing membrane comprises an enzyme layer, wherein the enzyme layer comprises an enzyme and a polymer comprising polyurethane and/or polyurea segments and one or more zwitterionic repeating units. The enzyme layer protects the enzyme and prevents it from deactivating by dynamic changes in its environment caused by endogenous and exogenous compounds, and other stress factors including temperature and pH. The enzyme layer can be from 0.01 μm to about 250 μm thick. In further examples of the devices of the disclosed devices the enzyme can selected from the group consisting of glucose oxidase, glucose dehydrogenase, galactose oxidase, cholesterol oxidase, amino acid oxidase, alcohol oxidase, lactate oxidase, and uricase. In certain examples, the enzyme is glucose oxidase.

In examples of devices of this aspect, the one or more zwitterionic repeating units comprise a betaine compound or derivative thereof. In examples of devices of this aspect, the one or more zwitterionic repeating units comprise a betaine compound or precursor thereof.

In examples of devices of this aspect, the one or more zwitterionic repeating units comprise at least one moiety selected from the group consisting of a carboxyl betaine, a sulfo betaine, a phosphor betaine, and derivatives thereof.

In examples of devices of this aspect, the one or more zwitterionic repeating units are derived from a monomer selected from the group consisting of:

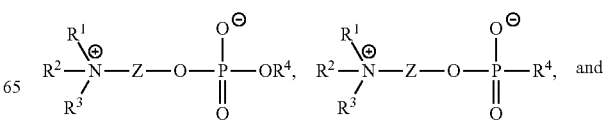

-continued

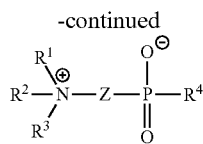

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$, $R^3$, and $R^4$ are independently chosen from alkyl, heteroalkyl, cycloalkyl, heterocycloalkyl, aryl, or heteroaryl; and wherein one or more of $R^1$, $R^2$, $R^3$, $R^4$, and Z are substituted with a polymerization group.

In examples of devices of this aspect, the one or more zwitterionic repeating units are derived from a monomer selected from the group consisting of:

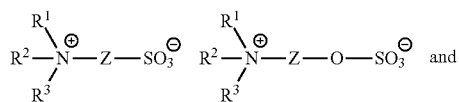

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$, are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

In examples of devices of this aspect, the one or more zwitterionic repeating units are derived from a monomer selected from the group consisting of:

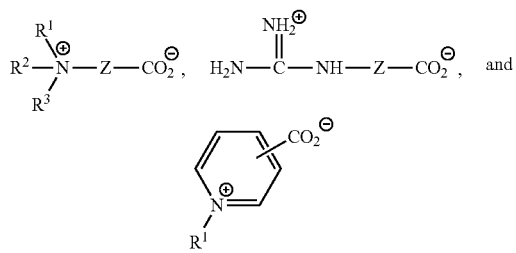

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$ are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

In examples of devices of this aspect, wherein the polymerization group is selected from alkene, alkyne, epoxide, lactone, amine, hydroxyl, isocyanate, carboxylic acid, anhydride, silane, halide, aldehyde, and carbodiimide.

In examples of devices of this aspect, the one or more zwitterionic repeating units is at least about 1 wt. % based on the total weight of the polymer.

In examples of devices of this aspect, the polyurethane and/or polyurea segments are from about 15 wt. % to about 75 wt. %, based on the total weight of the polymer.

In examples of devices of this aspect, the polymer in the enzyme layer further comprises at least one segment selected from the group consisting of epoxides, polyolefins, polysiloxanes, polyamide, polystylene, polyacrylate, polyethers, polyesters, and polycarbonates.

In examples of devices of this aspect, the polymer in the enzyme layer further comprises a polyethylene oxide segment, which in some examples is from about 5 wt. % to about 60 wt. %, based on the total weight of the enzyme layer polymer.

In examples of devices of this aspect, the polymer in the enzyme layer has a molecular weight of from about 10 kDa to about 500,000 kDa, a polydispersity index of from about 1.4 to about 3.5, and/or a contact angle of from about 10° to about 90°.

In a eight aspect, a device is provided where the enzyme layer further comprises a base polymer and enzyme stabilizing and/or immobilizing polymer, wherein the enzyme stabilizing and/or immobilizing polymer comprises a polymer chain having both hydrophilic and hydrophobic regions and one or more zwitterionic repeating units; and wherein the base polymer is selected from silicone, epoxide, polyolefin, polystylene, polyoxymethylene, polysiloxane, polyether, polyacrylic, polymethacrylic, polyester, polycarbonate, polyamide, poly(ether ketone), poly(ether imide), polyurethane, and polyurethane urea.

In a ninth aspect, a device is provided where the enzyme layer further comprises an enzyme stabilizing reagent. In certain examples the enzyme stabilizing reagent can be selected from the group consisting of one or more zwitterions selected from the group consisting of cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine), poly(sulfobetaine), and derivatives thereof.

In a tenth aspect, devices are provided for determining an analyte concentration (e.g., glucose), the devices comprising: a sensor configured to generate a signal associated with a concentration of an analyte and a sensing membrane located over the sensor. In certain embodiments disclosed herein are devices for measurement of an analyte concentration, the devices comprising a sensor configured to generate a signal associated with a concentration of an analyte; and a sensing membrane located over the sensor, the sensing membrane comprising a diffusion-resistance layer comprising a base polymer having a lowest glass transition temperature as measured using ASTM D3418 of greater than −50° C. and an ultimate tensile strength as measured by ASTM D1708 that is greater than 6000 psi. For example, the glass transition temperature of the base polymer can be greater than 0° C. and/or the ultimate tensile strength of the base polymer can be greater than 8250 psi.

In certain examples, the base polymer can be a segmented block copolymer. For example, the base polymer can comprise polyurethane and/or polyurea segments and one or more polycarbonate or polyester segments. In other examples, the base polymer can be a polyurethane copolymer chosen from a polyether-urethane-urea, polycarbonate-urethane, polyether-urethane, polyester-urethane, and/or copolymers thereof, so long as the lowest glass transition temperature is greater than −50° C. In other examples, the base polymer comprises a polymer selected from epoxies, polyolefins, polyoxymethylene, polyethers, polyacrylics, polymethacrylic, polyesters, polycarbonates, polyamide, poly(ether ketone), poly(ether imide), and/or copolymers thereof so long as the lowest glass transition temperature is greater than −50° C. In still other examples, the base polymer can be substantially free of silicone. In further examples, the diffusion-resistance layer further can comprise a hydrophilic polymer. For example, the hydrophilic polymer can be selected from polyvinyl alcohol, polyethylene glycol, polyacrylamide, polyacetate, polyethylene oxide, polyethyleneamine, polyvinylpyrrolidone (PVP), polyoxazoline (PDX), and copolymers and/or mixtures thereof. In other examples, the hydrophilic polymer can be blended with the base polymer or can be covalently bonded to the base polymer. In still other examples, the base polymer or hydrophilic polymer can comprise a crosslinker or several crosslinkers, where in the crosslinker comprise a polymer or oligomer selected from polyfunctional isocynate, polyfunctional aziridine, polyfunctional carbodiimide. In other examples, the diffusion-resistance layer can comprise a blend of a polycarbonate-urethane base polymer and polyvinylpyrrolidone. The diffusion-resistance layer can be from 0.01 μm to about 250 μm thick.

In certain embodiments, disclosed are sensors that have a drift of less than or equal to 10% over 10 days. The sensor can comprise an electrode and the device can be configured for continuous measurement of an analyte concentration, such as glucose.

In other aspects, disclosed are devices for measurement of an analyte concentration, the devices comprising: a sensor configured to generate a signal associated with a concentration of an analyte; and a sensing membrane located over the sensor, the sensing membrane comprising a diffusion resistance layer, wherein the sensor has less than 10% drift in the signal over 10 days.

In still other aspects, disclosed are devices for measurement of an analyte concentration, the devices comprising: a transcutaneous sensor configured to generate a signal associated with a concentration of an analyte; and a sensing membrane located over the sensor, the sensing membrane comprising a diffusion-resistance layer, wherein the diffusion-resistance layers comprises a polyurethane containing block copolymer and is substantially free of silicone.

In all of the devices disclosed herein, they can be configured for continuous measurement of an analyte concentration.

Additional advantages will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

DETAILED DESCRIPTION

Figure 1:
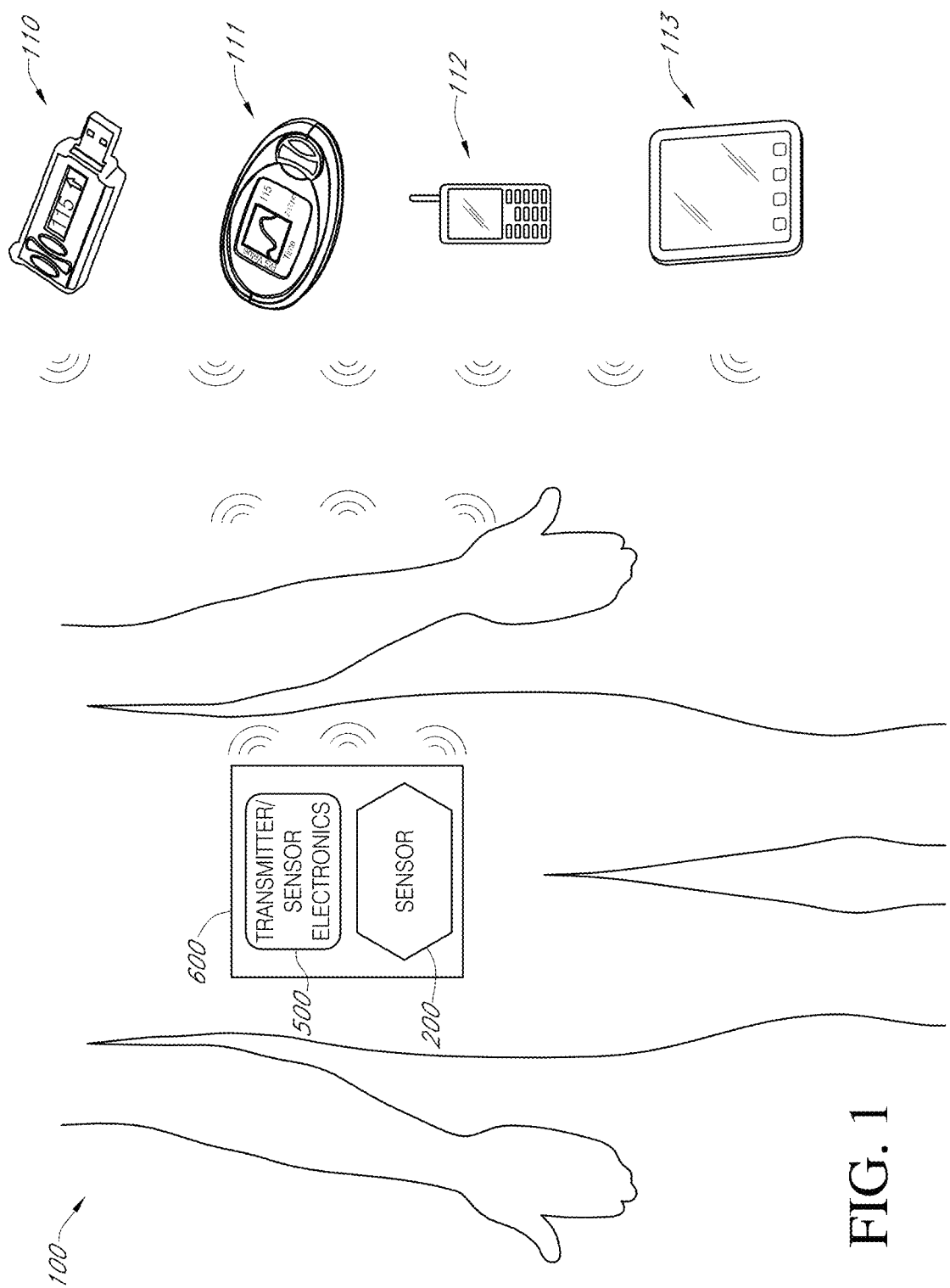
FIG. 1 is a schematic view of a continuous analyte sensor system attached to a host and communicating with other devices.

The methods, compositions, and devices described herein can be understood more readily by reference to the following detailed description of specific aspects of the disclosed subject matter and the Examples and Figures included therein.

Before the methods, compositions, and devices are disclosed and described, it is to be understood that the aspects described below are not limited to specific synthetic methods or specific reagents, as such can, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (e.g., blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; α-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, β-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-α-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, antinuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "baseline" as used herein is a broad term, and is to be given its ordinary and customary meaning to a person of ordinary skill in the art (and is not to be limited to a special or customized meaning), and refers without limitation to the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal.

The term "continuous (or continual) analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and or intermittently (but regularly) performed, for example, about every 5 to 10 minutes.

The term "counts" as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "dipole" or "dipolar compound" as used herein is a broad term, and is to be given its ordinary and customary meaning to a person of ordinary skill in the art (and is not to be limited to a special or customized meaning), and refer without limitation to compounds in which a neutral molecule of the compound has a positive and negative electrical charge at different locations within the molecule. The positive and negative electrical charges within the molecule can be any non-zero charges up to and including full unit charges.

The term "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include a membrane system having a biointerface domain and an enzyme domain. If the sensor is deemed to be the point of reference and the biointerface domain is positioned farther from the sensor than the enzyme domain, then the biointerface domain is more distal to the sensor than the enzyme domain.

The term "domain" as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (i.e., anisotropic) or provided as portions of the membrane.

The term "electrical potential" as used herein is a broad term, and is to be given its ordinary and customary meaning to a person of ordinary skill in the art (and is not to be limited to a special or customized meaning), and refers without limitation to the electrical potential difference between two points in a circuit which is the cause of the flow of a current.

The terms "electrochemically reactive surface" and "electroactive surface" as used herein are broad terms, and are to be given their ordinary and customary meaning to a person of ordinary skill in the art (and are not to be limited to a special or customized meaning), and refer without limitation to the surface of an electrode where an electrochemical reaction takes place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The term "host" as used herein is a broad term, and is to be given its ordinary and customary meaning to a person of ordinary skill in the art (and is not to be limited to a special or customized meaning), and refers without limitation to animals (e.g., humans) and plants. In some examples, a host can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. In other examples, a host can include a mammal, such as a primate or a human.

The terms "interferents" and "interfering species" as used herein are broad terms, and are to be given their ordinary and customary meaning to a person of ordinary skill in the art (and are not to be limited to a special or customized meaning), and refer without limitation to effects or species that interfere with the measurement of an analyte of interest in a sensor to produce a signal that does not accurately represent the analyte measurement. In an exemplary electrochemical sensor, interfering species can include compounds with an oxidation potential that overlaps with that of the analyte to be measured.

The terms "non-zwitterionic dipole" and "non-zwitterionic dipolar compound" as used herein are broad terms, and are to be given their ordinary and customary meaning to a person of ordinary skill in the art (and is not to be limited to a special or customized meaning), and refer without limitation to compounds in which a neutral molecule of the compound have a positive and negative electrical charge at different locations within the molecule. The positive and negative electrical charges within the molecule can be any non-zero, but less than full unit, charges.

The terms "operable connection," "operably connected," and "operably linked" as used herein are broad terms, and are to be given their ordinary and customary meaning to a person of ordinary skill in the art (and are not to be limited to a special or customized meaning), and refer without limitation to one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "optional" or "optionally" means that the subsequently described event or circumstance can or cannot occur, and that the description includes instances where the event or circumstance occurs and instances where it does not.

The term "polyampholytic polymer" as used herein is a broad term, and is to be given its ordinary and customary meaning to a person of ordinary skill in the art (and is not to be limited to a special or customized meaning), and refers without limitation to polymers comprising both cationic and anionic groups. Such polymers can be prepared to have about equal numbers of positive and negative charges, and thus the surface of such polymers can be about net neutrally charged. Alternatively, such polymers can be prepared to have an excess of either positive or negative charges, and thus the surface of such polymers can be net positively or negatively charged, respectively.

The term "polyzwitterions" as used herein is a broad term, and is to be given its ordinary and customary meaning to a person of ordinary skill in the art (and is not to be limited to a special or customized meaning), and refers without limitation to polymers where a repeating unit of the polymer chain is a zwitterionic moiety. Polyzwitterions are also known as polybetaines. Since polyzwitterions have both cationic and anionic groups, they are a type of polyampholytic polymer. They are unique, however, because the cationic and anionic groups are both part of the same repeating unit, which means a polyzwitterion has the same number of cationic groups and anionic groups whereas other polyampholytic polymers can have more of one ionic group than the other. Also, polyzwitterions have the cationic group and anionic group as part of a repeating unit. Polyampholytic polymers need not have cationic groups connected to anionic groups, they can be on different repeating units and thus may be distributed apart from one another at random intervals, or one ionic group may outnumber the other.

The term "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a biointerface layer and an enzyme layer. If the sensor is deemed to be the point of reference and the enzyme layer is positioned nearer to the sensor than the biointerface layer, then the enzyme layer is more proximal to the sensor than the biointerface layer.

The terms "raw data stream" and "data stream" as used herein are broad terms, and are to be given their ordinary and customary meaning to a person of ordinary skill in the art (and are not to be limited to a special or customized meaning), and refer without limitation to an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The terms "sensing membrane" and "membrane system" as used herein are broad terms, and are to be given their ordinary and customary meaning to a person of ordinary skill in the art (and are not to be limited to a special or customized meaning), and refers without limitation to a permeable or semi-permeable membrane that can comprise one or more domains or layers and constructed of materials of a few μm thickness or more, which are permeable to oxygen and may or may not be permeable to an analyte of interest. In one example, the sensing membrane or membrane system can comprise an immobilized glucose oxidase enzyme, which allows an electrochemical reaction to occur to measure a concentration of glucose.

The terms "sensing region," "sensor," and "sensing mechanism" as used herein are broad terms, and are to be given their ordinary and customary meaning to a person of ordinary skill in the art (and are not to be limited to a special or customized meaning), and refer without limitation to the region or mechanism of a monitoring device responsible for the detection of a particular analyte.

The term "sensitivity" as used herein is a broad term, and is to be given its ordinary and customary meaning to a person of ordinary skill in the art (and is not to be limited to a special or customized meaning), and refers without limitation to an amount signal (e.g., in the form of electrical current and/or voltage produced by a predetermined amount (unit) of the measured analyte. For example, in one embodiment, a sensor has a sensitivity (or slope) of from about 1 to about 100 picoAmps of current for every 1 mg/dL of glucose analyte.

The terms "zwitterion" and "zwitterionic compound" as used herein are broad terms, and are to be given their ordinary and customary meaning to a person of ordinary skill in the art (and is not to be limited to a special or customized meaning), and refer without limitation to compounds in which a neutral molecule of the compound has a unit positive and unit negative electrical charge at different locations within the molecule. Such compounds are a type of dipolar compounds, and are also sometimes referred to as "inner salts."

A "zwitterion precursor" or "zwitterionic compound precursor" as used herein are broad terms, and are to be given their ordinary and customary meaning to a person of ordinary skill in the art (and is not to be limited to a special or customized meaning), and refer without limitation to any compound that is not itself a zwitterion, but can become a zwitterion in a final or transition state through chemical reaction. In some embodiments described herein, devices comprise zwitterion precursors that can be converted to zwitterions prior to in vivo implantation of the device. Alternatively, in some embodiments described herein, devices comprise zwitterion precursors that can be converted to zwitterions by some chemical reaction that occurs after in vivo implantation of the device. Such reactions are known to the skilled in art and include ring opening reaction, addition reaction such as Michael addition. This method is especially useful when the polymerization of betaine containing monomer is difficult due to technical challenges such as solubility of betaine monomer to achieve desired physical properties such as molecular weight and mechanical strength. Post-polymerization modification or conversion of betaine precursor can be a practical way to achieve desired polymer structure and composition. Examples of such as precursors include tertiary amines, quaternary amines, pyridines, and others detailed herein.

A "zwitterion derivative" or "zwitterionic compound derivative" as used herein are broad terms, and are to be given their ordinary and customary meaning to a person of ordinary skill in the art (and is not to be limited to a special or customized meaning), and refer without limitation to any compound that is not itself a zwitterion, but rather is the product of a chemical reaction where a zwitterion is converted to a non-zwitterion. Such reactions can be reversible, such that under certain conditions zwitterion derivatives can act as zwitterion precursors. For example, hydrolyzable betaine esters formed from zwitterionic betaines are cationic zwitterion derivatives that under the appropriate conditions are capable of undergoing hydrolysis to revert to zwitterionic betaines.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min (minutes); s and sec (seconds); ° C. (degrees Centigrade).

Sensor System

FIG. 1 is a schematic of a continuous analyte sensor system 100 attached to a host and communicating with a number of other example devices 110-113. A transcutaneous analyte sensor system comprising an on-skin sensor assembly 600 is shown which is fastened to the skin of a host via a disposable housing (not shown). The system includes a transcutaneous analyte sensor 200 and an electronics unit (referred to interchangeably as "sensor electronics" or "transmitter") 500 for wirelessly transmitting analyte information to a receiver. During use, a sensing portion of the sensor 200 is under the host's skin and a contact portion of the sensor 200 is operably connected (e.g., electrically connected) to the electronics unit 500. The electronics unit 500 is engaged with a housing which is attached to an adhesive patch fastened to the skin of the host.

The on-skin sensor assembly 600 may be attached to the host with use of an applicator adapted to provide convenient and secure application. Such an applicator may also be used for inserting the sensor 200 through the host's skin. Once the sensor 200 has been inserted, the applicator detaches from the sensor assembly.

In general, the continuous analyte sensor system 100 includes any sensor configuration that provides an output signal indicative of a concentration of an analyte. The output signal including (e.g., sensor data, such as a raw data stream, filtered data, smoothed data, and/or otherwise transformed sensor data) is sent to receiver which may be e.g., a smart phone, smart watch, dedicated device and the like. In one embodiment, the analyte sensor system 100 includes a transcutaneous glucose sensor, such as is described in US Patent Publication No. US-2011-0027127-A1, the contents of which is hereby incorporated by reference in its entirety. In some embodiments, the sensor system 100 includes a continuous glucose sensor and comprises a transcutaneous sensor such as described in U.S. Pat. No. 6,565,509 to Say et al., for example. In another embodiment, the sensor system 100 includes a continuous glucose sensor and comprises a subcutaneous sensor such as described with reference to U.S. Pat. No. 6,579,690 to Bonnecaze et al. or U.S. Pat. No. 6,484,046 to Say et al., for example. In another embodiment, the sensor system 100 includes a continuous glucose sensor and comprises a subcutaneous sensor such as described with reference to U.S. Pat. No. 6,512,939 to Colvin et al. In another embodiment, the sensor system 100 includes a continuous glucose sensor and comprises an intravascular sensor such as described with reference to U.S. Pat. No. 6,477,395 to Schulman et al., for example. In another embodiment, the sensor system 100 includes a continuous glucose sensor and comprises an intravascular sensor such as described with reference to U.S. Pat. No. 6,424,847 to Mastrototaro et al. Other signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entireties. The sensor extends through a housing, which maintains the sensor on the skin and provides for electrical connection of the sensor to sensor electronics, provided in the electronics unit.

In one embodiment, the sensor is formed from a wire or is in a form of a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension of the elongated conductive body is less than about 0.1 inches (0.3 cm), less than about 0.075 inches (0.20 cm), less than about 0.05 inches (0.13 cm), less than about 0.025 inches (0.06 cm), less than about 0.01 inches (0.03 cm), less than about 0.004 inches (0.01 cm), or less than about 0.002 inches (0.005 cm). The sensor may have a circular cross-section. In some embodiments, the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, one or two additional conducting layers may be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

In certain embodiments, the materials used to form the elongated conductive body (e.g., stainless steel, titanium, tantalum, platinum, platinum-iridium, iridium, certain polymers, and/or the like) can be strong and hard, and therefore are resistant to breakage. For example, in some embodiments, the ultimate tensile strength of the elongated conductive body is from about 80 kPsi to about 500 kPsi. In another example, in some embodiments, the Young's modulus of the elongated conductive body is from about 160 GPa to about 220 GPa. In still another example, in some embodiments, the yield strength of the elongated conductive body is from about 60 kPsi to about 2200 kPsi. In some embodiments, the sensor's small diameter provides (e.g., imparts, enables) flexibility to these materials, and therefore to the sensor as a whole. Thus, the sensor can withstand repeated forces applied to it by surrounding tissue.

In addition to providing structural support, resiliency and flexibility, in some embodiments, the core (or a component thereof) provides electrical conduction for an electrical signal from the working electrode to sensor electronics (not shown). In some embodiments, the core comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is conductive material selected to provide electrical conduction between the core and the first layer, and/or to attach the first layer to the core (e.g., if the first layer is formed of a material that does not attach well to the core material). In another embodiment, the core is formed of a non-conductive material (e.g., a non-conductive metal and/or a non-conductive polymer) and the first layer is a conductive material, such as stainless steel, titanium, tantalum, a conductive polymer, and/or the like. The core and the first layer can be of a single (or same) material, e.g., platinum. One skilled in the art appreciates that additional configurations are possible.

In the illustrated embodiments, the electronics unit 500 is releasably attachable to the sensor 200. The electronics unit 500 includes electronic circuitry associated with measuring and processing the continuous analyte sensor data, and is configured to perform algorithms associated with processing and calibration of the sensor data. For example, the electronics unit 500 can provide various aspects of the functionality of a sensor electronics module as described in U.S. Patent Publication No. US-2009-0240120-A1 and U.S. patent application Ser. No. 13/247,856 filed Sep. 28, 2011 and entitled "ADVANCED CONTINUOUS ANALYTE MONITORING SYSTEM," the contents of which are hereby incorporated by reference in their entireties. The electronics unit 500 may include hardware, firmware, and/or software that enable measurement of levels of the analyte via a glucose sensor, such as an analyte sensor 200. For example, the electronics unit 500 can include a potentiostat, a power source for providing power to the sensor 200, other components useful for signal processing and data storage, and preferably a telemetry module for one- or two-way data communication between the electronics unit 500 and one or more receivers, repeaters, and/or display devices, such as devices 110-113. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. The electronics unit 500 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, and the like. Examples of systems and methods for processing sensor analyte data are described in more detail herein and in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entireties.

One or more repeaters, receivers and/or display devices, such as key fob repeater 110, medical device receiver 111 (e.g., insulin delivery device and/or dedicated glucose sensor receiver), smart phone 112, portable computer 113, and the like are operatively linked to the electronics unit, which receive data from the electronics unit 500, which is also referred to as the transmitter and/or sensor electronics body herein, and in some embodiments transmit data to the electronics unit 500. For example, the sensor data can be transmitted from the sensor electronics unit 500 to one or more of key fob repeater 110, medical device receiver 111, smart phone 112, portable computer 113, and the like. In one embodiment, a display device includes an input module with a quartz crystal operably connected to an RF transceiver (not shown) that together function to transmit, receive and synchronize data streams from the electronics unit 500. However, the input module can be configured in any manner that is capable of receiving data from the electronics unit 500.

Once received, the input module sends the data stream to a processor that processes the data stream, such as described in more detail below. The processor is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. The processor includes hardware that performs the processing described herein, for example read-only memory (ROM) provides permanent or semi-permanent storage of data, storing data such as sensor ID (sensor identity), receiver ID (receiver identity), and programming to process data streams (for example, programming for performing estimation and other algorithms described elsewhere herein) and random access memory (RAM) stores the system's cache memory and is helpful in data processing. An output module, which may be integral with and/or operatively connected with the processor, includes programming for generating output based on the sensor data received from the electronics unit (and any processing that incurred in the processor).

In some embodiments, analyte values are displayed on a display device. In some embodiments, prompts or messages can be displayed on the display device to convey information to the user, such as reference outlier values, requests for reference analyte values, therapy recommendations, deviation of the measured analyte values from the estimated analyte values, or the like. Additionally, prompts can be displayed to guide the user through calibration or troubleshooting of the calibration.

Additionally, data output from the output module can provide wired or wireless, one- or two-way communication between the receiver and an external device. The external device can be any device that interfaces or communicates with the receiver. In some embodiments, the external device is a computer, and the receiver is able to download current or historical data for retrospective analysis by a physician, for example. In some embodiments, the external device is a modem, and the receiver is able to send alerts, warnings, emergency messages, or the like, via telecommunication lines to another party, such as a doctor or family member. In some embodiments, the external device is an insulin pen, and the receiver is able to communicate therapy recommendations, such as insulin amount and time, to the insulin pen. In some embodiments, the external device is an insulin pump, and the receiver is able to communicate therapy recommendations, such as insulin amount and time to the insulin pump. The external device can include other technology or medical devices, for example pacemakers, implanted analyte sensor patches, other infusion devices, telemetry devices, or the like. The receiver may communicate with the external device, and/or any number of additional devices, via any suitable communication protocol, including radio frequency, Bluetooth, universal serial bus, any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, ANT, and/or a proprietary communication protocol.

The implementations described herein generally discuss sensors constituted by one or more sensor wires. However, it will be understood that the sensors are not limited to such wire shaped or linear arrangements. Rather, the sensors may be implemented as planar sensors, volumetric sensors, point sensors, or in other shapes as will be understood given this description.

Membrane Systems

Membrane systems disclosed herein are suitable for use with implantable devices in contact with a biological fluid. For example, the membrane systems can be utilized with implantable devices, such as devices for monitoring and determining analyte levels in a biological fluid, for example, devices for monitoring glucose levels for individuals having diabetes. In some embodiments, the analyte-measuring device is a continuous device. The analyte-measuring device can employ any suitable sensing element to provide the raw signal, including but not limited to those involving enzymatic, chemical, physical, electrochemical, spectrophotometric, polarimetric, calorimetric, radiometric, immunochemical, or like elements.

Although some of the description that follows is directed at glucose-measuring devices, including the described membrane systems and methods for their use, these membrane systems are not limited to use in devices that measure or monitor glucose. These membrane systems are suitable for use in any of a variety of devices, including, for example, devices that detect and quantify other analytes present in biological fluids (e.g. cholesterol, amino acids, alcohol, galactose, and lactate), cell transplantation devices (see, for example, U.S. Pat. Nos. 6,015,572, 5,964,745, and 6,083,523), drug delivery devices (see, for example, U.S. Pat. Nos. 5,458,631, 5,820,589, and 5,972,369), and the like, which are incorporated herein by reference in their entireties for their teachings of membrane systems.

In one embodiment, the analyte-measuring device is an implantable glucose sensor, such as described with reference to U.S. Pat. No. 6,001,067 and U.S. Patent Publication No. US-2005-0027463-A1, which are incorporated herein by reference in their entireties. In another embodiment, the analyte-measuring device is a glucose sensor, such as described with reference to U.S. Patent Publication No. US-2006-0020187-A1, which is incorporated herein by reference in its entirety. In still other embodiments, the sensor is configured to be implanted in a host vessel or extracorporeally, such as is described in U.S. Patent Publication No. US-2007-0027385-A1, U.S. Patent Publication No. US-2008-0119703-A1, U.S. Patent Publication No. US-2008-0108942-A1, and U.S. Patent Publication No. US-2007-0197890-A1, which are incorporated herein by reference in their entirety. In some embodiments, the sensor is configured as a dual-electrode sensor, such as described in U.S. Patent Publication No. US-2005-0143635-A1, U.S. Patent Publication No. US-2007-0027385-A1, U.S. Patent Publication No. US-2007-0213611-A1, and U.S. Patent Publication No. US-2008-0083617-A1, which are incorporated herein by reference in their entirety. In one alternative embodiment, the continuous glucose sensor comprises a sensor such as described in U.S. Pat. No. 6,565,509 to Say et al., for example. In another alternative embodiment, the continuous glucose sensor comprises a subcutaneous sensor such as described with reference to U.S. Pat. No. 6,579,690 to Bonnecaze et al. or U.S. Pat. No. 6,484,046 to Say et al., for example. In another alternative embodiment, the continuous glucose sensor comprises a refillable subcutaneous sensor such as described with reference to U.S. Pat. No. 6,512,939 to Colvin et al., for example. In yet another alternative embodiment, the continuous glucose sensor comprises an intravascular sensor such as described with reference to U.S. Pat. No. 6,477,395 to Schulman et al., for example. In another alternative embodiment, the continuous glucose sensor comprises an intravascular sensor such as described with reference to U.S. Pat. No. 6,424,847 to Mastrototaro et al. In some embodiments, the electrode system can be used with any of a variety of known in vivo analyte sensors or monitors, such as U.S. Pat. No. 7,157,528 to Ward; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; U.S. Pat. No. 6,122,536 to Sun et al.; European Patent Publication No. EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. 5,985,129 to Gough et al.; PCT International Publication No. WO4/021877 to Caduff; U.S. Pat. No. 5,494,562 to Maley et al.; U.S. Pat. No. 6,120,676 to Heller et al.; and U.S. Pat. No. 6,542,765 to Guy et al., which are incorporated by reference herein in their entireties. In general, it is understood that the disclosed embodiments are applicable to a variety of continuous analyte measuring device configurations.

In some embodiments, a long term sensor (e.g., wholly implantable or intravascular) is configured and arranged to function for a time period of from about 30 days or less to about one year or more (e.g., a sensor session). In some embodiments, a short term sensor (e.g., one that is transcutaneous or intravascular) is configured and arranged to function for a time period of from about a few hours to about 30 days, including a time period of about 1, 2, 3, 4, 5, 6, 7, 8, 9, 10, 11, 12, 13, 14, 15, 16, 17, 18, 19, 20, 21, 22, 23, 24, 25, 26, 27, 28 or 29 days (e.g., a sensor session). As used herein, the term "sensor session" is a broad term and refers without limitation to the period of time the sensor is applied to (e.g., implanted in) the host or is being used to obtain sensor values. For example, in some embodiments, a sensor session extends from the time of sensor implantation (e.g., including insertion of the sensor into subcutaneous tissue and placing the sensor into fluid communication with a host's circulatory system) to the time when the sensor is removed.

In general, the membrane system includes a plurality of domains, for example, an electrode domain, an interference domain, an enzyme domain, a resistance domain, and a biointerface domain. The membrane system can be deposited on the exposed electroactive surfaces using known thin film techniques (for example, vapor deposition, spraying, electrodepositing, dipping, brush coating, film coating, drop-let coating, and the like). Addition steps may be applied following the membrane material deposition, for example, drying, annealing, and curing (for example, UV curing, thermal curing, moisture curing, radiation curing, and the like) to enhance certain properties such as mechanical properties, signal stability, and selectivity. In a typical process, upon deposition of resistance layer membrane, a biointerface layer having a "dry film" thickness of from about 0.05 μm, or less, to about 1, 2, 3, 4, 5, 6, 7, 8, 9, 10, 11, 12, 13, 14, 15, or 16 μm. "Dry film" thickness refers to the thickness of a cured film cast from a coating formulation by standard coating techniques.

In certain embodiments, the biointerface layer is formed of a biointerface polymer, wherein the biointerface polymer comprises polyurethane and/or polyurea segments and one or more zwitterionic repeating units. In some embodiments, the biointerface layer coatings are formed of a polyurethane urea having carboxyl betaine groups incorporated in the polymer and non-ionic hydrophilic polyethylene oxide segments, wherein the polyurethane urea polymer is dissolved in organic or non-organic solvent system according to a pre-determined coating formulation, and is crosslinked with an isocyanate crosslinker and cured at moderate temperature of about 50° C. The solvent system can be a single solvent or a mixture of solvents to aid the dissolution or dispersion of the polymer. The solvents can be the ones selected as the polymerization media or added after polymerization is completed. The solvents are preferably selected from the ones having lower boiling point to facilitate drying and lower in toxicity for implant applications. Examples of these solvent includes aliphatic ketone, ester, ether, alcohol, hydrocarbons, and the likes. Depending on the final thickness of the biointerface layer and solution viscosity (as related to the percent of polymer solid), the coating can be applied in a single step or multiple repeated steps of the chosen process such as dipping to build the desired thickness. Yet in other embodiments, the biointerface polymers are formed of a polyurethane urea having carboxylic acid groups and carboxyl betaine groups incorporated in the polymer and non-ionic hydrophilic polyethylene oxide segments, wherein the polyurethane urea polymer is dissolved in organic or non-organic solvent system in a coating formulation, and is crosslinked with an a carbodiimide (e.g., 1-ethyl-3-(3-dimethylaminopropyl)carbodiimide (EDC) and cured at moderate temperature of about 50° C.

In certain embodiments, the biointerface layer is formed of a biointerface polymer. The biointerface polymer is a polyzwitterion. The biointerface polymer may also comprise polyurethane and/or polyurea segments. For example, the biointerface polymer can comprise a polyurethane copolymer such as polyether-urethane-urea, polycarbonate-urethane, polyether-urethane, silicone-polyether-urethane, silicone-polycarbonate-urethane, polyester-urethane, polyurethane-urea, and the like. Since these polyurethane and/or polyurea segments contain urea and/or urethane bonds formed from polyisocyanate and short chain polyol or polyamine, which are hydrogen bonding rich moieties, these segments are referred to herein as "hard segments." These segments can also be relatively hydrophobic. In addition to polyurethane and/or polyurea hard segments, the disclosed biointerface polymers can also comprise soft segments, which have relatively poor hydrogen bonding. Soft segment are usually composed of polyols of polycarbonates, polyesters, polyethers, polyarylene, and polyalkylene, and the like. The soft segments can be either hydrophobic or hydrophilic. In certain embodiments, the biointerface layer is formed of a biointerface polymer, wherein the biointerface polymer comprises polyurethane and/or polyurea segments and one or more zwitterionic repeating units. In some embodiments, the biointerface polymer is formed of a polyurethane urea having betaine groups incorporated in the polymer and non-ionic hydrophilic polyethylene oxide segments.

In other embodiments, the biointerface layer coatings are formed of a polyurethane urea having sulfo betaine groups incorporated in the polymer and non-ionic hydrophilic polyethylene oxide segments, wherein the polyurethane urea polymer is dissolved in organic or non-organic solvent system according to a pre-determined coating formulation, and is crosslinked with an isocyanate crosslinker and cured at moderate temperature of about 50° C. The solvent system can be a single solvent or a mixture of solvents to aid the dissolution or dispersion of the polymer. The solvents can be the ones selected as the polymerization media or added after polymerization is completed. The solvents are preferably selected from the ones having lower boiling point to facilitate drying and lower in toxicity for implant applications. Examples of these solvent includes aliphatic ketone, ester, ether, alcohol, hydrocarbons, and the likes. Depending on the final thickness of the biointerface layer and solution viscosity (as related to the percent of polymer solid), the coating can be applied in a single step or multiple repeated steps of the chosen process such as dipping to build the desired thickness. Yet in other embodiments, the biointerface polymers are formed of a polyurethane urea having unsaturated hydrocarbon groups and sulfo betaine groups incorporated in the polymer and non-ionic hydrophilic polyethylene oxide segments, wherein the polyurethane urea polymer is dissolved in organic or non-organic solvent system in a coating formulation, and is crosslinked in the presence of initiators with heat or irradiation including UV, LED light, electron beam, and the likes, and cured at moderate temperature of about 50° C. Examples of unsaturated hydrocarbon includes allyl groups, vinyl groups, acrylate, methacrylate, alkenes, alkynes, and the likes.

In certain embodiments, the enzyme layer is formed of an enzyme layer polymer and an active enzyme, wherein the enzyme layer polymer comprises polyurethane and/or polyurea segments and one or more zwitterionic repeating units. In some embodiments, the enzyme layer coatings are formed of a polyurethane urea having carboxyl betaine groups incorporated in the polymer and non-ionic hydrophilic polyethylene oxide segments, wherein the polyurethane urea polymer is dissolved in organic or non-organic solvent system according to a pre-determined coating formulation, and is crosslinked with an isocyanate crosslinker and cured at moderate temperature of about 50° C. The solvent system can be a single solvent or a mixture of solvents to aid the dissolution or dispersion of the polymer. The solvents can be the ones selected as the polymerization media or added after polymerization is completed. The solvents are preferably selected from the ones having lower boiling point to facilitate drying, having a lower potential to denature the enzyme, and lower in toxicity for implant applications. Examples of these solvents include water, aliphatic ketone, ester, ether, alcohol, hydrocarbons, and the likes. Depending on the final thickness of the enzyme layer and solution viscosity (as related to the percent of polymer solid), the coating can be applied in a single step or multiple repeated steps of the chosen process such as dipping to build the desired thickness. Yet in other embodiments, the enzyme layer polymers are formed of a polyurethane urea having carboxylic acid groups and carboxyl betaine groups incorporated in the polymer and non-ionic hydrophilic polyethylene oxide segments, wherein the polyurethane urea polymer is dissolved in organic or non-organic solvent system in a coating formulation, and is crosslinked with an a carbodiimide (e.g., 1-ethyl-3-(3-dimethylaminopropyl)carbodiimide (EDC) and cured at moderate temperature of about 50° C. Other crosslinkers can be used as well, such as polyfunctional aziridines.

In other embodiments, the enzyme layer is formed of a polyurethane urea having sulfo betaine groups incorporated in the polymer and non-ionic hydrophilic polyethylene oxide segments, wherein the polyurethane urea polymer is dissolved in organic or non-organic solvent system according to a pre-determined coating formulation, and is crosslinked with an isocyanate crosslinker and cured at moderate temperature of about 50° C. The solvent system can be a single solvent or a mixture of solvents to aid the dissolution or dispersion of the polymer. The solvents can be the ones selected as the polymerization media or added after polymerization is completed. The solvents are preferably selected from the ones having lower boiling point to facilitate drying and lower in toxicity for implant applications. Examples of these solvent includes aliphatic ketone, ester, ether, alcohol, hydrocarbons, and the likes. Depending on the final thickness of the enzyme layer and solution viscosity (as related to the percent of polymer solid), the coating can be applied in a single step or multiple repeated steps of the chosen process such as dipping to build the desired thickness. Yet in other embodiments, the enzyme layer polymers are formed of a polyurethane urea having unsaturated hydrocarbon groups and sulfo betaine groups incorporated in the polymer and non-ionic hydrophilic polyethylene oxide segments, wherein the polyurethane urea polymer is dissolved in organic or non-organic solvent system in a coating formulation, and is crosslinked in the presence of initiators with heat or irradiation including UV, LED light, electron beam, and the like, and cured at moderate temperature of about 50° C. Examples of unsaturated hydrocarbon includes allyl groups, vinyl groups, acrylate, methacrylate, alkenes, alkynes, and the likes.

Figure 3A:
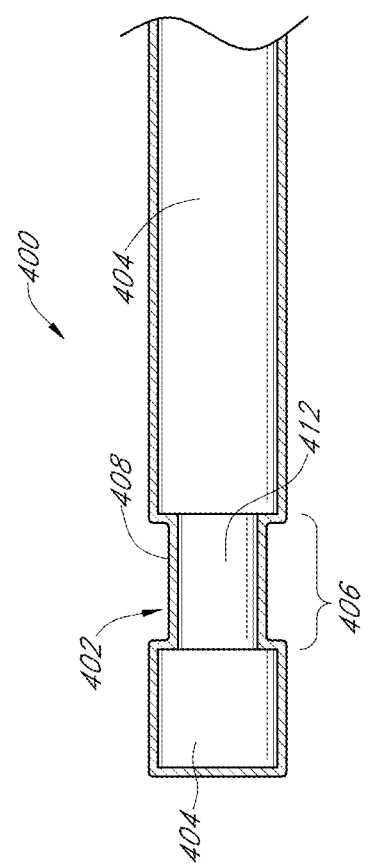
FIG. 3A is a side view schematic illustrating an in vivo portion of a continuous analyte sensor, in one embodiment.
Figure 3B:
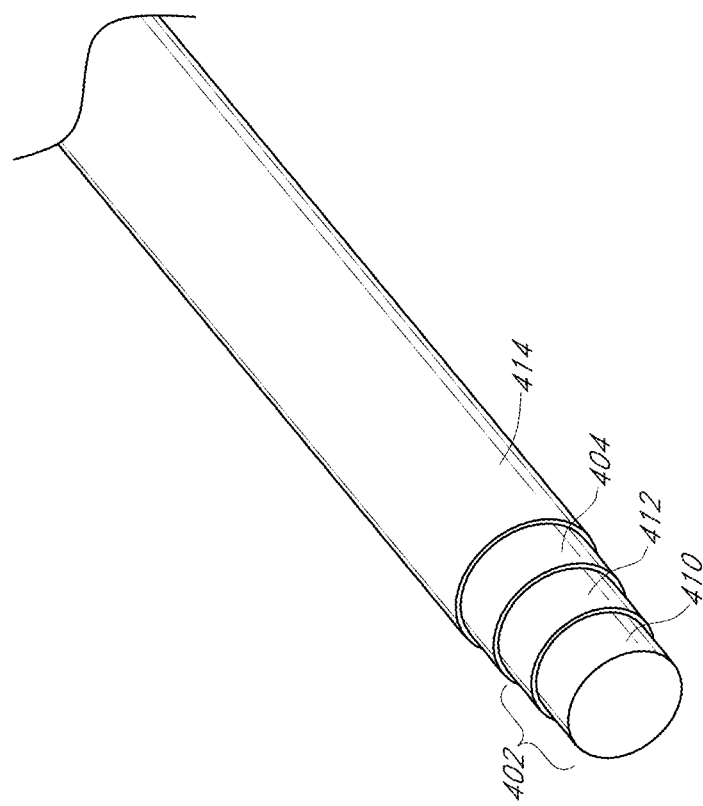
FIG. 3B is a perspective view schematic illustrating an in vivo portion of a continuous analyte sensor, in one embodiment.
Figure 3C:
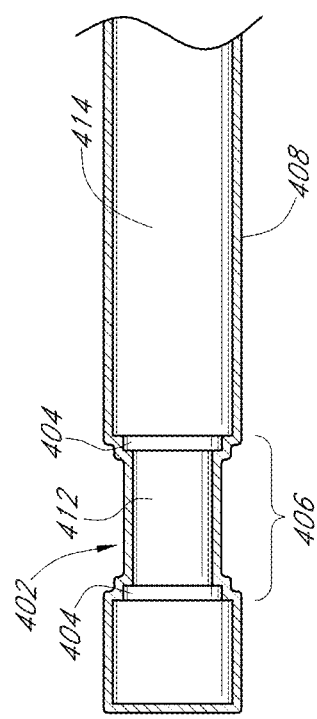
FIG. 3C is a side view schematic illustrating an in vivo portion of a continuous analyte sensor, in one embodiment.

FIGS. 3A through 3C illustrate an embodiment of the in vivo portion of a continuous analyte sensor 400, which includes an elongated conductive body 402. The elongated conductive body 402 includes a core 410 (see FIG. 3B) and a first layer 412 at least partially surrounding the core. The first layer includes a working electrode (for example, located in window 406) and a membrane 408 located over the working electrode. In some embodiments, the core and first layer can be of a single material (such as, for example, platinum). In some embodiments, the elongated conductive body is a composite of at least two materials, such as a composite of two conductive materials, or a composite of at least one conductive material and at least one non-conductive material. In some embodiments, the elongated conductive body comprises a plurality of layers. In certain embodiments, there are at least two concentric or annular layers, such as a core formed of a first material and a first layer formed of a second material. However, additional layers can be included in some embodiments. In some embodiments, the layers are coaxial.

The elongated conductive body can be long and thin, yet flexible and strong. For example, in some embodiments, the smallest dimension of the elongated conductive body is less than about 0.1 inches, 0.075 inches, 0.05 inches, 0.025 inches, 0.01 inches, 0.004 inches, or 0.002 inches. While the elongated conductive body is illustrated in FIGS. 3A through 3C as having a circular cross-section, in other embodiments the cross-section of the elongated conductive body can be ovoid, rectangular, triangular, polyhedral, star-shaped, C-shaped, T-shaped, X-shaped, Y-Shaped, irregular, or the like. In one embodiment, a conductive wire electrode is employed as a core. To such a clad electrode, two additional conducting layers can be added (e.g., with intervening insulating layers provided for electrical isolation). The conductive layers can be comprised of any suitable material. In certain embodiments, it can be desirable to employ a conductive layer comprising conductive particles (i.e., particles of a conductive material) in a polymer or other binder.

The materials used to form the elongated conductive body (such as, for example, stainless steel, titanium, tantalum, platinum, platinum-iridium, iridium, certain polymers, and/or the like) can be strong and hard, and therefore are resistant to breakage. In some embodiments, the sensor's small diameter provides flexibility to these materials, and therefore to the sensor as a whole. Thus, the sensor can withstand repeated forces applied to it by surrounding tissue.

In addition to providing structural support, resiliency and flexibility, in some embodiments, the core 410, or a component thereof, provides electrical conduction for an electrical signal from the working electrode to sensor electronics (not shown). In some embodiments, the core 410 comprises a conductive material, such as stainless steel, titanium, tantalum, a conductive polymer, and/or the like. However, in other embodiments, the core is formed from a non-conductive material, such as a non-conductive polymer. In yet other embodiments, the core comprises a plurality of layers of materials. For example, in one embodiment the core includes an inner core and an outer core. In a further embodiment, the inner core is formed of a first conductive material and the outer core is formed of a second conductive material. For example, in some embodiments, the first conductive material is stainless steel, titanium, tantalum, a conductive polymer, an alloy, and/or the like, and the second conductive material is a conductive material selected to provide electrical conduction between the core and the first layer, and/or to attach the first layer to the core (that is, if the first layer is formed of a material that does not attach well to the core material). In another embodiment, the core is formed of a non-conductive material (such as, for example, a non-conductive metal and/or a non-conductive polymer) and the first layer is formed of a conductive material, such as stainless steel, titanium, tantalum, a conductive polymer, and/or the like. The core and the first layer can be of a single (or same) material, such as platinum. One skilled in the art appreciates that additional configurations are possible.

Referring again to FIGS. 3A through 3C, the first layer 412 can be formed of a conductive material and the working electrode can be an exposed portion of the surface of the first layer 412. Accordingly, the first layer 412 can be formed of a material configured to provide a suitable electroactive surface for the working electrode, a material such as, but not limited to, platinum, platinum-iridium, gold, palladium, iridium, graphite, carbon, a conductive polymer, an alloy and/or the like.

As illustrated in FIG. 3B and FIG. 3C, a second layer 404 surrounds at least a portion of the first layer 412, thereby defining the boundaries of the working electrode. In some embodiments, the second layer 404 serves as an insulator and is formed of an insulating material, such as polyimide, polyurethane, parylene, or any other known insulating materials. For example, in one embodiment the second layer is disposed on the first layer and configured such that the working electrode is exposed via window 406. In some embodiments, an elongated conductive body, including the core, the first layer and the second layer, is provided. A portion of the second layer can be removed to form a window 406, through which the electroactive surface of the working electrode (that is, the exposed surface of the first layer 412) is exposed. In some embodiments, a portion of the second and (optionally) third layers can be removed to form the window 406, thus exposing the working electrode. Removal of coating materials from one or more layers of the elongated conductive body (for example, to expose the electroactive surface of the working electrode) can be performed by hand, excimer lasing, chemical etching, laser ablation, grit-blasting, or the like.

The sensor can further comprise a third layer 414 comprising a conductive material. For example, the third layer 414 can comprise a reference electrode, which can be formed of a silver-containing material that is applied onto the second layer 404 (that is, the insulator).

The elongated conductive body 402 can further comprise one or more intermediate layers (not shown) located between the core 410 and the first layer 412. For example, the intermediate layer can be one or more of an insulator, a conductor, a polymer, and/or an adhesive.

It is contemplated that the ratio between the thickness of the silver/silver chloride layer and the thickness of an insulator (such as, for example, polyurethane or polyimide) layer can be controlled, so as to allow for a certain error margin (that is, an error margin associated with the etching process) that would not result in a defective sensor (for example, due to a defect resulting from an etching process that cuts into a depth more than intended, thereby unintentionally exposing an electroactive surface). This ratio can be different depending on the type of etching process used, whether it is laser ablation, grit blasting, chemical etching, or some other etching method. In one embodiment in which laser ablation is performed to remove a silver/silver chloride layer and a polyurethane layer, the ratio of the thickness of the silver/silver chloride layer and the thickness of the polyurethane layer can be from about 1:5 to about 1:1, or from about 1:3 to about 1:2.

In some embodiments, the core 410 comprises a non-conductive polymer and the first layer 412 comprises a conductive material. Such a sensor configuration can advantageously provide reduced material costs, in that it replaces a typically expensive material with an inexpensive material. For example, the core 410 can be formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

Figure 2A:
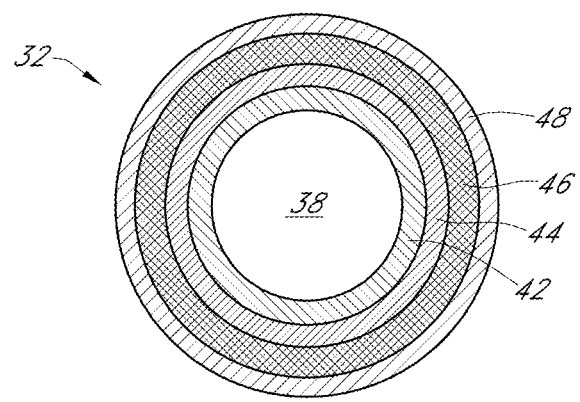
FIGS. 2A-2C are cross-sectional views of a sensor illustrating various embodiments of the membrane system.
Figure 2B:
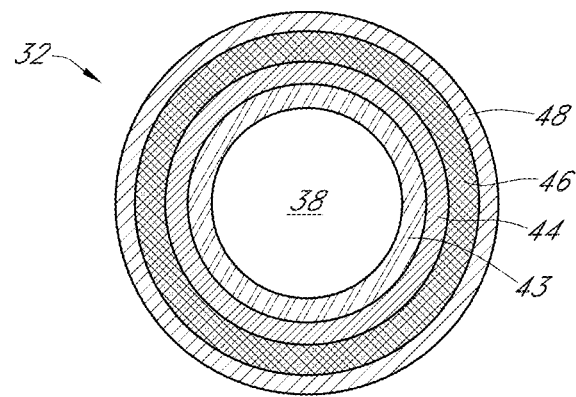
Figure 2C:
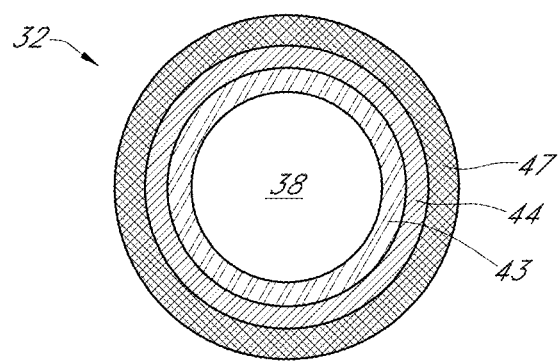
Figure 3D:
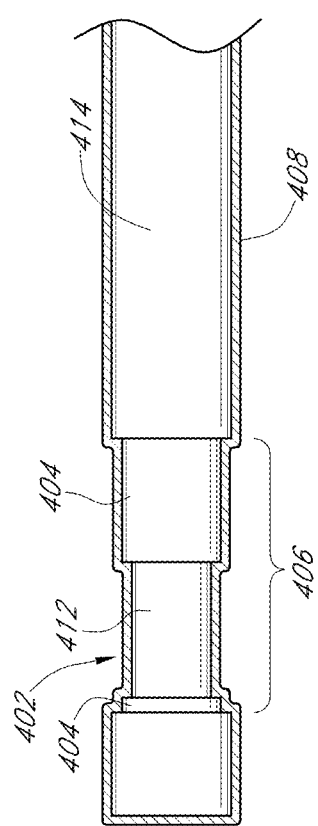
FIG. 3D is a cross-sectional/side-view schematic illustrating an in vivo portion of a continuous analyte sensor, in one embodiment.

As illustrated in FIG. 3C and FIG. 3D, the sensor can also include a membrane 408, such as those discussed elsewhere herein, for example, with reference to FIGS. 2A through 2C. The membrane 408 can include an enzyme layer (not shown), as described elsewhere herein. For example, the enzyme layer can include a catalyst or enzyme configured to react with an analyte. For example, the enzyme layer can be an immobilized enzyme layer including glucose oxidase. In other embodiments, the enzyme layer can be impregnated with other oxidases, including, for example, galactose oxidase, cholesterol oxidase, amino acid oxidase, alcohol oxidase, lactate oxidase, or uricase.

FIG. 3B is a schematic illustrating an embodiment of an elongated conductive body 402, or elongated body, wherein the elongated conductive body is formed from at least two materials and/or layers of conductive material, as described in greater detail elsewhere herein. The term "electrode" can be used herein to refer to the elongated conductive body, which includes the electroactive surface that detects the analyte. In some embodiments, the elongated conductive body provides an electrical connection between the electroactive surface (that is, the working electrode) and the sensor electronics (not shown). In certain embodiments, each electrode (that is, the elongated conductive body on which the electroactive surface is located) is formed from a fine wire with a diameter of from about 0.001 inches (0.003 cm) or less to about 0.01 inches (0.03 cm) or more. Each electrode can be formed from, for example, a plated insulator, a plated wire, or bulk electrically conductive material. For example, in some embodiments, the wire and/or elongated conductive body used to form a working electrode is about 0.002, 0.003, 0.004, 0.005, 0.006, 0.007, 0.008, 0.009, 0.01, 0.015, 0.02, 0.025, 0.03, 0.035, 0.04 or 0.045 inches in diameter.

Furthermore, the first layer can comprise an electroactive surface (that is, the portion exposed through the window 406). The exposed electroactive surface can be the working electrode. For example, if the sensor is an enzymatic electrochemical analyte sensor, the analyte enzymatically reacts with an enzyme in the membrane covering at least a portion of the electroactive surface. The reaction can generate electrons (e$^-$) that are detected at the electroactive surface as a measurable electronic current. For example, in the detection of glucose wherein glucose oxidase produces hydrogen peroxide as a byproduct, hydrogen peroxide reacts with the surface of the working electrode producing two protons (2H$^+$), two electrons (2e$^-$) and one molecule of oxygen (O$_2$), which produces the electronic current being detected.

As previously described with reference to FIG. 3A and as illustrated in FIG. 3C, an insulator 404 is disposed on at least a portion of the elongated conductive body 402. In some embodiments, the sensor is configured and arranged such that the elongated body includes a core 410 and a first layer 412, and a portion of the first layer 412 is exposed via window 406 in the insulator 404. In other embodiments, the sensor is configured and arranged such that the elongated body 402 includes a core 410 embedded in an insulator 404, and a portion of the core 410 is exposed via the window 406 in the insulator 404. For example, the insulating material can be applied to the elongated body 402 (by, for example, screen-, ink-jet and/or block-print) in a configuration designed to leave at least a portion of the first layer's 412 surface (or the core's 410 surface) exposed. For example, the insulating material can be printed in a pattern that does not cover a portion of the elongated body 402. Alternatively, a portion of the elongated body 402 can be masked prior to application of the insulating material. Removal of the mask, after insulating material application, can expose the portion of the elongated body 402.

In some embodiments, the insulating material 404 comprises a polymer, for example, a non-conductive (that is, dielectric) polymer. Dip-coating, spray-coating, vapor-deposition, printing and/or other thin film and/or thick film coating or deposition techniques can be used to deposit the insulating material on the elongated body 402 and/or core 410. For example, in some embodiments, the insulating material is applied as a layer of from about less than 5 μm, or from about 5, about 10 or about 15 μm to about 20, about 25, about 30, or about 35 μm or more in thickness. The insulator can be applied as a single layer of material, or as two or more layers, which are comprised of either the same or different materials, as described elsewhere herein. Alternatively, the conductive core does not require a coating of insulator. In some embodiments, the insulating material defines an electroactive surface of the analyte sensor (that is, the working electrode). For example, a surface of the conductive core (such as, for example, a portion of the first layer 412) can either remain exposed during the insulator application, or a portion of applied insulator can be removed to expose a portion of the conductive core's surface, as described above.

In some embodiments, in which the sensor has an insulated elongated body or an insulator disposed upon a conductive structure, a portion of the insulating material can be stripped or otherwise removed, for example, by hand, excimer lasing, chemical etching, laser ablation, grit-blasting (such as, for example, with sodium bicarbonate or other suitable grit), or the like, to expose the electroactive surfaces. In one exemplary embodiment, grit blasting is implemented to expose the electroactive surface(s), for example, by utilizing a grit material that is sufficiently hard to ablate the polymer material yet also sufficiently soft so as to minimize or avoid damage to the underlying metal electrode (for example, a platinum electrode). Although a variety of "grit" materials can be used (such as, for example, sand, talc, walnut shell, ground plastic, sea salt, and the like), in some embodiments, sodium bicarbonate is an advantageous grit-material because it is sufficiently hard to ablate, e.g., a parylene coating without damaging, e.g., an underlying platinum conductor. An additional advantage of sodium bicarbonate blasting includes its polishing action on the metal as it strips the polymer layer, thereby eliminating a cleaning step that might otherwise be necessary. Alternatively, a portion of an electrode or other conductive body can be masked prior to depositing the insulator in order to maintain an exposed electroactive surface area.

The electroactive surface of the working electrode can be exposed by formation of a window 406 in the insulator 404. The electroactive window 406 of the working electrode can be configured to measure the concentration of an analyte.

In some embodiments, a silver wire is formed onto and/or fabricated into the sensor and subsequently chloridized to form a silver/silver chloride reference electrode. Advantageously, chloridizing the silver wire as described herein enables the manufacture of a reference electrode with good in vivo performance. By controlling the quantity and amount of chloridization of the silver to form silver/silver chloride, improved break-in time, stability of the reference electrode and extended life can be obtained in some embodiments. Additionally, use of silver chloride as described above allows for relatively inexpensive and simple manufacture of the reference electrode.

Referring to FIG. 3B and FIG. 3C, the reference electrode 414 can comprise a silver-containing material (e.g., silver/silver chloride) applied over at least a portion of the insulating material 404, as discussed in greater detail elsewhere herein. For example, the silver-containing material can be applied using thin film and/or thick film techniques, such as but not limited to dipping, spraying, printing, electro-depositing, vapor deposition, spin coating, and sputter deposition, as described elsewhere herein. For example, a silver or silver chloride-containing paint (or similar formulation) can be applied to a reel of the insulated conductive core. Alternatively, the reel of insulated elongated body (or core) is cut into single unit pieces (that is, "singularized"), and silver-containing ink is pad printed thereon. In still other embodiments, the silver-containing material is applied as a silver foil. For example, an adhesive can be applied to an insulated elongated body, around which the silver foil can then be wrapped in. Alternatively, the sensor can be rolled in Ag/AgCl particles, such that a sufficient amount of silver sticks to and/or embeds into and/or otherwise adheres to the adhesive for the particles to function as the reference electrode. In some embodiments, the sensor's reference electrode includes a sufficient amount of chloridized silver that the sensor measures and/or detects the analyte for at least three days.

FIG. 2A is a cross-sectional view through a sensor illustrating one embodiment of the membrane system 32. In this particular embodiment, the membrane system includes an electrode layer 42, an enzyme layer 44, a diffusion resistance layer 46, and a biointerface layer 48, all of which are located around a working electrode of the sensor 38, and all of which are described in more detail elsewhere herein. In some embodiments, a unitary diffusion resistance domain and biointerface layer can be included in the membrane system (e.g., wherein the functionality of both layers is incorporated into one domain). In some embodiments, the sensor is configured for short-term implantation (e.g., from about 1 to 30 days). However, it is understood that the membrane system 32 can be modified for use in other devices, for example, by including only one or more of the domains, or additional domains.

FIG. 2B is a cross-sectional view through one embodiment of the sensor, illustrating another embodiment of the membrane system 32. In this particular embodiment, the membrane system includes an interference reduction or blocking layer 43, an enzyme layer 44, a diffusion resistance layer 46, and a biointerface layer 48 located around the working electrode of a sensor 38, all of which are described in more detail elsewhere herein.

FIG. 2C is a cross-sectional view through one embodiment of the sensor, illustrating still another embodiment of the membrane system 32. In this particular embodiment, the membrane system includes an interferent reduction or blocking layer 43, an enzyme layer 44, and a unitary diffusion resistance/biointerface layer 47 located around the working electrode of a sensor, all of which are described in more detail elsewhere herein.

In some embodiments, the membrane system can include a biointerface layer 48, comprising a surface-modified biointerface polymer as described in more detail elsewhere herein. However, the sensing membranes 32 of some embodiments can also include a plurality of domains or layers including, for example, an electrode domain (e.g., as illustrated in the FIG. 2A), an interference reduction or blocking domain (e.g., as illustrated in FIGS. 2B and 2C), or a cell disruptive domain (not shown), such as described in more detail elsewhere herein and in U.S. Patent Publication No. US-2006-0036145-A1, which is incorporated herein by reference in its entirety.

It is to be understood that sensing membranes modified for other sensors, for example, can include fewer or additional layers. For example, in some embodiments, the membrane system can comprise one electrode layer, one enzyme layer, and two biointerface layers, but in other embodiments, the membrane system can comprise one electrode layer, two enzyme layers, and one biointerface layer. In some embodiments, the biointerface layer can be configured to function as the diffusion resistance domain and control the flux of the analyte (e.g., glucose) to the underlying membrane layers.

In some embodiments, one or more domains of the sensing membranes can be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, polyurethane ureas, cellulosic polymers, poly(ethylene oxide), poly(propylene oxide) and copolymers and blends thereof, polysulfones and block copolymers thereof including, for example, di-block, tri-block, alternating, random and graft copolymers.

In some embodiments, the sensing membrane can be deposited on the electroactive surfaces of the electrode material using known thin or thick film techniques (for example, spraying, electro-depositing, dipping, or the like). It should be appreciated that the sensing membrane located over the working electrode does not have to have the same structure as the sensing membrane located over the reference electrode; for example, the enzyme domain deposited over the working electrode does not necessarily need to be deposited over the reference or counter electrodes.

Although the exemplary embodiments illustrated in FIGS. 2A through 2C involve circumferentially extending membrane systems, the membranes described herein can be applied to any planar or non-planar surface.

Sensor Electronics

In general, analyte sensor systems have electronics associated therewith, also referred to as a "computer system" that can include hardware, firmware, or software that enable measurement and processing of data associated with analyte levels in the host. In one exemplary embodiment of an electrochemical sensor, the electronics include a potentiostat, a power source for providing power to the sensor, and other components useful for signal processing. In additional embodiments, some or all of the electronics can be in wired or wireless communication with the sensor or other portions of the electronics. For example, a potentiostat disposed on the device can be wired to the remaining electronics (e.g. a processor, a recorder, a transmitter, a receiver, etc.), which reside on the bedside. In another example, some portion of the electronics is wirelessly connected to another portion of the electronics (e.g., a receiver), such as by infrared (IR) or radiofrequency (RF). It is contemplated that other embodiments of electronics can be useful for providing sensor data output, such as those described in U.S. Patent Publication No. US-2005-0192557-A1, U.S. Patent Publication No. US-2005-0245795-A1, U.S. Patent Publication No. US-2005-0245795-A1, U.S. Patent Publication No. US-2005-0245795-A1, U.S. Patent Publication No. US-2008-0119703-A1, and U.S. Patent Publication No. US-2008-0108942-A1, each of which is incorporated herein by reference in its entirety.

In one preferred embodiment, a potentiostat is operably connected to the electrode(s) (such as described elsewhere herein), which biases the sensor to enable measurement of a current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device. In some embodiments, the electronics include an A/D converter that digitizes the analog signal into a digital signal, also referred to as "counts" for processing. Accordingly, the resulting raw data stream in counts, also referred to as raw sensor data, is directly related to the current measured by the potentiostat.

In general, the electronics include a processor module that includes the central control unit that controls the processing of the sensor system. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing or replacement of signal artifacts such as is described in U.S. Patent Publication No. US-2005-0043598-A1). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like.

In some embodiments, the processor module comprises a digital filter, for example, an infinite impulse response (IIR) or finite impulse response (FIR) filter, configured to smooth the raw data stream. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter.

In some embodiments, the processor module is configured to build the data packet for transmission to an outside source, for example, an RF transmission to a receiver. Generally, the data packet comprises a plurality of bits that can include a preamble, a unique identifier identifying the electronics unit, the receiver, or both, (e.g., sensor ID code), data (e.g. raw data, filtered data, or an integrated value) or error detection or correction. Preferably, the data (transmission) packet has a length of from about 8 bits to about 128 bits, preferably about 48 bits; however, larger or smaller packets can be desirable in certain embodiments. The processor module can be configured to transmit any combination of raw or filtered data. In one exemplary embodiment, the transmission packet contains a fixed preamble, a unique ID of the electronics unit, a single five-minute average (e.g. integrated) sensor data value, and a cyclic redundancy code (CRC).

In some embodiments, the processor further performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, and the like. In such cases, the processor includes hardware and software that performs the processing described herein, for example flash memory provides permanent or semi-permanent storage of data, storing data such as sensor ID, receiver ID, and programming to process data streams (e.g., programming for performing estimation and other algorithms described elsewhere herein) and random access memory (RAM) stores the system's cache memory and is helpful in data processing. Alternatively, some portion of the data processing (such as described with reference to the processor elsewhere herein) can be accomplished at another (e.g., remote) processor and can be configured to be in wired or wireless connection therewith.

In some embodiments, an output module, which is integral with or operatively connected with the processor, includes programming for generating output based on the data stream received from the sensor system and it's processing incurred in the processor. In some embodiments, output is generated via a user interface.

Interferents

Interferents are molecules or other species that can cause a sensor to generate a false positive or negative analyte signal (e.g., a non-analyte-related signal). Some interferents become reduced or oxidized at the electrochemically reactive surfaces of the sensor, while other interferents interfere with the ability of the enzyme (e.g., glucose oxidase) used to react with the analyte being measured. Yet other interferents react with the enzyme (e.g., glucose oxidase) to produce a by-product that is electrochemically active. Interferents can exaggerate or mask the response signal, thereby leading to false or misleading results. For example, a false positive signal can cause the host's analyte concentration (e.g., glucose concentration) to appear higher than the true analyte concentration. False-positive signals can pose a clinically significant problem in some conventional sensors. For example in a severe hypoglycemic situation, in which the host has ingested an interferent (e.g., acetaminophen), the resulting artificially high glucose signal can lead the host to believe that he is euglycemic or hyperglycemic. In response, the host can make inappropriate treatment decisions, such as by injecting himself with too much insulin, or by taking no action, when the proper course of action would be to begin eating. In turn, this inappropriate action or inaction can lead to a dangerous hypoglycemic episode for the host. Accordingly, certain embodiments contemplated herein include a membrane system that substantially reduces or eliminates the effects of interferents on analyte measurements. These membrane systems can include one or more domains capable of blocking or substantially reducing the flow of interferents onto the electroactive surfaces of the electrode can reduce noise and improve sensor accuracy as described in more detail in U.S. Patent Publication No. US-2009-0247856-A1.

Drift

The term "drift" as used herein is a broad term, and is to be given its ordinary and customary meaning to a person of ordinary skill in the art (and is not to be limited to a special or customized meaning), and refers without limitation to a change in the sensitivity of a sensor over time. Drift can be driven by a change in permeability of the sensor membrane system, which can be particularly evident in embodiments which use a polyurethane diffusion resistance domain. Without wishing to be bound by theory, it is believed that the change in permeability in such systems arises from the rearrangement of the diffusion resistance domain polyurethane polymer chains to either bring more hydrophilic components to the surface or otherwise rearrange in some way to allow for greater access to hydrophilic polymer components during hydration of the membrane system. Because of this, increasing the speed of hydration or increasing the wettability of the membrane system reduces system drift.

Due to electrostatically induced hydration, polymers and cross-linked coatings of zwitterionic compounds have near instantaneous wetting properties. As discussed in greater detail below, including one or more zwitterionic compounds, precursors or derivatives thereof (such as hydrolyzable cationic esters) in the outermost domain of a membrane system or applying a coating of such compounds to the surface of the membrane system results in reduced sensor drift. Further, as discussed in greater detail below, including a base polymer having a lowest glass transition temperature as measured using ASTM D3418 of greater than −50° C. and an ultimate tensile strength as measured by ASTM D1708 that is greater than 6000 psi can result in reduced sensor drift. The drift can be characterized by less than 10% change in signal at 2 hrs after start.

Membrane Fabrication

Polymers of the preferred embodiments can be processed by solution-based techniques such as spraying, dipping, casting, electrospinning, vapor deposition, spin coating, coating, and the like. Water-based polymer emulsions can be fabricated to form membranes by methods similar to those used for solvent-based materials. In both cases the evaporation of a volatile liquid (e.g., organic solvent or water) leaves behind a film of the polymer. Cross-linking of the deposited film or layer can be performed through the use of multi-functional reactive ingredients by a number of methods. The liquid system can cure by heat, moisture, high-energy radiation, ultraviolet light, or by completing the reaction, which produces the final polymer in a mold or on a substrate to be coated.

In some embodiments, the wetting property of the membrane (and by extension the extent of sensor drift exhibited by the sensor) can be adjusted and/or controlled by creating covalent cross-links between surface-active group-containing polymers, functional-group containing polymers, polymers with zwitterionic groups (or precursors or derivatives thereof), and combinations thereof. Cross-linking can have a substantial effect on film structure, which in turn can affect the film's surface wetting properties. Crosslinking can also affect the film's tensile strength, mechanical strength, water absorption rate and other properties.

Cross-linked polymers can have different cross-linking densities. In certain embodiments, cross-linkers are used to promote cross-linking between layers. In other embodiments, in replacement of (or in addition to) the cross-linking techniques described above, heat is used to form cross-linking. For example, in some embodiments, imide and amide bonds can be formed between two polymers as a result of high temperature. In some embodiments, photo cross-linking is performed to form covalent bonds between the polycationic layers(s) and polyanionic layer(s). One major advantage to photo-cross-linking is that it offers the possibility of patterning. In certain embodiments, patterning using photo-cross linking is performed to modify the film structure and thus to adjust the wetting property of the membrane.

Polymers with domains or segments that are functionalized to permit cross-linking can be made by methods known in the art. For example, polyurethaneurea polymers with aromatic or aliphatic segments having electrophilic functional groups (e.g., carbonyl, aldehyde, anhydride, ester, amide, isocyano, epoxy, allyl, or halo groups) can be cross-linked with a crosslinking agent that has multiple nucleophilic groups (e.g., hydroxyl, amine, urea, urethane, or thio groups). In further embodiments, polyurethaneurea polymers having aromatic or aliphatic segments having nucleophilic functional groups can be crosslinked with a crosslinking agent that has multiple electrophilic groups. Still further, polyurethaneurea polymers having hydrophilic segments having nucleophilic or electrophilic functional groups can be crosslinked with a crosslinking agent that has multiple electrophilic or nucleophilic groups. Unsaturated functional groups on the polyurethane urea can also be used for crosslinking by reacting with multivalent free radical agents. Non-limiting examples of suitable cross-linking agents include isocyanate, carbodiimide, glutaraldehyde, aziridine, silane, or other aldehydes, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final film.

Polymers disclosed herein can be formulated into mixtures that can be drawn into a film or applied to a surface using any method known in the art (e.g., spraying, painting, dip coating, vapor depositing, molding, 3-D printing, lithographic techniques (e.g., photolithograph), micro- and nano-pipetting printing techniques, silk-screen printing, etc.). The mixture can then be cured under high temperature (e.g., 50-150° C.). Other suitable curing methods can include ultraviolet or gamma radiation, for example.

Biointerface Domain

The biointerface layer is the domain or layer of an implantable device configured to interface with (i.e., contact) a biological fluid when implanted in a host or connected to the host (e.g., via an intravascular access device providing extracorporeal access to a blood vessel). When present on an analyte sensor, e.g., a continuous analyte sensor implanted into a host, the biointerface layer can increase sensor longevity and decrease sensor inaccuracy by reducing the biomaterial-associated inflammation response. The antifouling properties of the biointerface layer can inhibit the accumulation of cells, proteins, and other biological species on the sensor. In some embodiments, the biointerface domain may be formed of a biointerface domain described in U.S. Provisional Application No. 62/273,142, filed Dec. 30, 2015, which is hereby incorporated by reference herein in its entirety.

The biointerface layers disclosed herein can be mechanically robust, resist damage upon implantation, and withstand degradation during the sensor implantation. Further, the disclosed biointerface layers do not materially affect the response time of the sensor or the diffusion resistance layer's properties. Also, the disclosed biointerface layers can have hydrophilic properties that can have large amounts of water uptake, and fast water uptake and quick stabilization, so that sensor start-up is not negatively affected. The disclosed biointerface layers are also permeable to analytes (e.g., glucose) but resist adsorption of proteins.

Some embodiments described herein can include membranes that comprise a biointerface layer 48 (see FIGS. 2A and 2B).

Furthermore, the disclosed biointerface layer can be the host of pharmaceutical or bioactive agent that upon release from the biointerface layer to the local tissue can effectively reduce or delay inflammation. The anti-inflammatory agents can be steroidal or non-steroidal drugs and can be the scavengers of reactive oxygen species (ROS). Suitable anti-inflammatory agents include but are not limited to, for example, nonsteroidal anti-inflammatory drugs (NSAIDS) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In some embodiments, the biointerface layer can comprise a polymer described as a bioprotective layer in US Patent Publication 2014-0094671, which is incorporated by reference herein at least for its teachings of bioprotective layers in sensor membranes.

Figure 12:
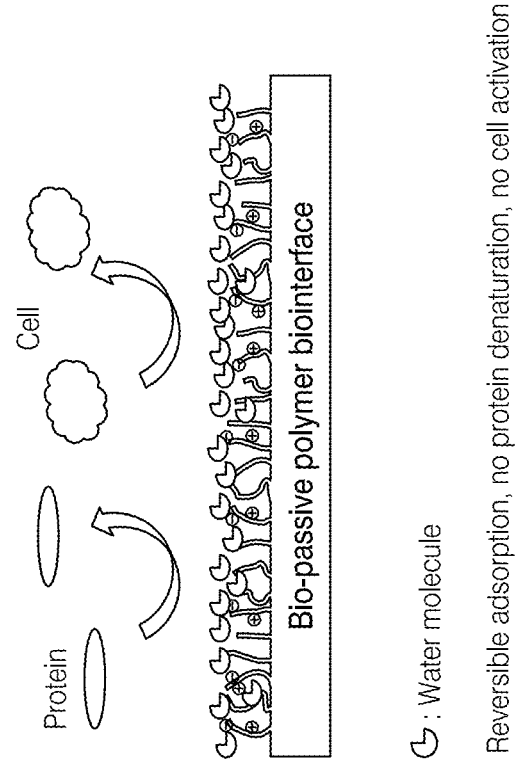
FIG. 12 is a diagram illustrating possible mechanism for the antifouling characteristics of a biointerface polymer layer.

While not wishing to be bound by theory, it is believed that zwitterion groups in the biointerface layer can attract, retain, and order the structure of water at the polymer-biologic interface, resulting in reversible adsorption, no or reduced protein denaturization, and no or reduced cell activation (see FIG. 12). Other possible mechanisms for the antifouling properties of the biointerface layer are significant swelling, which can fill in spaces at the site of implantation and act as buffering zone (see FIG. 16).

In further examples, the biointerface layer can comprise materials that repel the adhesion and/or absorption of carbohydrates. While not wishing to be bound by theory, the attachment or absorption of carbohydrates at the sensor membrane may affect the operation of the sensor. Thus having materials that repel the adhesion and/or absorption of carbohydrates can help alleviate this problem.

In further examples, Factor H can be covalently conjugated onto the surface of the biointerface layer. Factor H is one of the principal regulators of a complement system that play a vital role in the immune response. Its regular functions include controlling proteins that generate proinflammatory anaphylatoxins; maintaining tissue integrity by identifying "self" from "non-self" and harnessing direct anti-inflammatory properties. Thus, Factor H is an important protein that regulates complement activation. This regulation occurs by multiple mechanisms which include disruption of C3 convertase formation and acceleration of its decay. Factor H also acts as a cofactor to factor I in the degradation of C3b, and competes with factor B for binding to C3b.

Factor H for use as a medical device surface coating can be beneficial because of its link between complement-triggered inflammations, the regulatory role of Factor H in stopping complement triggered inflammation and tissue damage.

In this embodiment, Factor H can be covalently conjugated onto the surface of biointerface layer by methods disclosed herein. Factor H can then be released upon environmental changes and control inflammation. Control of inflammation can help reduce issues associated with first day signal reduction or loss after the sensor is implanted. Factor H can also help increase the longevity and decrease in vivo variability.

Figure 33:
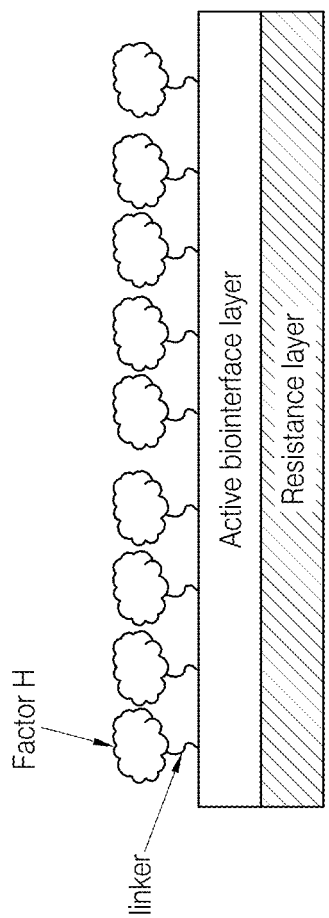
FIG. 33 is a schematic of a biointerface layer with Factor H covalently linked thereto through a linker.

Thus, disclosed herein in a certain embodiment is a sensor comprising a biointerface layer comprising a covalently connected active Factor H to the surface of the biointerface layer. The covalent attachment can be a linker, e.g., an alkyl, alkoxyl, ester, triazole, polyether, polyester, polyalkeneoxide, and the like. In some examples, the linker can be sensitive to cleavage by internal or external stimuli, such as pH, heat, UV-Vis, or protease attack. The linker can also be an oligo peptide sequence which can be cleaved by MMP (Matrix metallopeptidase), which are upregulated in atherosclerosis and inflammation. A schematic of a biointerface layer with conjugated Factor H is shown in FIG. 33. The layer comprises three parts: (i) the biointerface polymer as disclosed herein; (ii) stimuli responsive linker, which can be cleaved by changing of environment; and (iii) active Factor H, which is covalently connected to linker.

The biointerface layer comprises a biointerface polymer. In some embodiments, the biointerface polymer is a polyzwitterion. Polyzwitterions are polymers where a repeating unit of the polymer chain is a zwitterionic moiety. As such, these polymers have the same number of cationic and anionic groups, due to each zwitterion repeating unit having both a positive and negative charge, and thus have an overall charge of zero, often through a wide pH range.

Polyzwitterions are distinguishable from other polyampholytes in that, which polyampholytes contain anionic and cationic groups, the ionic groups are not correlated with one another as part of the same repeating unit. So the anionic and cationic groups may be distributed apart from one another, at random intervals, or one ionic group may outnumber the other. It is thus typical for a polyampholyte to have a net charge, except perhaps at some narrow pH range.

The disclosed polyzwitterions can have a variety of repeating units, which are illustrated as i) through vii) below, where n is some integer from 2 to 1000:

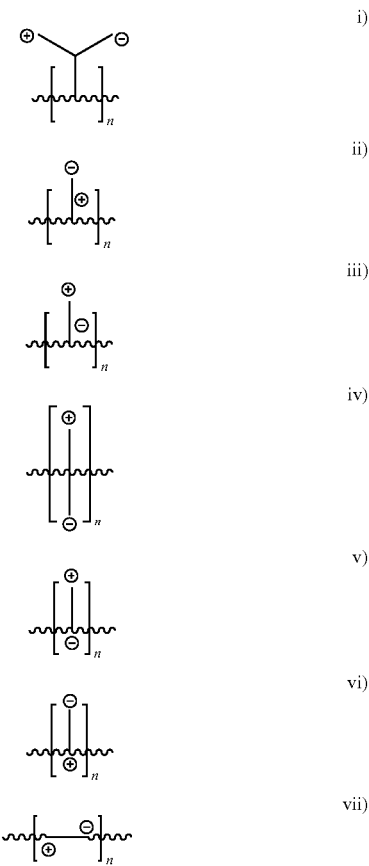

In structures i) through iv) the zwitterionic unit is connected to the backbone chain (~~~~) and the charges are on side-groups that are pendant to the chain. In structures v) through vii) the zwitterionic unit is such that one or both charges is on the chain itself.

Examples of suitable zwitterionic monomers that can be used to produce a polyzwitterion of any of structures i) through vii) include:

ammoniophosphates (phosphobetaines or lecithin analogues), ammoniophosphonates (phosphonobetaines), or ammoniophosphinates (phosphinobetaines), respectively having the structures

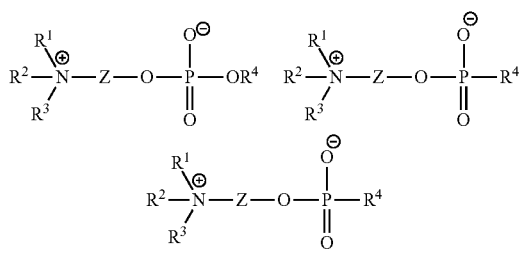

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$, $R^3$, and $R^4$ are independently chosen from alkyl, heteroalkyl, cycloalkyl, heterocycloalkyl, aryl, or heteroaryl; wherein one or more of $R^1$, $R^2$, $R^3$, $R^4$, and Z are substituted with a polymerization group;

ammoniosulfonates (sulfobetaines), ammoniosulfates, respectively having the structures:

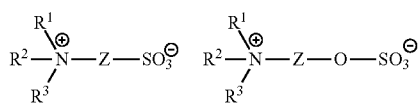

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$, are independently chosen from alkyl, heteroalkyl, cycloalkyl, heterocycloalkyl, aryl, or heteroaryl; wherein one or more of R', $R^2$, $R^3$, and Z are substituted with a polymerization group; and ammoniocarboxylates having the structures:

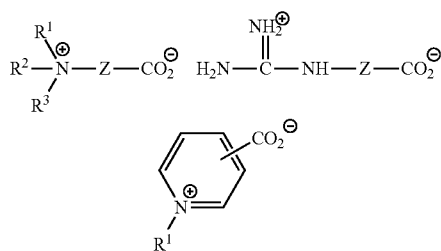

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$ are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

In each of these monomers Z can have a length of from 1 to 12 atoms, e.g., from 1, 2, 3, 4, 5, 6, 7, 8, 9, 10, 11, or 12 atoms, where any of these values can form an upper or lower endpoint of a range.

In a step-growth polymerization, a matching pair of functional groups are selected to promote polymerization, for example, to polymerize a zwitterionic monomer bearing di-hydroxyl group, a diisocyanate, epoxide, or di-carboxylic acid group containing co-monomer can be chosen to afford polymers formed with urethane, ether, and ester linkages.

Additional examples of zwitterion precursors that be modified and formed into monomers for the disclosed biointerface polymers include ammoniocarboxylate (caboxylbetaine) or ammoniosulfonates (sulfobetaine), phosphobetaines (ammoniophosphates or lecithin analogues), phosphatidylcholine, poly(carboxybetaine), poly(sulfobetaine), and precursors or derivatives; trigonelline, ectoine, 3-dimethylsulfoniopropanoate, arsenobetaine, ammoniophosphonates (phosphonobetaines), ammoniophosphinates (phosphinobetaines), ammoniosulfonamides, ammonisulfon-imides, guanidiniocarboxylates (asparagine analogs), pyridiniocarboxylates, ammonio(alokoxy)dicyanoethenolates, ammonioboronates, sulfoniocarboxylates, phosphoniosulfonates, phosphoniocarboxylates, squaraine dyes, and oxypyridine betaines.

These monomers can be prepared by methods known to those of skilled in the art, e.g., as detailed in Laschewsky, "Structures and synthesis of zwitterionic polymers," Polymers 6:1544-1601, 2014. In certain examples, the disclosed polyzwitterions can have repeating zwitterionic units obtained from any of the zwitterionic monomers disclosed above.

The biointerface polymer may also comprises polyurethane and/or polyurea segments. For example, the biointerface polymer can comprise a polyurethane copolymer such as polyether-urethane-urea, polycarbonate-urethane, polyether-urethane, silicone-polyether-urethane, silicone-polycarbonate-urethane, polyester-urethane, polyurethane-urea, and the like. Since these polyurethane and/or polyurea segments contain urea and/or urethane bonds formed from polyisocyanate and short chain polyol or polyamine, which are hydrogen bonding rich moieties, these segments are referred to herein as "hard segments." These segments can also be relatively hydrophobic.

In addition to polyurethane and/or polyurea hard segments, the disclosed biointerface polymers can also comprise soft segments, which have relatively poor hydrogen bonding. Soft segment are usually composed of polyols of polycarbonates, polyesters, polyethers, polyarylene, and polyalkylene, and the like. The soft segments can be either hydrophobic or hydrophilic.

Although the biointerface polymer in some embodiments comprises polyurethane and/or polyurea, in other embodiments, the biointerface polymer may be a polymer that does not comprise polyurethane and/or polyurea.

Biointerface polymers useful for certain embodiments can include linear or branched polymer on the backbone structure of the polymer. Thus, either the hard or soft segments can contain branching or linear backbones.

The zwitterionic monomers can be part of either the hard or soft segments, or both, as described herein.

In some embodiments, the hard segment portion of the biointerface polymer can comprise from about 5% to about 50% by weight of the polymer, sometimes from about 15% to 20%, and other times from about 25% to 40%. The hard segments can have a molecular weight of from about 160 daltons to about 10,000 daltons, and sometimes from about 200 daltons to about 2,000 daltons. In some embodiments, the molecular weight of the soft segments can be from about 200 daltons to about 10,000,000 daltons, and sometimes from about 500 daltons to about 5,000 daltons, and sometimes from about 500 daltons to about 2,000 daltons.

As noted the hard segments can be polyurethanes or polyureas. Polyurethane is a polymer produced by the condensation reaction of a diisocyanate and a difunctional hydroxyl-containing material. A polyurea is a polymer produced by the condensation reaction of a diisocyanate and a difunctional amine-containing material. Preferred diisocyanates include aliphatic diisocyanates containing from about 4 to about 9 methylene units. Diisocyanates containing cycloaliphatic moieties can also be useful in the preparation of the polymer and copolymer components of the membranes of preferred embodiments.

The soft segments used in the preparation of the biointerface polymer can be a polyfunctional aliphatic polyol, a polyfunctional aliphatic or aromatic amine, or the like that can be useful for creating permeability of the analyte (e.g., glucose) therethrough, and can include, for example, polyoxazoline, poly(ethylene glycol) (PEG), polyacrylamide, polyimine, polypropylene oxide (PPO), PEG-co-PPO diol, silicone-co-PEG diol, Silicone-co-PPO diol, polyethylacrylate (PEA), polyvinylpyrrolidone (PVP), and variations thereof (e.g., PVP vinyl acetate), and wherein PEG and variations thereof can be preferred for their hydrophilicity.

In some of the embodiments, the soft segment portion of the biointerface polymer can comprise from about 5% to about 50% by weight of the polymer, sometimes from about 15% to 20%, and other times from about 25% to 40%. The soft segments can have a molecular weight of from about 160 daltons to about 10,000 daltons, and sometimes from about 200 daltons to about 2,000 daltons. In some embodiments, the molecular weight of the soft segments can be from about 200 daltons to about 10,000,000 daltons, and sometimes from about 500 daltons to about 5,000 daltons, and sometimes from about 500 daltons to about 2,000 daltons.

In some embodiments, the biointerface polymer, including hard and soft segments, and zwitterionic repeating units, can have a molecular weight of from about 10 kDa to about 500,000 kDa, for example, from about 10 kDa to about 100,000 kDa, from about 1000 kDa to about 500,000 kDa, from about 10,000 kDa to about 100,000 kDa, and from about 100,000 kDa to about 500,000 kDa.

The hard and soft segments can each be selected for their properties, such as, but not limited to, tensile strength, flex life, modulus, and the like. For example, polyurethanes are relatively strong and provide numerous reactive pathways, which properties can be advantageous as bulk properties for a membrane domain of the continuous sensor.

In some specific examples, the segments can be chosen to result in a biointerface polymer with high Tg. Having a high Tg segment or polymer in the biointerface layer can result in stronger mechanical properties. Further, a hig Tg segment or polymer can allow for more hydrophilic soft segments, which can allow for the incorporation of bioactive agents like anti-inflammatory drugs (e.g., dexamethasone). As an example, the zwitterionic feature of the betaine can bind salt form of dexamethasone more efficiently because of the electron static interactions. As such, disclosed herein are examples of biointerface polymers wherein the hydrophobic segments can be composed of high glass transition temperature ($T_g$) hydrophilic polymers (e.g., polycarbonates). The high $T_g$ hydrophobic segments can have strong mechanical properties and thus construct the porous scaffold which could absorb and encapsulate water and drug molecules inside for continuous drug delivery. The materials can also covalently incorporate functional reactive groups for further chemical reaction or crosslinking (those groups include carboxylic acid, azide, alkyne, alkene, thiol).

As noted, the biointerface polymer contains one or more zwitterionic repeating units; thus these groups are "internal" in reference to the polymer backbone. Such "internal" repeating units are distinguished from a material that is found at the end of a polymer chain since such a moiety would only be bonded to the polymer chain at one location. The disclosed biointerface polymers can, in some embodiments, have one or more zwitterionic groups at the terminal ends of the polymer chains; however, such groups are not the only zwitterionic groups in the chain; there is at least one internal zwitterionic group in the backbone.

In some preferred embodiments, zwitterion moieties are selected for desirable properties, for example, non-constant noise-blocking ability, break-in time (reduced), ability to repel charged species, cationic or anionic blocking, surface wettability, antifouling, or the like. In some embodiments, the zwitterion or zwitterion precursor exists as zwitterionic groups while the device is in vivo. As such, these groups present mixed charged areas of the device surface to the surrounding environment, thereby increasing surface hydration of the device, and potentially reducing nonspecific protein adsorption and cell adhesion.

In some embodiments, the biointerface polymer includes at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, to about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54% or about 55% zwitterionic repeating units by weight of the polymer.

The zwitterionic repeating unit can be a betaine such as a carboxyl, sulfo, or phosphor betaine compound, precursor or derivative thereof (for example alkylbetaines or aminobetaines). These segments or moieties can be incorporated into the biointerface polymer, whether in the hard segment, the soft segment, or both, for example up to about 55 wt. % of the biointerface polymer.

Although in some embodiments, using two or more different zwitterion or zwitterion precursor segments or moieties are used, in other embodiments, a single zwitterion or zwitterion precursor segment or moiety can be used in the biointerface polymer.

Figure 4:
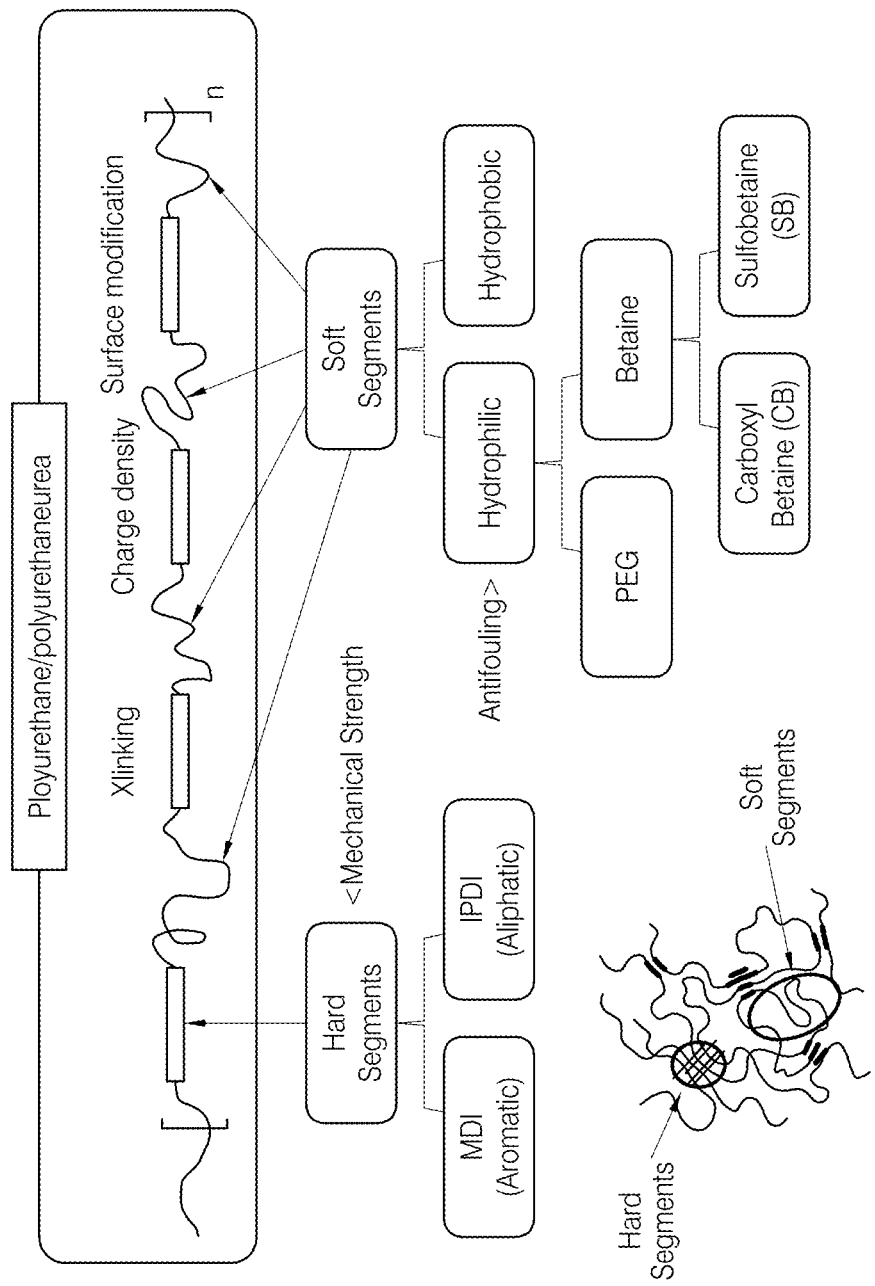
FIG. 4 is a schematic showing certain embodiments of a biointerface polymer.

Some examples of a biointerface polymer are schematically illustrated in FIG. 4. Generally, the biointerface polymer comprises one or more hard segments and one or more soft segments. The hard segments can be aliphatic or aromatic monomers. The soft segments can be hydrophilic or hydrophobic oligomers of, for example, polyalkylene glycols, polycarbonates, polyesters, polyethers, polyvinylalcohol, polyvinypyrrolidone, polyoxazoline, and the like. The zwitterionic groups (e.g., betaines) can be part of the soft segment, the hard segments, or both. As illustrated, in FIG. 4, various hard and soft segments can be present, which permits one to tune the properties of the biointerface polymer by using different segments, different segments lengths, functionalization on certain segments, crosslinking certain segments, and the like. In some embodiments, biocompatible segmented block polyurethane copolymers comprising hard and soft segments can be used for the biointerface layer.

Incorporation of these zwitterionic repeating units into a polymer can be achieved by using zwitterionic monomers that have diols or diamines (e.g., at position Z), or can be attached to diols or diamines at any of $R^1$ through $R^4$. Attaching a diol or diamine at $R^1$-$R^4$ can be accomplished by reacting the corresponding precursor with a halo-substituted diamine or halo-substituted diol. Examples of such monomers are shown below:

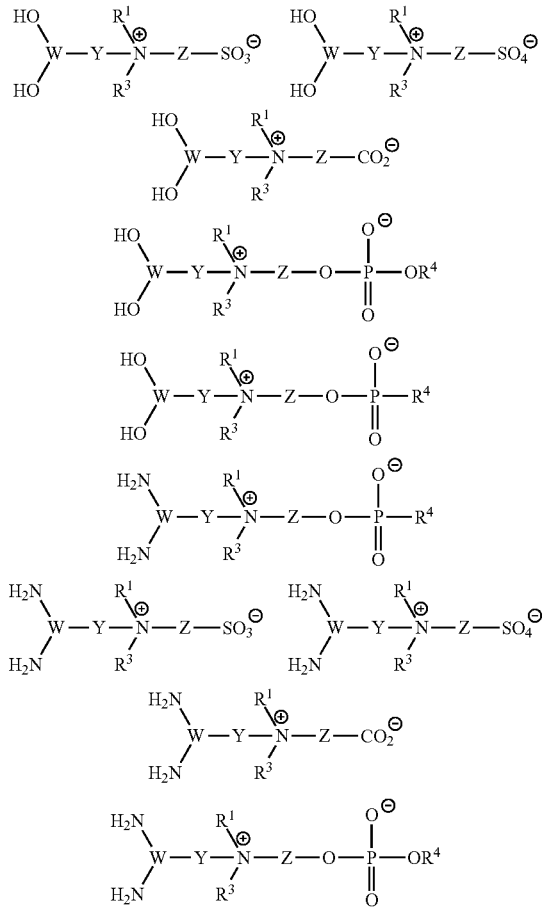

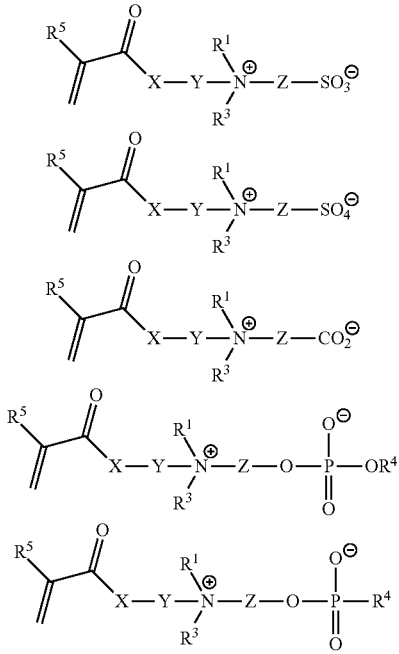

where W, Y, and Z are, independently, branched or straight chain alkyl, heteroalkyl, cycloalkyl, cycloheteroalkyl, aryl, or heteroaryl, any of which can be optionally substituted with O, OH, halogen, amido, or alkoxyl; $R^1$ is H, alkyl, heteroalkyl, cycloalkyl, cycloheteroalkyl, aryl, or heteroaryl; and $R^2$, $R^3$, and $R^4$, are independently chosen from alkyl, heteroalkyl, cycloalkyl, cycloheteroalkyl, aryl, or heteroaryl. In specific examples W is $C_1$-$C_4$ alkyl. In specific examples Y is $C_1$-$C_4$ alkyl. In other examples Z is $C_1$-$C_4$ alkyl.

These compounds can be reacted with a diisocyanate to form a polyurethane or polyurea. Alternatively, the carboxylates, sulfonates, phosphinates, or phophonates moieties can be protected and then the protection group can be removed after polymerization. In another alternative, the amine can be a tertiary amine, which is then quaternized by alkylation after polymerization.

Another method involves the radical polymerization of zwitterionic monomers having unsaturated moieties substituted at position Z in the monomers shown above. In other examples zwitterionic monomers where an unsaturated moiety is attached to the ammonium group can be used in a radical polymerization. Examples of such monomers are shown below:

where X is O, NH, or $NR^4$, Y and Z are, independently, branched or straight chain alkyl, heteroalkyl, cycloalkyl, cycloheteroalkyl, aryl, or heteroaryl, and of which can be optionally substituted with OH, halogen, or alkoxyl; $R^1$ is H, alkyl, heteroalkyl, cycloalkyl, cycloheteroalkyl, aryl, or heteroaryl; and $R^3$ and $R^5$ are independently chosen from heteroalkyl, cycloalkyl, cycloheteroalkyl, aryl, or heteroaryl. In specific examples, $R^5$ is H or $CH_3$. In other examples, X is O. In still other examples, X is NH or $NCH_3$. In specific examples Y is $C_1$-$C_4$ alkyl. In other examples Z is $C_1$-$C_4$ alkyl.

Additional examples of suitable zwitterionic monomers include N-(2-methacryloyloxy)ethyl-N,N-dimethylammonio propanesulfonate, N-(3-methacryloylimino)propyl-N,N-dimethylammonio propanesulfonate, 2-(methacryloyloxy)ethylphosphatidylcholine, and 3-(2'-vinyl-pyridinio) propanesulfonate.

In other embodiments, the biointerface polymer is cross-linked. For example, polyurethaneurea polymers with aromatic or aliphatic segments having electrophilic functional groups (e.g., carbonyl, aldehyde, anhydride, ester, amide, isocyanate, epoxy, allyl, or halo groups) can be crosslinked with a crosslinking agent that has multiple nucleophilic groups (e.g., hydroxyl, amine, urea, urethane, or thio groups). In further embodiments, polyurethaneurea polymers having aromatic or aliphatic segments having nucleophilic functional groups can be crosslinked with a crosslinking agent that has multiple electrophilic groups. Still further, polyurethaneurea polymers having hydrophilic segments having nucleophilic or electrophilic functional groups can be crosslinked with a crosslinking agent that has multiple electrophilic or nucleophilic groups. Unsaturated functional groups on the polyurethane urea can also be used for crosslinking by reacting with multivalent free radical agents.

Non-limiting examples of suitable cross-linking agents include isocyanate, carbodiimide, gluteraldehyde or other aldehydes, aziridine, silane, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final layer.

Further, the disclosed biointerface layer can have zwitterions entrapped or embedded within the polymer network by non-covalent interactions. Thus, in further embodiments, the disclosed biointerface layer can comprise a biointerface polymer and additional betaines blended therewith. For example, the biointerface polymer can be blended with cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic compounds or precursors or derivatives thereof can be applicable and that this list of exemplary betaines is not intended to limit the scope of the embodiments.

The biointerface layer can further comprise a biointerface domain, wherein the biointerface domain comprises a surface modifying polymer added to a base polymer, wherein the surface modifying polymer comprises a polymer chain having both hydrophilic and hydrophobic regions and wherein one or more zwitterionic compounds are covalently bonded to an internal region of the polymer, wherein the base polymer can be selected from silicone, epoxies, polyolefins, polystylene, polyoxymethylene, polysiloxanes, polyethers, polyacrylics, polymethacrylic, polyesters, polycarbonates, polyamide, poly(ether ketone), poly(ether imide), polyurethane, and polyurethane urea.

In some embodiments, the biointerface layer can comprise a combination of one or more biointerface polymer(s), for example, polyurethane or polyurethane urea and one or more hydrophilic polymers, such as, PVA, PEG, polyacrylamide, polyacetates, polyzwitterions, PEO, PEA, PVP, and variations thereof (e.g., PVP vinyl acetate), e.g., as a physical blend or admixture wherein each polymer maintains its unique chemical nature.

In some embodiments, the biointerface layer 48 is positioned most distally to the sensing region such that its outer most domain contacts a biological fluid when inserted in vivo. In some embodiments, the biointerface layer is resistant to cellular attachment, impermeable to cells, and can be composed of a biostable material. While not wishing to be bound by theory, it is believed that when the biointerface domain 48 is resistant to cellular attachment (for example, attachment by inflammatory cells, such as macrophages, which are therefore kept a sufficient distance from other domains, for example, the enzyme domain), hypochlorite and other oxidizing species are short-lived chemical species in vivo and biodegradation does not generally occur. Additionally, the materials preferred for forming the biointerface domain 48 can be resistant to the effects of these oxidative species and have thus been termed biodurable. In some embodiments, the biointerface domain controls the flux of oxygen and other analytes (for example, glucose) to the underlying enzyme domain (e.g. wherein the functionality of the diffusion resistance domain is built-into the biointerface domain such that a separate diffusion resistance domain is not required).

In some embodiments, the one or more zwitterionic compounds or precursors thereof applied to the surface of the membrane system are hydrolyzable cationic esters of zwitterionic compounds. In these embodiments, the hydrolyzable cationic esters provide the added benefit that hydrolysis of the cationic esters into nonfouling zwitterionic groups can kill microbes (such as bacteria) or condense DNA. Further, the mixed-charge nature of the resulting zwitterionic groups result in inhibition of nonspecific protein adsorption on the surface of the sensors. In these embodiments, cationic betaine esters, such as cationic pCB esters are preferable.

Figure 17:
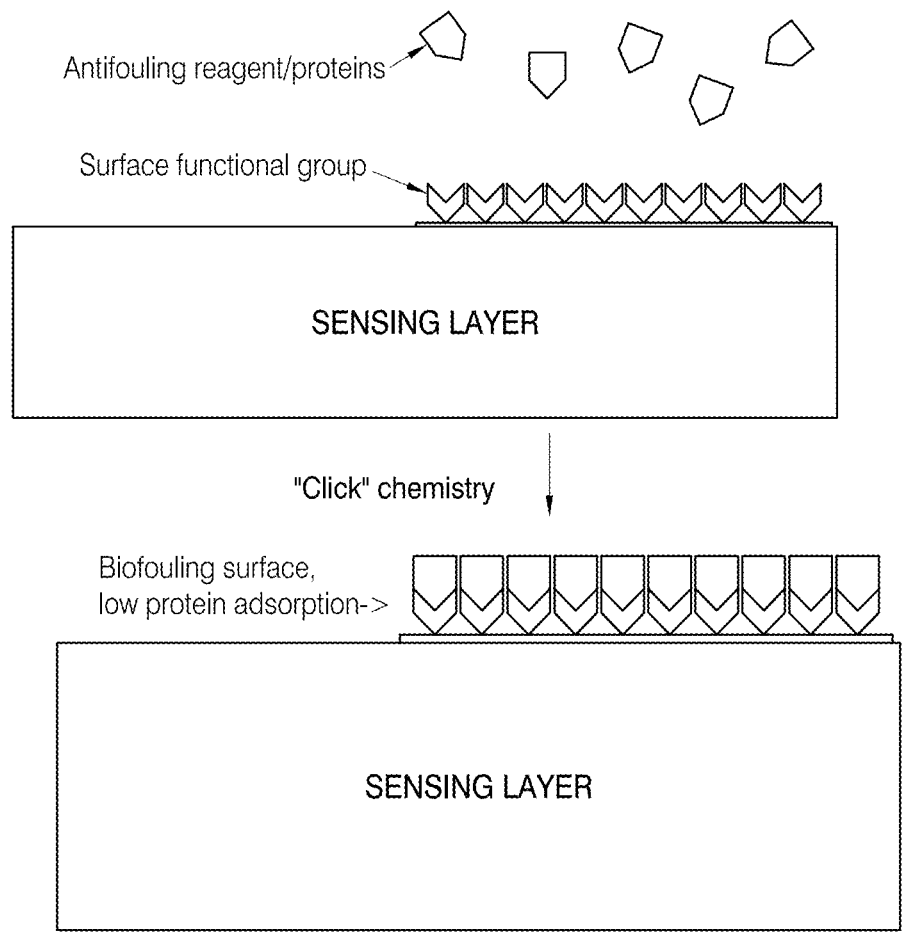
FIG. 17 is a diagram illustrating the use of additional functionality on the biointerface layer. This functionality can be used to attach, e.g., via click chemistry, antifouling reagents or proteins.

In certain embodiments, the biointerface polymer can comprise reactive groups that can be available for further functionalization. For example, unsaturated functional groups like alkynes can be used to attach various moieties attached to dipolar groups likes azides to form covalent linkages. Such Huisgen cycloaddition chemistry is often referred to as click chemistry. Thus, in certain embodiments herein the biointerface layer can comprise alkyne functional groups pendant on the polymer backbone. Antifouling agents such as proteins, cytokines, anti-inflammatory agent, steroids, and other bioactive agents disclosed herein, which are attached to a dipolar group like an azide, can be conveniently attached to the polymer, resulting in a triazole group. Thus, disclosed herein are biointerface layers, sensors containing such layers, that comprise an alkyne, triazole, or both. These reactive groups can be present in the zwitterion repeating units (e.g., as substituents on Z or Y). A schematic of these products is shown in FIG. 17.

It has been found that incorporation of zwitterion or zwitterion precursor segments or moieties internally in the polymer backbone can be challenging due to the solubility issues associated with the monomers of the zwitterion or zwitterion precursors. Such groups typically can only be dissolved in highly polar solvents such as methanol and water, which are not favorable in the synthesis of some the biointerface polymers (e.g., polyurethanes). Thus, the available functional groups that could be used chemically incorporated into the biointerface polymer's backbone by solution based polycondensation synthesis was limited. As an alternative method of incorporating zwitterion or zwitterion precursor segments or moieties into the base-polymer's backbone, precursors or derivatives of the zwitterion or zwitterion precursors can be used. For example, zwitterion precursors and/or zwitterionic derivatives, which have more desirable solubility characteristics in low polarity organic solvents, can be used as monomers. The biointerface polymer (e.g., polyurethaneureas) can be synthesized by polycondensation reactions and form well-defined polymers with high molecular weight and low polydispersity index. These polymers can then be converted to zwitterion group containing polymers via chemical reaction (such as hydrolysis, deprotection, heat-triggered rearrangement, and UV-triggered degradation) or biological triggered reaction after in vivo implantation of the device.

Figure 14:
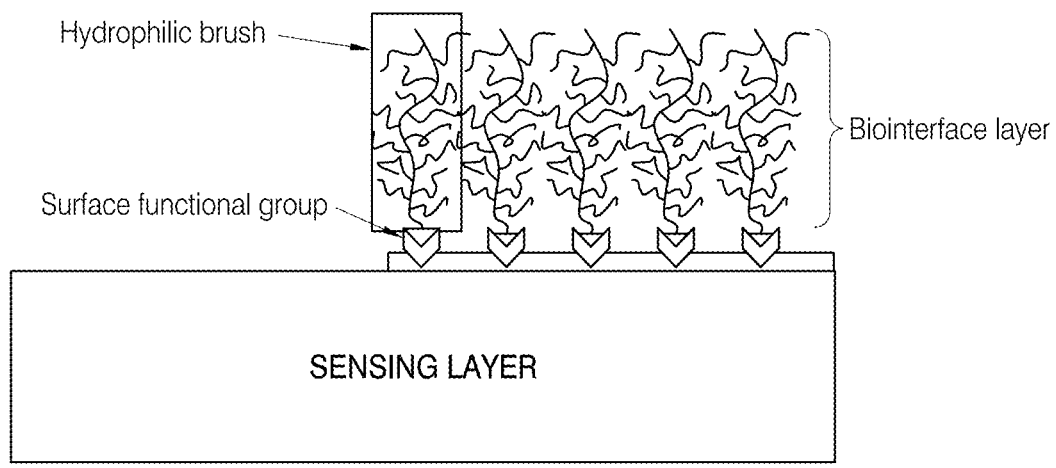
FIG. 14 is a diagram illustrating a biointerface layer made of densely packed hydrophilic brushes. The biointerface layer is grafted onto surface functional groups in an adjacent layer (e.g., resistance layer).

In some embodiments, the hydrophilic segment of the biointerface domain comprises a "brush" polymer where a linear polymer backbone is functionalized with oligomers of hydrophilic branches (e.g., PEG). That is, in the biointerface domain, the biointerface polymer can comprises a polymer chain having both hydrophilic and hydrophobic regions and the hydrophilic regions can comprise a liner polymer chain having hydrophilic oligomers bound thereto and the linear polymer can be grafted to the biointerface polymer. The liner polymer can be a non-biodegradable polymer, e.g., polyacrylate, that is functionalized at one end (e.g., azide) to permit attachment to functional groups located on main chain of the biointerface domain. For example, a copper catalyzed azide-alkyne Huisgen cycloaddition reaction (CuAAC) can be used to attach multiple brush polymers to alkyne functional groups on the biointerface domain. The brush polymers can be prepared from Atom Transfer Radical Polymerization from homopolymers with a defined chain length (e.g., PEG-acrylate monomers). In some embodiments, the biointerface layer is grafted onto surface functional groups in an adjacent layer (e.g., resistance layer) (see e.g., FIG. 14).

Figure 15:
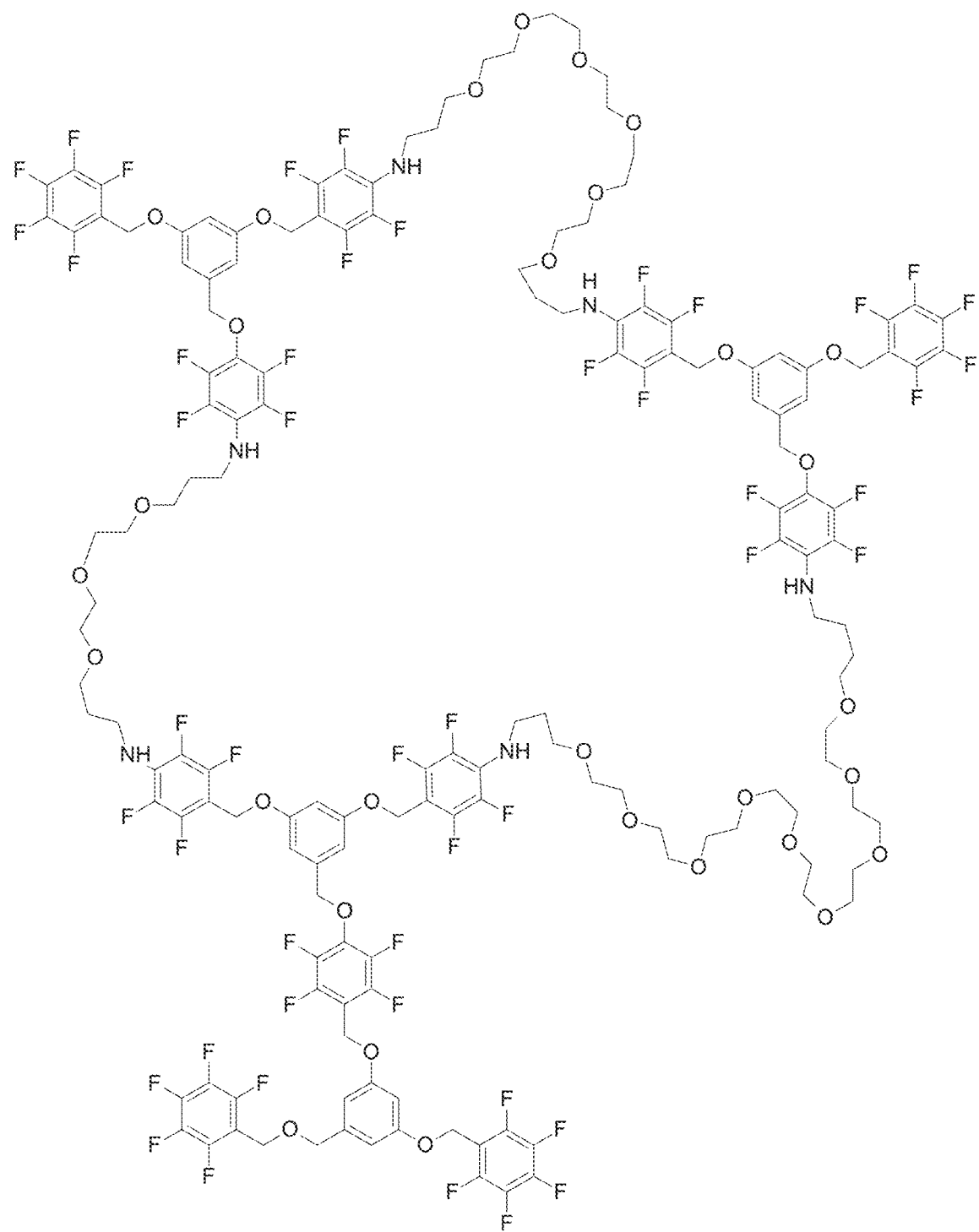
FIG. 15 contains a chemical structure for a biointerface layer using hydrophobic hyperbranched fluoropolymer (HBFP)-rich domains and hydrophilic PEG domains.

In another embodiment, the biointerface layer can comprise an amphiphilic copolymer of a hydrophobic, hyperbranched fluoropolymer (HBFP) and hydrophilic polymer such as polyalkyloxide, polyvinylalcohol, or polyester (see e.g., FIG. 15). These networks can be prepared from hyperbranched fluoropolymer (Mn from 1 to 100 kDa, e.g., from 5 to 15 kDa), by atom transfer radical-self condensing vinyl copolymerization and linear diamine-terminated hydrophilic polymer such as diamino-poly(ethylene glycol) (Mn from 1 to 20,000 Da). Thus, disclosed herein is a continuous analyte sensor comprising a amphiphilic copolymer comprising hyperbranched, fluoropolymer segments and hydrophilic polyethyleneglycol segments. Examples of such polymers are disclosed in Gudipati et al. J. Polymer Sci. (42:6193-6208, (2004); and Muller et al., Macromolecules 31:776, (1998), which are incorporated by reference herein for their teachings of amphiphilic polymers comprising HBFP.

In another embodiment, a fluorescent dye (e.g., Rhodamine) can be covalently incorporated into the biointerface domain. This domain can permit the tracking of the domain, sensing layer, and/or sensor with confocal microscopy. This feature can aid in tracking the degradation or phase separation of the polymers in the sensing membrane. Such polymers can be prepared by a two-step polycondensation. It certain embodiments, the fluorescent dye incorporated biointerface domains can be combined and blended with other biointerface domains as disclosed herein. Examples of suitable fluorescent dyes include, but are not limited to, benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable fluorescent dyes include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-tetrapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris(4,7-diphenyl-1,10-phenanthroline) (Ru (dpp)$_3$); Ru (II) tris(1,10-phenanthroline) (Ru(phen)$_3$), tris(2,2'-bipyridine)ruthenium (II) chloride hexahydrate (Ru (bpy)$_3$); erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphthalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorescein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; derivatives or combinations thereof.

The fluorescent labeled biointerface domain can contain from about 0.05 wt. % to about 20 wt. % fluorescence dye, for example, from about 0.1, about 0.5, about 1, about 2, about 3, about 4, about 5, about 6, about 7, about 8, about 9, about 10, about 15, or about 20 wt. %, where any of the stated values can form an upper or lower endpoint of a range.

In certain embodiments, the thickness of the biointerface domain can be from about 0.1, about 0.5, about 1, about 2, about 4, about 6, about 8 µm or less to about 10, about 15, about 20, about 30, about 40, about 50, about 75, about 100, about 125, about 150, about 175, about 200 or about 250 µm or more. In some of these embodiments, the thickness of the biointerface domain can be sometimes from about 1 to about 5 µm, and sometimes from about 2 to about 7 µm. In other embodiments, the biointerface domain can be from about 20 or about 25 µm to about 50, about 55, or about 60 µm thick. In some embodiments, the glucose sensor can be configured for transcutaneous or short-term subcutaneous implantation, and can have a thickness from about 0.5 µm to about 8 µm, and sometimes from about 4 µm to about 6 µm. In one glucose sensor configured for fluid communication with a host's circulatory system, the thickness can be from about 1.5 µm to about 25 µm, and sometimes from about 3 to about 15 µm. It is also contemplated that in some embodiments, the biointerface layer or any other layer of the electrode can have a thickness that is consistent, but in other embodiments, the thickness can vary. For example, in some embodiments, the thickness of the biointerface layer can vary along the longitudinal axis of the electrode end.

The biointerface layer can be hydrophilic as measured by contact angle. For example, the biointerface layer can have a contact angle of from about 20° to about 90°, from about 60 to about 90°, from about 70 to about 90°, from about 80 to about 90°, from about 60 to about 80°, at least about 50°, at least about 60°, or at least about 70°.

The biointerface layer can also have a low polydispersity index. For example, the polymer can have a polydispersity index of from about 1.4 to about 3.5, from about 1.75 to about 2.25, from about 1.75 to about 2.5, or about 2. The biointerface layer can also not materially affect the T95 response time of a sensor. T95 response time is the amount of time required for the electrical response to reach 95% of the difference between a $1^{st}$ and $2^{nd}$ glucose step's response. For example, a sensor with a biointerface layer as disclosed herein can have a T95 response time that is the same, or within 5% of, the T95 response time of a sensor that is otherwise identical but without the biointerface layer.

Diffusion Resistance Domain

One shortcoming of some current diffusion-resistance layers, also called the dufussion resistance domain, is that they tend to cause significant sensor drift within a few days of the sensor usage, as indicated by both in-vitro testing and in-vivo data. While not wishing to be bound by theory, sensitivity is related, in part, to hydrophilic polymers in the diffusion-resistance layer. If the hydrophilic polymer leaches out over time from the layer when under hydrated conditions, changes in sensitivity and decreases in accuracy and longevity can occur.

Further, un-equilibrated phase separation among the two polymers can result in unpredictable sensitivity changes over time and can require extra calibrations during sensor use. An equilibrated and reproducible phase separation between the hydrophilic and hydrophobic polymers can improve senor accuracy, better consistency and reproducibility and sensor longevity. In some embodiments, the diffusion resistance domain may be formed of a diffusion resistance domain described in U.S. Provisional Application No. 62/273,219, filed Dec. 30, 2015, which is hereby incorporated by reference herein in its entirety.

The diffusion resistance membrane also requires strong mechanical stability to resist rubbing against tissue in vivo and keep the phase separated microstructure unchanging. Strong mechanical resistance layer can also minimize the membrane rearrangement, improve under layer stability (due to increased hoop strength), and reduce tip breach failure (due to improved puncture resistance).

Disclosed herein is a stable, semipermeable diffusion-resistance layer. The disclosed diffusion-resistance layer comprises a base polymer capable of providing a structurally stable matrix. The disclosed diffusion-resistance layer also contains a hydrophilic analyte permeable phase that resides throughout the layer. The layer has a microphase-separated morphology where the analyte permeable phases is percolated throughout a main, hydrophobic polymer matrix. The main matrix polymer provides structural support as required by the membrane application as well as influence on the analyte permeable phase separation, the size and distribution of its microstructure. It is the size and distribution of analyte permeable phase that determine the permeability, hence the sensitivity of a given electrochemical sensor. It is therefore understandable and desirable to maintain the size and distribution of analyte permeable phase upon initial deployment to minimize the sensitivity change over time of actual use and resist temperature and mechanical stress fluctuation.

In specific embodiments, the disclosed diffusion-resistance layer comprises a polymer blend composed of a base polymer, which is a hydrophobic segmented block copolymer, and hydrophilic polymer. The hydrophobic segmented block copolymer has a high glass transition temperature ($T_g$) to afford increase dimensional stability and resistance to swelling caused by hydration, temperature and mechanical challenges. By using a polymer with a high $T_g$, a more rigid matrix can be formed, which can limit the swelling induced by the hydration and maintain the size and distribution of hydrophilic analyte permeable microphase.

At low temperature polymers are brittle, glassy since there is no sufficient energy present to encourage local or segmental chain movement. As the temperature is increased and at some point there is sufficient energy available to allow some chain mobility. For a polymer containing both amorphous and crystalline phases or is only amorphous, the onset of this segmental chain mobility for the amorphous segments is called the glass transition temperature, $T_g$. Because there is unoccupied volume in the amorphous polymer phase some segmental chain movement occurs. This segmental chain movement is sometimes depicted as a snake slithering "in place" within the glass. The localized chain movement causes a further increase in unoccupied volume, and larger segments are able to move eventually, allowing the snake further movement in the glass. Further increase in temperature can lead to the energy sufficient to break up the crystalline phase, and this temperature is often referred to as the melt transition temperature, $T_m$. In gas and liquid separation membrane, mass transfer occurs in the amorphous phase.

The flexibility of amorphous polymers is reduced drastically when they are cooled below a characteristic transition temperature ($T_g$). At temperature below $T_g$ there is no ready segmental motion and as such a polymer with desirable glass transition temperature be selected for application that restrict the segmental mobility and afford structural and dimensional stability. As a property associated with the polymer, $T_g$ values are most often related to the onset of segmental motion in the principle polymer backbone, the more rigid and bulky is the polymer segment the high the $T_g$ is. In a multi-block urethane copolymer, multiple $T_g$'s associated with different soft-segments can present, for example, an extremely low $T_g$ of −120° C., which can occur if silicone is used as co-soft segment. Likewise, a relatively high $T_g$ of −50° C. or higher can be related to a more rigid polycarbonate co-soft-segment.

Figure 43:
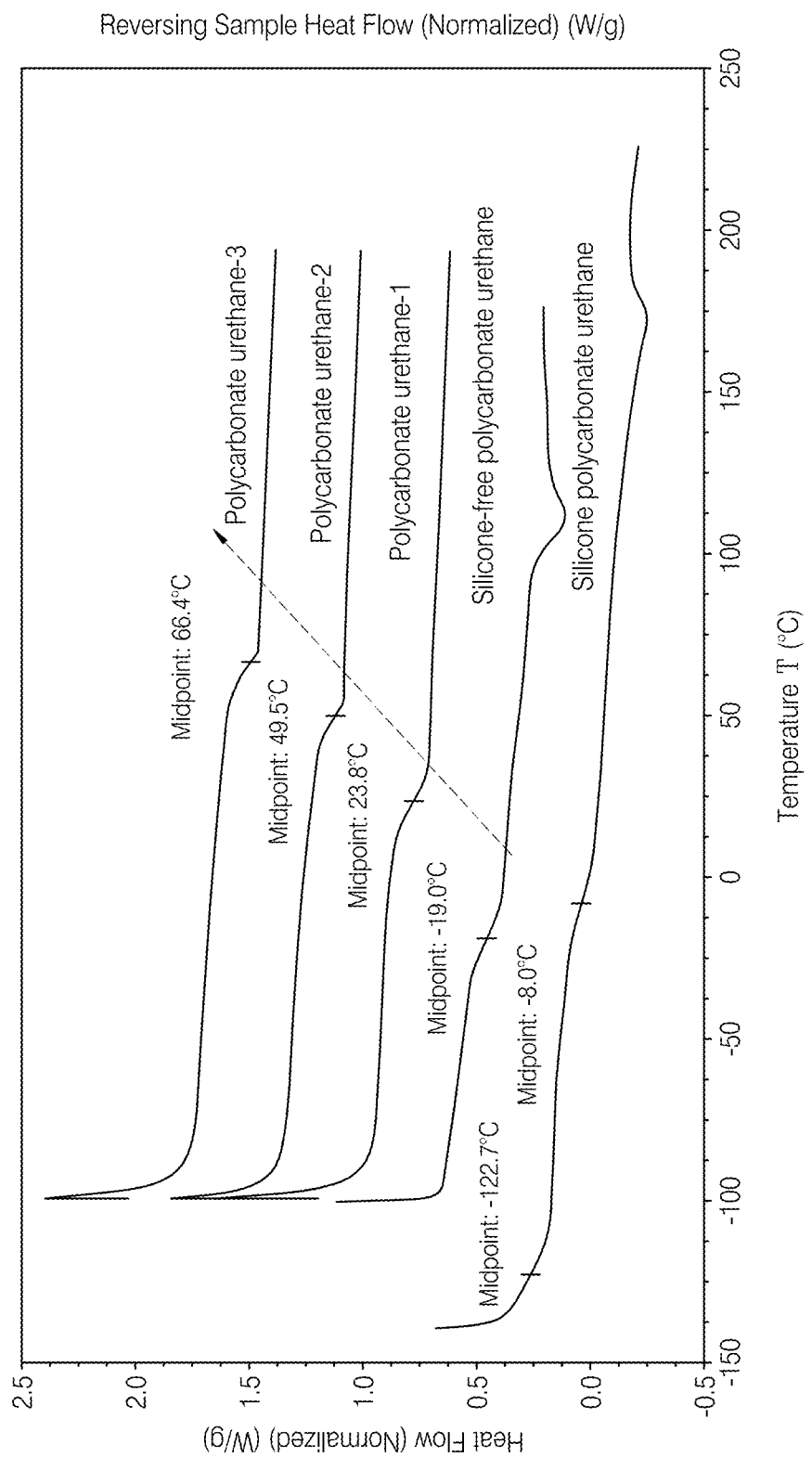
FIG. 43 is a plot of differential scanning calorimetry heating scans performed with TA Instrument Q2000 DSC using aluminum sample pans on resistance layer polyurethane polymer samples.

The glass transition temperature of the hydrophobic segmented block copolymer component of the diffusion resistance layer can be measured using ASTM D3418. In specific examples the lowest glass transition temperature of the hydrophobic segmented block copolymer can be greater than −50° C., e.g., greater than −40, greater than −30, greater than −20, greater than −10, or greater than 0° C. In other examples, the hydrophobic segmented block copolymer can have a lowest glass transition temperature of from 0° C. to −50° C., from −10° C. to −50° C., from −20° C. to −50° C., from 0 to −40° C., from −10° C. to −40° C., from −20° C. to −40° C., from 0° C. to −30° C., from −10° C. to −30° C., or from 0° C. to −30° C. A copolymer can have $T_g$'s associated with different segments. Thus, when there are multiple $T_g$'s, the Tg's referenced here refer to the lowest $T_g$ the copolymer has. As illustrated in FIG. 43, the $T_g$ of polyurethane block copolymer can be altered by changing the amount and type of soft-segment incorporated in polyurethane block-copolymer synthesis. The silicone containing polyurethane exhibits a low $T_g$ at around −120° C. associated with silicone and is absent from the silicone-free polycarbonate urethane. The $T_g$ can be further increased by incorporating a more rigid soft-segment, such as polycarbonate diols.

The disclosed hydrophobic segmented block copolymer can also have an ultimate tensile strength as measured by ASTM D1708 that is greater than 6000 psi, e.g., greater than 8000 psi, greater than 8250 psi, greater than 8500 psi, or greater than 8750 psi. For example, the hydrophobic segmented block copolymer can have an ultimate tensile strength from 7900 to 8750 psi, from 8250 to 8750 psi, from 8500 to 8700 psi, or from 7900 psi to 8250 psi.

In some embodiments, the base polymer can be synthesized to include a polyurethane membrane with both hydrophilic and hydrophobic regions to control the diffusion of glucose and oxygen to an analyte sensor. A suitable hydrophobic polymer component can be a polyurethane or polyether urethane urea. Polyurethane is a polymer produced by the condensation reaction of a diisocyanate and a difunctional hydroxyl-containing material. A polyurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and copolymers, mixtures or combinations thereof.

In specific embodiments, the base polymer can be substantially free (e.g., less than 1 wt. %) of silicone.

In another embodiment of a suitable base polymer, a hydrophilic soft segment polymer component can be polyethylene oxide. For example, one useful hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane. In this case, the lowest $T_g$ of polymer domain formed of hydrophobic soft-segment or hard-segment is higher than −50° C.

Having a homogeneous segmented block copolymer can help ensure that the hydrophilic segments are more evenly distributed throughout the diffusion-resistance layer. The membrane's phase separation properties (or controlled location of hydrophilic/hydrophobic regions for creation of membrane permeation channels) can be controlled to a greater degree by altering the size and length of the monomers/oligomers involved in the membrane synthesis. Since, in this embodiment, only one polymer used in the resistance layer, sensitivity change because of the hydrophilic polymer leaching out will be minimum.

Alternatively, in some embodiments, the diffusion resistance layer can comprise a combination or blend of a base polymer (e.g., segmented polyurethane block copolymers as disclosed herein) and one or more hydrophilic polymers (e.g., PVA, PEG, polyacrylamide, acetates, PEO, PEA, PVP, PDX, and, copolymers, blends, and/or variations thereof). It is contemplated that any of a variety of combination of polymers can be used to yield a blend with desired glucose, oxygen, and interference permeability properties. The hydrophilic polymer can be blended with the base polymer or can be covalently attached to the base polymer.

When the hydrophilic polymer is covalently attached to the base polymer, one way to create an aqueous dispersion is to dissolve the polymer in acetone and add the solution dropwise to an aqueous solvent mixing at high shear. The aqueous solvent can be distilled water or water with stabilizing water-soluble additives such as PVP, salts, or SDS. While any variation can be used, one example for a diffusion-resistance layer would use an aqueous dispersion with either an aqueous solvent of PVP in water (0-50% PVP) with a PVP concentration that yields desired sensor sensitivity, or a pure water solvent to which a concentrated PVP solution can be added after the dispersion is created.

In some specific embodiments, a tri-block polymer of PVP can be used as the hydrophobic polymer in the diffusion-resistance layer. In still other examples, the hydrophilic polymer can be a PVP that is functionalized with silane, alcohol, fluorine, or acrylate. In still other examples, silica or similar nanocomposite materials can be used in the blend in place of or in addition to the hydrophilic polymer. So, for example, a diffusion-resistance layer can be formed from a blend of a hydrophobic block copolymer like a polycarbonate-urethane base polymer as disclosed herein and silica or a nanocomposite.

In yet further examples, the hydrophilic polymer can be crosslinked with, e.g., vinyl lactams. In a specific example, crosslinked polyvinylpyrrolidone (PVP) polymers can be made by reaction between epoxide-containing PVP copolymers and tertiary-amine-containing PVP copolymers in solution at a predetermined temperature. Crosslinkable copolymers of (a) 80-99% by wt. vinylpyrrolidone (VP) and 1-20% by wt. of a tertiary-amine-containing polymerizable monomer, e.g. vinylimidazole (VI) or 4-vinylpyridine (VPy), and (b) 80-99% by wt. VP and 1-20% by wt. of an epoxide-containing polymerizable monomer, e.g. allyl glycidyl ether (AGE) or glycidyl acrylate (GA), are reacted in solution, e.g. water, alcohol, or mixtures thereof, at a predetermined temperature, e.g. 50°-70° C., in a wt. ratio (solids basis) of (a):(b) of about 2:1 to 1:2, preferably about 1:1, in a solution concentration of about 10-30% of each, to provide a crosslinked PVP product. In another example, a diffusion-resistance layer can be formed from a blend of a hydrophobic block copolymer like a polycarbonate-urethane base polymer as disclosed herein and a crosslinked PVP and/or PVP functionalized with silanes, alcohol, or fluorine.

In some embodiments, the diffusion-resistance layer can be formed from a blend of a polycarbonate-urethane base polymer as disclosed herein and a PVP hydrophilic polymer. In some of the embodiments involving the use of PVP, the PVP portion of the polymer blend can comprise from about 5% to about 50% by weight of the polymer blend, sometimes from about 15% to about 20%, and other times from about 25% to about 40%. It is contemplated that PVP of various molecular weights can be used. For example, in some embodiments, the molecular weight of the PVP used can be from about 25,000 daltons to about 5,000,000 daltons, sometimes from about 50,000 daltons to about 2,000,000 daltons, and other times from about 6,000,000 daltons to about 10,000,000 daltons. The same percentages can apply when using PDX instead of PVP.

Figure 49:
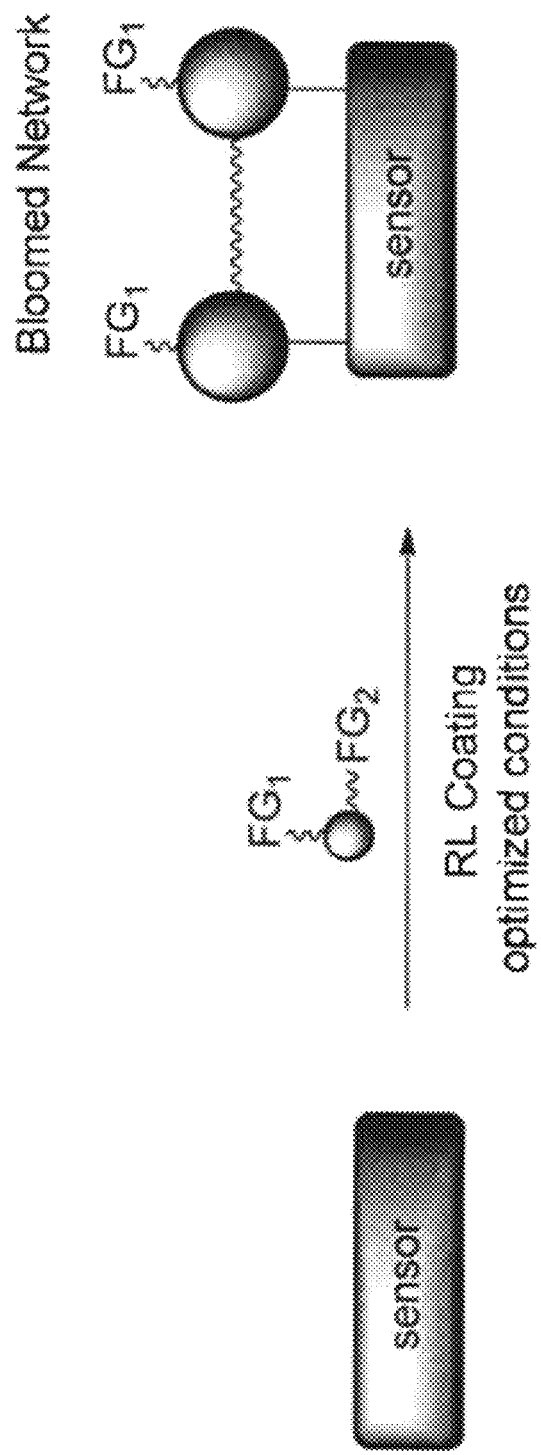
FIG. 49 is a schematic showing an embodiment of a blooming moiety and a networking moiety.

In some other embodiments, the base polymer can be endcapped with groups that can be used to link polymers together (so called networking moieties) and groups that can bloom to the surface and impact the surface properties (so called blooming moieties). These are shown in the schematic of FIG. 49, where FG1 is a blooming moiety and FG2 is a networking moiety.

Figure 50:
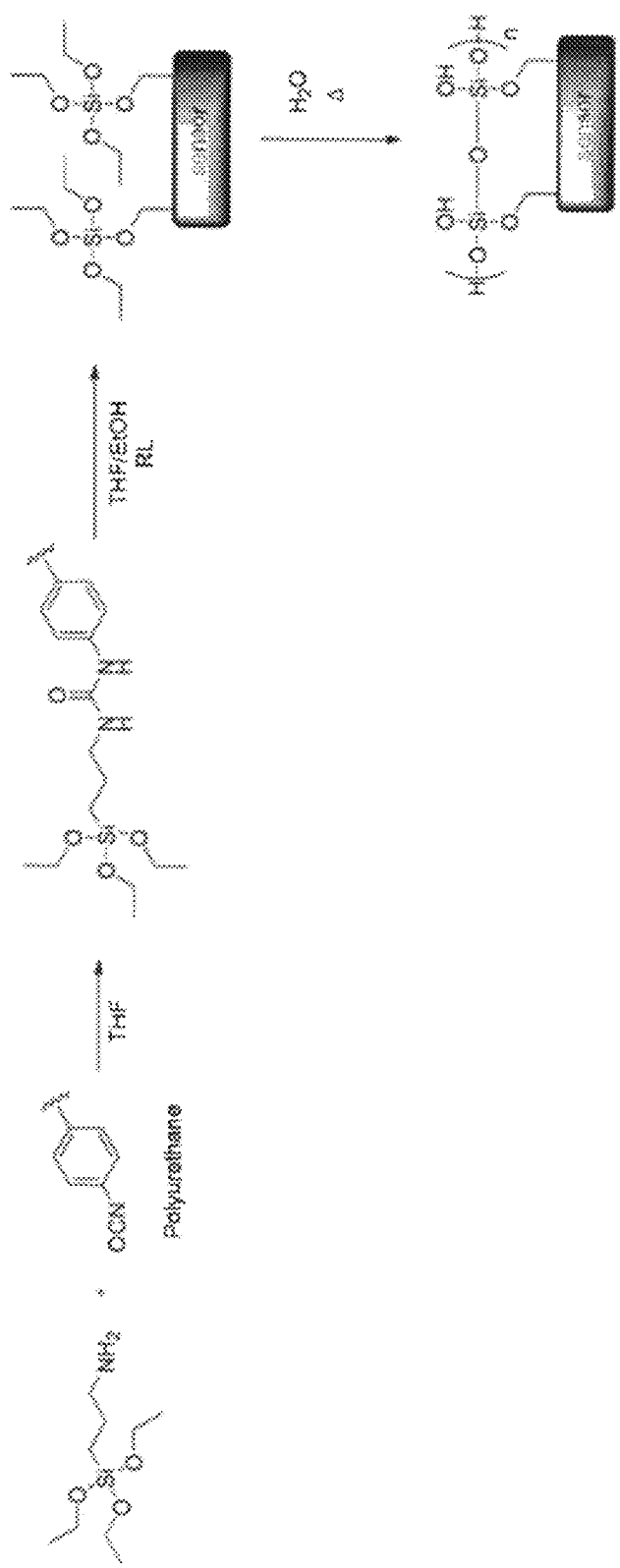
FIG. 50 is a schematic showing an embodiment where the blooming and networking moiety is a siloxane.

It is also contemplated that the blooming moiety and networking moiety can be the same, as is shown in FIG. 50 where the blooming and networking moiety is a siloxane.

Figure 51:
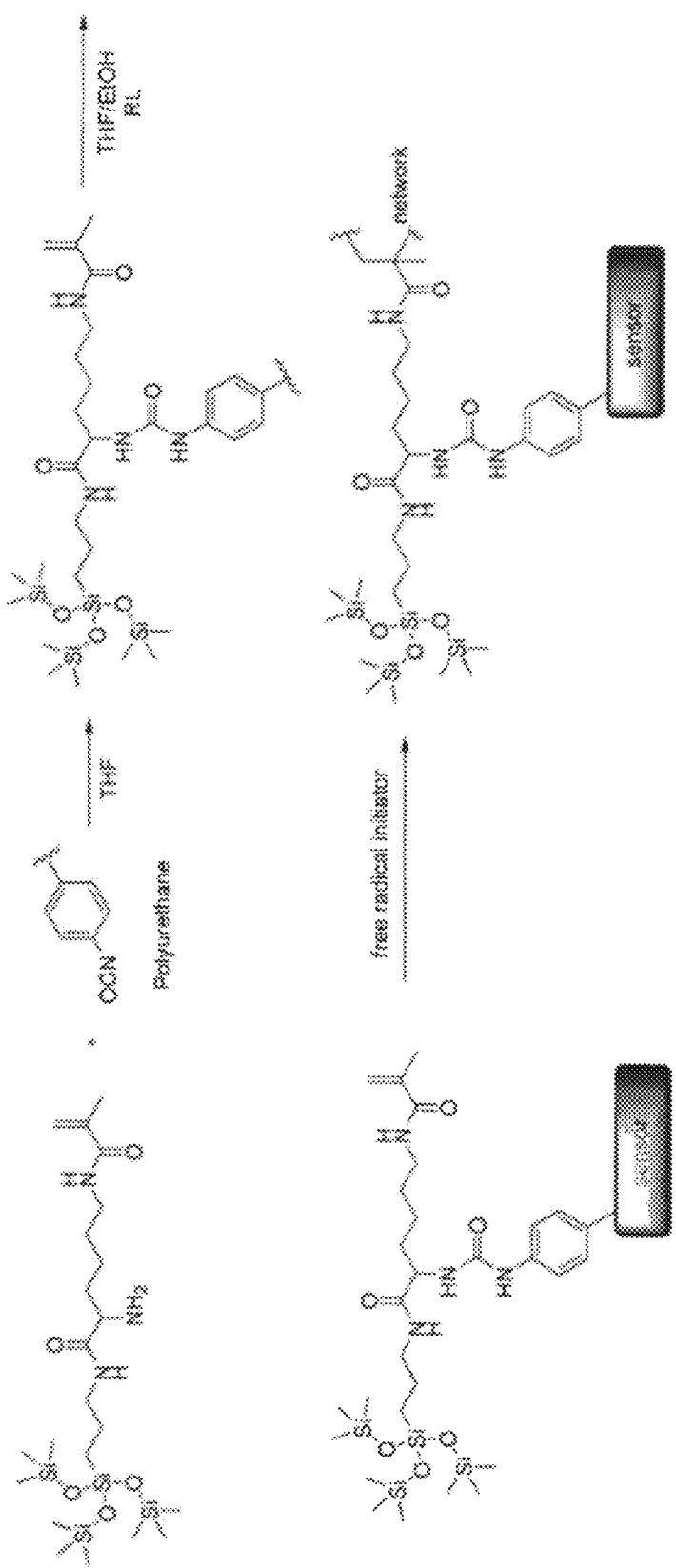
FIG. 51 is a schematic showing an embodiment wherein the blooming moiety is tris(trimethylsilyl)siloxane and the networking moiety is methacrylamide.
Figure 52:
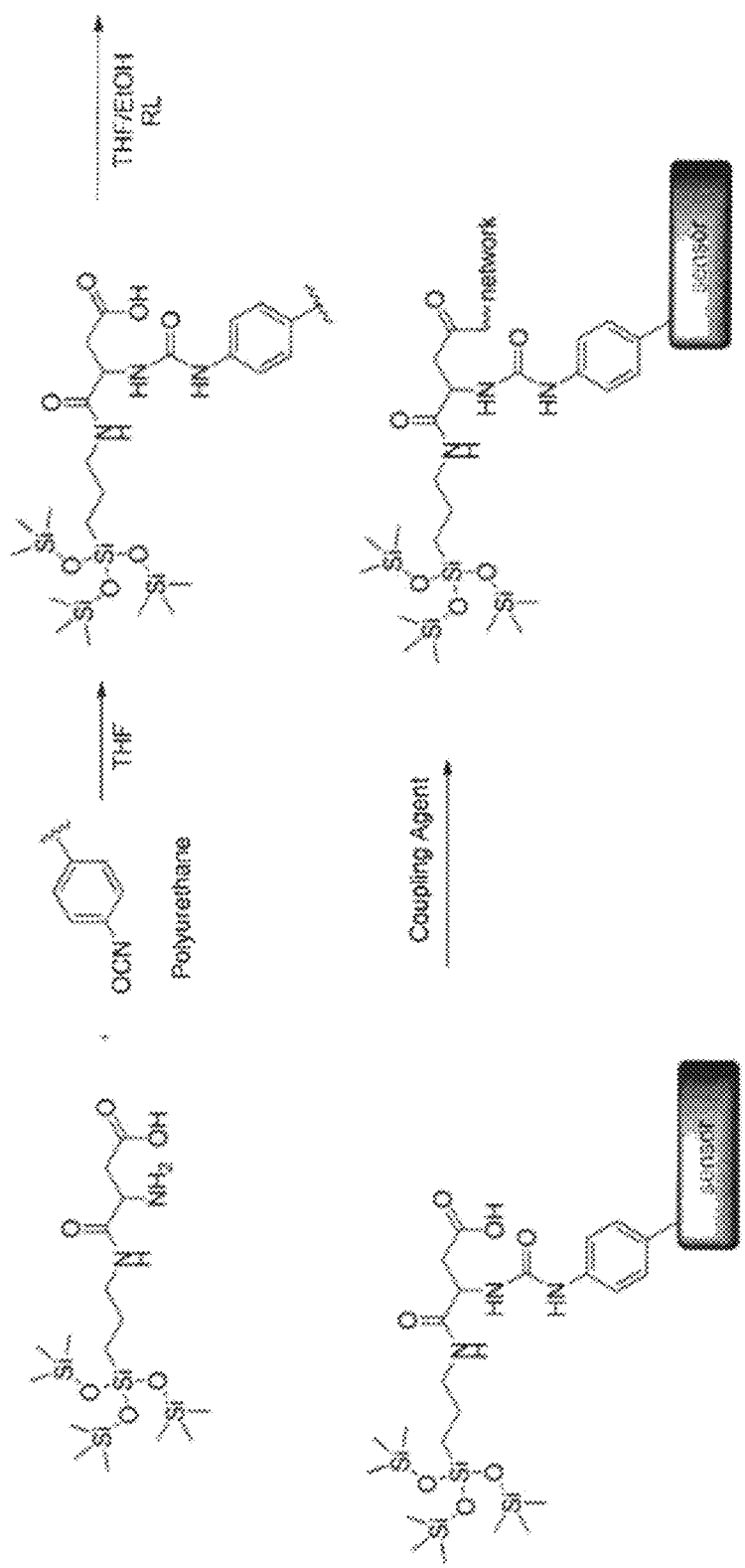
FIG. 52 is a schematic showing an embodiment wherein the blooming moiety is tris(trimethylsilyl)siloxane and the networking moiety is carboxylic acid.

In other examples, the networking and blooming moieties are different, as is shown in FIG. 51, where the blooming moiety is tris(trimethylsilyl)siloxane and the networking moiety is methacrylamide, or in FIG. 52, where the blooming moiety is tris(trimethylsilyl)siloxane and the networking moiety is carboxylic acid.

Additional examples of blooming moieties are fluorocarbons. Additional examples of networking moieties are vinyl groups (e.g., vinylalcohol, vinylbenzyl) isocyanates, amines, amides, alcohols, azides, thiols, alkenes, alkynes, esters, and the like. In some other embodiments, the networking moiety can be groups that complex iron (Fe(II) or Fe(III)).

Further, the disclosed diffusion-resistance layer can have zwitterions entrapped or embedded within the polymer network by non-covalent interactions. Thus, in further embodiments, the disclosed diffusion-resistance layer can comprise a base polymer and a hydrophilic polymer and additional betaines blended therewith. For example, the diffusion-resistance layer can be blended with cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic compounds or precursors or derivatives thereof can be applicable and that this list of exemplary betaines is not intended to limit the scope of the embodiments.

Sensors containing the disclosed diffusion-resistance layers can have a minimum drift (e.g., ≤10%) over extended time. For example, disclosed herein are sensors that have a drift of less than 9%, 8%, 7%, 6%, 5%, 4%, 3%, 2%, or 1% over 10 days.

A sensor having a diffusion resistance layer is shown as 46 in FIGS. 2A and 2B; there it is situated more proximal to the implantable device relative to the biointerface layer. In some embodiments, the functionality of the diffusion resistance domain can be built into the biointerface layer. Accordingly, it is to be noted that the description herein of the diffusion resistance domain can also apply to the biointerface layer. The diffusion resistance domain serves to control the flux of oxygen and other analytes (for example, glucose) to the underlying enzyme domain.

The diffusion resistance domain 46 includes a semipermeable membrane that controls the flux of oxygen and glucose to the underlying enzyme domain 42, preferably rendering oxygen in non-rate-limiting excess. As a result, the upper limit of linearity of glucose measurement is extended to a much higher value than that which is achieved without the diffusion resistance domain. In some embodiments, the diffusion resistance domain exhibits an oxygen-to-glucose permeability ratio of approximately 200:1, but in other embodiments the oxygen-to-glucose permeability ratio can be approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion can provide sufficient excess oxygen at all reasonable glucose and oxygen concentrations found in the subcutaneous matrix (see Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane or electroactive surfaces. By enhancing the oxygen supply through the use of a silicone composition, for example, glucose concentration can be less of a limiting factor. In other words, if more oxygen is supplied to the enzyme or electroactive surfaces, then more glucose can also be supplied to the enzyme without creating an oxygen rate-limiting excess.

In some embodiments, the diffusion-resistance layer 46 can be formed as a unitary structure with the biointerface domain 48; that is, the inherent properties of the diffusion resistance domain 46 are incorporated into biointerface domain 48 such that the biointerface domain 48 functions as a diffusion resistance domain 46.

In some embodiments, a diffusion resistance layer 46 can be used and can be situated more proximal to the implantable device relative to the biointerface layer. In some embodiments, the functionality of the diffusion resistance domain can be built into the biointerface layer that comprises the polyzwitterionic biointerface polymer. Accordingly, it is to be noted that the description herein of the diffusion resistance domain can also apply to the biointerface layer. The diffusion resistance domain serves to control the flux of oxygen and other analytes (for example, glucose) to the underlying enzyme domain. As described in more detail elsewhere herein, there exists a molar excess of glucose relative to the amount of oxygen in blood, i.e., for every free oxygen molecule in extracellular fluid, there are typically more than 100 glucose molecules present (see Updike et al., Diabetes Care 5:207-21 (1982)). However, an immobilized enzyme-based sensor employing oxygen as cofactor is supplied with oxygen in non-rate-limiting excess in order to respond linearly to changes in glucose concentration, while not responding to changes in oxygen tension. More specifically, when a glucose-monitoring reaction is oxygen-limited, linearity is not achieved above minimal concentrations of glucose. Without a semipermeable membrane situated over the enzyme domain to control the flux of glucose and oxygen, a linear response to glucose levels can be obtained only up to about 40 mg/dL. However, in a clinical setting, a linear response to glucose levels is desirable up to at least about 500 mg/dL.

The diffusion resistance domain 46 includes a semipermeable membrane that controls the flux of oxygen and glucose to the underlying enzyme domain 44, preferably rendering oxygen in non-rate-limiting excess. As a result, the upper limit of linearity of glucose measurement is extended to a much higher value than that which is achieved without the diffusion resistance domain. In some embodiments, the diffusion resistance domain exhibits an oxygen-to-glucose permeability ratio of approximately 200:1, but in other embodiments the oxygen-to-glucose permeability ratio can be approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion can provide sufficient excess oxygen at all reasonable glucose and oxygen concentrations found in the subcutaneous matrix (see Rhodes et al., Anal. Chem., 66:1520-1529 (1994)). In some embodiments, a lower ratio of oxygen-to-glucose can be sufficient to provide excess oxygen by using a high oxygen soluble domain (for example, a silicone material) to enhance the supply/transport of oxygen to the enzyme membrane or electroactive surfaces. By enhancing the oxygen supply through the use of a silicone composition, for example, glucose concentration can be less of a limiting factor. In other words, if more oxygen is supplied to the enzyme or electroactive surfaces, then more glucose can also be supplied to the enzyme without creating an oxygen rate-limiting excess.

In some embodiments, the diffusion resistance domain is formed of a base polymer synthesized to include a polyurethane membrane with both hydrophilic and hydrophobic regions to control the diffusion of glucose and oxygen to an analyte sensor. A suitable hydrophobic polymer component can be a polyurethane or polyether urethane urea. Polyurethane is a polymer produced by the condensation reaction of a diisocyanate and a difunctional hydroxyl-containing material. A polyurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the diffusion resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In one embodiment of a polyurethane-based resistance domain, a hydrophilic soft segment polymer component can be polyethylene oxide. For example, one useful hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

Alternatively, in some embodiments, the diffusion resistance domain can comprise a combination of a base polymer (e.g., polyurethane) and one or more hydrophilic polymers (e.g., PVA, PEG, polyacrylamide, acetates, PEO, PEA, PVP, and variations thereof). It is contemplated that any of a variety of combination of polymers can be used to yield a blend with desired glucose, oxygen, and interference permeability properties. For example, in some embodiments, the diffusion resistance domain can be formed from a blend of a silicone polycarbonate-urethane base polymer and a PVP hydrophilic polymer, but in other embodiments, a blend of a polyurethane, or another base polymer, and one or more hydrophilic polymers can be used instead. In some of the embodiments involving the use of PVP, the PVP portion of the polymer blend can comprise from about 5% to about 50% by weight of the polymer blend, sometimes from about 15% to about 20%, and other times from about 25% to about 40%. It is contemplated that PVP of various molecular weights can be used. For example, in some embodiments, the molecular weight of the PVP used can be from about 25,000 daltons to about 5,000,000 daltons, sometimes from about 50,000 daltons to about 2,000,000 daltons, and other times from about 6,000,000 daltons to about 10,000,000 daltons.

In some embodiments, the diffusion resistance domain 46 can be formed as a unitary structure with the biointerface domain 48; that is, the inherent properties of the diffusion resistance domain 46 are incorporated into biointerface domain 48 such that the biointerface domain 48 functions as a diffusion resistance domain 46.

In certain embodiments, the thickness of the diffusion resistance domain can be from about 0.05 µm or less to about 200 µm or more. In some of these embodiments, the thickness of the diffusion resistance domain can be from about 0.05, about 0.1, about 0.15, about 0.2, about 0.25, about 0.3, about 0.35, about 0.4, about 0.45, about 0.5, about 1, about 1.5, about 2, about 2.5, about 3, about 3.5, about 4, about 6, about 8 µm to about 9, about 10, about 11, about 12, about 13, about 14, about 15, about 16, about 17, about 18, about 19, about 19.5, about 20, about 30, about 40, about 50, about 60, about 70, about 75, about 80, about 85, about 90, about 95, or about 100 µm. In some embodiments, the thickness of the diffusion resistance domain is from about 2, about 2.5, or about 3 µm to about 3.5, about 4, about 4.5, or about 5 µm in the case of a transcutaneously implanted sensor or from about 20 or about 25 µm to about 40 or about 50 µm in the case of a wholly implanted sensor.

Enzyme Domain

The enzyme layer, also referred to as an enzyme domain, is the domain or layer of an implantable device configured to immobilize an active enzyme, which reacts with an analyte, when implanted in a host or connected to the host (e.g., via an intravascular access device providing extracorporeal access to a blood vessel). In some embodiments, the enzyme domain may be formed of an enzyme resistance domain described in U.S. Provisional Application No. 62/273,155, filed Dec. 30, 2015, which is hereby incorporated by reference herein in its entirety.

The enzyme layers disclosed herein can be mechanically robust, resist physiochemical degradation upon implantation, and withstand adhesive degradation during the sensor implantation. Further, the disclosed enzyme layers do not affect the response time of the sensor, permeable to analytes, and do not alter the glucose rate limiting control by resistance layer. The disclosed enzyme layers can have hydrophilic properties that have a water uptake of great than 10% relative to the dry weight, and fast water uptake and quick in reaching stabilization, so that sensor start-up is not affected negatively.

In some embodiments, the enzyme domain can comprise one surface-active end group containing polymer, or a blend of two or more (e.g., two, three, four, five, or more) surface-active end group-containing polymers, as described above. For example, in some embodiments the enzyme domain can comprise one surface-active end group containing polymer that comprises surface-active end groups that are zwitterionic, or are precursors or derivatives thereof. In other embodiments, one surface-active group containing polymer in a blend of two or more surface-active group containing polymers comprises zwitterionic surface-active groups, or precursors or derivatives thereof. In other embodiments, a blend can comprise a polymer with positively charged surface-active groups and a polymer with negatively charged surface-active groups.

In some embodiments where the enzyme domain comprises one or more zwitterionic surface-active groups, or precursors or derivatives thereof, the zwitterionic surface-active group can comprise a betaine moiety such as a carboxyl, sulfo, or phosphor betaine group, or precursors or derivatives thereof (for example alkylbetaines or aminobetaines), for example up to about 0.1, about 0.2, about 0.5, about 1, about 2, or about 5% wt. of the domain. Exemplary betaines include cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic groups, or precursors or derivatives thereof, can be applicable and that this list of exemplary betaines is not intended to limit the scope of the embodiments. In some embodiments, hydrolyzable cationic esters of zwitterionic groups (as discussed elsewhere) can be used at similar concentrations for incorporation into the enzyme domain.

In some other embodiments, a blend of two or more surface-active group-containing polymers comprises one surface-active group that is negatively charged and one surface-active group that is positively charged. In some embodiments, the number of negatively and positively charged surface-active groups is such that an enzyme domain formed from the blend is about net neutrally charged. In other embodiments, the number of positively charged and negatively charged surface-active groups can be unequal, with either more positively charged or negatively charged surface-active groups being present.

In some embodiments, the catalyst (enzyme) can be impregnated or otherwise immobilized into the biointerface or diffusion resistance domain such that a separate enzyme domain 44 is not required (e.g., wherein a unitary domain is provided including the functionality of the biointerface domain, diffusion resistance domain, and enzyme domain). In some embodiments, the enzyme domain 44 is formed from a polyurethane, for example, aqueous dispersions of colloidal polyurethane polymers including the enzyme.

In some embodiments, the enzyme layers disclosed herein may comprise an enzyme layer polymer. The enzyme layer polymer may be a polyzwitterion. Polyzwitterions are polymers where a repeating unit of the polymer chain is a zwitterionic moiety. As such, these polymers have the same number of cationic and anionic groups, due to each zwitterion repeating unit having both a positive and negative charge, and thus have an overall charge of zero, often through a wide pH range. While not wishing to be bound by theory, it is believed that zwitterion groups in the enzyme layer polymer provide a charge center for strong charge-charge interaction with ionic groups in enzyme and can help immobilize the enzymes in the enzyme layer and decrease leaching of enzymes out of the enzyme layer (and sometimes into the host). Further, the zwitterionic groups are highly hydrophilic and retain water and help prevent enzyme from denaturing.

The enzyme layer polymers can be polyzwitterions, which are distinguishable from other polyampholytes in that, which polyampholytes contain anionic and cationic groups, the ionic groups are not correlated with one another as part of the same repeating unit. So the anionic and cationic groups may be distributed apart from one another, at random intervals, or one ionic group may outnumber the other. It is thus typical for a polyampholyte to have a net charge, except perhaps at some narrow pH range.

The disclosed polyzwitterions can have a variety of repeating units, which are illustrated as i) through vii) below, where n is some integer from 2 to 1000:

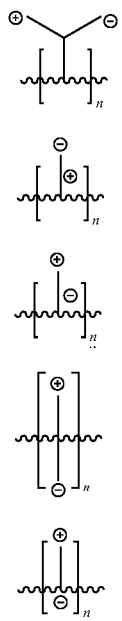

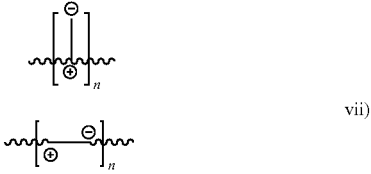

In structures i) through iv) the zwitterionic unit is connected to the backbone (~~~) and the charges are on side-groups that are pendant to the chain. In structures v) through vii) the zwitterionic unit is such that one or both charges is on the chain itself.

Examples of suitable zwitterionic monomers that can be used to produce a polyzwitterion of any of structures i) through vii) include:

ammoniophosphates (phosphobetaines or lecithin analogues), ammoniophosphonates (phosphonobetaines), or ammoniophosphinates (phosphinobetaines), respectively having the structures

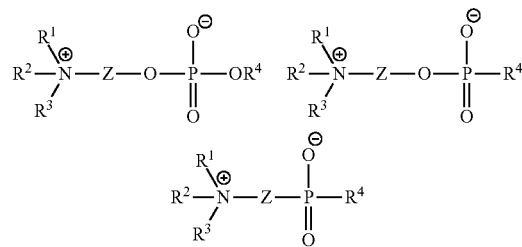

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$, $R^3$, and $R^4$ are independently chosen from alkyl, heteroalkyl, cycloalkyl, heterocycloalkyl, aryl, or heteroaryl; wherein one or more of $R^1$, $R^2$, $R^3$, $R^4$, and Z are substituted with a polymerization group.

By "polymerization group," it is meant a functional group that permits polymerization of the monomer with itself to form a homopolymer or together with different monomers to form a copolymer. Depending on the type of polymerization methods employed, the polymerization group can be selected from alkene, alkyne, epoxide, lactone, amine, hydroxyl, isocyanate, carboxylic acid, anhydride, silane, halide, aldehyde, and carbodiimide. In a step-growth polymerization, a matching pair of functional groups are selected to promote polymerization, for example, to polymerize a zwitterionic monomer bearing di-hydroxyl group, a diisocyanate, epoxide, or di-carboxylic acid group containing co-monomer can be chosen to afford polymers formed with urethane, ether, and ester linkages.

Further examples of suitable zwitterionic monomers that can be used to produce a polyzwitterion of any of structures i) through vii) include ammoniosulfonates (sulfobetaines), ammoniosulfates, respectively having the structures:

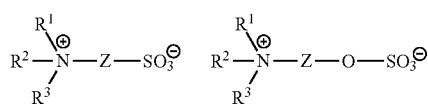

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$, are independently chosen from alkyl, heteroalkyl, cycloalkyl, heterocycloalkyl, aryl, or heteroaryl; wherein one or more of $R^1$, $R^2$, $R^3$, and Z are substituted with a polymerization group; and ammoniocarboxylates having the structures:

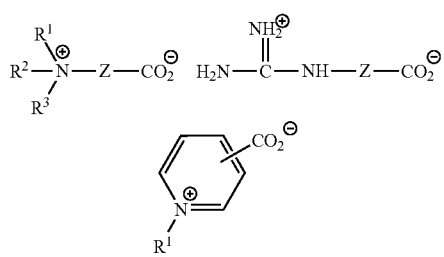

where Z is branched or straight chain alkyl, heteroalkyl, cycloalkyl, cycloheteroalkyl, aryl, or heteroaryl; $R^1$ is H, alkyl, heteroalkyl, cycloalkyl, heterocycloalkyl, aryl, or heteroaryl; and $R^2$ and $R^3$ are independently chosen from alkyl, heteroalkyl, cycloalkyl, heterocycloalkyl, aryl, or heteroaryl; wherein one or more of $R^1$, $R^2$, $R^3$, and Z are substituted with a polymerization group.

In each of these monomers Z can have a length of from 1 to 12 atoms, e.g., from 1, 2, 3, 4, 5, 6, 7, 8, 9, 10, 11, or 12 atoms, where any of these values can form an upper or lower endpoint of a range.

These monomers can be prepared by methods known to those of skilled in the art, e.g., as detailed in Laschewsky, "Structures and synthesis of zwitterionic polymers," Polymers 6:1544-1601, 2014. In certain examples, the disclosed polyzwitterions can have repeating zwitterionic units obtained from any of the zwitterionic monomers disclosed above.

The enzyme layer polymer may also comprises polyurethane and/or polyurea segments. For example, the enzyme layer polymer can comprise a polyurethane copolymer such as polyether-urethane-urea, polycarbonate-urethane, polyether-urethane, silicone-polyether-urethane, silicone-polycarbonate-urethane, polyester-urethane, polyurethane-urea, and the like. Since these polyurethane and/or polyurea segments contain urea and/or urethane bonds formed from polyisocyanate and short chain polyol or polyamine, which are hydrogen bonding rich moieties, these segments are referred to herein as "hard segments." These segments can also be relatively hydrophobic.

In addition to polyurethane and/or polyurea hard segments, the disclosed enzyme layer polymers can also comprise soft segments, which have relatively poor hydrogen bonding. Soft segment are usually composed of polyols of polycarbonates, polyesters, polyethers, polyarylene, and polyalkylene, and the like. The soft segments can be either hydrophobic or hydrophilic.

Enzyme layer polymers useful for certain embodiments can include linear or branched polymers on the backbone structure of the polymer. Thus, either the hard or soft segments can contain branching or linear backbones.

The zwitterionic monomers can be part of either the hard or soft segments, or both, as described herein.

In some embodiments, the hard segment portion of the enzyme layer polymer can comprise from about 5% to about 50% by weight of the polymer, sometimes from about 15% to 20%, and other times from about 25% to 40%. The hard segments can have a molecular weight of from about 160 daltons to about 10,000 daltons, and sometimes from about 200 daltons to about 2,000 daltons. In some embodiments, the molecular weight of the soft segments can be from about 200 daltons to about 10,000,000 daltons, and sometimes from about 500 daltons to about 5,000 daltons, and sometimes from about 500 daltons to about 2,000 daltons.

As noted the hard segments can be polyurethanes or polyureas. Polyurethane is a polymer produced by the condensation reaction of a diisocyanate and a difunctional hydroxyl-containing material. A polyurea is a polymer produced by the condensation reaction of a diisocyanate and a difunctional amine-containing material. Preferred diisocyanates include aliphatic diisocyanates containing from about 4 to about 9 methylene units. Diisocyanates containing cycloaliphatic moieties can also be useful in the preparation of the polymer and copolymer components of the membranes of preferred embodiments.

The soft segments used in the preparation of the enzyme layer polymer can be a polyfunctional aliphatic polyol, a polyfunctional aliphatic or aromatic amine, or the like that can be useful for creating permeability of the analyte (e.g., glucose) therethrough, and can include, for example, polyoxazoline, poly(ethylene glycol) (PEG), polyacrylamide, polyimine,polypropylene oxide (PPO), PEG-co-PPO diol, silicone-co-PEG diol, Silicone-co-PPO diol, polyethylacrylate (PEA), polyvinylpyrrolidone (PVP), and variations thereof (e.g., PVP vinyl acetate), and wherein PEG and variations thereof can be preferred for their hydrophilicity.

In some of the embodiments, the soft segment portion of the enzyme layer polymer can comprise from about 5% to about 70% by weight of the polymer, sometimes from about 15% to 20%, and other times from about 25% to 40%. The soft segments can have a molecular weight of from about 160 daltons to about 10,000 daltons, and sometimes from about 200 daltons to about 2,000 daltons. In some embodiments, the molecular weight of the soft segments can be from about 200 daltons to about 10,000,000 daltons, and sometimes from about 500 daltons to about 5,000 daltons, and sometimes from about 500 daltons to about 2,000 daltons.

In some embodiments, the enzyme layer polymer, including hard and soft segments, and zwitterionic repeating units, can have a molecular weight of from about 10 kDa to about 500,000 kDa, for example, from about 10 kDa to about 100,000 kDa, from about 1000 kDa to about 500,000 kDa, from about 10,000 kDa to about 100,000 kDa, and from about 100,000 kDa to about 500,000 kDa.

The hard and soft segments can each be selected for their properties, such as, but not limited to, tensile strength, flex life, modulus, and the like. For example, polyurethanes are relatively strong and provide numerous reactive pathways, properties can be advantageous for a membrane domain of the continuous sensor.

As noted, the enzyme layer polymer contains one or more zwitterionic repeating units; thus these groups are "internal" in reference to the polymer backbone. Such "internal" repeating units are distinguished from a material that is found at the end of a polymer chain since such a moiety would only be bonded to the polymer chain at one location. The disclosed enzyme layer polymers can, in some embodiments, have one or more zwitterionic groups at the terminal ends of the polymer chains; however, such groups are not the only zwitterionic groups in the chain; there is at least one internal zwitterionic group in the backbone.

In some embodiments, the enzyme layer polymer includes at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, to about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54% or about 55% zwitterionic repeating units by weight of the polymer. In a preferred example, the enzyme layer polymer includes at least about 20% zwitterionic repeating units by weight of the polymer.

The zwitterionic repeating unit can be a betaine such as a carboxyl, sulfo, or phosphor betaine compound, precursor or derivative thereof (for example alkylbetaines or aminobetaines). These segments or moieties can be incorporated into the enzyme layer polymer, whether in the hard segment, the soft segment, or both, for example up to about 55 wt. % of the enzyme layer polymer.

Although in some embodiments, using two or more different zwitterion or zwitterion precursor segments or moieties are used, in other embodiments, a single zwitterion or zwitterion precursor segment or moiety can be used in the enzyme layer polymer.

Some examples of an enzyme layer polymer are schematically illustrated in FIG. 4. Generally, the enzyme layer polymer comprises one or more hard segments and one or more soft segments. The hard segments can be aliphatic or aromatic monomers. The soft segments can be hydrophilic or hydrophobic oligomers of, for example, polyalkylene glycols, polycarbonates, polyesters, polyethers, polyvinylalcohol, polyvinypyrrolidone, polyoxazoline, and the like. The zwitterionic groups (e.g., betaines) can be part of the soft segment, the hard segments, or both. As illustrated, in FIG. 4, various hard and soft segments can be present, which permits one to tune the properties of the enzyme layer polymer by using different segments, different segments lengths, functionalization on certain segments, crosslinking certain segments, and the like. In some embodiments, biocompatible segmented block polyurethane copolymers comprising hard and soft segments can be used for the enzyme layer.

Incorporation of these zwitterionic repeating units into a polymer can be achieved by using zwitterionic monomers that have diols or diamines (e.g., at position Z), or can be attached to diols or diamines at any of $R^1$ through $R^4$. Attaching a diol or diamine at $R^1$-$R^4$ can be accomplished by reacting the corresponding precursor with a halo-substituted diamine or halo-substituted diol. Examples of such monomers are shown below:

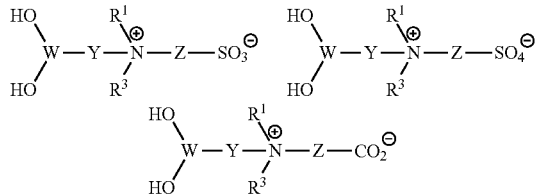

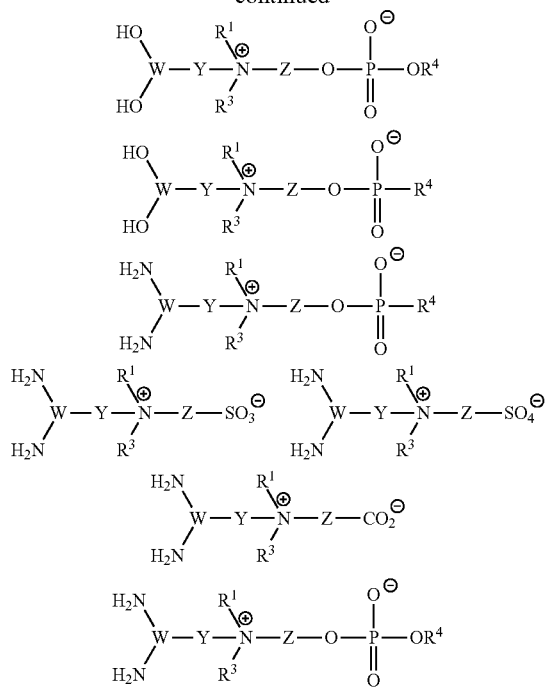

where W, Y, and Z are, independently, branched or straight chain alkyl, heteroalkyl, cycloalkyl, cycloheteroalkyl, aryl, or heteroaryl, any of which can be optionally substituted with O, OH, halogen, amido, or alkoxyl; $R^1$ is H, alkyl, heteroalkyl, cycloalkyl, cycloheteroalkyl, aryl, or heteroaryl; and $R^2$, $R^3$, and $R^4$, are independently chosen from alkyl, heteroalkyl, cycloalkyl, cycloheteroalkyl, aryl, or heteroaryl. In specific examples W is $C_1$-$C_4$ alkyl. In specific examples Y is $C_1$-$C_4$ alkyl. In other examples Z is $C_1$-$C_4$ alkyl.

These compounds can be reacted with a diisocyanate to form a polyurethane or polyurea. Alternatively, the carboxylates, sulfonates, phosphinates, or phophonates moieties can be protected and then the protection group can be removed after polymerization. In another alternative, the amine can be a tertiary amine, which is then quaternized by alkylation after polymerization.

Another method involves the radical polymerization of zwitterionic monomers having unsaturated moieties substituted at position Z in the monomers shown above. In other examples zwitterionic monomers where an unsaturated moiety is attached to the ammonium group can be used in a radical polymerization. Examples of such monomers are shown below:

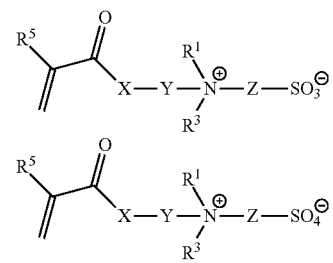

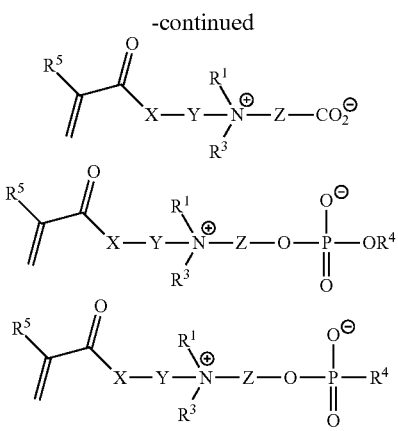

where X is O, NH, or NR⁴, Y and Z are, independently, branched or straight chain alkyl, heteroalkyl, cycloalkyl, cycloheteroalkyl, aryl, or heteroaryl, and of which can be optionally substituted with OH, halogen, or alkoxyl; $R^1$ is H, alkyl, heteroalkyl, cycloalkyl, cycloheteroalkyl, aryl, or heteroaryl; and $R^3$ and $R^5$ are independently chosen from heteroalkyl, cycloalkyl, cycloheteroalkyl, aryl, or heteroaryl. In specific examples, $R^5$ is H or $CH_3$. In other examples, X is O. In still other examples, X is NH or $NCH_3$. In specific examples Y is $C_1$-$C_4$ alkyl. In other examples Z is $C_1$-$C_4$ alkyl.

Additional examples of suitable zwitterionic monomers include N-(2-methacryloyloxy)ethyl-N,N-dimethylammonio propanesulfonate, N-(3-methacryloylimino)propyl-N,N-dimethylammonio propanesulfonate, 2-(methacryloyloxy)ethylphosphatidylcholine, and 3-(2'-vinyl-pyridinio) propanesulfonate.

In other embodiments, the enzyme layer polymer can be crosslinked. For example, polyurethaneurea polymers with aromatic or aliphatic segments having electrophilic functional groups (e.g., carbonyl, aldehyde, anhydride, ester, amide, isocyanate, epoxy, allyl, or halo groups) can be crosslinked with a crosslinking agent that has multiple nucleophilic groups (e.g., hydroxyl, amine, urea, urethane, or thio groups). In further embodiments, polyurethaneurea polymers having aromatic or aliphatic segments having nucleophilic functional groups can be crosslinked with a crosslinking agent that has multiple electrophilic groups. Still further, polyurethaneurea polymers having hydrophilic segments having nucleophilic or electrophilic functional groups can be crosslinked with a crosslinking agent that has multiple electrophilic or nucleophilic groups. Unsaturated functional groups on the polyurethane urea can also be used for crosslinking by reacting with multivalent free radical agents.

Non-limiting examples of suitable cross-linking agents include isocyanate, carbodiimide, gluteraldehyde or other aldehydes, aziridine, silane, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final layer.

Further, the disclosed enzyme layer can have zwitterions entrapped or embedded within the polymer network by non-covalent interactions. Thus, in further embodiments, the disclosed enzyme layer can comprise an enzyme layer polymer and additional betaines blended therewith. For example, the enzyme layer polymer can be blended with cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, glycine betaine, poly(carboxybetaine) (pCB), and poly(sulfobetaine) (pSB). It will be appreciated that many more zwitterionic compounds or precursors or derivatives thereof can be applicable and that this list of exemplary betaines is not intended to limit the scope of the embodiments.

In certain embodiments, the enzyme layer can comprise the polyzwitterionic enzyme layer polymer and the enzyme. In other embodiments, the enzyme layer can comprise the polyzwitterionic enzyme layer polymer blended with a base polymer, and the enzyme. Suitable base polymers may include, but are not limited to, silicone, epoxies, polyolefins, polystyrene, polyoxymethylene, polysiloxanes, polyethers, polyacrylics, polymethacrylic, polyesters, polycarbonates, polyamide, poly(ether ketone), poly(ether imide), polyurethane, and polyurethane urea, wherein polyurethanes and polyurethane urea may include polyurethane copolymers such as polyether-urethane-urea, polycarbonate-urethane, polyether-urethane, silicone-polyether-urethane, silicone-polycarbonate-urethane, polyester-urethane, and the like. In some embodiments, base polymers may be selected for their bulk properties, such as, but not limited to, tensile strength, flex life, modulus, and the like. For example, polyurethanes are known to be relatively strong and to provide numerous reactive pathways, which properties may be advantageous as bulk properties for a membrane domain of the continuous sensor.

In some embodiments, a base polymer including biocompatible segmented block polyurethane copolymers comprising hard and soft segments may be used. In some embodiments, the hard segment of the copolymer may have a molecular weight of from about 160 daltons to about 10,000 daltons, and sometimes from about 200 daltons to about 2,000 daltons. In some embodiments, the molecular weight of the soft segment may be from about 200 daltons to about 10,000,000 daltons, and sometimes from about 500 daltons to about 5,000,000 daltons, and sometimes from about 500,00 daltons to about 2,000,000 daltons. It is contemplated that polyisocyanates used for the preparation of the hard segments of the copolymer may be aromatic or aliphatic diisocyanates. The soft segments used in the preparation of the polyurethane may be a polyfunctional aliphatic polyol, a polyfunctional aliphatic or aromatic amine, or the like that may be useful for creating permeability of the analyte (e.g. glucose) therethrough, and may include, for example, polyvinyl acetate (PVA), poly(ethylene glycol) (PEG), polyacrylamide, acetates, polyethylene oxide (PEO), polyethylacrylate (PEA), polyvinylpyrrolidone (PVP), Poly (2-oxazoline (PDX), and variations thereof (e.g. PVP vinyl acetate), and wherein PVP, PDX and variations thereof may be preferred for their hydrolytic stability in some embodiments.

In some embodiments, the one or more zwitterionic compounds or precursors thereof applied to the surface of the membrane system are hydrolyzable cationic esters of zwitterionic compounds. In these embodiments, the hydrolyzable cationic esters provide the added benefit that hydrolysis of the cationic esters into nonfouling zwitterionic groups can kill microbes (such as bacteria) or condense DNA. Further, the mixed-charge nature of the resulting zwitterionic groups result in inhibition of nonspecific protein adsorption on the surface of the sensors. In these embodiments, cationic betaine esters, such as cationic pCB esters are preferable.

It has been found that incorporation of zwitterion or zwitterion precursor segments or moieties internally in the polymer backbone can be challenging due to the solubility issues associated with the monomers of the zwitterion or zwitterion precursors. Such groups typically can only be dissolved in highly polar solvents such as methanol and water, which are not favorable in the synthesis of some the enzyme layer polymers (e.g., polyurethanes). Thus, the available functional groups that could be used chemically incorporated into the enzyme layer polymer's backbone by solution based polycondensation synthesis was limited. As an alternative method of incorporating zwitterion or zwitterion precursor segments or moieties into the base-polymer's backbone, precursors or derivatives of the zwitterion or zwitterion precursors can be used. For example, zwitterion precursors and/or zwitterionic derivatives, which have more desirable solubility characteristics in low polarity organic solvents, can be used as monomers. The enzyme layer polymer (e.g., polyurethaneureas) can be synthesized by polycondensation reactions and form well-defined polymers with high molecular weight and low polydispersity index. These polymers can then be converted to zwitterion group containing polymers via chemical reaction (such as hydrolysis, deprotection, heat-triggered rearrangement, and UV-triggered degradation) or biological triggered reaction after in vivo implantation of the device.

In some embodiments, enzymes included in an enzyme layer are susceptible to thermal or pH induced degradation. In some related embodiments, the enzyme layer may also comprise one or more enzyme stabilizing agents. Such agents improve the enzyme's ability to resist thermal or pH induced denaturing. Inclusion of enzyme stabilizing agents thus facilitates device fabrication by allowing for use of fabrication processes which would otherwise compromise the enzyme's activity. Inclusion of these agents has the added benefits of extending useable and shelf lives of the sensors. Any material which improves thermal and/or pH stability of the enzyme, without affecting analyte or oxygen permeability of the enzyme layer to the point that the enzyme layer is no longer suitable for use in a sensor, may be used as an enzyme stabilizing agent. In some embodiments, an enzyme stabilizing agent may be dipolar. Without wishing to be bound by theory, it is believed that dipolar enzyme stabilizing agents stabilize the enzyme by orienting around the enzyme in such a way as to provide a charged local environment that stabilizes the enzyme's tertiary structure.

Dipolar enzyme stabilizing agents may be zwitterionic or non-zwitterionic. That is, dipolar enzyme stabilizing agents are neutral molecules with a positive and negative electrical charge at different locations. In some embodiments, the positive and negative electrical charges are full unit charges (i.e., the molecules are zwitterionic). In other embodiments, the positive and negative charges are less than full unit charges (i.e., the molecules are dipolar, but non-zwitterionic).

In some embodiments, a zwitterionic enzyme stabilizing agent may be a betaine, such as glycine betaine, poly (carboxybetaine) (pCB), or poly(sulfobetaine) (pSB), or some other zwitterion, such as cocamidopropyl betaine, oleamidopropyl betaine, octyl sulfobetaine, caprylyl sulfobetaine, lauryl sulfobetaine, myristyl sulfobetaine, palmityl sulfobetaine, stearyl sulfobetaine, betaine (trimethylglycine), octyl betaine, phosphatidylcholine, ectoine, or hydroxyectoine. In preferred embodiments, the zwitterionic enzyme stabilizing agent is glycine betaine. In some embodiments, a non-zwitterionic enzyme stabilizing reagent may be an amine oxide.

The enzyme stabilizing reagents, if used, can be present at up to about 0.1, about 0.2, about 0.5, about 1, about 2, or about 5% wt. of the enzyme layer. It will be appreciated that many more zwitterionic groups, or precursors or derivatives thereof, can be applicable and that this list of exemplary betaines is not intended to limit the scope of the embodiments. In some embodiments, hydrolyzable cationic esters of zwitterionic groups (as discussed elsewhere) can be used at similar concentrations for incorporation into the enzyme layer.

In embodiments where the enzyme layer comprises an enzyme stabilizing reagent, the amount of enzyme stabilizing reagent present in the enzyme domain is sufficient to provide an improvement in the thermal and/or pH stability of the enzyme, while not disrupting the permeability characteristics of the enzyme layer so that the sensor retains high glucose sensitivity. The identity and amount of enzyme stabilizing reagent used in the enzyme layer may vary based on the particular enzyme used in the sensor; however, the amount of enzyme stabilizing reagent is generally less than about 50% wt. of the amount of the enzyme; such as less than about 25% wt; such as less than about 10 wt. %. In a preferred embodiment, the enzyme is glucose oxidase and the enzyme stabilizing reagent is a betaine, such as glycine betaine.

In some embodiments, the enzyme and enzyme layer polymer, and optional enzyme stabilizing agents, can be impregnated or otherwise immobilized into the biointerface layer or diffusion resistance domain such that a separate enzyme layer is not required (e.g. wherein a unitary domain is provided including the functionality of the biointerface layer, diffusion resistance domain, interference domain, and enzyme layer). In some embodiments, the enzyme layer is formed from a polyurethane, for example, aqueous dispersions of colloidal polyurethane polymers including the enzyme and enzyme stabilizing reagent. Again, it is contemplated that in some embodiments, the polymer system of the enzyme layer may not be crosslinked, but in other embodiments, crosslinking may be used and achieved by any of a variety of methods, for example, by adding a crosslinking agent.

In some other embodiments, a blend of two or more surface-active group-containing polymers comprises one surface-active group that is negatively charged and one surface-active group that is positively charged. In some embodiments, the number of negatively and positively charged surface-active groups is such that an enzyme domain formed from the blend is about net neutrally charged. In other embodiments, the number of positively charged and negatively charged surface-active groups can be unequal, with either more positively charged or negatively charged surface-active groups being present.

In some embodiments, disclosed are membranes that comprise an enzyme layer 44 (see FIGS. 2A through 2C). The enzyme layers disclosed herein can comprise the enzyme layer polymer and an enzyme, or in an alternative embodiment, the enzyme layer can comprise the enzyme layer polymer and one or more other polymers, forming a polymer blend, and an enzyme.

In some embodiments, the enzyme layer 44, can be used and is situated less distal from the electrochemically reactive surfaces than the diffusion resistance domain 46. The enzyme layer comprises an enzyme configured to react with an analyte. In one embodiment, the membrane comprises an immobilized enzyme layer 44 including glucose oxidase. In other embodiments, the enzyme layer 44 can be impregnated with other oxidases, for example, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration. In other embodiments, the enzyme may be a dehydrogenase, such as a glucose dehydrogenase.

In some embodiments, the enzyme can be impregnated or otherwise immobilized into the biointerface or diffusion resistance domain such that a separate enzyme domain 44 is not required (e.g., wherein a unitary domain is provided including the functionality of the biointerface domain, diffusion resistance domain, and enzyme domain). In some embodiments, the enzyme domain 44 is formed from a polyurethane, for example, aqueous dispersions of colloidal polyurethane polymers including the enzyme.

In some embodiments, the thickness of the enzyme domain can be from about 0.01, about 0.05, about 0.6, about 0.7, or about 0.8 µm to about 1, about 1.2, about 1.4, about 1.5, about 1.6, about 1.8, about 2, about 2.1, about 2.2, about 2.5, about 3, about 4, about 5, about 6, about 8, about 10, about 15, about 20, about 30, about 40, about 50, about 60, about 70, about 75, about 80, about 90, about 100 µm, about 125, about 150, about 175, about 200 or about 250 µm. In some of these embodiments, the thickness of the enzyme domain can be from about 0.05, about 0.1, about 0.15, about 0.2, about 0.25, about 0.3, about 0.35, about 0.4, about 0.45, about 0.5, about 1, about 1.5, about 2, about 2.5, about 3, about 4, or about 5 µm to about 6, about 7, about 8, about 9, about 10, about 11, about 12, about 13, about 14, about 15, about 16, about 17, about 18, about 19, about 19.5, about 20, about 25, or about 30 µm. In some of these embodiments, the thickness of the enzyme layer can be sometimes from about 1 to about 5 µm, and sometimes from about 2 to about 7 µm. In other embodiments, the enzyme layer can be from about 20 or about 25 µm to about 50, about 55, or about 60 µm thick. In even further embodiments, the thickness of the enzyme domain is from about 2, about 2.5, or about 3 µm to about 3.5, about 4, about 4.5, or about 5 µm; in the case of a transcutaneously implanted sensor is from about 6, about 7, or about 8 µm to about 9, about 10, about 11, or about 12 µm in the case of a wholly implanted sensor. In some embodiments, the glucose sensor can be configured for transcutaneous or short-term subcutaneous implantation, and can have a thickness from about 0.5 µm to about 8 µm, and sometimes from about 4 µm to about 6 µm. In one glucose sensor configured for fluid communication with a host's circulatory system, the thickness can be from about 1.5 µm to about 25 µm, and sometimes from about 3 to about 15 µm. It is also contemplated that in some embodiments, the enzyme layer or any other layer of the electrode can have a thickness that is consistent, but in other embodiments, the thickness can vary. For example, in some embodiments, the thickness of the enzyme layer can vary along the longitudinal axis of the electrode end.

In another aspect, the enzyme layer can have a biomimetic adhesive polymer as an additive blended into the enzyme layer to enhance the adherence of the enzyme layer to the diffusion resistance domain and interference domain and decrease delamination. Suitable biomimetic adhesive polymers that can be used in this embodiment are 3,4-dihydroxy-L-phenylalanine containing polymers. 3,4-dihydroxy-L-phenylalanine (DOPA), the active ingredient in marine mussel proteins, can be converted into polymerizable monomers and them polymerized to form linear nondegradable homo or copolymers.

Interference Domain

It is contemplated that in some embodiments, such as in the sensor configuration illustrated in FIG. 2B, an interference domain 43, also referred to as the interference layer, may be provided in addition to (or in replacement of) the biointerface layer. The interference domain 43 may substantially reduce the permeation of one or more interferents into the electrochemically reactive surfaces. The interference domain 43 can be configured to be much less permeable to one or more of the interferents than to the measured species. It is also contemplated that in some embodiments, where interferent blocking may be provided by the biointerface layer (e.g., via a surface-active group-containing polymer of the biointerface layer), a separate interference domain is not present. In other embodiments, the membrane includes both an interference domain and a biointerface layer, with both domains configured to reduce the permeation of one or more interferents. In further embodiments, the interference domain and the biointerface layer are each configured to reduce permeation of different interfering species. For example, the interference domain may have greater specificity than the biointerface layer with respect to reducing permeation of one type of interfering species, while the biointerface layer may have greater specificity than the interference domain with respect to reducing permeation of another type of interfering species. In some embodiments, both the interference domain and the biointerface layer are configured to target certain interference species for permeation reduction.

In certain embodiments, the implantable sensor employs a membrane system comprising a resistance domain, an enzyme domain, and an interference domain. The interference domain can be proximal to the sensor and the resistance domain can be distal to the sensor, with the enzyme domain therebetween. The interference domain can consist of a single layer or plurality of layers of the same material. However, in some embodiments, the interference domain comprises two or more different types of layers in an alternating configuration. For example, a first type of layer can be represented by X, a second type of layer can be represented by Y, and a third type of layer can be represented by Z. The interference domain including alternating layers can have the following exemplary configurations:

XY

YX

XYX

XYXYX

XYXYXY

XXYYXYXXYY

XXXYYXXXYYYXXX

XYXYXYXYXYXYX

XYZXYZXYZX

-continued
XYXZXYXZXYXZ

ZYYXZZZXYYYXZ

The above configurations, which are merely exemplary, illustrate various embodiments. In certain embodiments, the first and last layers are the same (e.g., X and X), in other embodiments, the first and last layers are different (e.g., X and Y). The domain can include one or more layers that are unitary (i.e., a single layer is deposited, e.g., X), or composite (e.g., a first layer of material is deposited, followed by the deposition of a second and third, etc. layer of the same material atop the first layer, e.g., XXX). The pattern of alternating layers can be regular (e.g., XYXYXYXYXY) or irregular (e.g., ZYXZXYZYZ).

In some embodiments, the alternating layers include polyanionic layers and polycationic layers. The following are exemplary interference domain configurations, wherein the polyanionic layers (unitary, composite, and/or contiguous with the same polyanion or with different polyanions) are represented by A and the polycationic layers by C (unitary, composite, and/or contiguous with the same polyanion or with different polyanions):

CA

CAC

CACA

CACAC

CACACA

CACACAC

CACACACA

CACACACAC

CACACACACA

CACACACACAC

CACACACACACA

CACACACACACAC

CACACACACACACA

CACACACACACACAC

CACACACACACACACA

CACACACACACACACAC

CACACACACACACACACA

CACACACACACACACACAC

CACACACACACACACACACA

CACACACACACACACACACAC

CACACACACACACACACACACA

CACACACACACACACACACACAC

CACACACACACACACACACACACA

CACACACACACACACACACACACAC

-continued
CACACACACACACACACACACACACA

CACACACACACACACACACACACACAC

AC

ACA

ACAC

ACACA

ACACAC

ACACACA

ACACACAC

ACACACACA

ACACACACAC

ACACACACACA

ACACACACACAC

ACACACACACACA

ACACACACACACAC

ACACACACACACACA

ACACACACACACACAC

ACACACACACACACACA

ACACACACACACACACAC

ACACACACACACACACACA

ACACACACACACACACACAC

ACACACACACACACACACACA

ACACACACACACACACACACAC

ACACACACACACACACACACACA

ACACACACACACACACACACACAC

ACACACACACACACACACACACACA

ACACACACACACACACACACACACAC

ACACACACACACACACACACACACACA

ACACACACACACACACACACACACACA

ACACACACACACACACACACACACACA

Other configurations (e.g., those including additional layers, and/or additional materials) are also contemplated for some embodiments. In some embodiments, each A layer is a unitary or composite layer of the same polyanion, and each C layer is a unitary or composite layer of the same polycation. The outermost layers of the interference domain can both be polycation layers, with polyanion layers present only as interior layers. Any suitable number of alternating layers can be employed in the interference domain, for example, 1, 2, 3, 4, 5, 6, 7, 8, 9, 10, 11, 12, 13, 14, 15, 16, 17, 18, 19, 20 or more bilayers (defined as a polycationic layer adjacent to a polyanionic layer). In some embodiments a final polycationic layer is added so as to yield an interference domain with polycationic layers as the outermost layers. In other embodiments a final anionic layer is added so as to yield an interference domain with polyanionic layers as the outermost layers.

Polyanions and polycations belong to the class of polymers commonly referred to as polyelectrolytes—polymers wherein at least some of the repeating units (or monomers) include one or more ionic moieties. Polyelectrolytes which bear both cationic and anionic moieties are commonly referred to as polyampholytes. Certain polyelectrolytes form self-assembled monolayers wherein one end of the molecule shows a specific, reversible affinity for a substrate such that an organized, close-packed monolayer of the polyelectrolyte can be deposited.

The polycation can be any biocompatible polycationic polymer. In some embodiments, the polycation is a biocompatible water-soluble polycationic polymer. In certain embodiments, water solubility may be enhanced by grafting the polycationic polymer with water-soluble polynonionic materials such as polyethylene glycol. Representative polycationic materials may include, for example, natural and unnatural polyamino acids having a net positive charge at neutral pH, positively charged polysaccharides, and positively charged synthetic polymers. Additional examples of suitable polycationic materials include polyamines having amine groups on either the polymer backbone or the polymer sidechains, such as poly-L-lysine and other positively charged polyamino acids of natural or synthetic amino acids or mixtures of amino acids, including poly(D-lysine), poly(ornithine), poly(arginine), and poly(histidine), and nonpeptide polyamines such as poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(diallyldimethyl ammonium chloride), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), and natural or synthetic polysaccharides such as chitosan, poly(allylamine hydrochloride), poly(diallyldimethylammonium chloride), poly(vinylbenzyltriamethylamine), polyaniline or sulfonated polyaniline, (p-type doped), polypyrrole (p-type doped), polyallylamine gluconolactone, and poly(pyridinium acetylene).

The polyanionic material can be any biocompatible polyanionic polymer, for example, any polymer having carboxylic acid groups attached as pendant groups. The polyionic layers can be hydrophilic (e.g., a material or portion thereof which will more readily associate with water than with lipids). In some embodiments, the polyanionic polymer is a biocompatible water-soluble polyanionic polymer. Suitable materials include, but are not limited to, alginate, carrageenan, furcellaran, pectin, xanthan, hyaluronic acid, heparin, heparan sulfate, chondroitin sulfate, dermatan sulfate, dextran sulfate, polymethacrylic acid, polyacrylic acid, poly(vinyl sulfate), poly(thiophene-3-acetic acid), poly(-styrene-sulfonic acid), poly(styrene sulfonate), (poly[1-[4-(3-carboxy-4-hydroxy-phenylazo)benzene sulfonamido]-1,2-ethanediyl, sodium salt]), poly(4-[4-({4-[3-amino-2-(4-hydroxy-phenyl)propylcarbamoyl]-5-oxo-pentyl-}-methyl-amino)-phenylazo]-benzenesulfonic acid), oxidized cellulose, carboxymethyl cellulose and crosmarmelose, synthetic polymers, and copolymers containing pendant carboxyl groups, such as those containing maleic acid or fumaric acid in the backbone. Polyaminoacids of predominantly negative charge are also suitable. Examples of these materials include polyaspartic acid, polyglutamic acid, and copolymers thereof with other natural and unnatural amino acids. Polyphenolic materials, such as tannins and lignins, can be used if they are sufficiently biocompatible.

The molecular weight of the polyionic materials may be varied in order to alter coating characteristics, such as coating thickness. As the molecular weight is increased, the coating thickness generally increases. However, an increase in molecular weight may result in greater difficulty with handling. To achieve a balance of coating thickness, material handling, and other design considerations, the polyionic materials can have a particular average molecular weight Mn. In some embodiments, the average molecular weight of a polyionic material used is from about 1,000, 10,000, or 20,000 to about 25,000, 50,000, 100,000 or 150,000 g/mol.

Figure 26A:
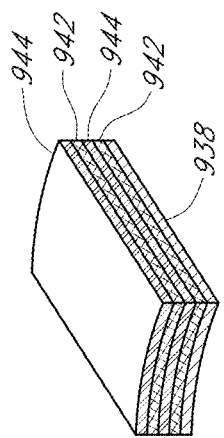
FIG. 26A is a schematic view of a portion of one embodiment of an interference domain that comprises a plurality of polycationic and polyanionic layers.
Figure 26B:
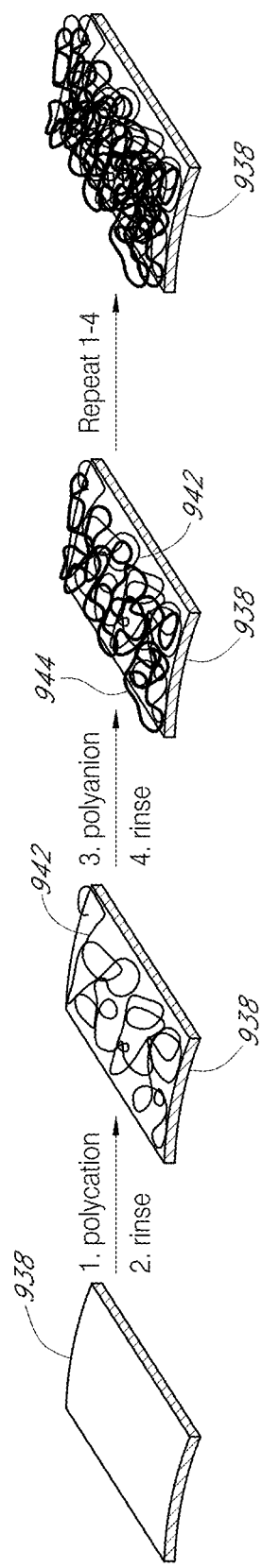
FIG. 26B illustrates one embodiment of a layer-by-layer deposition method, which employs alternating adsorption of polycations and polyanions to create a structure illustrated in FIG. 26A.

In some embodiments, the interference domain can be prepared using a layer-by-layer deposition technique, wherein a substrate (e.g., the sensor or membrane layer atop the sensor, e.g., the resistance or enzyme layer) is dipped first in a bath of one polyelectrolyte, then in a bath of an oppositely charged polyelectrolyte. Optionally, the substrate can be dipped in a bath of rinsing solution before or after the substrate is dipped into the polyelectrolyte bath. During each dip a small amount of polyelectrolyte is adsorbed and the surface charge is reversed, thereby allowing a gradual and controlled build-up of electrostatically cross-linked films (or hydrogen bonded films) of alternating polycation-polyanion layers. The method provides a technique for controlling functionality and film thickness and functionality. For example, it can be employed for depositing films as thin as one monolayer or for thicker layers. FIG. 26B illustrates one embodiment of a layer-by-layer deposition method, which employs alternating adsorption of polycations and polyanions to create a structure illustrated in FIG. 26A. Operationally, the embodiment illustrated in FIG. 26B, occurs through consecutive exposures of a substrate 938 to polycation and polyanion solutions, with rinsing to remove unadsorbed polymer after each deposition step. In a first step, a polycation 942 is deposited onto a substrate 938 (e.g., a wire with an electroactive surface or a flat wafer substrate) to form a polycationic layer 942. As described elsewhere herein in greater detail, the deposition of the layer can be performed using any of a variety of techniques, such as, dipping and/or spraying, for example. In a second step, rinsing is performed to remove unadsorbed polymer after deposition of the polycationic layer 942. Next, in a third step, a polyanion 944 is deposited onto the polycationic layer 942. Thereafter, in a fourth step, rinsing is performed to remove unadsorbed polymer after deposition of the polyanionic layer 944. These steps can be repeated until the desired interference domain configuration and/or structure is achieved. In an alternative embodiment, instead of depositing a polycationic layer as the first layer on top of the substrate 938, a polyanionic layer is deposited instead. Thereafter, a second layer formed of a polycation is deposited onto the first layer, i.e., the polyanionic layer. This process is continued until a certain desired interference domain configuration and/or structure is achieved.

In some embodiments, methods can also employ other interactions such as hydrogen bonding or covalent linkages. Depending upon the nature of the polyelectrolyte, polyelectrolyte bridging may occur, in which a single polyelectrolyte chain adsorbs to two (or more) oppositely charged macroions, thereby establishing molecular bridges. If only a monolayer of each polyelectrolyte adsorbs with each deposition step, then electrostatically cross-linked hydrogel-type materials can be built on a surface a few microns at a time.

If the substrate is not thoroughly rinsed between the application of polyionic films, thicker, hydrogel-like structures can be deposited.

In some embodiments, the interference blocking ability provided by the alternating polycationic layer(s) and polyanionic layer(s) can be adjusted and/or controlled by creating covalent cross-links between the polycationic layer(s) and polyanionic layer(s). Cross-linking can have a substantial effect on mechanical properties and structure of the film, which in turn can affect the film's interference blocking ability. Cross-linked polymers can have different cross-linking densities. In certain embodiments, cross-linkers are used to promote cross-linking between layers. In other embodiments, in replacement of (or in addition to) the cross-linking techniques described above, heat is used to form cross-linking. For example, in some embodiments, imide and amide bonds can be formed between a polycationic layer and a polyanionic layer as a result of high temperature. In some embodiments, photo cross-linking is performed to form covalent bonds between the polycationic layers(s) and polyanionic layer(s). One major advantage to photo-cross-linking is that it offers the possibility of patterning. In certain embodiments, patterning using photo-cross linking is performed to modify the film structure and thus to adjust the interference domain's interference blocking ability. Blocking ability can correspond to, but is not limited to, the ability to reduce transport of a certain interfering species or to the selectivity for the transport of a desired species (e.g., $H_2O_2$) over an interfering species. Post-deposition reactions, such as cross-linking and reduction of metal ions to form nanoparticles, provide further ways to modify film properties. In some embodiments, cross-linking may be performed between deposition of adjacent polycationic or polyanionic layers in replacement of (or in addition to) a post-deposition cross-linking process.

The overall thickness of the interference layer can impact its permeability to interferents. The overall thickness of the interference domain can be controlled by adjusting the number of layers and/or the degree of rinsing between layers. With layer deposition through spraying, control of drop size and density can provide coatings of desired selected thickness without necessarily requiring rinsing between layers. Additionally, the excess (unbound) material can be removed via other means, for example, by an air jet. If the residual polyelectrolyte from the previous layer is substantially removed before adding the subsequent layer, the thickness per layer decreases. Accordingly, in one embodiment, the surface is first coated with a polycation, the excess polycation is then removed by rinsing the surface, afterwards the polyanion is added, the excess is then removed, and the process is repeated as necessary. In some embodiments, the polycations or polyanions from different adjacent layers may intertwine. In further embodiment, they may be intertwined over several layers.

In some embodiments, the level of ionization of polyions may be controlled, for example, by controlling the pH in the dip solution comprising the polycation or the polyanion. By changing the level of ionization of these polyions, the interference blocking ability of a certain layer of may be altered and/or controlled. For example, a first polycationic layer that has a higher level of ionization than a second polycationic layer may be better at interacting with and reducing the transport a first interfering species, while the second polycationic may be better at interacting with and reducing the transport of a second interfering species. Changes in the level of ionization of a polyion's charge groups can also affect the mechanical properties, structural properties, and other certain properties (e.g., diffusion properties) that may affect the interference domain's ability to reduce transport of (or entirely block) interfering species. For example, an alternating bilayer, comprising polycations and polyanions, both of which have high levels of ionization, may bond together more tightly than a corresponding bilayer with low levels of ionization. Thus, the structural difference between these two membranes, which can be in the form of mechanical properties or other properties (e.g., thickness of the domain), can affect the performance of the interference domain.

In some embodiments, the linear charge density of the polyelectrolyte may be controlled at least in part by the average charge spacing along the polyion chain. The spacing between charge groups on the polycationic and/or polyanionic polymers that form the interference domain may be controlled by polyelectrolyte polymer selection or polymer synthesis. How far the charged groups are spaced can greatly affect the structural properties of the interference domain. For example, a polyion having charged groups that are spaced closely to each other may result in small-sized pores in the interference domain, thereby resulting in a structure that excludes medium molecular-sized and large molecular-sized interfering species from passage therethough, while allowing passage therethrough of small-sized pores. Conversely, a polyion having charged groups that are spaced apart at a moderate distance from each other may result in medium-sized pores that exclude large molecular-sized interfering species and allow passage therethrough of medium-molecular sized and small molecular-sized interfering species. In certain embodiments, the linear charge density of the polyanionic polymer is from about 1 to 50 e/Å, sometimes from about 10 to 25 e/Å, sometimes from about 2 to 10 e/Å, and sometimes from 2 to 3 e/Å, where e is the elementary charge of an electron/proton and Å is distance in angstroms. In some embodiments, the linear charge density of the polycationic polymer is from about 1 to 50 e/Å, sometimes from about 10 to 15 e/Å, sometimes from about 2 to 10 e/Å, and sometimes from 2 to 3 e/Å.

In some embodiments, the linear charge density of polyanionic polymer is substantially similar to the linear charge density of the polycationic polymer. For example, in one embodiment, the polyanionic layer is formed of (i) poly (acrylic acid), which has an average linear charge density of about 2.5 e/Å and (ii) poly(allylamine hydrochloride), which also has an average linear charge density of about 2.5 e/Å. In certain embodiments, the polycationic and polyanionic layers may have an average linear charge density that is substantially equal with each other and that is from about 1 to 50 e/Å, sometimes from about 2 to 25 e/Å, sometimes from about 5 to 10 e/Å, other times from about 10 to 15 e/Å, and other times from about 15 to 25 e/Å.

By providing an interference domain with differing linear charge densities, an interference domain may be formed that comprises different polycationic/polyanionic bilayers that are designed specifically to exclude different interfering species based on certain characteristics (e.g., molecular size) of the targeted interfering species. For example, in one embodiment, an outermost bilayer of the interference domain is designed to have a medium average charge spacing, thereby resulting in a bilayer that only excludes large molecular-sized species, but allows passage therethrough of medium molecular-sized species and small molecular-sized species. Conversely, an innermost bilayer of the interference domain may be designed to have low average charge spacing, thereby resulting in a bilayer that excludes all molecules, except those with very small molecular sizes, for example, $H_2O_2$.

In some embodiments, the polycationic layers may be formed of the same or substantially the same material (e.g., poly(allylamine hydrochloride) (PAH) for polycation or poly(acrylic acid) (PAA) for polyanion), while having different levels of ionization. For example, in one embodiment, the interference domain comprises seven alternating polyelectrolyte layers, with the first, third, fifth, and seventh layers being polycationic layers, and with the second, fourth, and sixth layers being polyanionic layers, wherein the first and seventh layers form the outer layers of the interference domain. In one embodiment, each or some of the polycationic layers may have different levels of ionization. For example, in one embodiment, the first, third, fifth, and seventh layers may each have different levels of ionization, with the first layer having the highest level of ionization and the seventh layer having the lowest level of ionization, or vice versa. In an alternative embodiment, some of the polycationic layers may share substantially the same level of ionization. For example, in one embodiment, the first and seventh layers may have substantially the same levels of ionization, while the third and fifth layers may have a level of ionization that is different from the others. As described elsewhere herein, the ionization level of a polyion may be controlled by controlling the pH in the dip solution comprising the polycation or the polyanion. By changing the level of ionization of these polyions, the interference blocking ability of a certain layer of may be altered and/or controlled.

The design of an interference domain having layers with levels of ionization can also be applied to polyanionic layers as well. For example, in one embodiment with seven alternating polyelectrolyte layers, the second, fourth, and sixth layers are each polyanionic layers and may each have different levels of ionization, with the second layer having the highest level of ionization and the sixth layer having the lowest level of ionization, or vice versa. In an alternative embodiment, some of the polyanionic layers may share substantially the same level of ionization. For example, in one embodiment, the second and fourth layers may have substantially the same levels of ionization, while the sixth layer may have a substantially different level of ionization from the others.

In certain embodiments, the particular polycationic layer(s) and/or polyanionic layer(s) selected to form the interference layer may depend at least in part on their ability to block, reduce, or impede passage therethrough of one or more interferents. For example, the polyanionic layer can be selected for its ability to block, reduce, or impede passage of a first interferent, whereas the polycationic layer is selected for its ability to block, reduce, or impede passage of a second interferent. The layer may be designed to slow but not block passage of an interferent therethrough, or designed to substantially block (e.g., trap) an interferent therein. Additional polyionic layers can be included in the interference domain with particular selectivity towards still different interferents. Depending upon the position of the interference domain in the membrane system relative to the electrode or electroactive surface of the sensor, the permeability of the layer to substances other than the interferent can be important. In sensor systems wherein $H_2O_2$ (hydrogen peroxide) is produced by an enzyme-catalyzed reaction of an analyte being detected, the interference domain should be designed to allow $H_2O_2$ to pass through with minimal impedance if the interference domain is positioned between the electroactive surface and the enzyme layer. On the other hand, if in a different membrane design, the interference domain is positioned distal to the enzyme layer (with respect to the electroactive surface), then in some embodiments, the interference domain may be designed to block $H_2O_2$ not produced by the enzyme-catalyzed reaction from passing therethrough. In addition, with this particular membrane design, the interference domain may be configured to allow analyte and oxygen to pass therethrough with minimal impedance.

Application of the layers in forming the interference domain may be accomplished by various methods known in the art. One coating process embodiment involves solely dip-coating and dip-rinsing steps. Another coating process embodiment involves solely spray-coating and spray-rinsing steps. However, a number of alternative embodiments involve various use of a combination of spray-coating, dip-coating, and/or rinsing steps. For example, one dip-coating method involves the steps of applying a coating of a first polyionic material to a substrate (e.g., the sensor or membrane layer atop the sensor, e.g., the resistance or enzyme layer) by immersing the substrate in a first solution of a first polyionic material; rinsing the substrate by immersing the substrate in a rinsing solution; and, optionally, drying the substrate. This procedure is then repeated using a second polyionic material, with the second polyionic material having charges opposite of the charges of the first polyionic material, in order to form a polyionic bilayer. This bilayer formation process can be repeated a plurality of times in order to produce the interference domain. In some embodiments, the number of bilayers can be from 1 to about 16 bilayers, sometimes from 1 to about 10 bilayers, and sometimes from about 3 to about 7 bilayers. In certain embodiments, the final layer of oppositely charged polyionic material can be deposited, such that the first and the last layer have the same charges (both positive, or both negative). The immersion time for each of the coating and rinsing steps may vary depending on a number of factors. For example, immersion of the substrate into the polyionic solution can occur over a period of about 1 to 30 minutes, or from about 2 to 20 minutes, or from about 1 to 5 minutes. Rinsing may be accomplished in one step, but a plurality of rinsing steps can also be employed. Rinsing in a series from about 2 to 5 steps can be employed, with each immersion into the rinsing solution consuming, for example, from about 1 to about 3 minutes. In some embodiments, several polycationic solutions and/or several polyanion solutions may be used. For example, in certain embodiments, the dip-coating sequence may involve the steps of applying a coating of a first polycationic material to the substrate to form a first layer, then applying a first anionic material to the first layer to form a second layer, then applying a second polycationic material to the second layer to form a third layer, then applying a second polyanionic material to form a fourth layer, and then applying a first or second polycationic material to the fourth layer to form a fifth layer. In some of these embodiments, the dip-coating sequence described above may be interspersed with rinsing steps performed between coating steps. It is contemplated that any of a variety of permutations involving the steps and materials described may be employed. In alternative embodiments, the materials used to form the polycationic and/or polyanionic layers may be substantially the same. However, the individual polycationic layers may have a different level of ionization than one or more other polycationic layers in the inference domain, and the individual polyanionic layers may also have a different level of ionization than one or more other polyanionic layers. For example, in one embodiment, the dip-coating sequence method involves the use of a first solution at a first pH comprising a polycationic material, a second solution at a second pH comprising a polyanionic material, a third solution at a third pH comprising the aforementioned polycationic material, a fourth solution at a fourth pH comprising the aforementioned polyanionic material, and a fifth solution at a fifth pH comprising the aforementioned polycationic material. Even though the same polycationic material is used to form the first, third, and fifth layers, because the solution used to form the first, third, and fifth layers have different pHs, the ionization levels of the first, third, and fifth layers will be different. Likewise, even though the same polyanionic material is used to form the second and fourth layers, because the solution used to form the second and fifth layers have different pHs, the levels of ionization of the second and fourth layers will be different. This difference in ionization levels can affect, inter alia, the mechanical properties of the film, structural properties (e.g., porosity, roughness) of the film, diffusional properties of the film, and also the selectivity of a certain polyelectrolyte layer for a certain interfering species over another interfering species. All of these effects influence the ability of the individual polyelectrolyte layers and of the interference domain to reduce transport of a variety of interfering species. In certain embodiments, at least two polycationic and/or two polyanionic layers of the interference domain are formed from the same polycationic/polyanionic material, but through use of solutions at different pHs. In some of these embodiments, a first polycationic layer possesses a high selectivity for a particular interfering species over other interfering species, while a second polycationic layer possesses a high selectivity for a different interfering species over other interfering species.

Alternatively or additionally, spray coating techniques can be employed. In one embodiment, the coating process generally includes the steps of applying a coating of: a first polyionic material to the substrate by contacting the substrate with a first solution of a first polyionic material; rinsing the substrate by spraying the substrate with a rinsing solution; and (optionally) drying the substrate. Similar to the dip-coating process, the spray-coating process may then be repeated with a second polyionic material, with the second polyionic material having charges opposite to those of the first polyionic material. The contacting of the substrate with solution, either polyionic material or rinsing solution, may occur through a variety of methods. For example, the substrate may be dipped into both solutions. One alternative is to apply the solutions in a spray or mist form. Of course, various combinations are possible and within the scope of the contemplated embodiments, e.g., dipping the substrate in the polyionic material followed by spraying the rinsing solution. The spray coating application may be accomplished via a number of methods known in the art. For example, a conventional spray coating arrangement may be used, i.e., the liquid material is sprayed by application of fluid, which may or may not be at an elevated or lowered pressure, through a reduced diameter nozzle which is directed towards the deposition target. Another spray coating technique involves the use of ultrasonic energy, whereby the liquid is atomized by the ultrasonic vibrations of a spray forming tip and thereby changed to a spray.

Yet another technique involves electrostatic spray coating in which a charge is conveyed to the fluid or droplets to increase the efficiency of the coating. A further method of atomizing liquid for spray coating involves purely mechanical energy, e.g., through contacting the liquid with a high speed reciprocating member or a high speed rotating disk. Still another method of producing microdroplets for spray coatings involves the use of piezoelectric elements to atomize the liquid. These techniques can be employed with air assistance or at an elevated solution pressure. In addition, a combination of two or more techniques may prove more useful with certain materials and conditions. A method of spray application involves dispensing, with a metering pump, the polyanion or polycation solution to an ultrasonic dispensing head. The polyion layer is sprayed so as to allow the surface droplets to coalesce across the material surface. The resulting layer may then be allowed to interact for a period of time or immediately rinsed with water or saline solution (or other solution devoid of polyanion or polycation).

In some embodiments, the layers of the interference domain can include a polymer with a conjugated pi system. Polymers with conjugated pi systems can contain a delocalized electron system, and can be conductive. Layers of polymers with conjugated pi systems can interact with each other through intermolecular forces, such as electrostatic pi-pi interactions (i.e., pi-stacking). Conjugated polymers can provide beneficial properties to an interference domain, such as increasing the rigidity, integrity, and/or reproducibility of the domain. In some embodiments, the polymer with a conjugated pi system can be poly acetylene, polypyrrole, polythiophene, poly(p-phenylene), poly(p-phenylenevinylene) or poly(carbazole). The interference domain can include alternating layers of any of the conjugated polymers mentioned above. In some embodiments, the number of layers of conjugated polymers can be from 1 to about 20 layers, sometimes from about 3 to about 10 layers.

It is contemplated that in some embodiments, the thickness of the interference domain may be from about 0.01 microns or less to about 20 microns or more. In some of these embodiments, the thickness of the interference domain may be from about 0.01, 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. In some of these embodiments, the thickness of the interference domain may be from about 0.2, 0.4, 0.5, or 0.6, microns to about 0.8, 0.9, 1, 1.5, 2, 3, or 4 microns.

Polyimine Films

In some embodiments, certain polymeric films can be used to form interference domains. For example, certain polyimides prepared from 2,2'-dimethyl-4,4'-diaminobiphenyl and the corresponding dianhydride can be cast into films that can be employed as hydrogen peroxide-selective membranes. See, e.g., Ekinci et al., Turk. J. Chem. 30 (2006), 277-285. In one embodiment, a film is prepared using the following steps. First, n-methyl-2-pyrrolidene (NMP) is distilled over $CaH_2$ under reduced pressure and is stored over about 4 Å molecular sieves. Reagent grade pyromellitic dianhydride (PMDA) is sublimed at about 250° C. under reduced pressure and dried under vacuum at about 120° C. prior to use. The diamine is purified via recrystallization from ethanol to give shiny crystals. Next, 2,20-dimethyl-4,40-diaminobiphenyl, (about 1.06 g, about 5 mmol) is dissolved in NMP (about 15 mL) in a 50 mL Schlenk tube equipped with a nitrogen line, overhead stirrer, a xylene filled Dean-Stark trap, and a condenser. PMDA (about 1.09 g, about 5 mmol) is then added to the amine solution, followed by overnight stirring resulting in a viscous solution. After being stirred for about 3 hours, the solution is heated to reflux at about 200° C. for about 15 hours. During the polymerization process, the water generated from the imidization is allowed to distill from the reaction mixture together with about 1-2 mL of xylene. After being allowed to cool to ambient temperature, the solution is diluted with NMP and then slowly added to a vigorously stirred solution of 95% ethanol. The precipitated polymer is collected via filtration, washed with ethanol, and dried under reduced pressure at 150° C. Before coating, a substrate (e.g., Pt electrode) is cleaned and optionally polished with aqueous alumina slurry down to about 0.05 µm. Then about 20 µL of polymer solution prepared by dissolving about 70 mg of polyimide in about 2 mL of NMP is dropped onto the surface of the Pt electrode and allowed to dry at room temperature for about 3 days.

Self Assembly Techniques

A self-assembly process can be employed to build up ultrathin multilayer films comprising consecutively alternative anionic and cationic polyelectrolytes on a charged surface. See, e.g., Decher et al., Thin Solid Films, 210-211 (1992) 831-835. Ionic attraction between opposite charges is the driving force for the multilayer buildup. In contrast to chemisorption techniques that require a reaction yield of about 100% in order to maintain surface functional density in each layer, no covalent bonds need to be formed with a self-assembly process. Additionally, an advantage over the classic Langmuir-Blodgett technique is that a solution process is independent of the substrate size and topology. Exemplary polyelectrolytes for use in such a process include, but are not limited to, polystyrenesulfonate sodium salt, polyvinylsulfate potassium salt, poly-4-vinylbenzyl-(N, N-diethyl-N-methyl-)-ammonium iodide, and poly(allylamine hydrochloride). The buildup of multilayer films can be conducted as follows. A solid substrate with a positively charged planar surface is immersed in the solution containing the anionic polyelectrolyte and a monolayer of the polyanion is adsorbed. Since the adsorption is carried out at relatively high concentrations of polyelectrolyte, a number of ionic groups remain exposed to the interface with the solution and thus the surface charge is reversed. After rinsing in pure water the substrate is immersed in the solution containing the cationic polyelectrolyte. Again a monolayer is adsorbed but now the original surface charge is restored. By repeating both steps in a cyclic fashion, alternating multilayer assemblies of both polymers are obtained. This process of multilayer formation is based on the attraction of opposite charges, and thus requires a minimum of two oppositely charged molecules. Consequently, one is able to incorporate more than two molecules into the multilayer, simply by immersing the substrate in as many solutions of polyeletrolytes as desired, as long as the charge is reversed from layer to layer. Even aperiodic multilayer assemblies can easily be prepared. In this respect, the technique is more versatile than the Langmuir-Blodgett technique which is rather limited to periodically alternating layer systems. Another advantage is that the immersion procedure does not pose principal restrictions as to the size of the substrate or to the automation in a continuous process.

Specific examples of the preparation of such films are as follows. Polystyrenesulfonate (sodium salt, Mr=100,000) and polyvinylsulfate (potassium salt, Mr=245,000) and poly (allylamine hydrochloride), Mw=50,000-65,000) are obtained from commercial sources and employed without further purification. Poly-4-vinylbenzyl-(N,N-diethyl-N-methyl-)-ammonium iodide can be synthesized, as described in Decher et al., Ber. Bunsenges. Phys. Chem., 95 (1992) 1430. Alternating multilayer assemblies of all materials can be characterized by UV/vis spectroscopy and small angle X-ray scattering (SAXS) using techniques known in the art. Direct-light microscopy and SAXS measurements can be performed with multilayer assemblies on suitable substrates. The multilayer films can be deposited on, e.g., atop a platinum electrode or other metal electrode, or a suitable intervening layer atop an electrode. For the adsorption of the first layer, an aqueous acidic solution of polystyrenesulfonate or polyvinylsulfate can be used. Afterwards the substrate is rinsed with water. After the adsorption of the first layer, the substrates can be stored for some weeks without noticeable deterioration of the surface. Thereafter, the cationic polyelectrolyte polyallylamine is adsorbed from aqueous solution. In the case of the non-quarternized polyallylamine, the polycation is adsorbed from an acidic solution. All following layers (odd layer numbers) of the anionic polyelectrolytes are adsorbed from aqueous solution. In the case of samples containing polyallylamine as the previously adsorbed layer, polystyrenesulfonate layers can be adsorbed from an acidic solution. An adsorption time of about 20 minutes at ambient temperature can be employed, however, in certain embodiments longer or shorter adsorption times may be acceptable. A range of polymer concentrations (e.g., 20 to 30 mg per about 10 ml water) can provide acceptable results.

Multilayer molecular films of polyelectrolyte:calixarene and polyelectrolyte:cyclodextrin hosts can be fabricated by alternating adsorption of charged species in aqueous solutions onto a suitable substrate. See, e.g., X. Yang, Sensors and Actuators B 45 (1997) 87-92. Such a layer-by-layer molecular deposition approach can be used to integrate molecular recognition reagents into polymer films. The deposition process is highly reproducible and the resulting films are uniform and stable. Replacing polyanions, highly negatively charged molecular species can be used for film fabrication. These molecular reagents are capable of binding organic species and can be deposited as functional components into thin films. This approach incorporates polymer and molecular elements into the film and thus results in films with polymer's physical properties and molecular film's selectivity. Films can be prepared as follows. The substrate (e.g., Pt electrode) can be first treated with aminopropyltrimethoxysilane in chloroform, followed with deposition of PSS and then PDDA polyelectrolytes by dipping into the aqueous solutions of the polyelectrolytes, respectively. After this, alternating depositions of negatively charged molecular host species (e.g., calix[6]arene or p-t-butylcalix[4]arene) and PDDA can be carried out until the desired number of bilayers is reached. Between each deposition, the substrate is thoroughly rinsed with deionized water. The polyelectrolyte and molecular ion assembly can be monitored by UV-vis absorption spectroscopy and mass loading can be measured with surface acoustic wave (SAW) devices.

In some embodiments, the interference domain is formed from one or more cellulosic derivatives. In general, cellulosic derivatives can include polymers such as cellulose acetate, cellulose acetate butyrate, 2-hydroxyethyl cellulose, cellulose acetate phthalate, cellulose acetate propionate, cellulose acetate trimellitate, or blends and combinations thereof.

In some alternative embodiments, other polymer types that can be utilized as a base material for the interference domain include polyurethanes and/or polymers having controlled pore size. In one such alternative embodiment, the interference domain includes a thin, hydrophobic membrane that is non-swellable and restricts diffusion of low molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in U.S.

Pat. No. 7,074,307, U.S. Patent Publication No. US-2005-0176136-A1, U.S. Pat. No. 7,081,195, and U.S. Patent Publication No. US-2005-0143635-A1, each of which is incorporated by reference herein in its entirety.

It is contemplated that in some embodiments, the thickness of the interference domain can be from about 0.01 µm or less to about 20 µm or more. In some of these embodiments, the thickness of the interference domain can be from about 0.01, about 0.05, about 0.1, about 0.15, about 0.2, about 0.25, about 0.3, about 0.35, about 0.4, about 0.45, about 0.5, about 1, about 1.5, about 2, about 2.5, about 3, or about 3.5 µm and about 4, about 5, about 6, about 7, about 8, about 9, about 10, about 11, about 12, about 13, about 14, about 15, about 16, about 17, about 18, about 19, or about 19.5 µm. In some of these embodiments, the thickness of the interference domain can be from about 0.2, about 0.4, about 0.5, or about 0.6, µm to about 0.8, about 0.9, about 1, about 1.5, about 2, about 3, or about 4 µm.

In general, the membrane systems described herein can be formed or deposited on the exposed electroactive surfaces (e.g., one or more of the working and reference electrodes) using known thin film techniques (for example, casting, spray coating, drawing down, electro-depositing, dip coating, and the like); however, casting or other known application techniques can also be utilized. In some embodiments, the interference domain can be deposited by spray or dip coating. In one exemplary embodiment, the interference domain is formed by dip coating the sensor into an interference domain solution using an insertion rate of from about 0.5 inch/min to about 60 inches/min, and sometimes about 1 inch/min; a dwell time of from about 0.01 minutes to about 2 minutes, and sometimes about 1 minute; and a withdrawal rate of from about 0.5 inch/minute to about 60 inches/minute, and sometimes about 1 inch/minute; and curing (drying) the domain from about 1 minute to about 14 hours, and sometimes from about 3 minutes to about 15 minutes (and can be accomplished at room temperature or under vacuum, e.g., about 20 to about 30 mmHg). In one exemplary embodiment including a cellulose acetate butyrate interference domain, a 3-minute cure (i.e., dry) time is used between each layer applied. In another exemplary embodiment employing a cellulose acetate interference domain, a 15 minute cure time is used between each layer applied.

In some embodiments, the dip process can be repeated at least one time and up to 10 times or more. In other embodiments, only one dip is preferred. The preferred number of repeated dip processes can depend upon the cellulosic derivative(s) used, their concentration, conditions during deposition (e.g., dipping) and the desired thickness (e.g., sufficient thickness to provide functional blocking of certain interferents), and the like. In one embodiment, an interference domain is formed from three layers of cellulose acetate butyrate. In another embodiment, an interference domain is formed from 10 layers of cellulose acetate. In yet another embodiment, an interference domain is formed from 1 layer of a blend of cellulose acetate and cellulose acetate butyrate. In alternative embodiments, the interference domain can be formed using any known method and combination of cellulose acetate and cellulose acetate butyrate, as will be appreciated by one skilled in the art.

Curing a polymer layer deposited by solvent evaporation is sometimes helpful to prevent sensor drift by allowing the polymer chains and hydrophilic and hydrophobic components to rearrange into a low energy state that remains stable over time. The final polymer microstructure determines the analyte and oxygen permeability characteristics and ultimate sensor performance. Thus, an analyte sensor can be cured so that all rearrangement occurs before the sensor is calibrated and the sensor sensitivity does not change before or during use. The speed, type of rearrangement, and polymer layer microstructure can be controlled and directed through exposure to different conditions, typically humidity, temperature, and time. Aqueous solvent cure can be used to accelerate polymer rearrangement in polymer layers with mixed hydrophilic and hydrophobic domains to achieve a sensor with desirable stability, analyte permeability, and oxygen performance. Benefits over the current humidity and temperature curing process include the reduction in drift, a reduction in cure time, and less sensor-to-sensor variability.

Aqueous solvents for curing may contain water miscible solvents, salts, stabilizers, plasticizers, or other components to modify rearrangement. Solvent temperature can be in the range of 0° C.-100° C., more preferably 20° C.-70° C. Miscible solvents can be alcohols or polar organic solvents such as ethanol or THF. Salts may be of any variety, for example PBS, and can include modifying components such as biocides and interferent species. Process may involve multiple soak steps in different aqueous formulations at different temperatures to selectively induce particular sequential rearrangements or extract specific compounds.

Electrode Domain

It is contemplated that in some embodiments, such as the embodiment illustrated in FIG. 2A, an optional electrode domain 42, also referred to as the electrode layer, can be provided, in addition to the biointerface domain and the enzyme domain; however, in other embodiments, the functionality of the electrode domain can be incorporated into the biointerface domain so as to provide a unitary domain that includes the functionality of the biointerface domain, diffusion resistance domain, enzyme domain, and electrode domain.

In some embodiments, the electrode domain is located most proximal to the electrochemically reactive surfaces. To facilitate electrochemical reaction, the electrode domain can include a semipermeable coating that maintains hydrophilicity at the electrochemically reactive surfaces of the sensor interface. The electrode domain can enhance the stability of an adjacent domain by protecting and supporting the material that makes up the adjacent domain. The electrode domain can also assist in stabilizing the operation of the device by overcoming electrode start-up problems and drifting problems caused by inadequate electrolyte. The buffered electrolyte solution contained in the electrode domain can also protect against pH-mediated damage that can result from the formation of a large pH gradient between the substantially hydrophobic interference domain and the electrodes due to the electrochemical activity of the electrodes.

In some embodiments, the electrode domain includes a flexible, water-swellable, substantially solid gel-like film (e.g., a hydrogel) having a "dry film" thickness of from about 0.05 µm to about 100 µm, and sometimes from about 0.05, about 0.1, about 0.15, about 0.2, about 0.25, about 0.3, about 0.35, about 0.4, about 0.45, about 0.5, or about 1 µm to about 1.5, about 2, about 2.5, about 3, about 3.5, about 4, about 4.5, about 5, about 6, about 6.5, about 7, about 7.5, about 8, about 8.5, about 9, about 9.5, about 10, about 10.5, about 11, about 11.5, about 12, about 13, about 14, about 15, about 16, about 17, about 18, about 19, about 19.5, about 20, about 30, about 40, about 50, about 60, about 70, about 80, about 90, or about 100 µm. In some embodiments, the thickness of the electrode domain can be from about 2, about 2.5, or about 3 µm to about 3.5, about 4, about 4.5, or about 5 µm in the case of a transcutaneously implanted sensor, or from about 6, about 7, or about 8 µm to about 9, about 10, about 11, or about 12 µm in the case of a wholly implanted sensor. The term "dry film thickness" as used herein is a broad term, and is to be given its ordinary and customary meaning to a person of ordinary skill in the art (and is not to be limited to a special or customized meaning), and refers without limitation to the thickness of a cured film cast from a coating formulation onto the surface of the membrane by standard coating techniques. The coating formulation can comprise a premix of film-forming polymers and a cross-linking agent and can be curable upon the application of moderate heat.

In certain embodiments, the electrode domain can be formed of a curable mixture of a urethane polymer and a hydrophilic polymer. In some of these embodiments, coatings are formed of a polyurethane polymer having anionic carboxylate functional groups and non-ionic hydrophilic polyether segments, which are crosslinked in the presence of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND™; Mobay Corporation). These polymers are supplied in dispersion grades having a polycarbonate-polyurethane backbone containing carboxylate groups identified as XW-121 and XW-123; and a polyester-polyurethane backbone containing carboxylate groups, identified as XW-110-2. In some embodiments, BAYBOND™123, an aqueous anionic dispersion of an aliphate polycarbonate urethane polymer sold as a 35 wt. % solution in water and co-solvent N-methyl-2-pyrrolidone, can be used.

In some embodiments, the electrode domain is formed from a hydrophilic polymer that renders the electrode domain equally or more hydrophilic than an overlying domain (e.g., interference domain, enzyme domain). Such hydrophilic polymers can include, a polyamide, a polylactone, a polyimide, a polylactam, a functionalized polyamide, a functionalized polylactone, a functionalized polyimide, a functionalized polylactam or combinations thereof, for example.

In some embodiments, the electrode domain is formed primarily from a hydrophilic polymer, and in some of these embodiments, the electrode domain is formed substantially from PVP. PVP is a hydrophilic water-soluble polymer and is available commercially in a range of viscosity grades and average molecular weights ranging from about 18,000 to about 500,000, under the PVP K™ homopolymer series by BASF Wyandotte and by GAF Corporation. In certain embodiments, a PVP homopolymer having an average molecular weight of about 360,000 identified as PVP-K90 (BASF Wyandotte) can be used to form the electrode domain. Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

In certain embodiments, the electrode domain is formed entirely from a hydrophilic polymer. Useful hydrophilic polymers contemplated include, but are not limited to, poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, poly-acrylic acid, polyethylene oxide, poly-2-ethyl-oxazoline, copolymers thereof and mixtures thereof. A blend of two or more hydrophilic polymers can be preferred in some embodiments.

It is contemplated that in certain embodiments, the hydrophilic polymer used may not be crosslinked, but in other embodiments, crosslinking can be used and achieved by any of a variety of methods, for example, by adding a crosslinking agent. In some embodiments, a polyurethane polymer can be crosslinked in the presence of PVP by preparing a premix of the polymers and adding a cross-linking agent just prior to the production of the membrane. Suitable cross-linking agents contemplated include, but are not limited to, carbodiimides (e.g., 1-ethyl-3-(3-dimethylaminopropyl) carbodiimide hydrochloride, and UCARLNK™ XL-25 (Union Carbide)), epoxides and melamine/formaldehyde resins. Alternatively, it is also contemplated that crosslinking can be achieved by irradiation at a wavelength sufficient to promote crosslinking between the hydrophilic polymer molecules, which is believed to create a more tortuous diffusion path through the domain.

The flexibility and hardness of the coating can be varied as desired by varying the dry weight solids of the components in the coating formulation. The term "dry weight solids" as used herein is a broad term, and is to be given its ordinary and customary meaning to a person of ordinary skill in the art (and is not to be limited to a special or customized meaning), and refers without limitation to the dry weight percent based on the total coating composition after the time the crosslinker is included. In one embodiment, a coating formulation can contain from about 6 to about 20 dry wt. %, preferably about 8 dry wt. %, PVP; about 3 to about 10 dry wt. %, sometimes about 5 dry wt. % cross-linking agent; and from about 70 to about 91 wt. %, sometimes about 87 wt. % of a polyurethane polymer, such as a polycarbonate-polyurethane polymer, for example. The reaction product of such a coating formulation is referred to herein as a water-swellable cross-linked matrix of polyurethane and PVP.

In some embodiments, underlying the electrode domain is an electrolyte phase that when hydrated is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrode domain. It is contemplated that certain embodiments can use any suitable electrolyte solution, including standard, commercially available solutions. Generally, the electrolyte phase can have the same osmotic pressure or a lower osmotic pressure than the sample being analyzed. In preferred embodiments, the electrolyte phase comprises normal saline.

Bioactive Agents

It is contemplated that any of a variety of bioactive (therapeutic) agents can be used with the analyte sensor systems described herein, such as the analyte sensor system shown in FIG. 1. In specific embodiments, the bioactive agents can be in the biointerface layer of the disclosed devices. In some embodiments, the bioactive agent is an anticoagulant. The term "anticoagulant" as used herein is a broad term, and is to be given its ordinary and customary meaning to a person of ordinary skill in the art (and is not to be limited to a special or customized meaning), and refers without limitation to a substance the prevents coagulation (e.g., minimizes, reduces, or stops clotting of blood). In these embodiments, the anticoagulant included in the analyte sensor system can prevent coagulation within or on the sensor. Suitable anticoagulants for incorporation into the sensor system include, but are not limited to, vitamin K antagonists (e.g., Acenocoumarol, Clorindione, Dicumarol (Dicoumarol), Diphenadione, Ethyl biscoumacetate, Phenprocoumon, Phenindione, Tioclomarol, or Warfarin), heparin group anticoagulants (e.g. Platelet aggregation inhibitors: Antithrombin III, Bemiparin, Dalteparin, Danaparoid, Enoxaparin, Heparin, Nadroparin, Parnaparin, Reviparin, Sulodexide, Tinzaparin), other platelet aggregation inhibitors (e.g. Abciximab, Acetylsalicylic acid (Aspirin), Aloxiprin, Beraprost, Ditazole, Carbasalate calcium, Cloricromen, Clopidogrel, Dipyridamole, Epoprostenol, Eptifibatide, Indobufen, Iloprost, Picotamide, Ticlopidine, Tirofiban, Treprostinil, Triflusal), enzymes (e.g., Alteplase, Ancrod, Anistreplase, Brinase, Drotrecogin alfa, Fibrinolysin, Protein C, Reteplase, Saruplase, Streptokinase, Tenecteplase, Urokinase), direct thrombin inhibitors (e.g., Argatroban, Bivalirudin, Desirudin, Lepirudin, Melagatran, Ximelagatran, other antithrombotics (e.g., Dabigatran, Defibrotide, Dermatan sulfate, Fondaparinux, Rivaroxaban), and the like.

In one embodiment, heparin is incorporated into the analyte sensor system, for example by dipping or spraying. While not wishing to be bound by theory, it is believed that heparin coated on the catheter or sensor can prevent aggregation and clotting of blood on the analyte sensor system, thereby preventing thromboembolization (e.g., prevention of blood flow by the thrombus or clot) or subsequent complications. In some embodiments, heparin is admixed with one or more zwitterionic compounds or derivatives thereof, such as hydrolyzable cationic esters thereof (as described above), prior to dipping or spraying, thus providing the sensor system with a mixed coating of heparin and one or more zwitterionic compounds or derivatives thereof.

In some embodiments, an antimicrobial is coated on the catheter (inner or outer diameter) or sensor. In some embodiments, an antimicrobial agent can be incorporated into the analyte sensor system. The antimicrobial agents contemplated can include, but are not limited to, antibiotics, antiseptics, disinfectants and synthetic moieties, and combinations thereof, and other agents that are soluble in organic solvents such as alcohols, ketones, ethers, aldehydes, acetonitrile, acetic acid, methylene chloride and chloroform. The amount of each antimicrobial agent used to impregnate the medical device varies to some extent, but is at least of an effective concentration to inhibit the growth of bacterial and fungal organisms, such as staphylococci, gram-positive bacteria, gram-negative bacilli and Candida.

In some embodiments, an antibiotic can be incorporated into the analyte sensor system. Classes of antibiotics that can be used include tetracyclines (e.g., minocycline), rifamycins (e.g., rifampin), macrolides (e.g., erythromycin), penicillins (e.g., nafeillin), cephalosporins (e.g., cefazolin), other β-lactam antibiotics (e.g., imipenem, aztreonam), aminoglycosides (e.g., gentamicin), chloramphenicol, sulfonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole), and β-lactam inhibitors (e.g., sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

In some embodiments, an antiseptic or disinfectant can be incorporated into the analyte sensor system. Examples of antiseptics and disinfectants are hexachlorophene, cationic bisiguanides (e.g., chlorhexidine, cyclohexidine) iodine and iodophores (e.g., povidoneiodine), para-chloro-meta-xylenol, triclosan, furan medical preparations (e.g., nitrofurantoin, nitrofurazone), methenamine, aldehydes (glutaraldehyde, formaldehyde) and alcohols. Other examples of antiseptics and disinfectants will readily suggest themselves to those of ordinary skill in the art.

In some embodiments, an anti-barrier cell agent can be incorporated into the analyte sensor system. Anti-barrier cell agents can include compounds exhibiting effects on macrophages and foreign body giant cells (FBGCs). It is believed that anti-barrier cell agents prevent closure of the barrier to solute transport presented by macrophages and FBGCs at the device-tissue interface during FBC maturation. Anti-barrier cell agents can provide anti-inflammatory or immunosuppressive mechanisms that affect the wound healing process, for example, healing of the wound created by the incision into which an implantable device is inserted. Cyclosporine, which stimulates very high levels of neovascularization around biomaterials, can be incorporated into a biointerface membrane of a preferred embodiment (see U.S. Pat. No. 5,569,462 to Martinson et al.). Alternatively, Dexamethasone, which abates the intensity of the FBC response at the tissue-device interface, can be incorporated into a biointerface membrane of a preferred embodiment. Alternatively, Rapamycin, which is a potent specific inhibitor of some macrophage inflammatory functions, can be incorporated into a biointerface membrane of a preferred embodiment.

In some embodiments, an anti-inflammatory agent can be incorporated into the analyte sensor system to reduce acute or chronic inflammation adjacent to the implant or to decrease the formation of a FBC capsule to reduce or prevent barrier cell layer formation, for example. Suitable anti-inflammatory agents include but are not limited to, for example, nonsteroidal anti-inflammatory drugs (NSAIDS) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

In some embodiments, an immunosuppressive or immunomodulatory agent can be incorporated into the analyte sensor system in order to interfere directly with several key mechanisms necessary for involvement of different cellular elements in the inflammatory response. Suitable immunosuppressive and immunomodulatory agents include, but are not limited to, anti-proliferative, cell-cycle inhibitors, (for example, paclitaxel, cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARy ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

In some embodiments, an anti-infective agent can be incorporated into the analyte sensor system. In general, anti-infective agents are substances capable of acting against infection by inhibiting the spread of an infectious agent or by killing the infectious agent outright, which can serve to reduce an immuno-response without an inflammatory response at the implant site, for example. Anti-infective agents include, but are not limited to, anthelmintics (e.g., mebendazole), antibiotics (e.g., aminoclycosides, gentamicin, neomycin, tobramycin), antifungal antibiotics (e.g., amphotericin b, fluconazole, griseofulvin, itraconazole, ketoconazole, nystatin, micatin, tolnaftate), cephalosporins (e.g., cefaclor, cefazolin, cefotaxime, ceftazidime, ceftriaxone, cefuroxime, cephalexin), β-lactam antibiotics (e.g., cefotetan, meropenem), chloramphenicol, macrolides (e.g., azithromycin, clarithromycin, erythromycin), penicillins (e.g., penicillin G sodium salt, amoxicillin, ampicillin, dicloxacillin, nafcillin, piperacillin, ticarcillin), tetracyclines (e.g., doxycycline, minocycline, tetracycline), bacitracin, clindamycin, colistimethate sodium, polymyxin b sulfate, vancomycin, antivirals (e.g., acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine), quinolones (e.g., ciprofloxacin, levofloxacin); sulfonamides (e.g., sulfadiazine, sulfisoxazole), sulfones (e.g., dapsone), furazolidone, metronidazole, pentamidine, sulfanilamidum crystallinum, gatifloxacin, and sulfamethoxazole/trimethoprim.

In some embodiments, a vascularization agent can be incorporated into the analyte sensor system. Vascularization agents generally can include substances with direct or indirect angiogenic properties. In some cases, vascularization agents can additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however, while not wishing to be bound by theory, it is believed that some barrier-cell effects can result indirectly from the effects of vascularization agents.

Vascularization agents can provide mechanisms that promote neovascularization and accelerate wound healing around the membrane or minimize periods of ischemia by increasing vascularization close to the tissue-device interface. Sphingosine-1-Phosphate (S1P), a phospholipid possessing potent angiogenic activity, can be incorporated into the biointerface membrane. Monobutyrin, a vasodilator and angiogenic lipid product of adipocytes, can also be incorporated into the biointerface membrane. In another embodiment, an anti-sense molecule (for example, thrombospondin-2 anti-sense), which can increase vascularization, is incorporated into a biointerface membrane.

Vascularization agents can provide mechanisms that promote inflammation, which is believed to cause accelerated neovascularization and wound healing in vivo. In one embodiment, a xenogenic carrier, for example, bovine collagen, which by its foreign nature invokes an immune response, stimulates neovascularization, and is incorporated into a biointerface membrane of some embodiments. In another embodiment, Lipopolysaccharide, an immunostimulant, can be incorporated into a biointerface membrane. In another embodiment, a protein, for example, a bone morphogenetic protein (BMP), which modulates bone healing in tissue, can be incorporated into the biointerface membrane.

In some embodiments, an angiogenic agent can be incorporated into the analyte sensor system. Angiogenic agents are substances capable of stimulating neovascularization, which can accelerate and sustain the development of a vascularized tissue bed at the tissue-device interface, for example. Angiogenic agents include, but are not limited to, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-β), Transforming Growth Factor Alpha (TGFα), Hepatocyte Growth Factor, Tumor Necrosis Factor-Alpha (TNFα), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (e.g., decorin or vimentin), glenipin, hydrogen peroxide, nicotine, and Growth Hormone.

In some embodiments, a pro-inflammatory agent can be incorporated into the analyte sensor system. Pro-inflammatory agents are generally substances capable of stimulating an immune response in host tissue, which can accelerate or sustain formation of a mature vascularized tissue bed. For example, pro-inflammatory agents are generally irritants or other substances that induce chronic inflammation and chronic granular response at the wound-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, *S. aureus* peptidoglycan, and proteins.

These bioactive agents can be used alone or in combination. The bioactive agents can be dispersed throughout the material of the sensor, for example, incorporated into at least a portion of the membrane system, or incorporated into the device (e.g., housing) and adapted to diffuse through the membrane.

There are a variety of systems and methods by which a bioactive agent can be incorporated into the sensor membrane. In some embodiments, the bioactive agent can be incorporated at the time of manufacture of the membrane system. For example, the bioactive agent can be blended prior to curing the membrane system, or subsequent to membrane system manufacture, for example, by coating, imbibing, solvent-casting, or sorption of the bioactive agent into the membrane system. Although in some embodiments the bioactive agent is incorporated into the membrane system, in other embodiments the bioactive agent can be administered concurrently with, prior to, or after insertion of the device in vivo, for example, by oral administration, or locally, by subcutaneous injection near the implantation site. A combination of bioactive agent incorporated in the membrane system and bioactive agent administration locally or systemically can be preferred in certain embodiments.

In general, a bioactive agent can be incorporated into the membrane system, or incorporated into the device and adapted to diffuse therefrom, in order to modify the in vivo response of the host to the membrane. In some embodiments, the bioactive agent can be incorporated only into a portion of the membrane system adjacent to the sensing region of the device, over the entire surface of the device except over the sensing region, or any combination thereof, which can be helpful in controlling different mechanisms or stages of in vivo response (e.g., thrombus formation). In some alternative embodiments however, the bioactive agent can be incorporated into the device proximal to the membrane system, such that the bioactive agent diffuses through the membrane system to the host circulatory system.

The bioactive agent can include a carrier matrix, wherein the matrix includes one or more of collagen, a particulate matrix, a resorbable or non-resorbable matrix, a controlled-release matrix, or a gel. In some embodiments, the carrier matrix includes a reservoir, wherein a bioactive agent is encapsulated within a microcapsule. The carrier matrix can include a system in which a bioactive agent is physically entrapped within a polymer network. In some embodiments, the bioactive agent is cross-linked with the membrane system, while in others the bioactive agent is sorbed into the membrane system, for example, by adsorption, absorption, or imbibing. The bioactive agent can be deposited in or on the membrane system, for example, by coating, filling, or solvent casting. In certain embodiments, ionic and nonionic surfactants, detergents, micelles, emulsifiers, demulsifiers, stabilizers, aqueous and oleaginous carriers, solvents, preservatives, antioxidants, or buffering agents are used to incorporate the bioactive agent into the membrane system.

In some embodiments, the surface of the membrane system comprises a tie layer found on the outermost surface of the sensor membrane to which the bioactive agent reversibly binds. In some embodiments, this tie layer comprises one or more zwitterionic compounds, or precursors or derivatives thereof, which are bound to surface-active groups of the polymer comprising the outermost domain of the membrane system. In some embodiments, the zwitterionic compounds or precursors or derivatives thereof comprise one or more zwitterionic betaines, as described above. In some embodiments, the zwitterionic compounds or precursors or derivatives thereof comprise hydrolyzable cationic esters of a zwitterionic compound, as described above. In preferred embodiments, the tie layer comprises one or more hydrolyzable cationic betaine esters, such as hydrolyzable cationic pCB esters.

The bioactive agent also can be incorporated into a polymer using techniques such as described above, and the polymer can be used to form the membrane system, coatings on the membrane system, portions of the membrane system, or any portion of the sensor system.

The membrane system can be manufactured using techniques known in the art. The bioactive agent can be sorbed into the membrane system, for example, by soaking the membrane system for a length of time (for example, from about an hour or less to about a week, or more preferably from about 4, about 8, about 12, about 16, or about 20 hours to about 1, about 2, about 3, about 4, about 5, or about 7 days).

The bioactive agent can be blended into uncured polymer prior to forming the membrane system. The membrane system is then cured and the bioactive agent thereby crosslinked or encapsulated within the polymer that forms the membrane system.

In yet another embodiment, microspheres are used to encapsulate the bioactive agent. The microspheres can be formed of biodegradable polymers, most preferably synthetic polymers or natural polymers such as proteins and polysaccharides. As used herein, the term polymer is used to refer to both to synthetic polymers and proteins. U.S. Pat. No. 6,281,015 discloses some systems and methods that can be used in conjunction with the preferred embodiments. In general, bioactive agents can be incorporated in (1) the polymer matrix forming the microspheres, (2) microparticle(s) surrounded by the polymer which forms the microspheres, (3) a polymer core within a protein microsphere, (4) a polymer coating around a polymer microsphere, (5) mixed in with microspheres aggregated into a larger form, or (6) a combination thereof. Bioactive agents can be incorporated as particulates or by co-dissolving the factors with the polymer. Stabilizers can be incorporated by addition of the stabilizers to the factor solution prior to formation of the microspheres.

The bioactive agent can be incorporated into a hydrogel and coated or otherwise deposited in or on the membrane system. Some hydrogels suitable for use in the preferred embodiments include cross-linked, hydrophilic, three-dimensional polymer networks that are highly permeable to the bioactive agent and are triggered to release the bioactive agent based on a stimulus.

The bioactive agent can be incorporated into the membrane system by solvent casting, wherein a solution including dissolved bioactive agent is disposed on the surface of the membrane system, after which the solvent is removed to form a coating on the membrane surface.

The bioactive agent can be compounded into a plug of material, which is placed within the device, such as is described in U.S. Pat. Nos. 4,506,680 and 5,282,844, which are incorporated by reference herein in their entireties. In some embodiments, it is preferred to dispose the plug beneath a membrane system; in this way, the bioactive agent is controlled by diffusion through the membrane, which provides a mechanism for sustained-release of the bioactive agent in the host.

Release of Bioactive Agents

Numerous variables can affect the pharmacokinetics of bioactive agent release. The bioactive agents of the disclosed embodiments can be optimized for short- or long-term release. In some embodiments, the bioactive agents of the disclosed embodiments are designed to aid or overcome factors associated with short-term effects (e.g., acute inflammation or thrombosis) of sensor insertion. In some embodiments, the bioactive agents are designed to aid or overcome factors associated with long-term effects, for example, chronic inflammation or build-up of fibrotic tissue or plaque material. In some embodiments, the bioactive agents combine short- and long-term release to exploit the benefits of both.

As used herein, "controlled," "sustained," or "extended" release of the factors can be continuous or discontinuous, linear or non-linear. This can be accomplished using one or more types of polymer compositions, drug loadings, selections of excipients or degradation enhancers, or other modifications, administered alone, in combination or sequentially to produce the desired effect.

Short-term release of the bioactive agent in the disclosed embodiments generally refers to release over a period of from about a few minutes or hours to about 2, about 3, about 4, about 5, about 6, or about 7 days or more.

Loading of Bioactive Agents

The amount of loading of the bioactive agent into the membrane system can depend upon several factors. For example, the bioactive agent dosage and duration can vary with the intended use of the membrane system, for example, the intended length of use of the device and the like; differences among patients in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above.

In some embodiments, in which the bioactive agent is incorporated into the membrane system without a carrier matrix, the preferred level of loading of the bioactive agent into the membrane system can vary depending upon the nature of the bioactive agent. The level of loading of the bioactive agent is preferably sufficiently high such that a biological effect (e.g., thrombosis prevention) is observed. Above this threshold, the bioactive agent can be loaded into the membrane system so as to imbibe up to 100% of the solid portions, cover all accessible surfaces of the membrane, or fill up to 100% of the accessible cavity space. Typically, the level of loading (based on the weight of bioactive agent(s), membrane system, and other substances present) is from about 1 ppm or less to about 1000 ppm or more, preferably from about 2, about 3, about 4, or about 5 ppm up to about 10, about 25, about 50, about 75, about 100, about 200, about 300, about 400, about 500, about 600, about 700, about 800, or about 900 ppm. In certain embodiments, the level of loading can be about 1 wt. % or less up to about 50 wt. % or more, preferably from about 2, about 3, about 4, about 5, about 6, about 7, about 8, about 9, about 10, about 15, or about 20 wt. % up to about 25, about 30, about 35, about 40, or about 45 wt. %.

When the bioactive agent is incorporated into the membrane system with a carrier matrix, such as a gel, the gel concentration can be optimized, for example, loaded with one or more test loadings of the bioactive agent. It is generally preferred that the gel contain from about 0.1 or less to about 50 wt. % or more of the bioactive agent(s), preferably from about 0.2, about 0.3, about 0.4, about 0.5, about 0.6, about 0.7, about 0.8, or about 0.9 wt. % to about 6, about 7, about 8, about 9, about 10, about 15, about 20, about 25, about 30, about 35, about 40, or about 45 wt. % or more bioactive agent(s), more preferably from about 1, about 2, or about 3 wt. % to about 4 or about 5 wt. % of the bioactive agent(s). Substances that are not bioactive can also be incorporated into the matrix.

Referring now to microencapsulated bioactive agents, the release of the agents from these polymeric systems generally occurs by two different mechanisms. The bioactive agent can be released by diffusion through aqueous filled channels generated in the dosage form by the dissolution of the agent or by voids created by the removal of the polymer solvent or a pore forming agent during the original micro-encapsulation. Alternatively, release can be enhanced due to the degradation of the encapsulating polymer. With time, the polymer erodes and generates increased porosity and microstructure within the device. This creates additional pathways for release of the bioactive agent.

In some embodiments, the sensor is designed to be bioinert, e.g., by the use of bioinert materials. Bioinert materials do not substantially cause any response from the host. As a result, cells can live adjacent to the material but do not form a bond with it. Bioinert materials include but are not limited to alumina, zirconia, titanium oxide or other bioinert materials generally used in the "catheter/catheterization" art. While not wishing to be bound by theory, it is believed that inclusion of a bioinert material in or on the sensor can reduce attachment of blood cells or proteins to the sensor, thrombosis or other host reactions to the sensor.

EXAMPLES

Example 1 Biointerface Polymers and Characterization

Various biointerface polymers were prepared using different amounts of hard segments, PEG, and sulfobetaines. The hard segments (HS) were polyurethanes or polyureas prepared from diisocyanates reacted with diol or diamine chain extenders of less than 12 carbon units. The particular formulations are shown in Table 1.

TABLE 1

| Name | PEG (wt. %) | Betaine (wt. %) | HS (wt. %) | Mn (Da) | PDI (Mw/Mn) |
|---|---|---|---|---|---|
| SBL-3 | 20 | 18 | 35 | 107,000 | 1.7 |
| SBL-10 | 35 | 40 | 25 | 127,000 | 1.6 |
| SBL-1 | 21 | 0 | 35 | 61,000 | 1.6 |
| SBL-9 | 27 | 34 | 31 | 77,400 | 1.7 |
| SBL-8 | 23 | 27 | 35 | 140,000 | 2.1 |
| RL-7* | 0 | 0 | 42 | 45,000 | 1.7 |

*Comparative.

Example 2 Characterization Analysis

Figure 5:
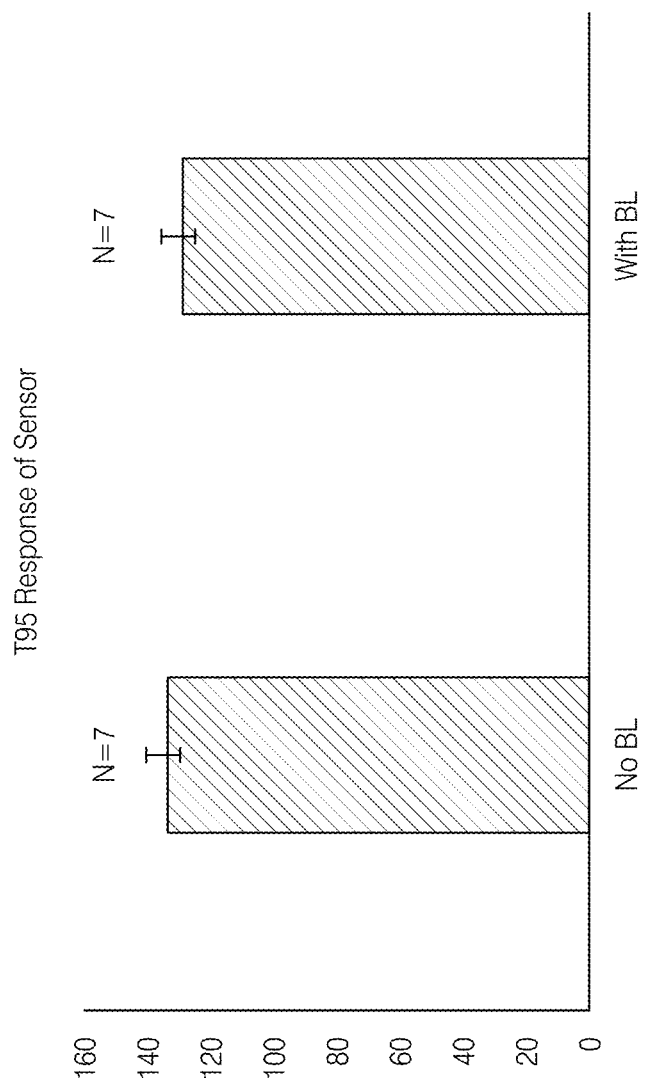
FIG. 5 is a graph showing the T95 response (in seconds) of a continuous sensor without a biointerface layer ("no BL") and one with a biointerface layer ("with BL"), as described herein. There is no significant difference in T95 response times between the sensors.

Sensors were built as described in the section entitled "sensor systems." The in vitro response time was tested and compared to a sensor without the biointerface layer. It was found that the sensor with the biointerface layer had the same T95 response time as the sensor without the biointerface layer, indicating that the biointerface layer did not slow the response times of a glucose sensor (FIG. 5)

Figure 6:
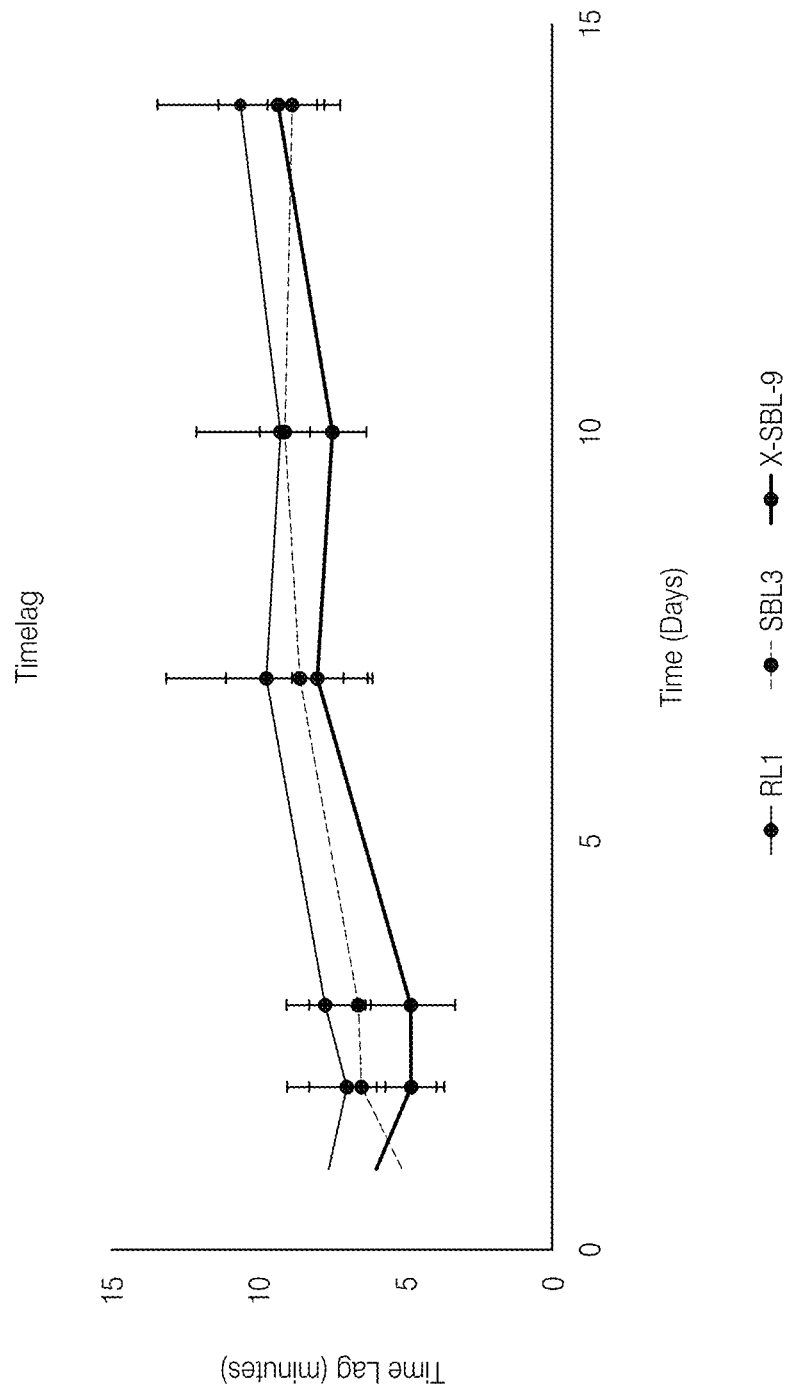
FIG. 6 is a graph showing the time lag from continuous glucose sensors without a biointerface layer ("RL") and with biointerface layer SBL-3 or X-SBL-9 in a pig model. Polymers SBL-3 is from Table 1. Polymer X-SBL-9 is from Table 1 but crosslinked.

The in vivo response time was also tested in pig over the course of 15 days. In particular continuous sensors with SBL-3 and crosslinked SBL-9 biointerface layers were compared to a sensor without a biointerface layers. It was likewise found that there was no difference in response times for the sensors with and without the biointerface layer (FIG. 6). This again showed that the biointerface domain did not affect the glucose sensor response time.

Figure 7:
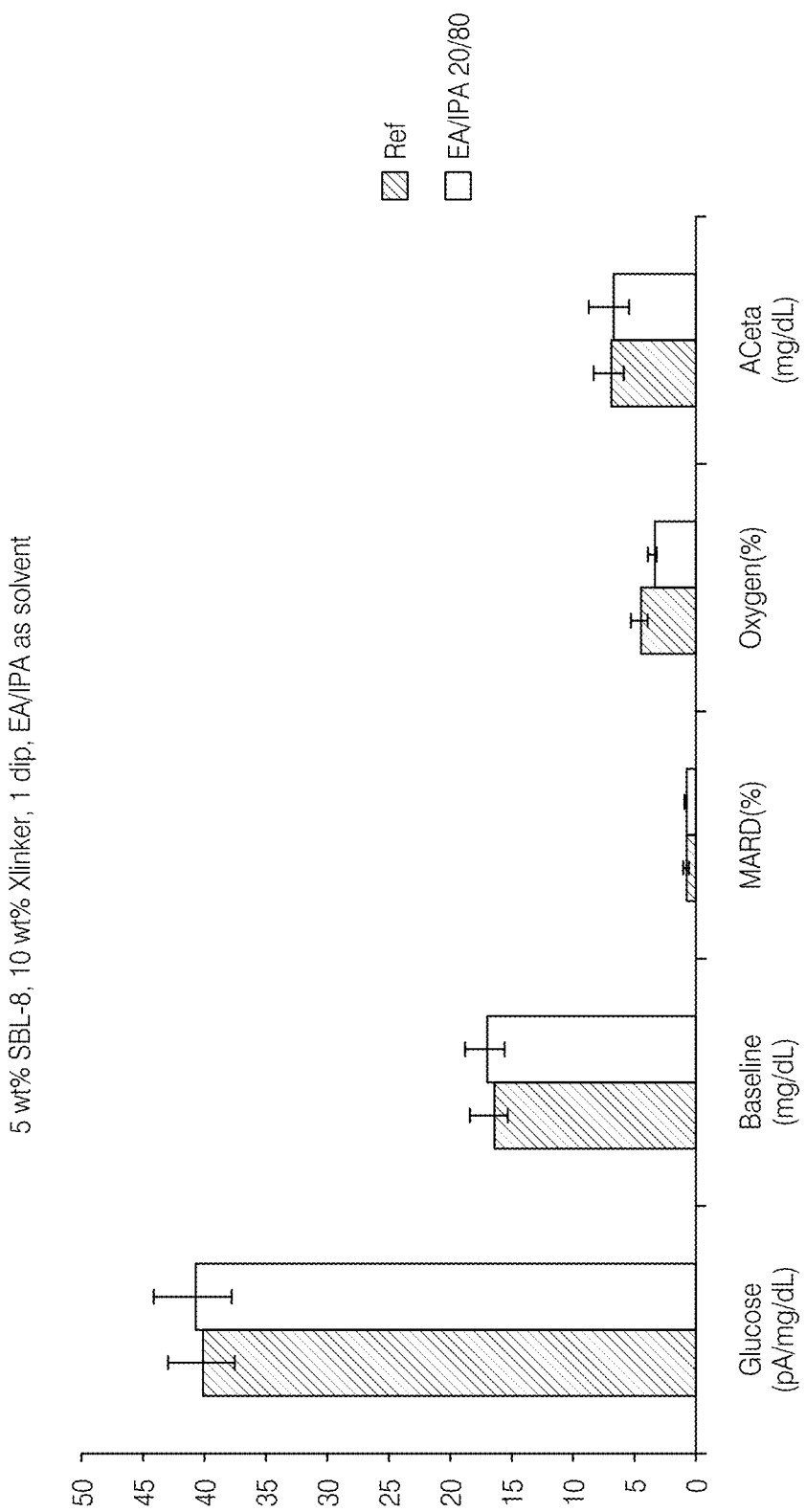
FIG. 7 is a graph showing the calibration check performance of continuous glucose sensors with and without a biointerface layer (SBL-8 with 10% crosslinking). The biointerface layer did not significantly affect the bench performance of the sensor.

The cal-check performance of sensors without a biointerface layer and sensors dip coated with 5 wt. % SBL-8 were compared. The results are shown in FIG. 7. In this cal-check test, the following characteristics were measured:

i. Glucose Slope (pA/mg/dL)—Ordinary least-squares linear regression analysis of the electrical response of the sensor when placed in buffer solutions of increasing glucose concentration. It is also referred to as glucose sensitivity.

ii. Baseline Equivalent (mg/dL)—mg/dL equivalent of the non-glucose related signal.

iii. MARD (%)—Mean Absolute Relative Difference, the measure of variation away from the ideal line.

iv. Low Oxygen Response—Defined as the percent change in electrical response under reduced oxygen conditions (i.e., at 0.25±0.05 mg $O_2$/L) compared with signal obtained under atmospheric conditions. It is also referred to as Oxygen Performance.

v. Acetaminophen Bias—the mg/dL equivalent signal from a 2 mg/dL concentration of acetaminophen. Also referred to as glucose equivalence.

Figure 8:
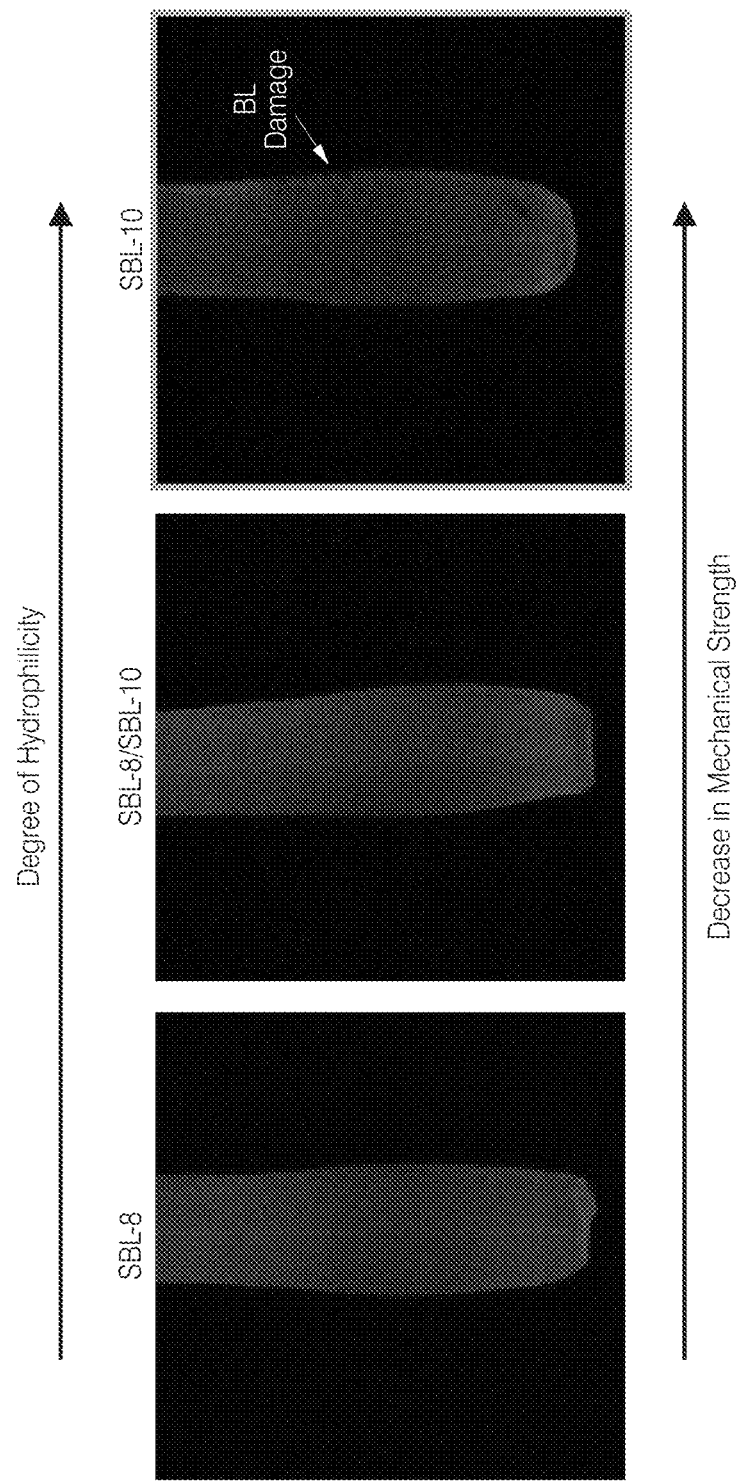
FIG. 8 is a group of photographs of sensors coated with three different biointerface layers. SBL-8 and SBL-10 are polymers from Table 1. SBL8/10 is a 50/50 wt. % blend of polymers SBL-8 and SBL-10. As the hydrophilicity of the biointerface layer increases (as referenced by the percentage of the polyethylene oxide in the polymer), the mechanical strength decreases. The decrease in mechanical strength is evident by the small dark areas, which indicate compromises in the layer.

The mechanical strength was also visually inspected by viewing sensors with BL-8, a blend of SBL-8 and SBL-10, and SBL-10. The BL-10 layer had various inclusions, which suggests that as the hydrophilicity of the layer increases, the mechanical strength decreases (FIG. 8). The hydrophilicity could also be adjusted by blending bionterface layers with different hydrophilicities (e.g., blending a polymer that is more hydrophilic with one that is less hydrophilic to arrive at a desired hydrophilicity and strength).

Figure 9:
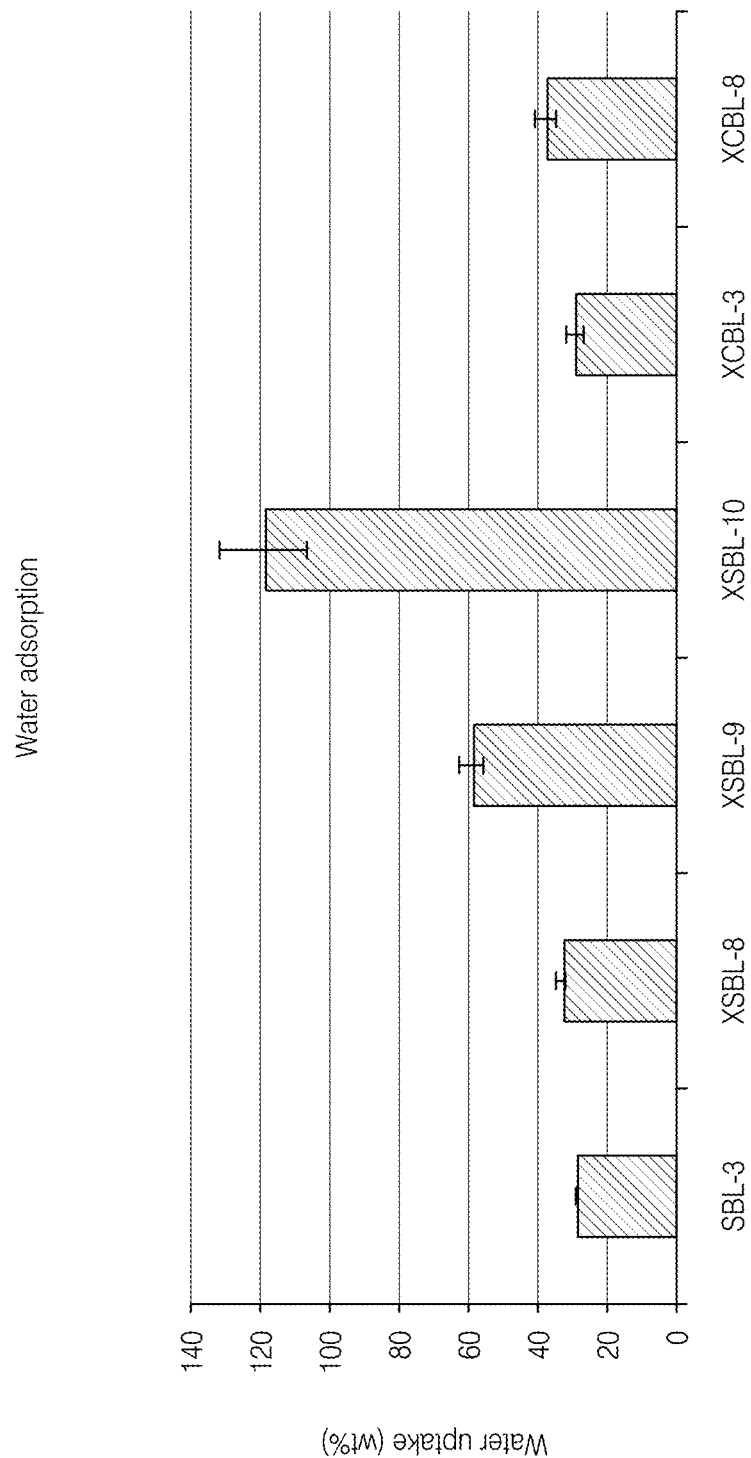
FIG. 9 is a graph of the hydrophobicity of various biointerface layers as measured by the amount of water uptake. SBL-3 is from Table 1. X-SBL-8 is polymer SBL-8 from Table 1 crosslinked. X-SBL-9 is polymer SBL-9 from Table 1 crosslinked. X-SBL-10 is polymer SBL-10 from Table 1 crosslinked. X-CBL-3 is polymer SBL-3 from Table 1 where the sulfobetaines are replaced with carboxyl betaines and crosslinked. X-CBL-8 is polymer SBL-8 from Table 1 where the sulfobetaines are replaced with carboxyl betaines and crosslinked. As the percentage of hydrophilic segments (e.g., PEG) increases from SBL-3 to SBL-10, the amount of water uptake, and thus hydrophilicity, increases.

The hydrophilicity of various biointerface layers were tested by measuring the wt. % of water they absorbed. Crosslinked SBL-10 (XSBL-10), with sulfobetaines in the backbone, was the most hydrophilic polymer tested (FIG. 9). These data indicate that the disclosed biointerface polymers are very hydrophilic, much more so than current sensors without such layers. Further, one can use crosslinking to affect the hydrophilicity of the polymer.

Figure 10A:
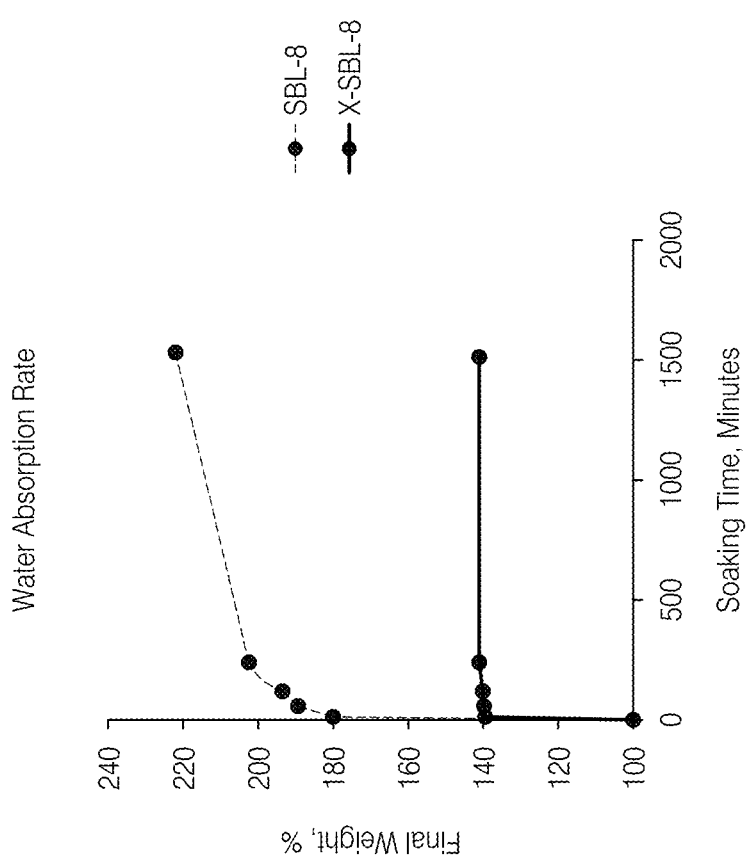
FIG. 10A is a graph of water absorption rate and tensile strength data for crosslinked (X-SBL-8) and uncrosslinked (SBL-8) biointerface polymer. The data show that crosslinking results in faster water absorption and equilibration.
Figure 10B:
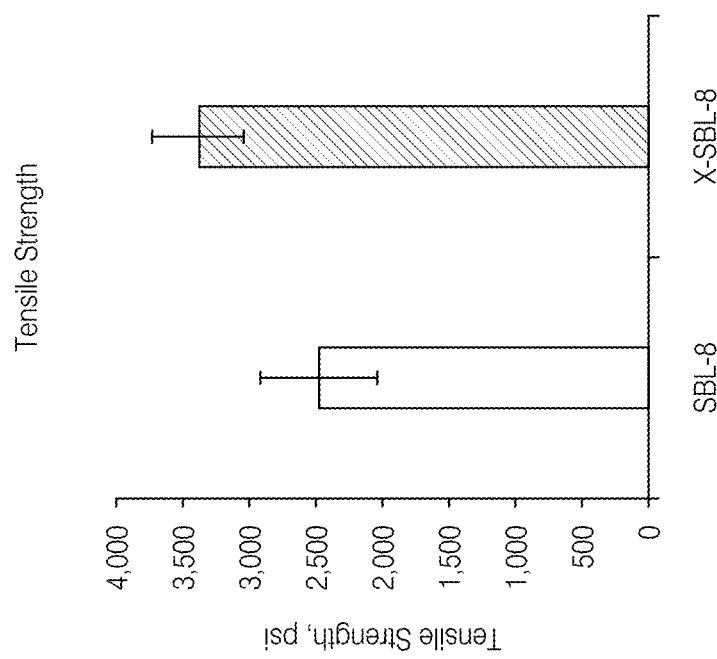
FIG. 10B is a graph of tensile strength data for crosslinked (X-SBL-8) and uncrosslinked (SBL-8) biointerface polymer. The data show that crosslinking increases the tensile strength.

The effect crosslinking had on the rate water is absorbed and the tensile strength was also tested. Specifically, crosslinked (XSBL-8) and uncrosslinked (SBL-8) with sulfobetaines in the backbone were soaked in water over time and weighed. The uncrosslinked polymer absorbed more water over time. The crosslinked polymer absorbed less water and reached equilibrium quicker. The crosslinked polymer also had significantly more strength (FIG. 10A and FIG. 10B).

Figure 18:
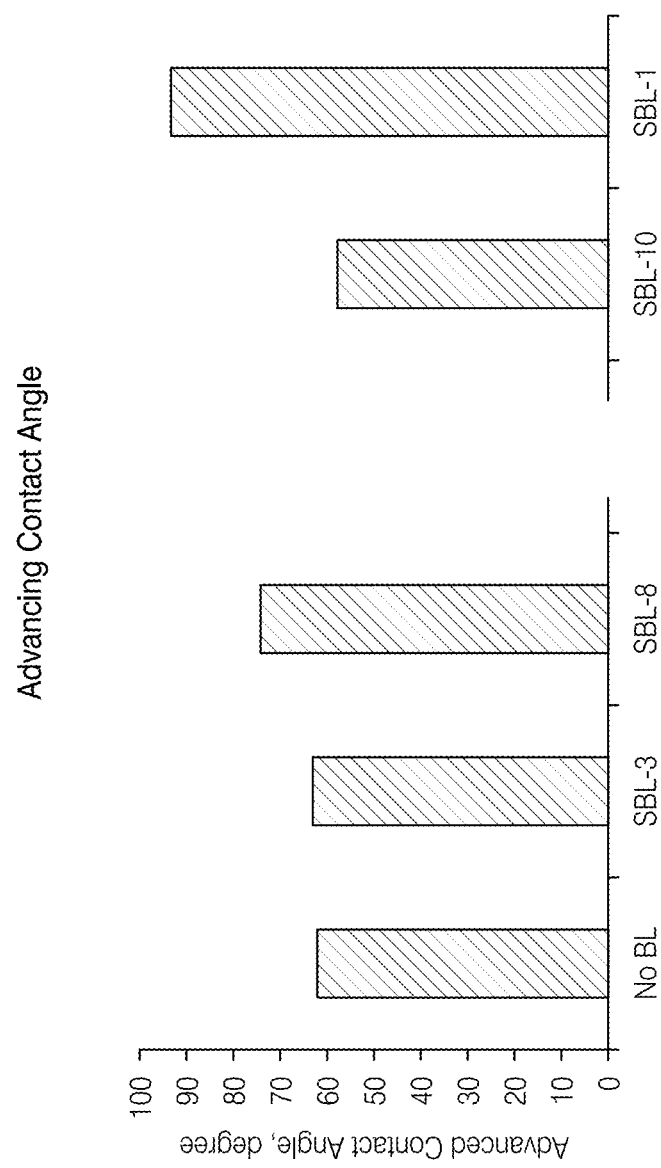
FIG. 18 is a graph showing the contact angle of various biointerface layers from Table 1. The variation of contact angle indicate that the wettability of the biointerface layer can be tuned by varying the amounts of hydrophobic and/or hydrophilic segments.

Hydrophobicity was also measured by contact angle experiments. Specifically, the advancing contact angles were measured using Attension Sigma force tensiometer 701 (Biolin Scientific product) on sensor wire coated with different polymer coatings. The sensors were submerged in deionized water at 25° C. and allowed to retract and advance repeatedly and the average values of advancing contact angles were calculated. The more hydrophilic and wettable surface the coating is, the lower value would be. The baseline value for sensors without a biointerface layer was 60°. The contact angle of the biointerface layers tested ranged from about 50 to about 90° (FIG. 18).

Figure 11:
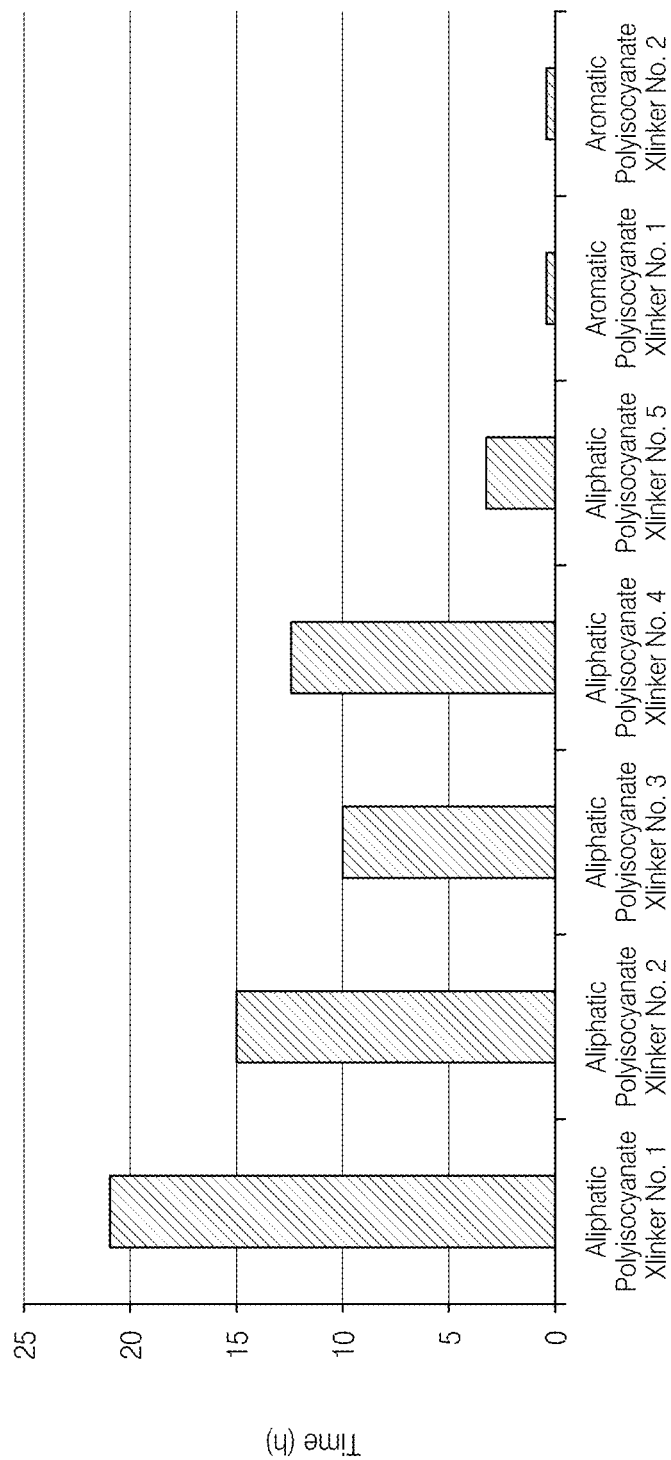
FIG. 11 is a graph of crosslinking reaction kinetics as measured by FT-IR. The crosslinking reaction was done on polymer SBL-10 using different isocyanate-based crosslinkers.

The cure rate of various crosslinkers were tested and the data is shown in FIG. 11. The curing rate is measured by the time to reach 50% of conversion of the functional group such as isocyanate groups. In practice, the fast curing rate can help improve conversion and accelerate the process however may compromise the pot-life. It is desirable to select a curing chemistry and crosslinker that yields balanced pot-life and curing rate. This can be achieve by screening different type of crosslinker and select the one giving optimum properties.

Figure 28:
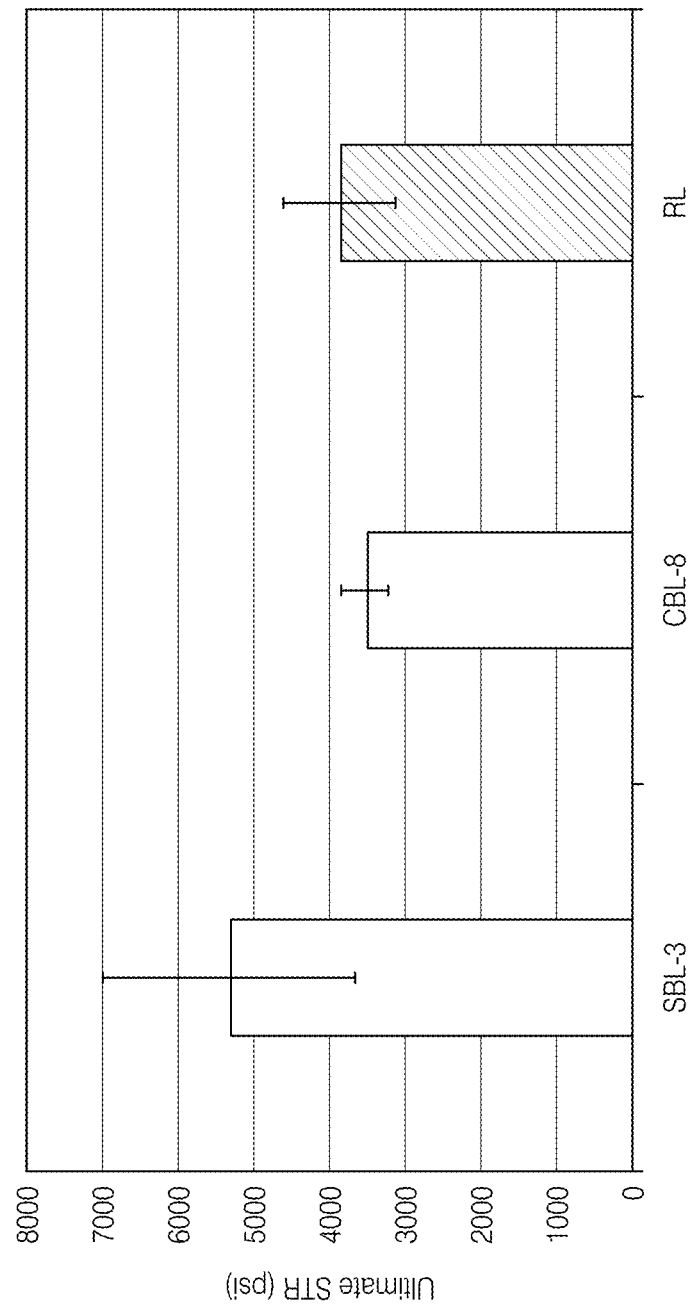
FIG. 28 is a graph of ultimate tensile strength of SBL-3 and CBL-8, with a resistance layer as the control (RL) (i.e., a membrane in which there was no biointerface layer and the resistance layer formed the outermost layer).
Figure 29:
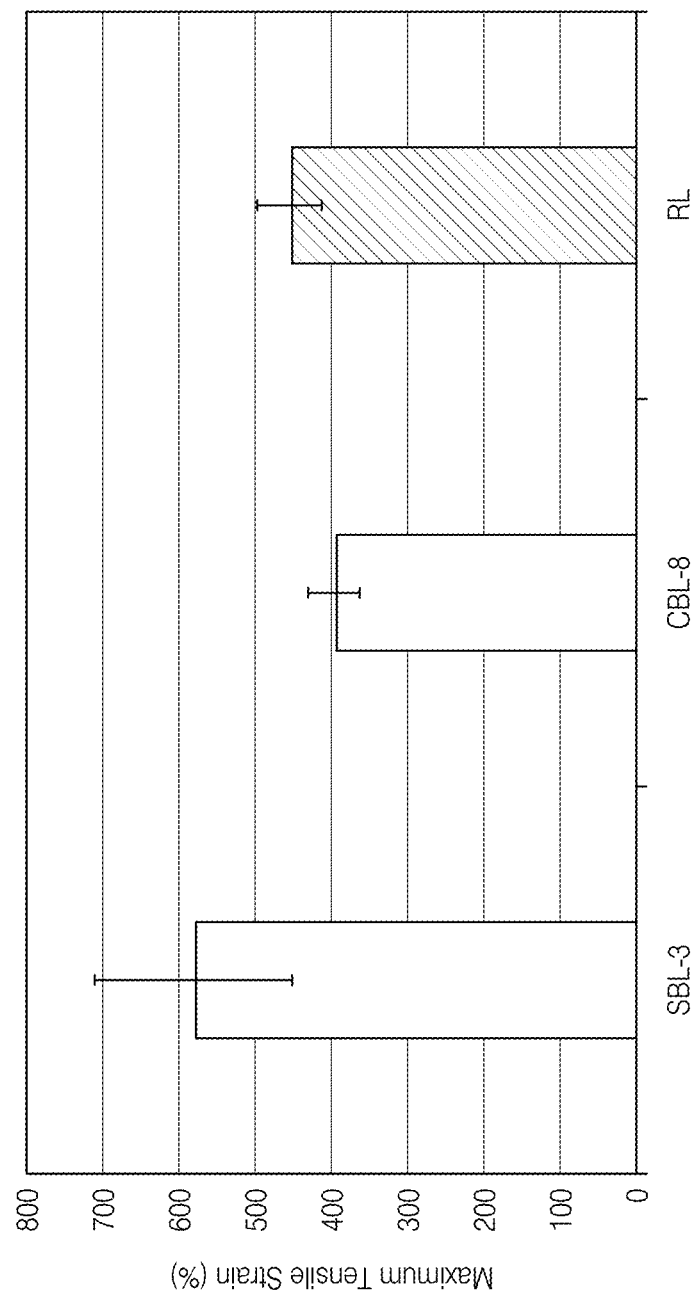
FIG. 29 is a graph of tensile strain at maximum load of SBL-3 and CBL-8, with a resistance layer as the control (RL).
Figure 30:
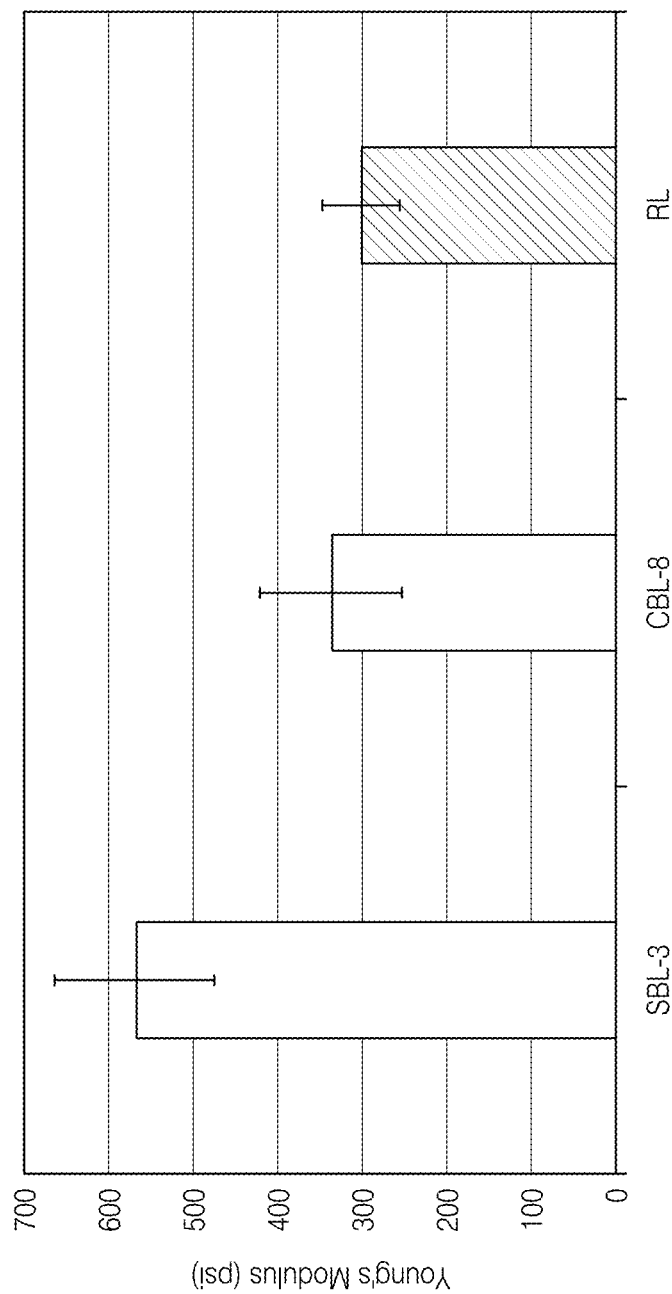
FIG. 30 is a graph of Young's modulus at 100% extension of SBL-3 and CBL-8, with a resistance layer as the control (RL).

Films of SBL-3, CBL-8, and resistance layer (i.e., a membrane in which there was no biointerface layer and the resistance layer formed the outermost layer) were prepared by casting polymer solutions onto polycarbonate sheets and a draw bar coater to cast flat films. This process was repeated until dried films were at desired thickness (3-4 thou). Films were then cut into dog-bones using a dog-bone cutter and a hand press. Dog-bone films were subject to tensile test using an Instron 3345 and stress-strain curves were generated. Five dog-bones were measured for each sample and data were presented by using average with standard deviation as error bar. Ultimate tensile strength, tensile strain and max load, and Young's modulus at 100% extension were calculated from these curves. The ultimate tensile strength of SBL-3 is higher than that of CBL-8 and the resistance layer film (FIG. 28). The tensile strain at maximum load for SBL-3 is higher than CBL-8 and the resistance layer film (FIG. 29). The tensile strain at maximum load for CBL-8 is significantly lower than that of SBL-3 (600% vs. 400%). The Young's modulus at 100% extension follows a similar trend as ultimate tensile strength, with the SBL-3 having significantly higher Young's modulus compared to both CBL-8 and resistance layer control (FIG. 30).

In terms of bulk mechanical properties, SBL-3 has higher ultimate tensile strength, tensile train at break and Young's modulus than CBL-8. In terms of solvent pairs used in polymer synthesis, SBL-3 made with THF/EtOH has stronger mechanical properties than SBL-3 made with THF/IPA solvent pair. In addition, dry SBL-3 with high solution viscosity (>90 cps in THF/EtOH at 10.5 wt % solid content) demonstrated improved film mechanical properties than the resistance layer control.

Example 3 Antifouling Properties

Figure 13:
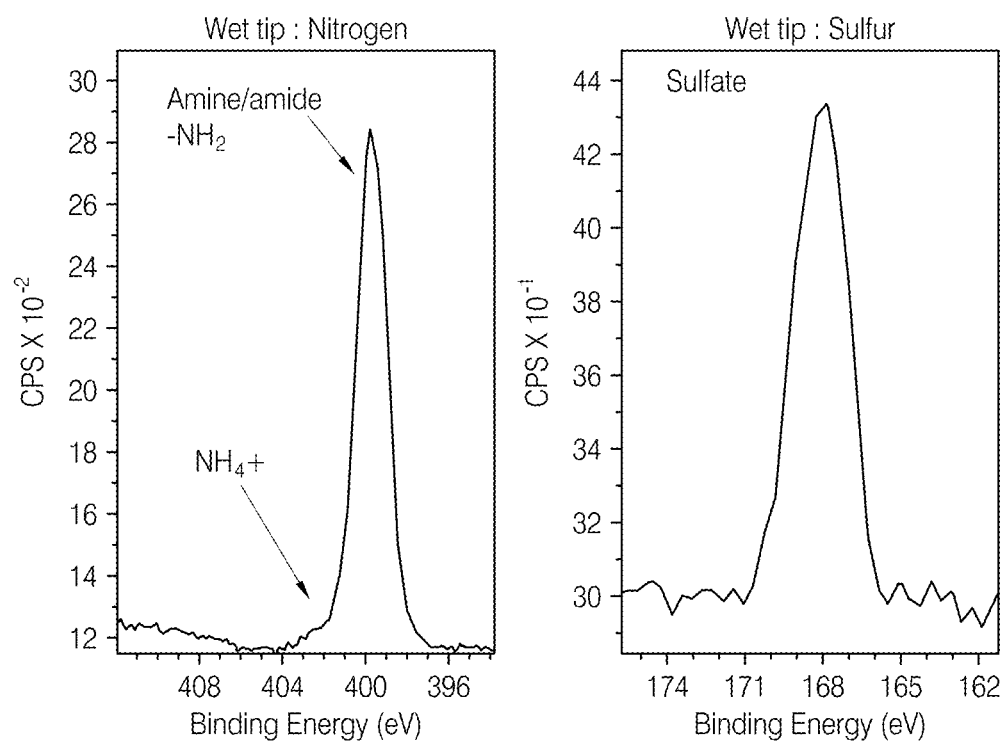
FIG. 13 contains data for XPS studies on polymer SBL-3, SBL-10 dry, and SBL-10 soaked. The data show that there is no preferential migration of betaine to the surface of the biointerface layer when the sensor is soaked in water (supported by comparing the element S atom ratio of SBL-10 coated dry sensor and SBL-10 coated sensor soaked). The XPS data also indicate sulfobetaine groups appear on the surface of sensor tips with both SBL-3 and SBL-10 coated sensors (supported by observing element S on the sensor tips). The increased amount of S atom detected on the surface of BL-10 sample as compared to BL-3 sample is the result of the increased loading of sulfo betaine in the polymer backbone.

The mechanisms of protein adsorption and antifouling properties of the biointerface layer were explored. The use of zwitterions embedded within and physically, rather than covalently, contained in a polymer are believed to work via the migration of these hydrophilic species to the interface between the polymer and the environment. Biointerface layer made from SBL-10 was tested by X-ray photoelectron spectroscopy (XPS) in a dry state and after soaking. It was found that the atomic concentration of Sulfur on the SBL-10 coated surface of sensor tip did not increase before soaking (dry state, 0.3%) and after soaking (0.2%), which indicate there was no migration to the surface of the zwitterionic segments in the polymer chain (FIG. 13). Thus, while not wishing to be bound by theory, it is believed that the biointerface layer creates a loosely bonded water layer at the surface which prevents the adsorption of proteins and cells (FIG. 12).

Figure 16:
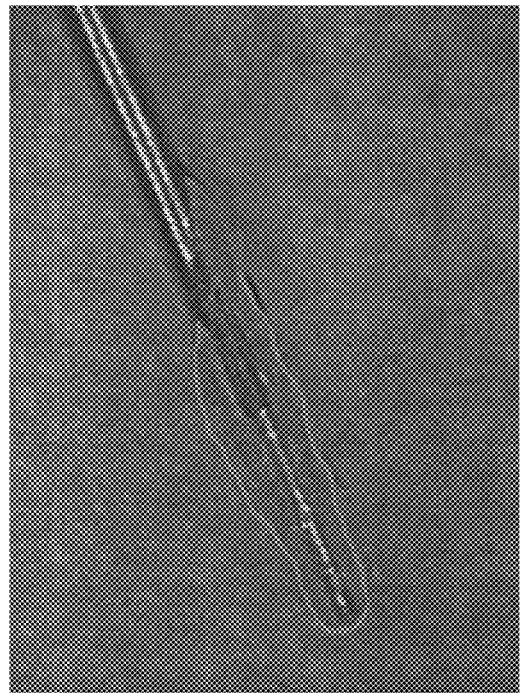
FIG. 16 is a pair of photographs showing a dry sensor coated with a biointerface layer and the same sensor after a 3-minute soak in phosphate buffer solution. The images show the biointerface layer swells (from 50 to 400%) after the soak, which indicates that the biointerface layer can be beneficial for excluding inflammatory cytokines from the implantation site.
Figure 16:
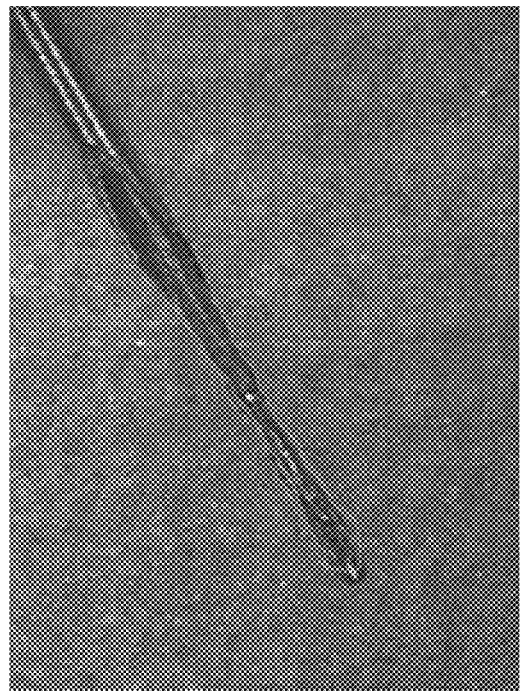

As another theory for the antifouling characteristics of the disclosed biointerface layers, the swelling ability of the biointerface layer. The ability of the disclosed biointerface layer to swell from 50 to 400% is illustrated in FIG. 16. While not wishing to be bound by theory, the ability to swell at the site of implant is believed to fill in void spaces, helping exclude cells, proteins, and cytokines from the cite that may contribute to fouling.

Figure 19:
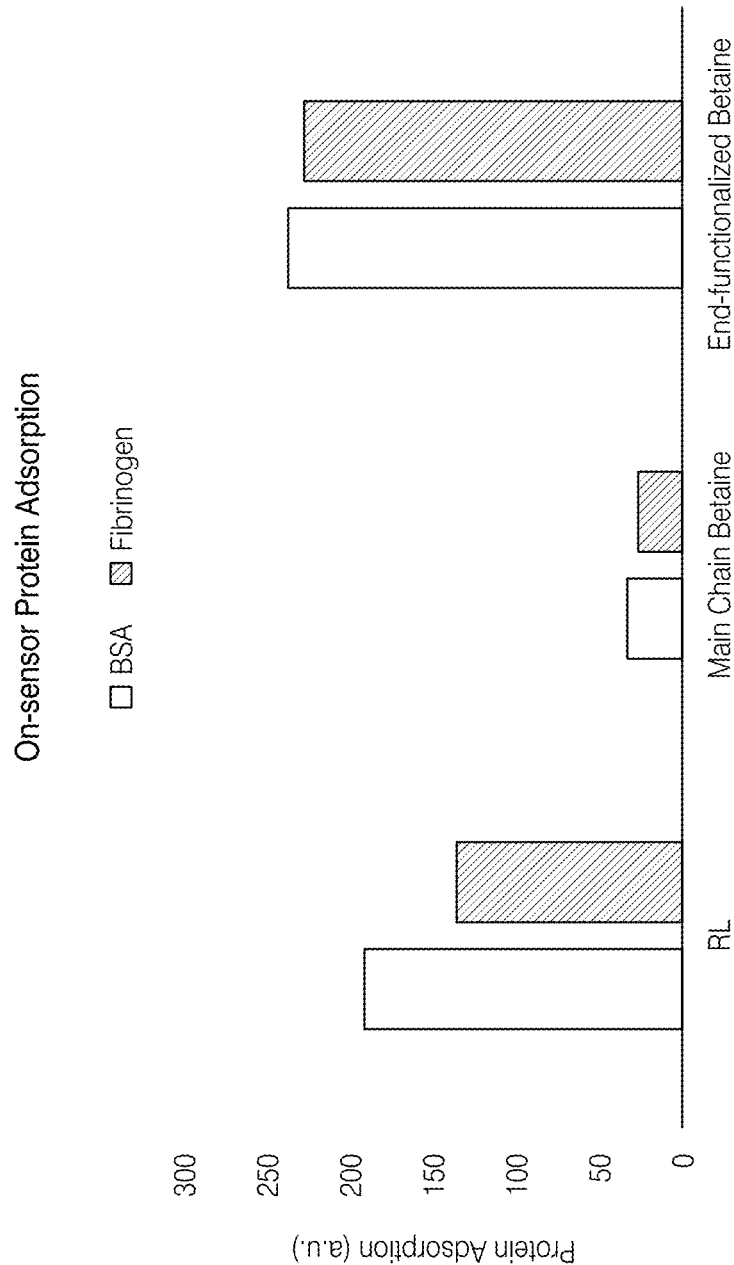
FIG. 19 is a graph showing the amount of protein (bovine serum albumin (BSA) or fibrinogen) absorption on different biointerface layers. The reference layer (RL) does not contain a biointerface polymer. Biointerface layers where a betaine is within the main polymer chain are compared with layers where the betaine is only at the ends of the polymer chain.
Figure 20:
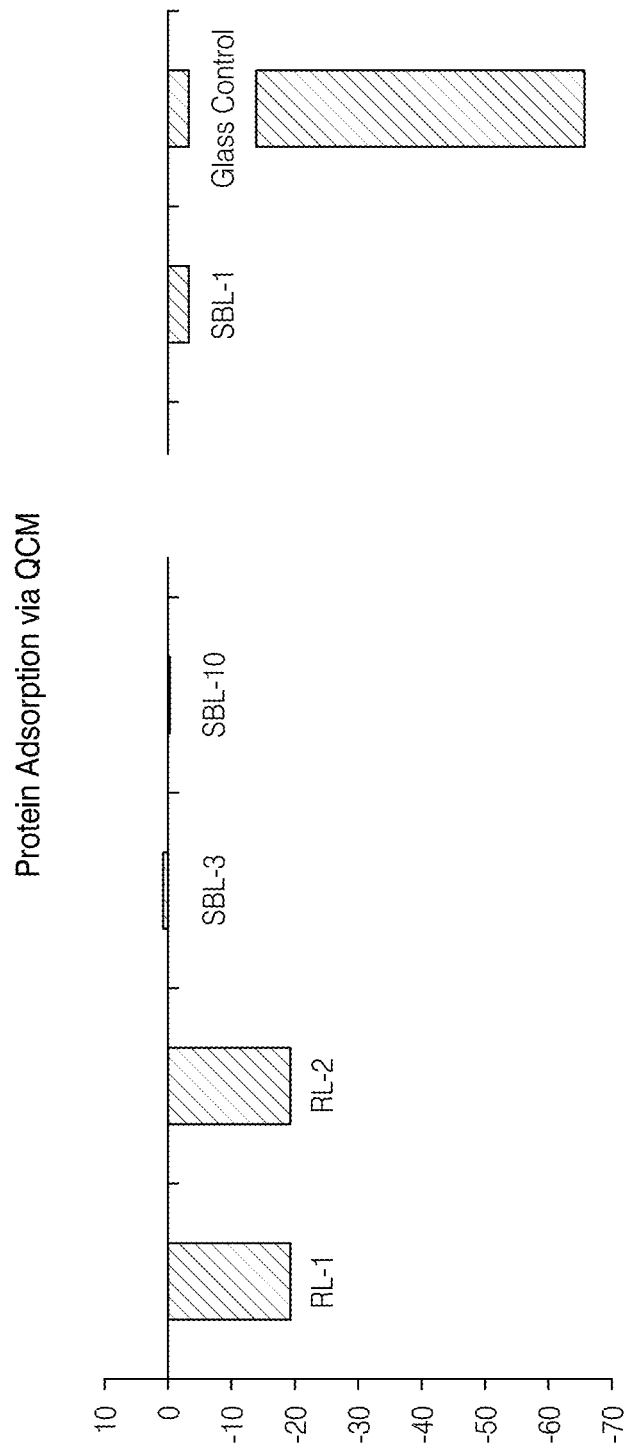
FIG. 20 is a graph showing the protein adsorption via the QCM method on various sensors without biointerface polymers and those with biointerface polymers. A silicone polycarbonate urethane layer corresponds to RL-1 and a silicone-free polycarbonate urethane corresponds to RL-2. Biointerface layers SBL-1, SBL-3, and SBL-10 are from Table 1. As is seen when compared to sensors without a biointerface layer, the amount of protein adsorption is significantly less.

The amount of protein adsorption was determined for a continuous glucose sensor having no biointerface layer, a continuous glucose sensor having a polyurethaneurea with betaines in the main polymer chain, and a continuous glucose sensor having polyurethaneurea with betaines at only the ends of the polymer chain. Fluorescently conjugated constructs of bovine serum albumin and human fibrinogen were incubated with these sensor configurations for 1hr. These sensors were then washed in DPBS and imaged as a z-stack on a laser scanning confocal. Maximum intensity projections were made of this image stack and the fluorescent intensities of protein adsorbed on the outer membrane above the sensor active electrode region was measured and the results (a.u.) are shown in FIG. 19. A similar test was performed using polymers SBL-1, SBL-3, and SBL-10, as compared to a silicone polycarbonate urethane layer (RL-1) and a silicone-free polycarbonate urethane layer (RL-2) (see FIG. 20). The data show that having the betaine groups within the polymer chain resulted in significantly less protein adsorption than when the betaine groups are on the ends of the polymer chains.

Figure 21:
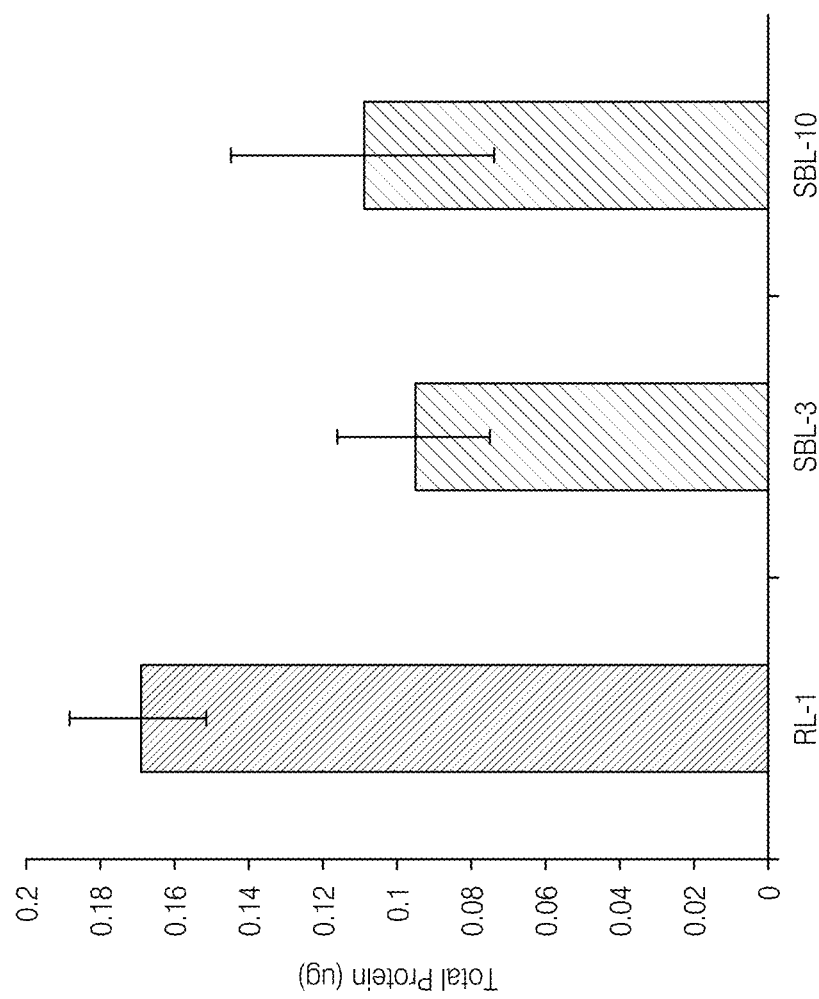
FIG. 21 is a graph of protein adsorption using an on-sensor micro-BCA method. The sensor without the biointerface layer (RL-1) had significantly more protein than sensors coated with biointerface layers SBL-3 and SBL-10.

The protein results were confirmed using an in vitro on sensor assay using the micro-bca extraction method. Sensors were placed into human plasma for 1hr. The protein adsorbed on the surface was extracted with a detergent solution and was tested for total protein using the micro-BCA (bicinchoninic acid assay). Again it was found that the biointerface polymers SBL-3 and SBL-10 resulted in significant reductions in total protein adsorption as compared to sensors without a biointerface layer (FIG. 21).

Figure 22:
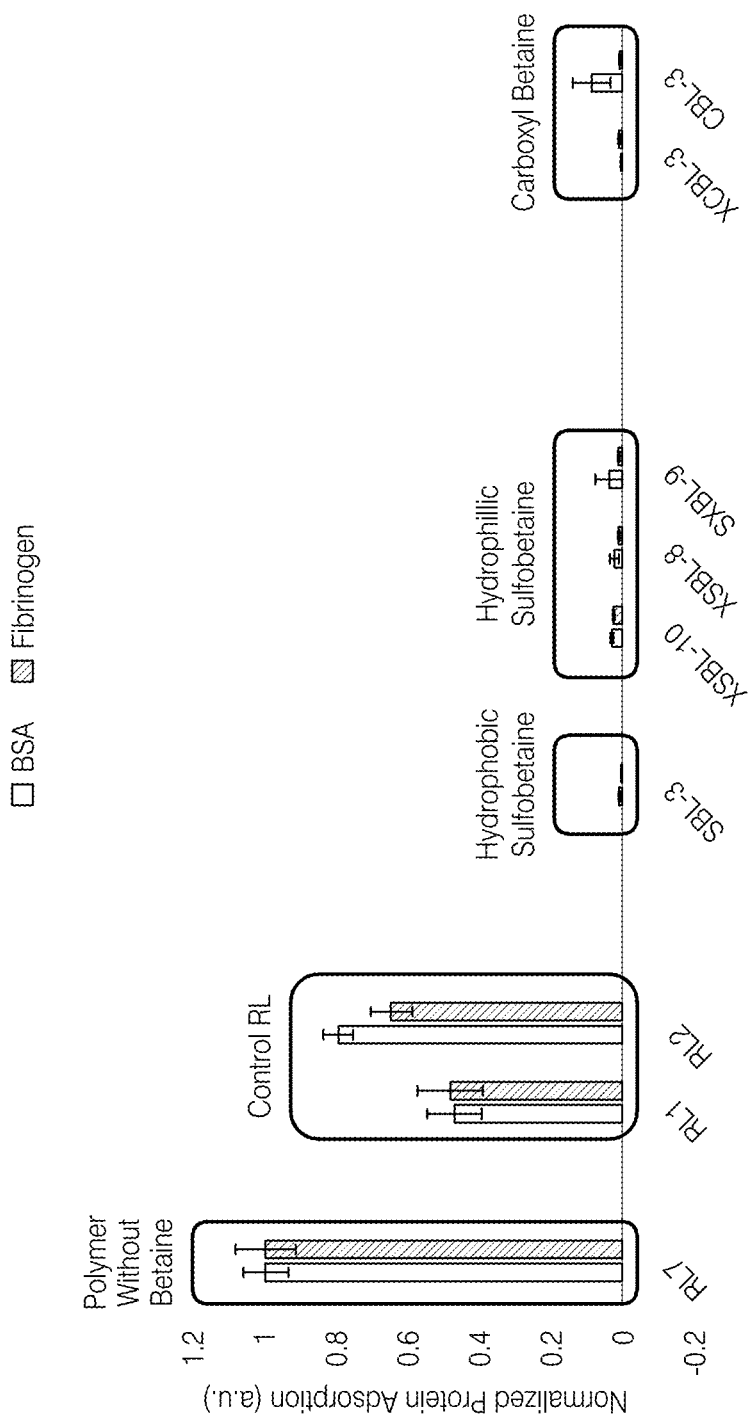
FIG. 22 is a graph of protein adsorption using a dye-labeled protein adsorption screening method. Sensors with a layer lacking betaines (RL-7 from Table 1) and control sensors without a biointerface layer (RL-1 and RL-2) showed significantly more protein adsorption than SBL-3, crosslinked versions of SBL-10, SBL-8, and SBL-9 (XSBL-10, XSBL-8, and XSBL-9, respectively), and crosslinked and uncrosslinked versions of SBL-3 with carboxylbetains instead of sulfobetaines (XCBL-3 and CBL-3, respectively).
Figure 31:
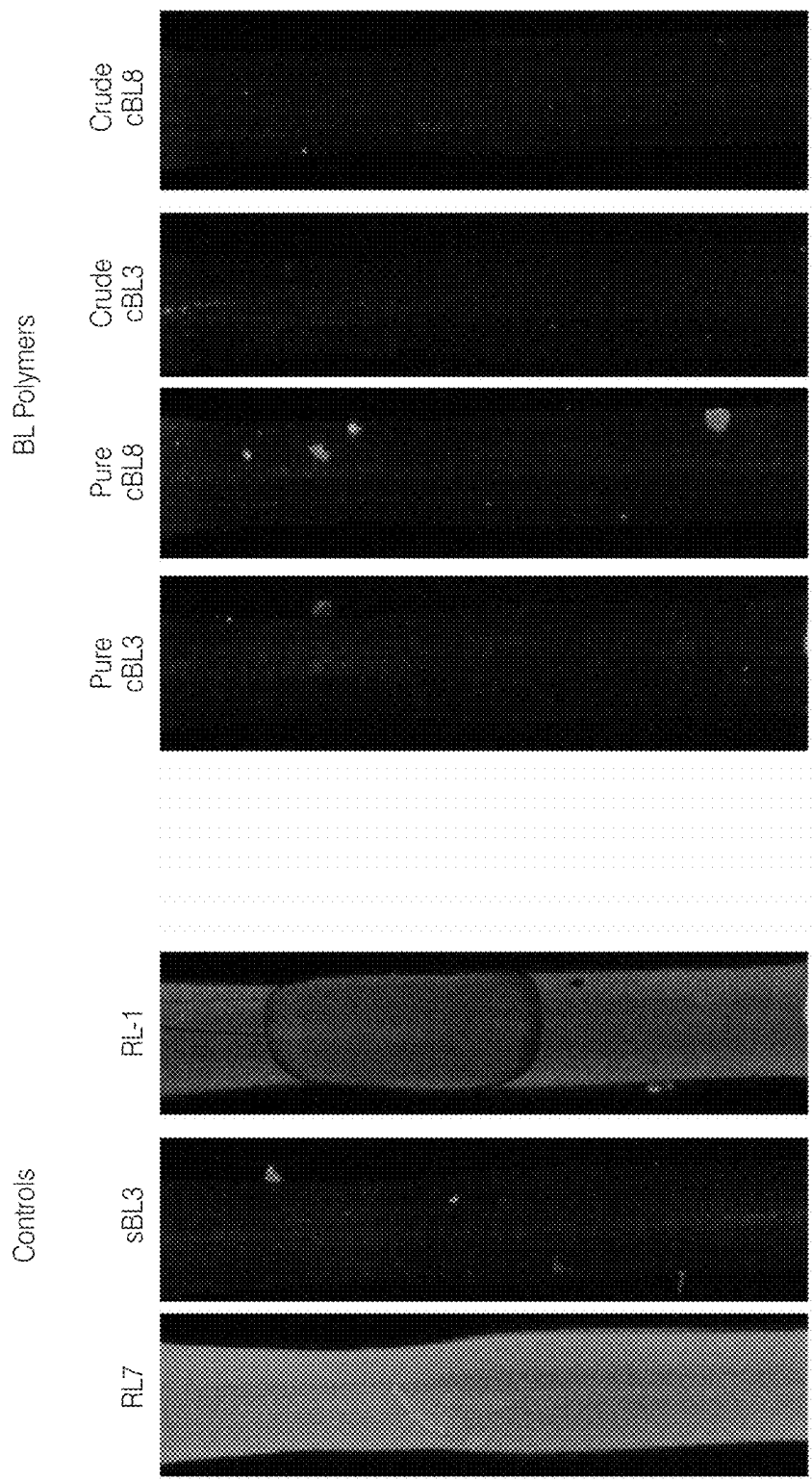
FIG. 31 contains images of the skive regions of sensors with BSA-488 incubated on various polymer surfaces after 1 hour.
Figure 32:
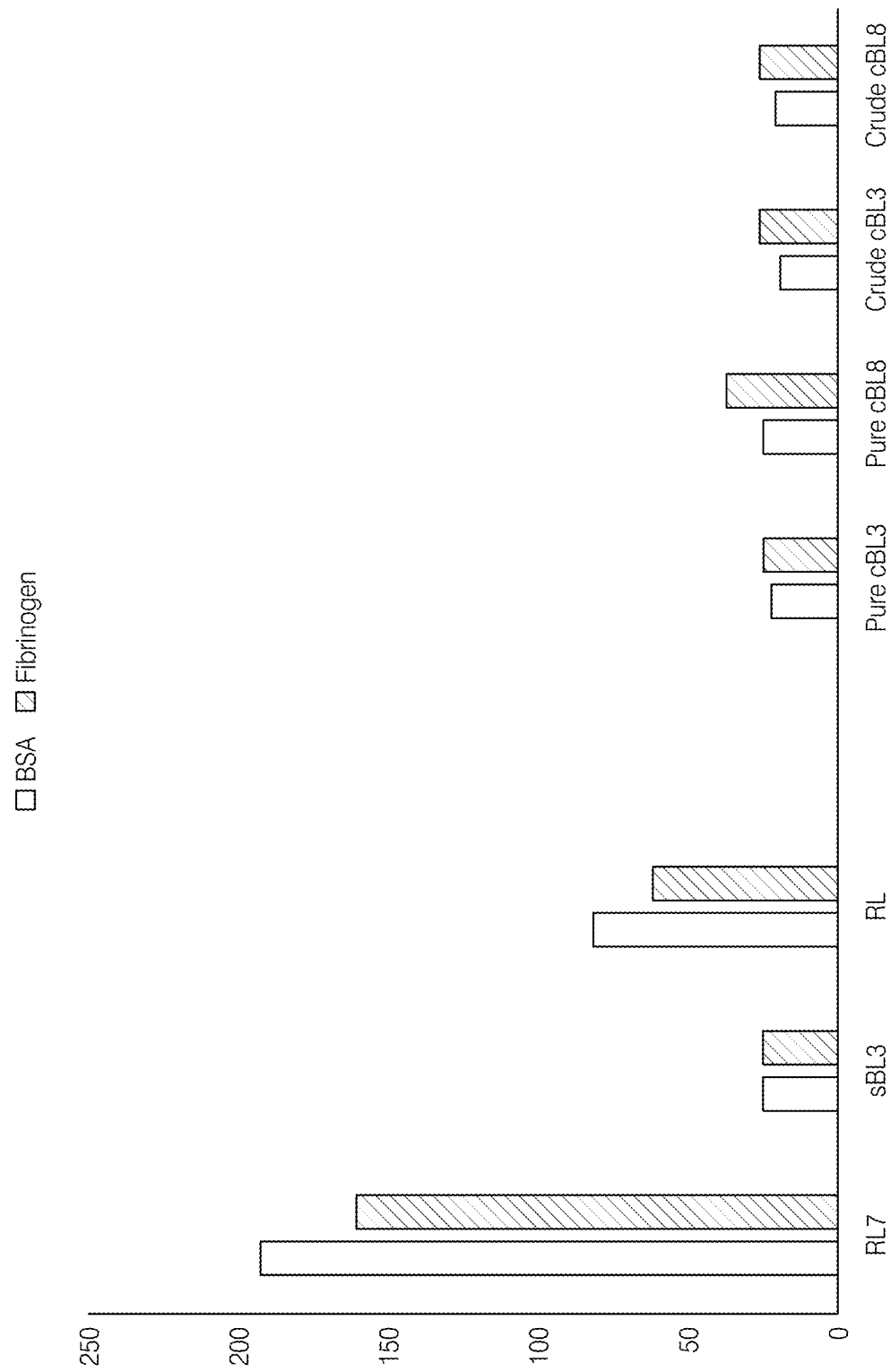
FIG. 32 is a graph of normalized protein adsorption based on ImageJ quantification of fluorescence intensity in skive region of sensor.

Normalized protein adsorption of BSA or fibrinogen for sensors without a biointerface layer (RL-1 and RL-2), a sensor without betaines or PEG in the backbone (RL-7), and sensors with biointerface layers SBL-3, crosslinked versions of SBL-10, SBL-8, and SBL-9 (XSBL-10, XSL-8, and XSL-9, respectively), and crosslinked and uncrosslinked versions of SBL-3 where the sulfobetaines have been replaced with carboxylbetains (XCBL-3 and CBL-3, respectively). The significant reduction in protein adsorption with the biointerface layers is evident (FIG. 22). Z-stack images of certain polymers were taken in skive region of these sensors (FIG. 31). Both SBL-3 and CBL-8 performed very well and have minimal protein adsorption to their surfaces (indicated in green) compared to both RL-7 (non-betaine control) and a resistance layer. FIG. 32 provides the quantification results based on images in FIG. 31.

Both carboxyl and sulfo-betaine type coatings evaluated on spin-coated glass discs and dip coated onto sensors had protein adsorption that was significantly less than both non-betaine and non-coated RL controls.

Figure 23:
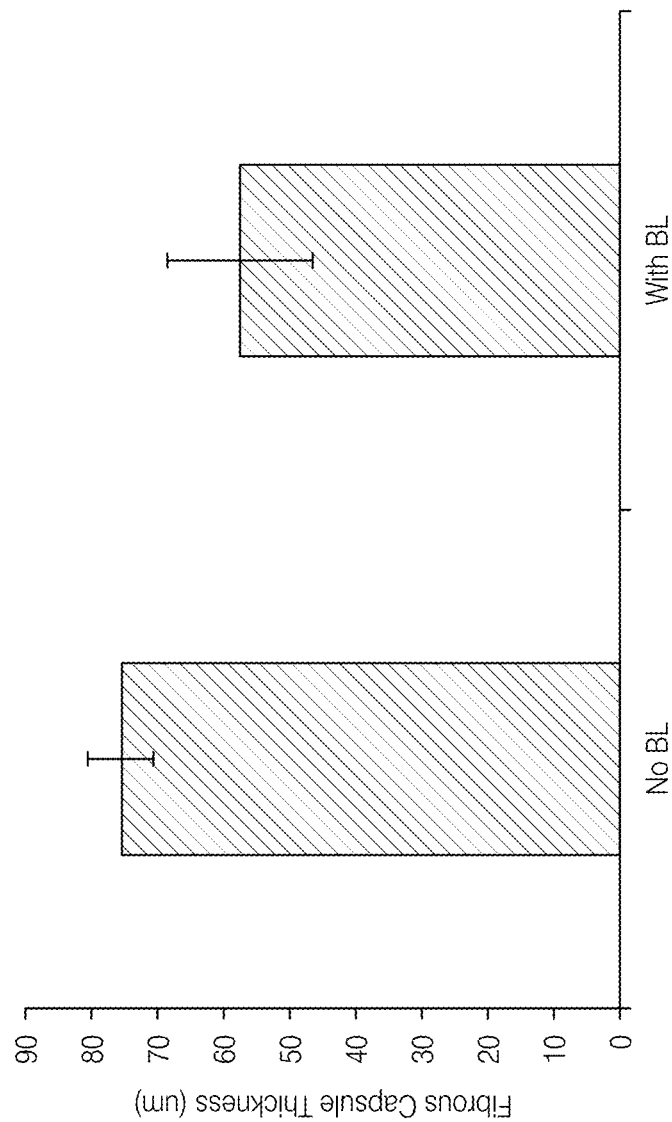
FIG. 23 is a graph showing the fibrous capsule thickness of a sensor with ("BL") and without ("No BL") a biointerface layer. The biointerface polymer in the BL was SBL-3 from Table 1. The reduction in fibrous capsule thickness when using a biointerface layers is significant.

The thicknesses of fibrous capsules were also measured. Fibrous capsules are a step in the biomaterial-associated inflammation response. It was found that the thickness of fibrous capsules was approximately 26% less when using a biointerface polymer (SBL-3) versus no biointerface layer (FIG. 23).

Figure 24:
FIG. 24 is a group of photographs showing stability of a sensor coated with a biointerface layer. The stable explant was coated with SBL-8 and the unstable explant was coated with SBL-10. The dark areas indicate compromises in the layer.
Figure 25A:
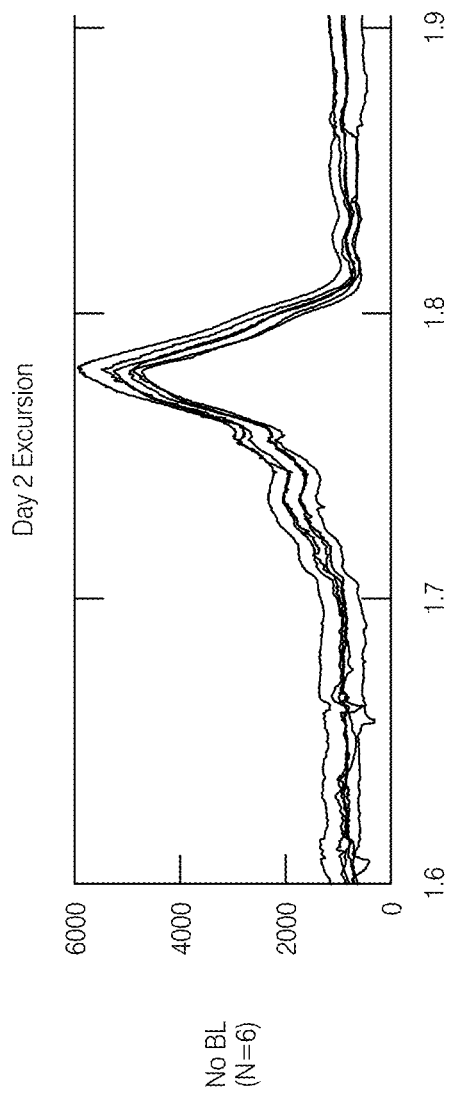
FIGS. 25A-D comprise a group of graphs showing the raw counts from various sensors at 2 days and 14 days post implant. In the sensor without the biointerface layer ("No BL") the spread of data points is more pronounced at day 14 than at day 2, indicating a shift raw counts that is due to biofouling. In contrast, the sensor with the biointerface layer ("with BL") had very little spread of data points at 14 days; it was similar to the spread at day 2, indicating that there was less biofouling.
Figure 25B:
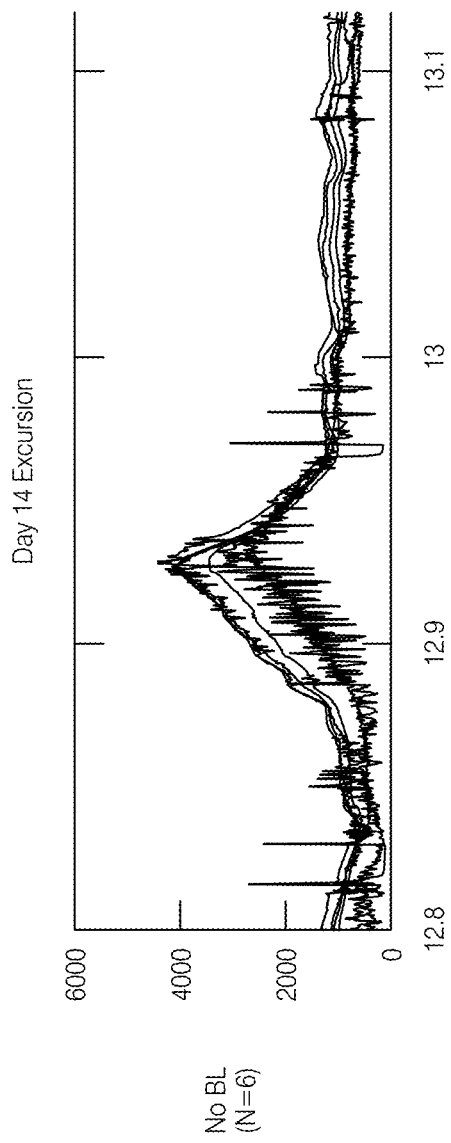
Figure 25C:
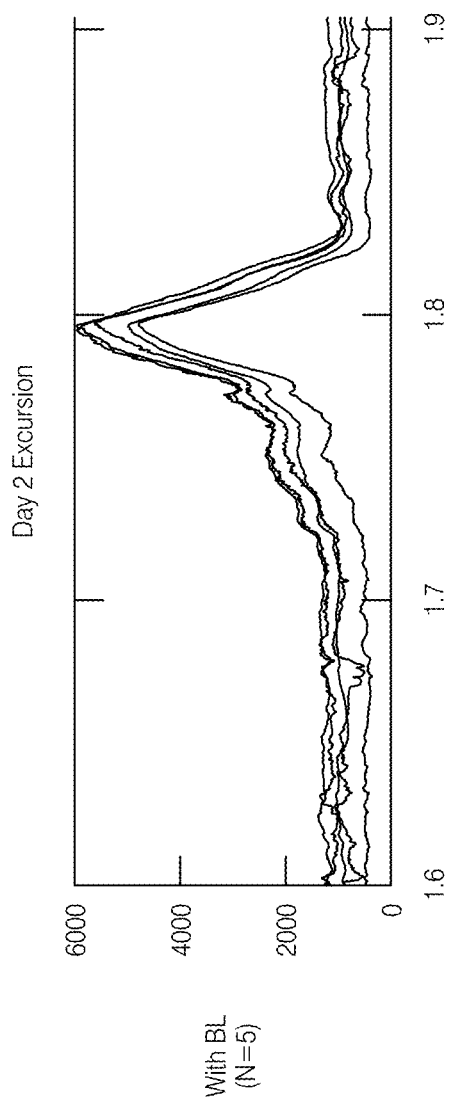
Figure 25D:
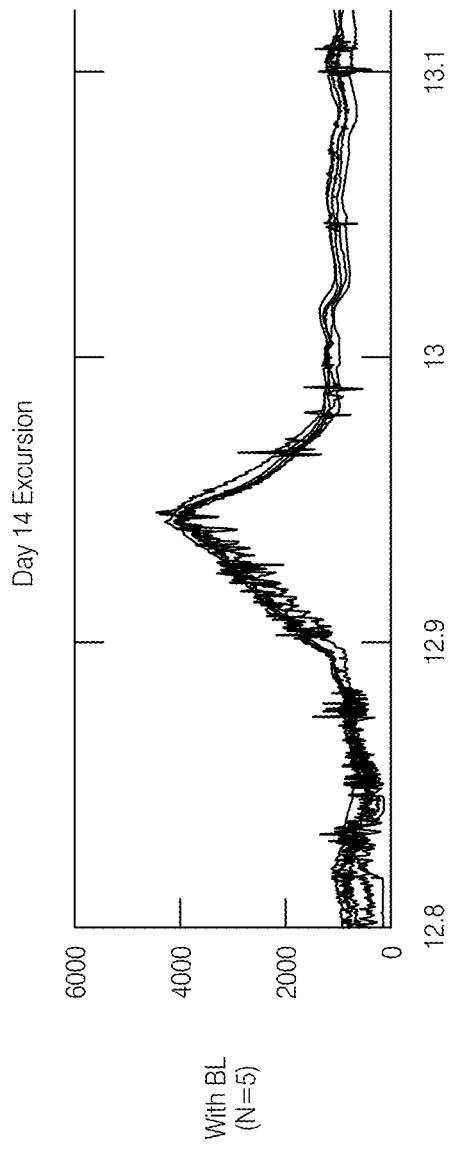

The stability of the biointerface layer after 14 days in vivo was visually confirmed. The layer before implant can be compared to SBL-3 (middle-row) and SBL-10 (bottom row). The SBL-10 showed more degradation than SBL-3 (FIG. 24).

The raw counts of data from continuous glucose sensors were plotted at day 2 and day 14. It was found that without the biointerface layer, there was a greater difference between sensors at day 14 than with sensors that had the biointerface layer. This data suggests that biofouling was a more significant factor, leading to more variance in the measurements, when no biointerface layer is used (FIG. 25).

Example 4 Noise Analysis

An ambulatory pig model was developed for the in vivo assessment of sensor performance. Using hair-less Yucatan pigs, sensors and wearable pods were adhered to their skin, which is similar to humans. Two 10 french external vascular access ports that allow infusion and withdrawal of fluids and blood from central venous circulation were installed into the descending right/left jugular veins. Animals were allowed to recover for 5-7 days before study. Pigs were induced with 5% isoflurane using Surgivet anesthesia machine for 5-10 minutes. Pigs were maintained at 2.5%-4% isoflurane during the duration of the sensor insertion. A pulse oximeter was used to track pig telemetry and pO2. The pigs' skin was cleaned using soap and chlorhexidine surgical scrub. The pigs' skin was then cleaned with alcohol gauze and then prepared with skin tac and allowed to air dry. The sensor was inserted and active transmitter in logging mode was snapped in. Animal patch overlays were used to secure the patch to the skin for long duration wear. Tegaderm (4" inch wide) was used to protect patch edges from lifting and waterproofing all sensors.

Figure 27:
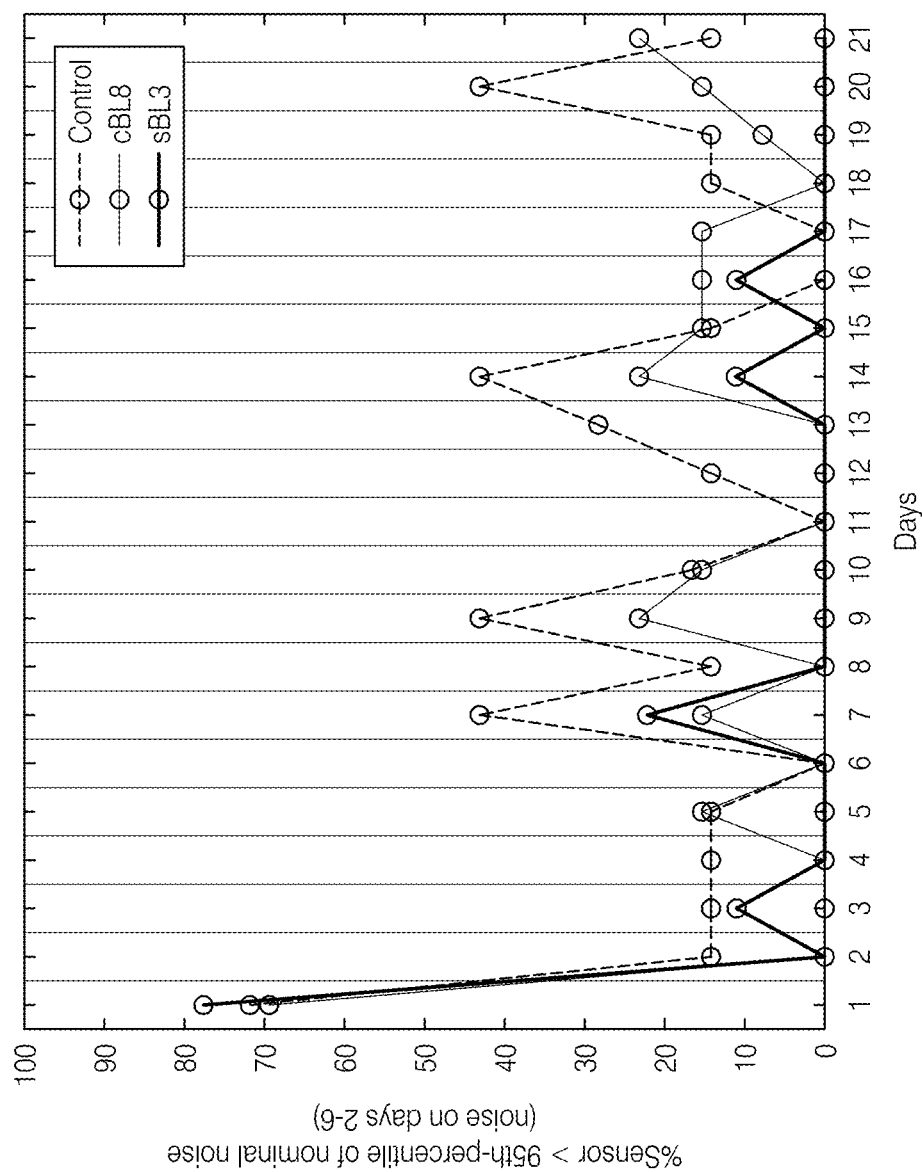
FIG. 27 is a graph of the 95% confidence interval for nominal noise for sensors coated with CBL-8 and SBL3.

A 25% dextrose bag was prepared from 0.9% saline bag mixed (1000 mL) with 50% dextrose. Baseline measurements were taken from sampling blood from the vascular access ports. The 25% dextrose bag was hooked up to infuse the vascular access port and started at a basal drip rate of 1-1.5 drops per second. Measurements were taken every 10 minutes for the duration of the excursion. Data was downloaded from transmitters and data was processed in MATLAB for time lag, sensitivity, noise, EOL, and MARD. There was minimal differences between groups in terms of time lag improvement, slope stability, and MARD calculation. Thus the biointerface layers do not affect cal-check or drift profiles. Further SBL-3 exhibits lowest levels of noise compared to CBL-8 and SBL-3 groups (FIG. 27). There are no apparent detriments in performance between groups in terms of time lag, slope, or MARD.

Example 5 Fluorescent Incorporation

A fluorescent dye labeled polyurethaneurea (FPUU) was synthesized by two step polycondensation reaction using erythrosine B dye (0.21 wt. %). The FPUU can be made in ethyl acetate and isopropanol mixed solvent and form homogeneous transparent red solution. The polymer can be precipitated in hexane. The polymer precipitation has strong bright red color, while the supernatant hexane is colorless transparent, which indicate that all the dye was covalently incorporated into polymer. After soaking the polymers in water for one week, no free dye leached out.

Example 6 Synthesis of SBL-8

The biointerface polymer is a polyurethaneurea that was synthesized via a two-step polycondensation reaction. In the first step, a homogeneous polyurethane prepolymer with isocyanate end groups on both prepolymer chain ends was prepared. In the second step, a small molecular diamine were used as chain extenders. These diamines react with prepolymer in dilute solution to obtain well-defined polyurethaneurea with high molecular weight.

Using SBL-8 as a representative example, the prepolymer was prepared by adding isophorone diisocyanate (IPDI), polyethylene oxide diol (YMER™ N120), polycarbonate diol (Ravecarb 107 polycarbonate diol), and sulfobetaine prepolymer into a dry 200 mL reaction jar fitted with a nitrogen sparge tube and a mechanical stirrer at room temperature. The reaction was heated to 65° C. for 30 min under nitrogen with mechanical stirring (200 rpm) until all the reactants dissolved. 400 ppm of catalyst were added into the reaction, which was kept at 65° C. for 1 h. The reaction temperature was raised to 85° C. and kept for 3 h until no bubbles were observed in the reaction mixture. The reaction mixture was allowed to stir for an additional 2 h at 100° C. to complete the formation of the prepolymer. The viscous prepolymer was cooled to 50° C. and dissolved in ethyl acetate to form a transparent solution.

For the chain extension step, isophorone diamines were used as chain extenders and were added to a dry 700 mL reaction jar equipped with a mechanical stirrer and diluted with ethyl acetate/isopropanol solvent mixture. The polyurethane prepolymer solution was added dropwise into the chain extender solution at room temperature under aggressive stirring (600 rpm). During the addition of chain extender solution, certain amount of solvent mixture (ethyl acetate/isopropanol) was added into the reaction mixture to maintain the reaction mixture at a suitable viscosity. After adding all the prepolymer solution into the jar, the reaction mixture was kept stirring for additional 5 h at room temperature to complete the chain extension. Similar procedures can be followed in order to provide other biointerface polymers, as detailed herein.

Example 7 Synthesis of Enzyme Layer Polymer and Characterization Thereof

A betaine containing polyurethaneurea polymer was synthesized via a two-step polycondensation reaction in organic solvents. In the first step, a homogeneous polyurethane prepolymer with isocyanate end groups on both chain ends was prepared. In the second step, small molecular diamine(s) was/were used as chain extender(s). These diamines react with prepolymer in dilute organic solution to obtain well-defined polyurethaneurea with linear structure and narrow molecular weight distribution.

As a representative example, the prepolymer was prepared by adding isophorone diisocyanate (IPDI), polyethylene oxide diol, polycarbonate diol, 2,2-bis(hydroxymethyl) propionic acid (Bis-MPA), and sulfobetaine prepolymer into a dry 200 mL reaction jar fitted with a nitrogen sparge tube and a mechanical stirrer at room temperature. The reaction was heated to 65° C. for 30 min under nitrogen with mechanical stirring (200 rpm) until all the reactants dissolved. 400 ppm of catalyst was added into the reaction, which was kept at 65° C. for 1 h. The reaction temperature was raised to 85° C. and kept for 3 h until no bubbles were observed in the reaction mixture. The reaction mixture was allowed to stir for an additional 2 h at 100° C. to complete the formation of the prepolymer. The viscous prepolymer was cooled to 50° C. and dissolved in ethyl acetate to form a transparent solution.

For the chain extension step, isophorone diamines were used as chain extenders and were added to a dry 700 mL reaction jar equipped with a mechanical stirrer and diluted with ethyl acetate/isopropanol solvent mixture. The polyurethane prepolymer solution was added dropwise into the chain extender solution at room temperature under aggressive stirring. During the addition of chain extender solution, certain amount of solvent mixture (ethyl acetate/isopropanol) was added into the reaction mixture to maintain the reaction mixture at a suitable viscosity. After adding all the prepolymer solution into the reaction mixture, the reaction was kept stirring for additional 5 h at room temperature to complete the chain extension. The polymer thus formed was dried in an oven at 50° C. under nitrogen flow to remove the solvent and re-dissolved or dispersed in a waterborne polyurethane dispersion along with enzyme and optionally cross-linking agent. The enzyme layer film was cast and dried at 50° C. for further characterization.

An active enzyme leaching assay measuring enzyme activity was used to determine the amount of active enzyme leaching from a film. A film is soaked in solution and aliquots of the leachate at specific time points are measured for enzyme activity. Enzyme activity is determined by the rate of hydrogen peroxide generated in the presence of excess glucose. A reactive dye in conjunction with peroxidase is quantitatively converted by hydrogen peroxide to a colored compound and monitored spectroscopically. The rate of colormetric change is related to the activity of the sample, which reflects the active enzyme loading. Experiments are done on 200 µm thick films cast that are dried overnight in a 50° C. convection oven.

Figure 34:
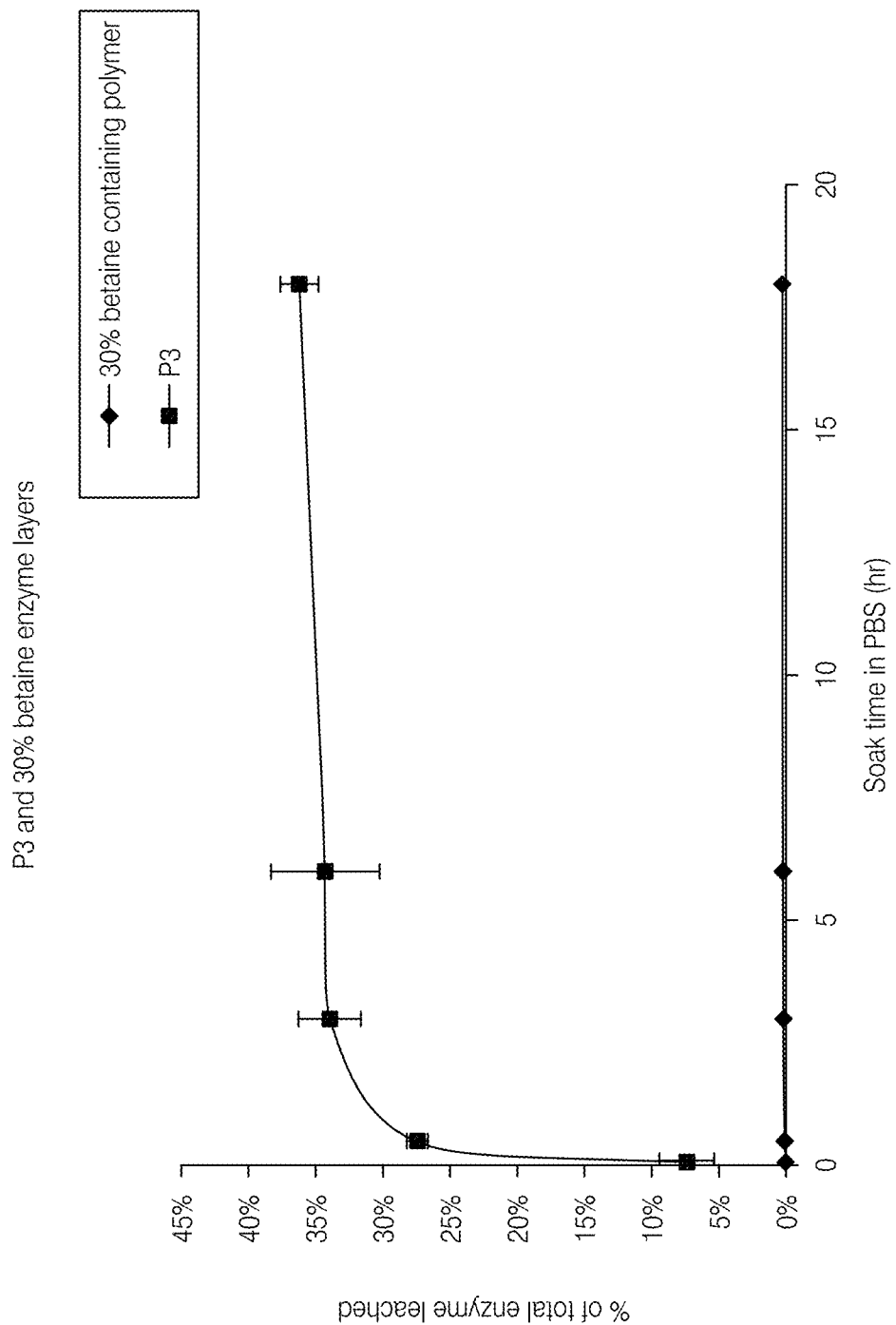
FIG. 34 is a graph showing the % of active enzyme leached out over time into water from a 200 μm thick film of a control polymer blend with a hydrophilic polymer additive not containing betaine (P3) or from a polymer blend with hydrophilic polymer additive containing betaine in the polymer backbone as disclosed herein.

FIG. 34 illustrates % of enzyme leached from a control film (P3) and a film prepared from the same polymer binder used in P3 but with 30 wt % of betaine-containing polymer as enzyme immobilization polymer additive, baseline subtracted. The results indicate effective GOX enzyme immobilization with a betaine containing polymer.

Figure 35:
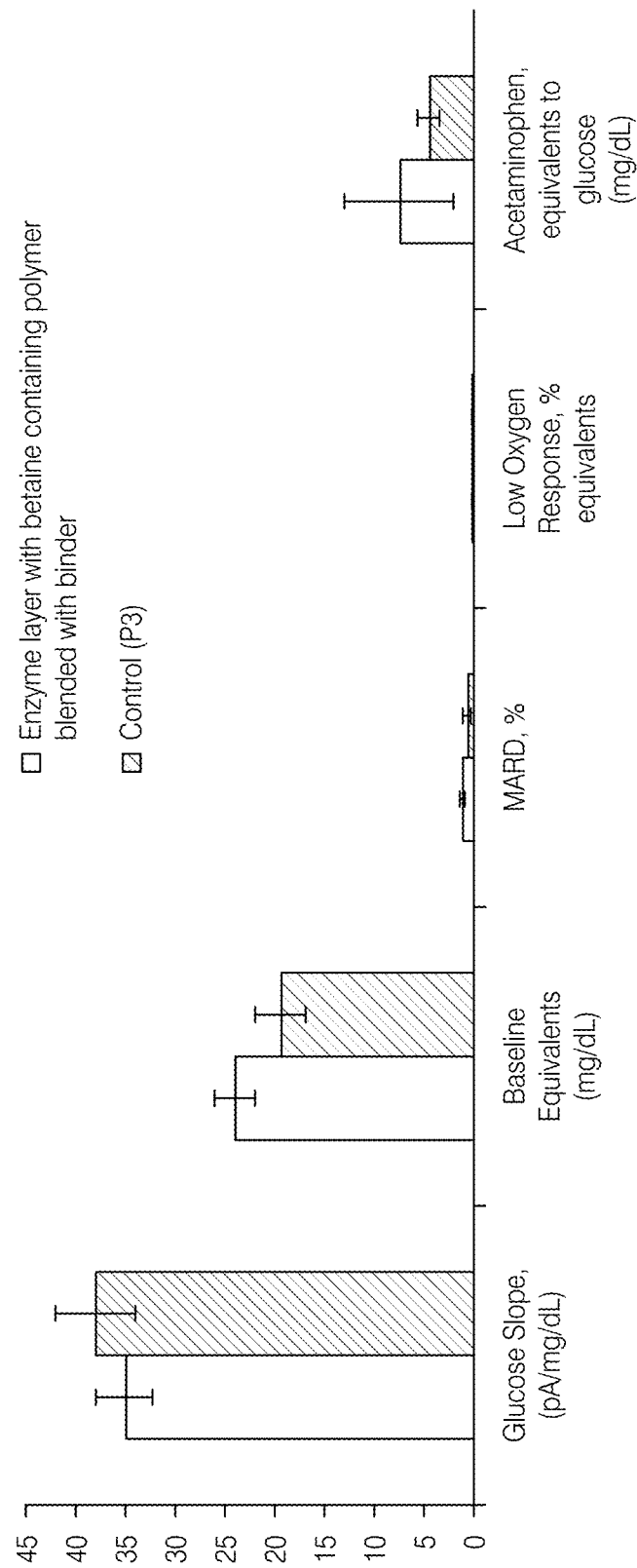
FIG. 35 is a graph comparing various sensor metrics for glucose sensors constructed with an enzyme layer formed of the same polymer binder used in (P3) but with 30 wt % of betaine containing polymer as enzyme immobilization polymer additive vs. glucose sensors (P3) constructed with an enzyme layer without the above-described 30 wt % betaine containing polymer.

Sensors were evaluated on calcheck metrics including sensitivity, baseline signal, oxygen sensitivity, linearity, and acetaminophen blocking. FIG. 35 shows certain sensor metrics (e.g. MARD and glucose slope) for sensors having an enzyme layer formed of the same polymer binder used in P3 but with 30 wt % of betaine containing polymer as enzyme immobilization polymer additive. Their performance under the various metrics are comparable. In this cal-check test, the following characteristics were measured:
  i. Glucose Slope (pA/mg/dL)—Ordinary least-squares linear regression analysis of the electrical response of the sensor when placed in buffer solutions of increasing glucose concentration. It is also referred to as glucose sensitivity.
  ii. Baseline Equivalent (mg/dL)—mg/dL equivalent of the non-glucose related signal.
  iii. MARD (%)—Mean Absolute Relative Difference, the measure of variation away from the ideal line.
  iv. Low Oxygen Response—Defined as the percent change in electrical response under reduced oxygen conditions (i.e., at 0.25±0.05 mg $O_2$/L) compared with signal obtained under atmospheric conditions. It is also referred to as Oxygen Performance.
  v. Acetaminophen Bias—the mg/dL equivalent signal from a 2 mg/dL concentration of acetaminophen. Also referred to as glucose equivalence.

TABLE 2

Enzyme layer polymer and characterization

| Name | PEG (wt. %) | Betaine (wt. %) | HS (wt. %) | Mn (Da) | PDI (Mw/Mn) |
|---|---|---|---|---|---|
| Betaine-containing polymer additive | 55 | 7.6 | 25 | 91,900 | 1.7 |
| WB-7 | 17 | 3.2 | 51 | 107,112 | 1.7 |
| WB-8 | 17 | 3.2 | 51 | 45,000 | 1.7 |
| WB-9 | 16.6 | 3.2 | 50 | N/A | N/A |
| WB-14 | 15.9 | 3.2 | 50 | N/A | N/A |

Example 8 Synthesis of Enzyme Layer Polymer and Characterization thereof

A betaine containing polyurethaneurea polymer in aqueous solution was synthesized via a two-step polycondensation reaction in water. In the first step, a homogeneous polyurethane prepolymer with isocyanate end groups on both chain ends was prepared. In the second step, small molecular diamine(s) was/were used as chain extender(s). These diamines react with prepolymer in dilute aqueous solution to obtain waterborne polyurethaneurea solution.

As a representative example, the prepolymer was prepared by adding polyether diol, and 2,2-bis(hydroxymethyl) propionic acid into a dry 200 mL reaction jar fitted with a nitrogen sparge tube and a mechanical stirrer at room temperature. The reaction mixture was heated to 90° C. for 30 min under nitrogen with mechanical stirring (200 rpm) until all the reactants melted and form transparent liquid. The reaction was allowed to cool to 80° C. and added carboxybetaine diol, stir at 80° C. for 1 h. The reaction mixture was cooled down to 65° C. and then added isophorone diisocyanate (IPDI). 400 ppm of catalyst was added into the reaction, and reaction was kept at 85° C. for 4 h under nitrogen with mechanical stirring. The reaction was neutralized with trimethylamine and then added into water dropwise to form prepolymer aqueous emulsion.

For the chain extension step, ethylenediamine were used as chain extenders and were added to a 700 mL reaction jar equipped with a mechanical stirrer and diluted with water. The polyurethane prepolymer aqueous emulsion was added dropwise into the chain extender solution at room temperature under aggressive stirring. After adding all the prepolymer solution into the reaction mixture, the reaction was kept stirring for additional 5 h at room temperature to complete the chain extension.

In a different assay as that detailed in Example 1, total enzyme leaching from enzyme layer films was determined using two separate tests. FIG. 34 uses a bicinchoninic acid test, which determines total protein content by peptide bond reducing of copper II ion to copper I with an associated color change of copper I complexing with bicinchoninic acid. This color change is measured via an absorption measurement at 562 nm using a UV spectrophotometer.

Figure 36:
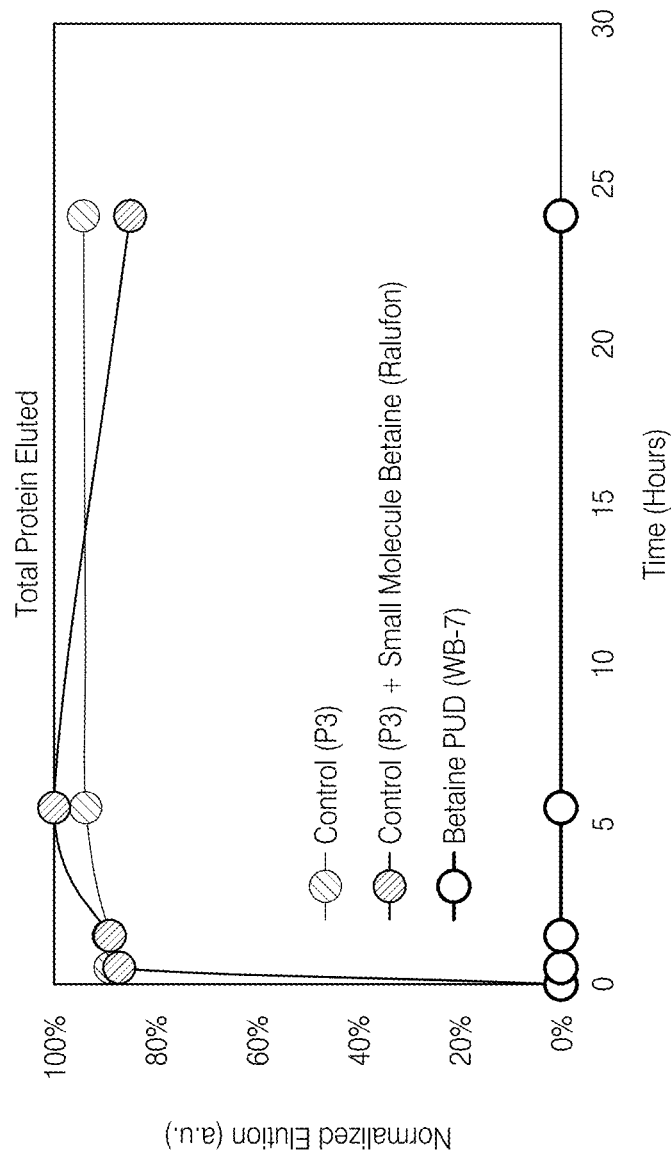
FIG. 36 is a graph showing the normalized elution of total protein enzyme over time into water from a 200 μm thick film of a control polymer without betaines, a control polymer with small molecule betaines added to the formulation, or a polymer with betaines in the polymer backbone as disclosed herein.

Total eluted protein was also measured by a gel electrophoresis method with subsequent protein band quantification in FIG. 36. FIG. 36 shows the comparison of enzyme leaching from film samples prepared from standard formulation (control, P3), standard formulation with the addition of small molecule betaine additive (Ralufon), and film prepared from waterborne polyurethane dispersion with betaine incorporated into the polymer as building-block, as disclosed in this example. Within 30 minutes at room temperature, 200 μm thick samples of enzyme formulation control (P3) leaches much more (2 orders of magnitudes) enzyme, than waterborne polyurethane dispersion betaine films, indicating that the enzyme is immobilized within the film. In addition, addition of equivalent amount (3 wt %) of small molecule sulfo betaine Ralufon to the P3 control formulation failed to improve the enzyme retention. Testing was continued to 24 hours, and waterborne polyurethane dispersion films continue to effectively retain enzyme.

Figure 37:
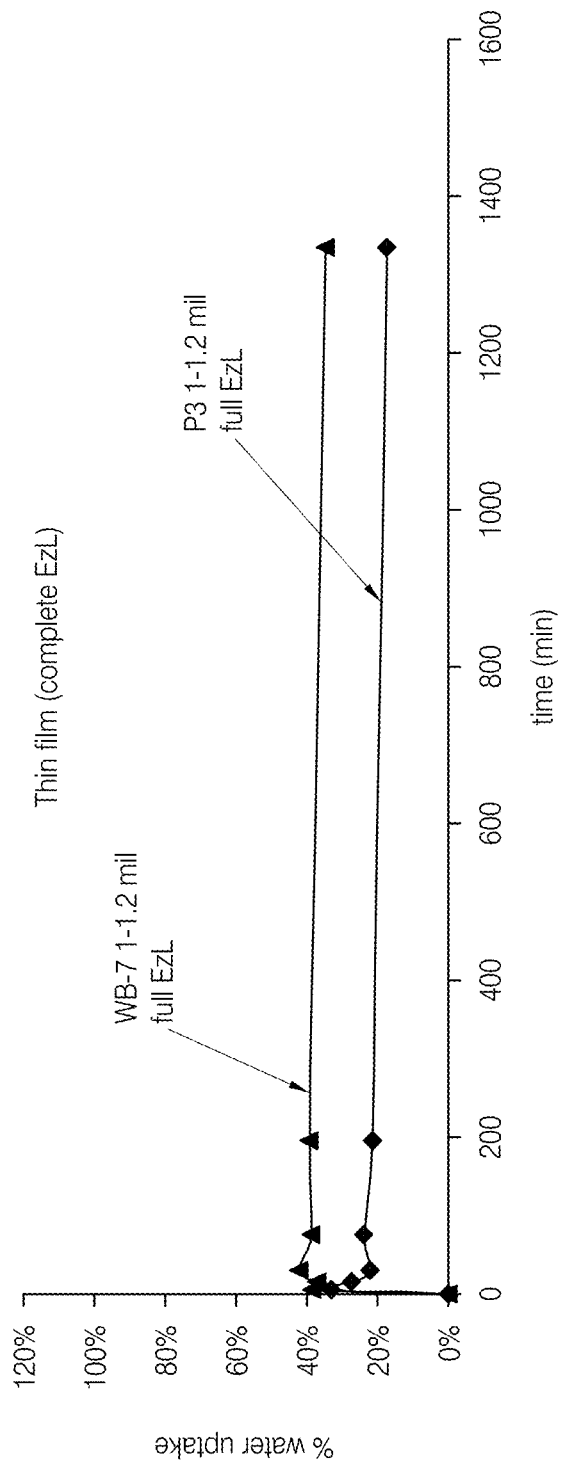
FIG. 37 is a graph showing the water uptake over time for enzyme layer prepared from WB-7 and a control polymer, without betaines, (P3).

Water adsorption of films made from enzyme layer solutions was performed at room temperature in water on 25-50 μm thick films. FIG. 37 indicates that betaine containing polymers as prepared in this example, WB-7 and standard (P3) enzyme layer films both absorb most of the water they take up within the first 5 minutes. The control films, however, almost immediately start leaching a large amount of hydrophilic molecules, resulting in 10% loss of water, by weight, after 24 hours. Films prepared from betaine containing polyurethane dispersions with built-in betaine have a stable hydrated state over time and are more hydrophilic and absorb more water than control enzyme formulation films.

Figure 38:
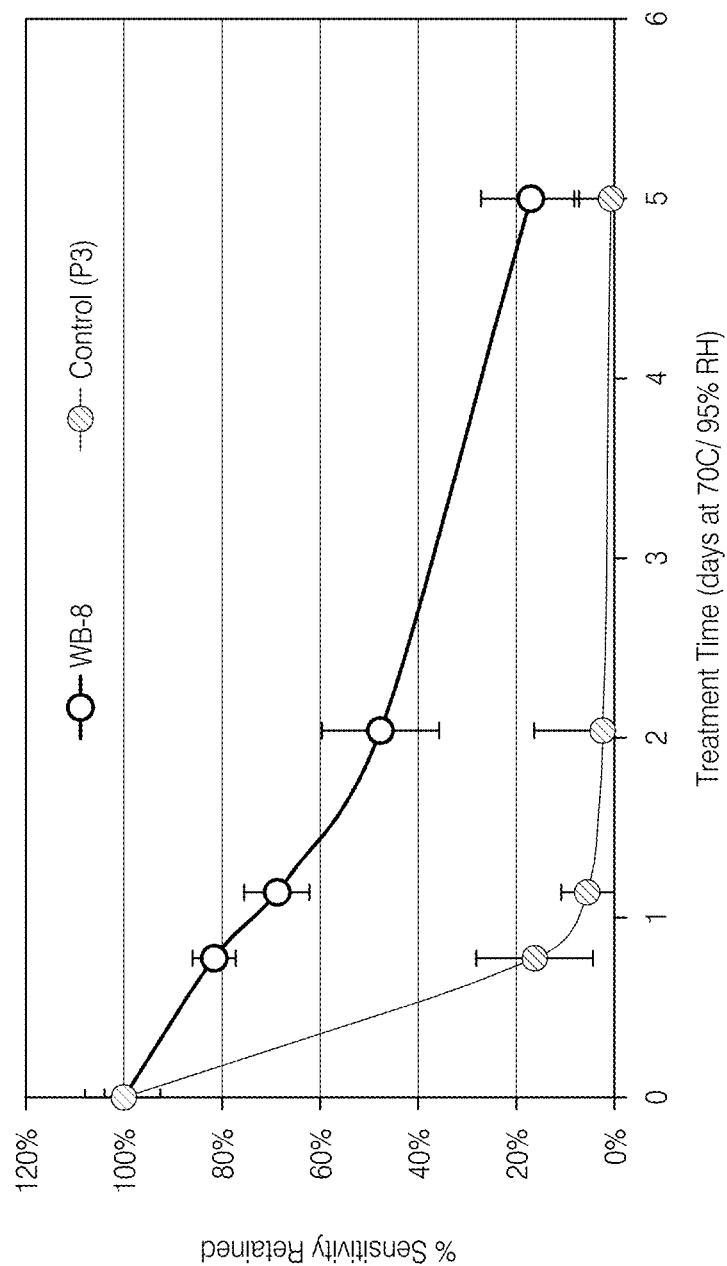
FIG. 38 is a graph showing the sensitivity of a sensor with a betaine containing polymer in the enzyme layer and a sensor without such a polymer. The sensors coated with enzyme layers were treated at 70° C. and at 95% humidity. After this accelerated ageing treatment, the resistance layer was added and sensitivity was measured. The data show a steady dip in sensitivity for the sensor without the betaine containing polymer, which is the result of enzyme deactivation due to thermal stress and/or high humidity.

Half sensors (sensors with all the components except a resistance layer) containing enzyme layer were subjected to high heat and humidity treatment 70° C. and 95% humidity. A standard resistance layer was then applied after the treatment to avoid the effect of treatment on resistance layer and sensitivity was measured (FIG. 38). The data show that higher sensitivity was maintained when using betaine containing polymers in the enzyme layer.

Figure 39:
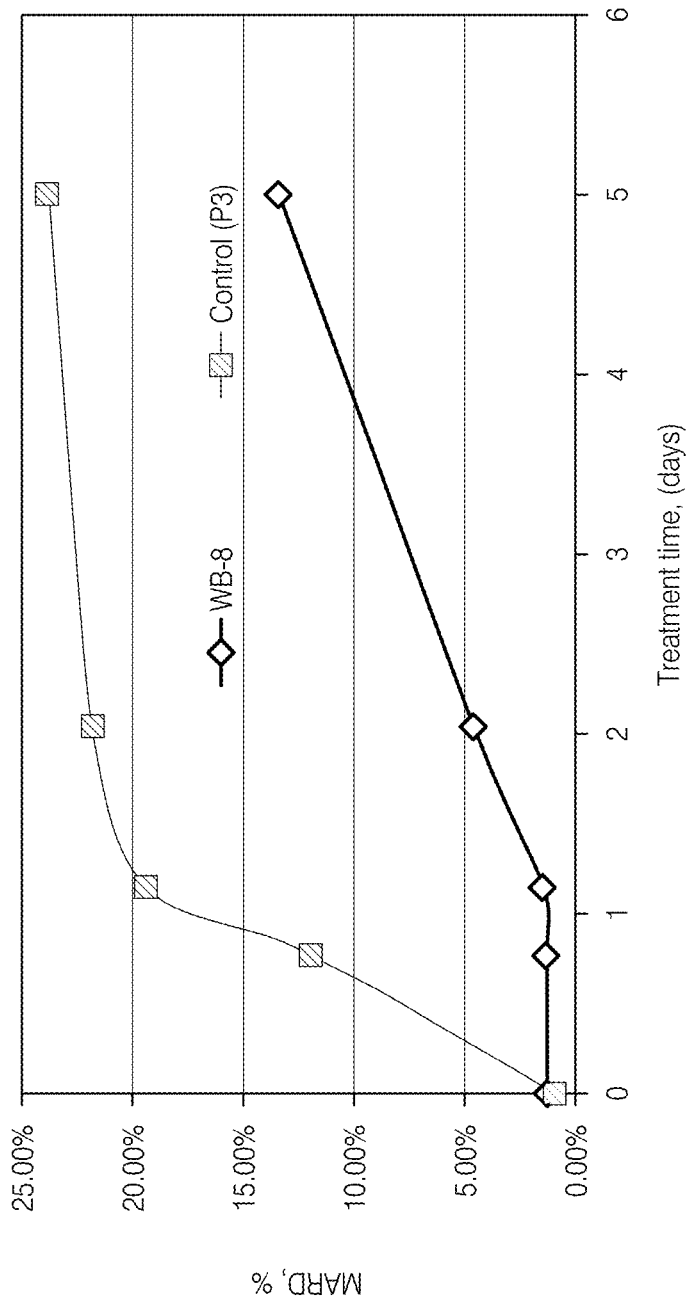
FIG. 39 is a graph showing the accuracy of a sensor with a betaine containing polymer in the enzyme layer and a sensor without such a polymer. The sensors were coated with enzyme layers and treated 70° C. and at 95% humidity. After this accelerated ageing treatment, the resistance layer was added sensor performance in the form of sensor accuracy was measured and expressed as mean absolute relative difference (MARD), which is calculated from the average of absolute relative difference of calculated value from least square linear fitting and actual value: Average of $|(V_{cal}-V_{actual})/V_{actual}|$ for each steps of glucose concentration.

The linearity was also determined and, as shown in FIG. 39, after the humidity treatment the control (P3) enzyme sensors had poorer linearity and accuracy when compared to the sensors with betaine containing polymers in the backbone.

Figure 40:
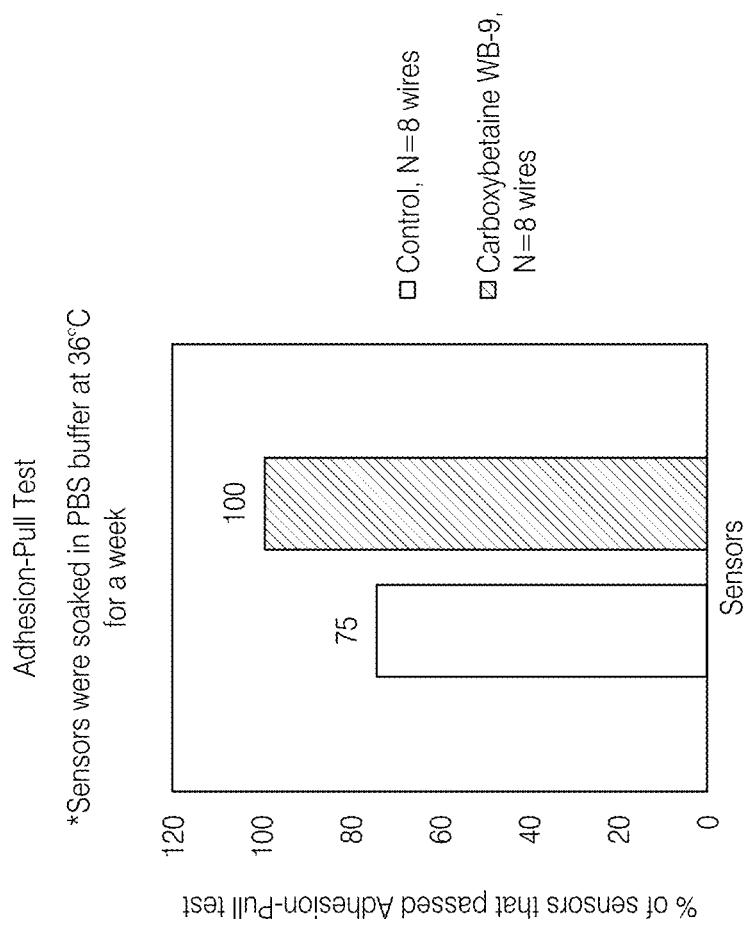
FIG. 40 is a graph showing results from an adhesion pull test.
Figure 41:
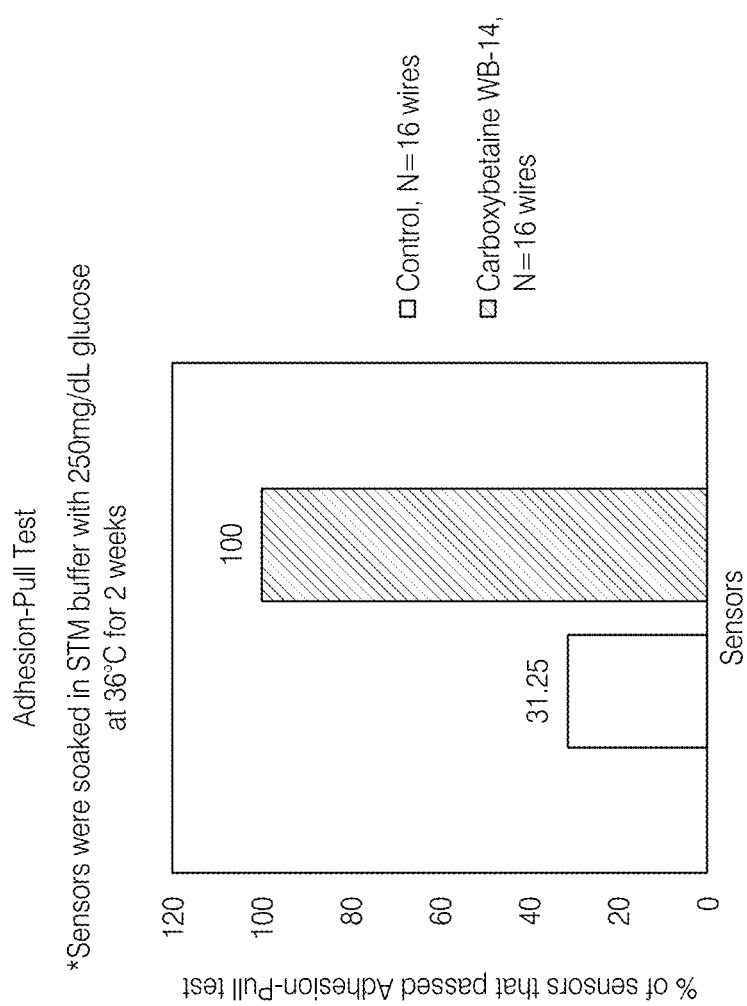
FIG. 41 is a graph showing other results from the adhesion pull test.

Sensors containing enzyme layer WB-9 and WB-14 were prepared. A control sensor (P3) was also used, which had a standard enzyme layer. After a period of soaking in heated buffer solution with and without glucose, membrane-coated sensors were transferred from a sensor fixture to a clamp fixture with a rubber pad. A silicone tube was transferred to the back end of the membrane-coated sensor using a syringe needle. A silicone tube was placed on the syringe needle, the sensor was inserted inside the needle aperture (to protect membrane-coated area on sensor), and the silicone tube was then slide over the needle to reach back end of sensor. The silicone tube has a diameter small enough to be held tightly in place on sensor. This was repeated for all sensors to be tested. The clamp with sensors inserted in the silicone tube were soaked in same soaking buffer and temperature for 7 mins. Using a sensor dipper the control P3 and carboxybetaine waterborne polymer sensors WB-9 and WB-14 were pulled at the same time with a fixed pulling speed, forcing the sensor tip and skived region to go through silicone tube. This force and speed motion is responsible of folding the membrane coating on sensors that do not have good layer adhesion. Sensors were examined under optical microscopy after the pulling test to identify the obvious membrane delamination. The percent of sensors that passed the adhesion-pull test was determined by dividing the number of sensors that failed test (showed delamination) by the total amount of sensors that were tested, times 100. The results are shown in FIG. 40 and FIG. 41. In both cases the waterborne polymers WB-9 and WB-14 outperformed the standard enzyme layers.

Example 9 Diffusion Resistance Layer

Figure 42:
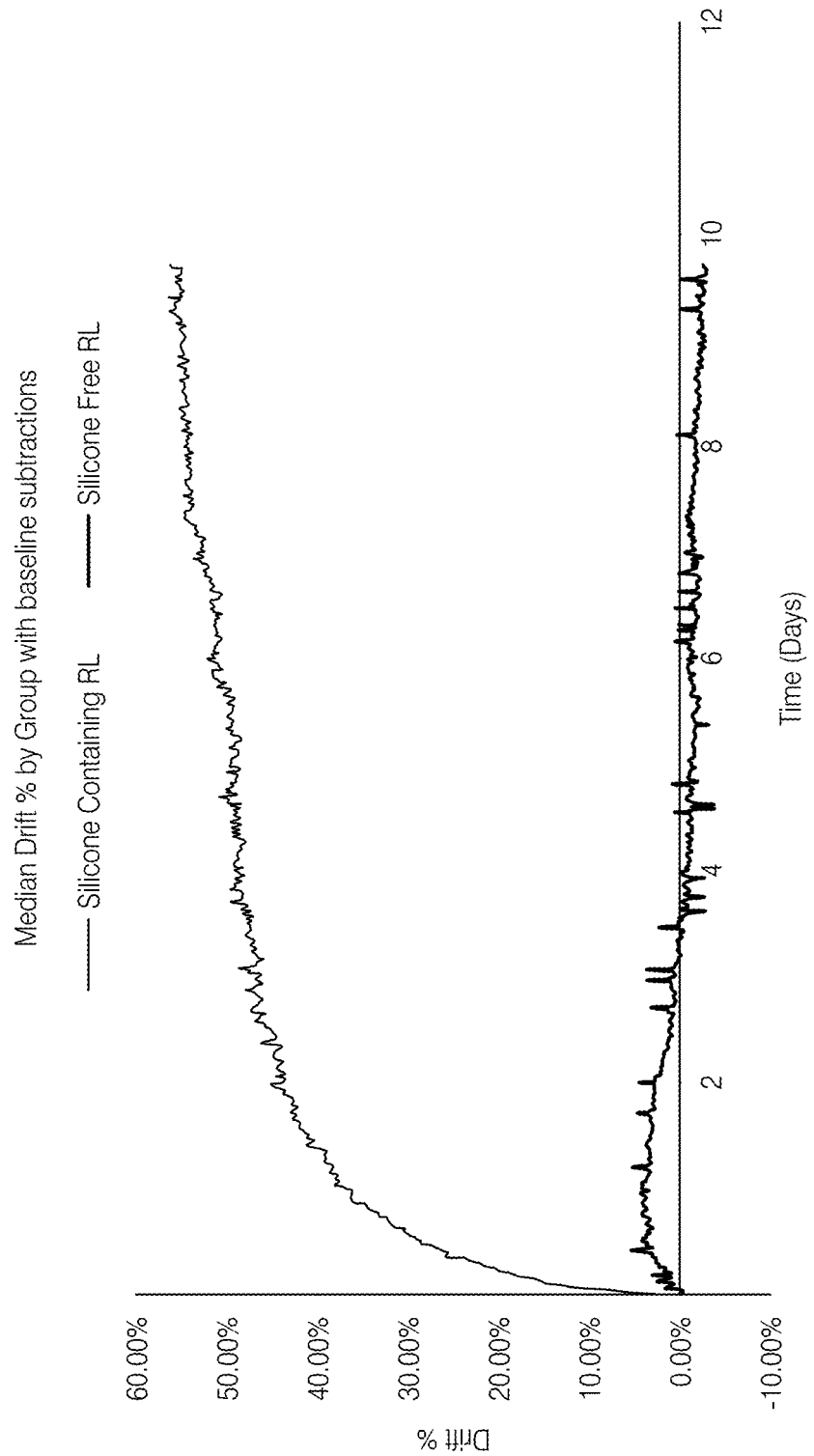
FIG. 42 is a graph showing drift testing of sensors constructed from silicone containing diffusion resistance layer (RL) membrane (thin line) and silicone free diffusion resistance (RL) membrane (thick line).
Figure 44A:
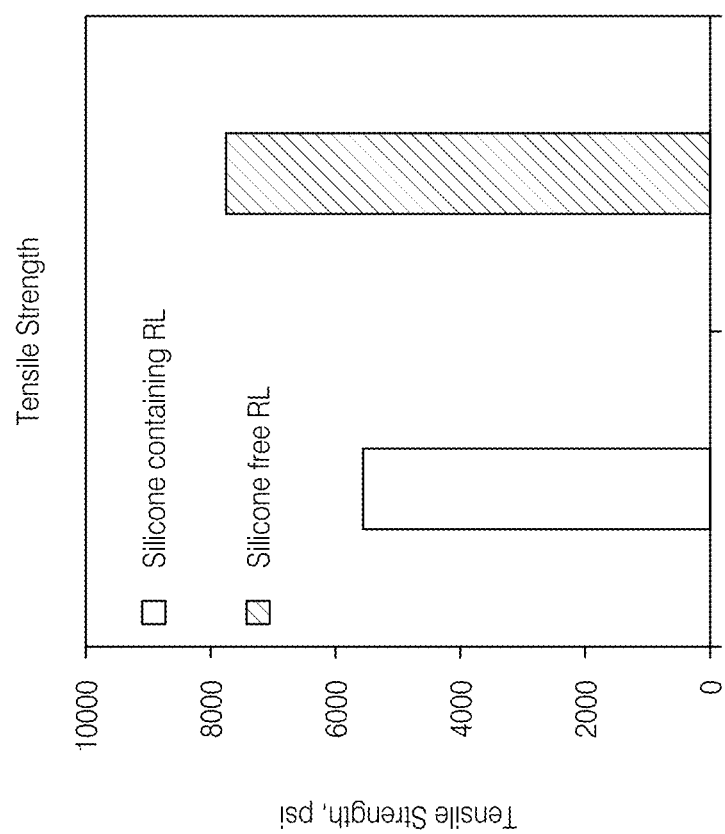
FIGS. 44A and 44B are a pair of graphs showing the tensile strength and puncture resistance of silicone containing diffusion resistance (RL) membrane and silicone free diffusion resistance (RL) membrane. The data for the tensile strength was obtained on membranes without blending with a hydrophilic polymer like PVP. The puncture resistance data was obtained on wet membranes with blending with PVP.
Figure 44B:
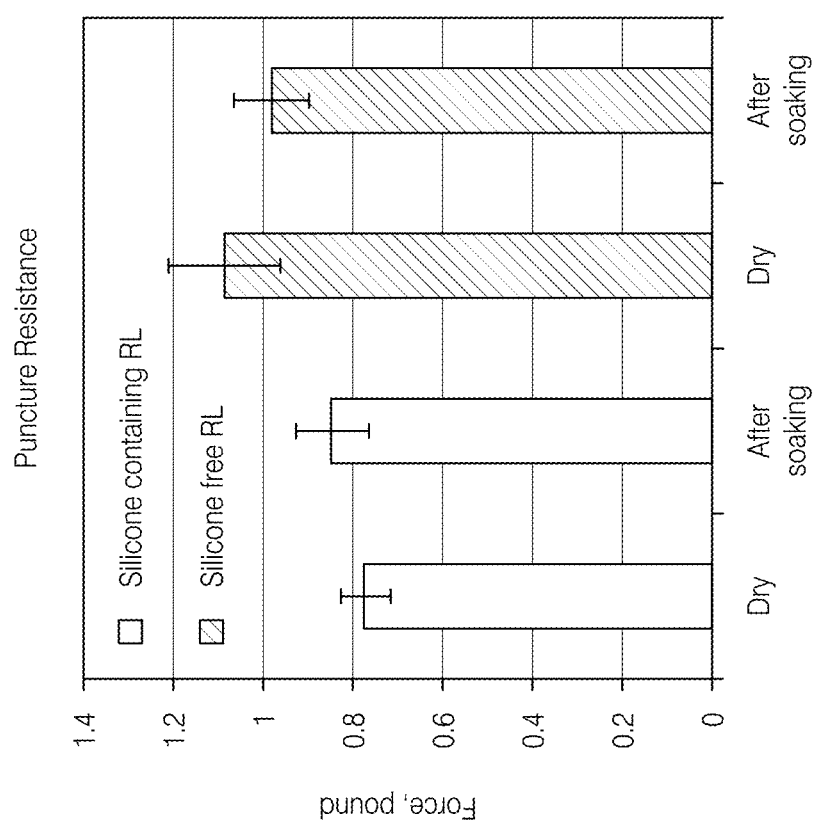

Sensors were prepared that contained a diffusion resistance layer comprising a blend of PVP and a polyurethane urea-polycarbonate block copolymer either with or without silicone. The block copolymer with silicone had a $T_g$ as shown in FIG. 43. The tensile strength of two block copolymers are shown in FIG. 44A, and the puncture resistance is shown in FIG. 44B. The sensitivity of the sensors were measured in an in vitro model over 200 hours and the results are shown in FIG. 42. The sensors with the high $T_g$ and high tensile strength, silicone free polymer in the diffusion resistance layer had minimal drift (less than 10%) over the course of the experiment, as compared to the sensors with lower Tg and tensile strength and silicone.

Figure 47A:
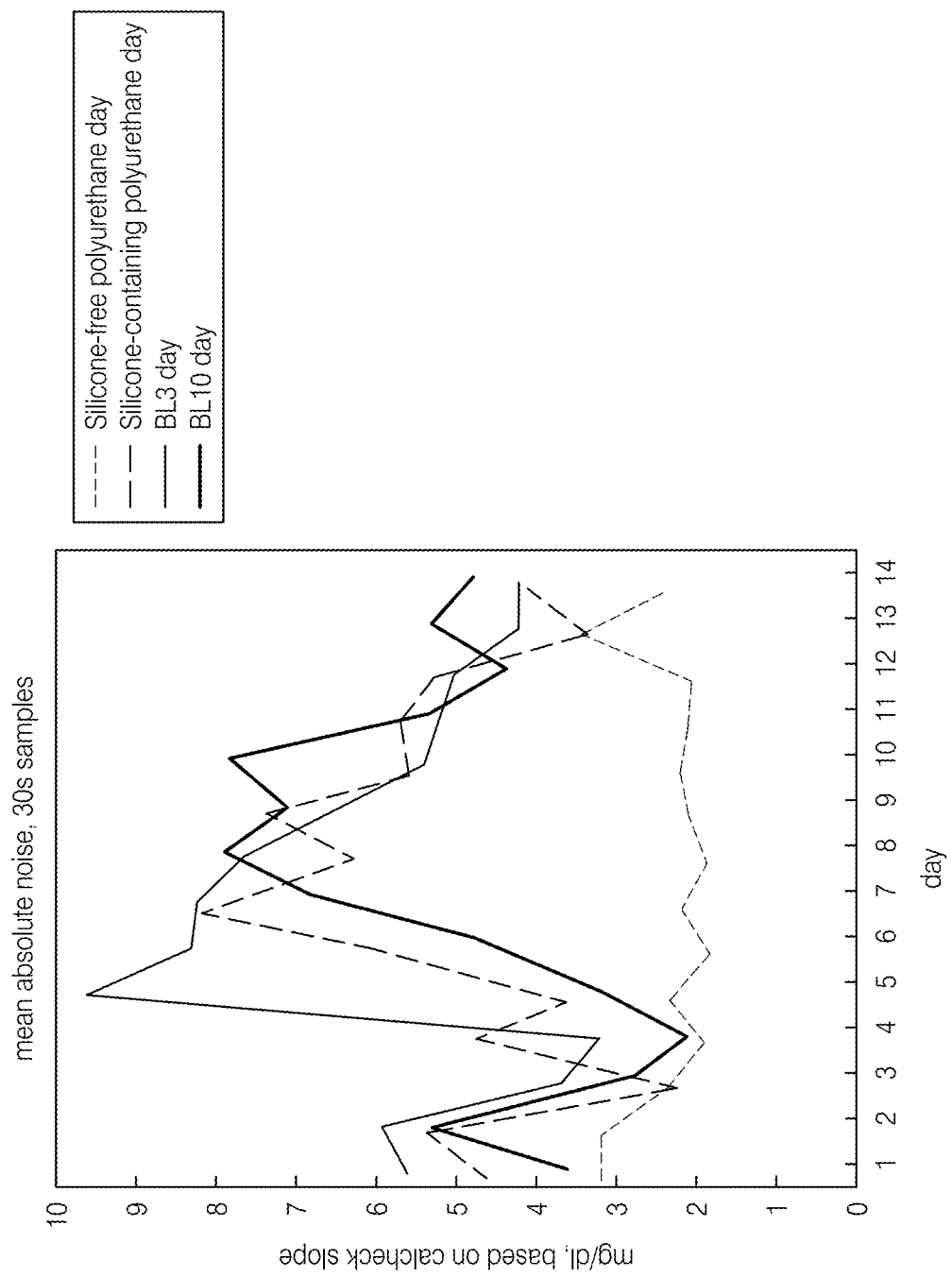
FIGS. 47A and 47B are a pair of graphs showing the sensor data in a pig model using sensors with a silicone containing diffusion resistance (RL) and sensors without silicone in the diffusion resistance RL.
Figure 47B:
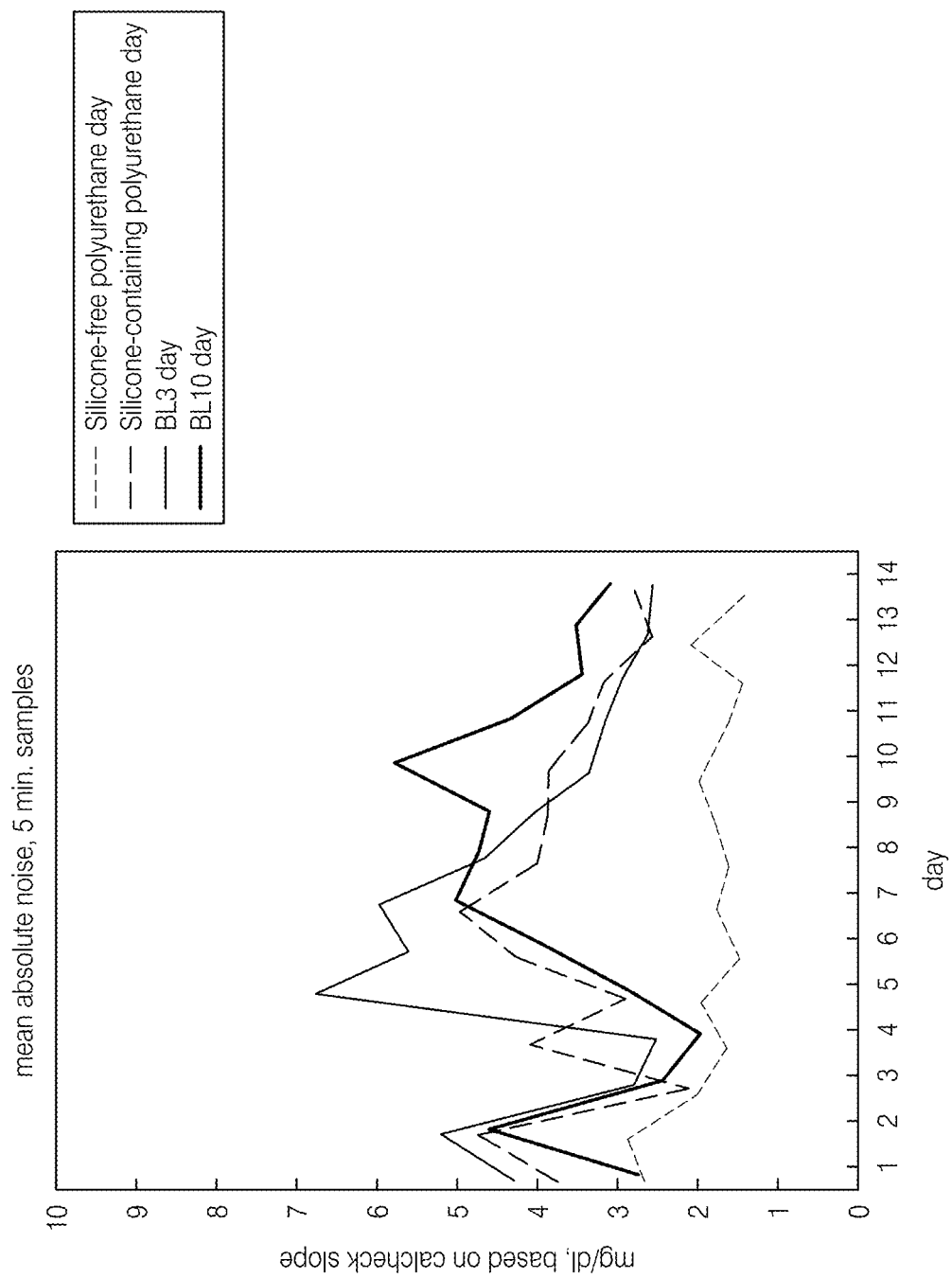

Further the sensor noise was determined and the data is shown in FIGS. 47A and 47B. The sensors with the high $T_g$ and high tensile strength, silicone free polymer in the diffusion resistance layer exhibited less in vivo noise in the 14 day study.

Example 10

Figure 45:
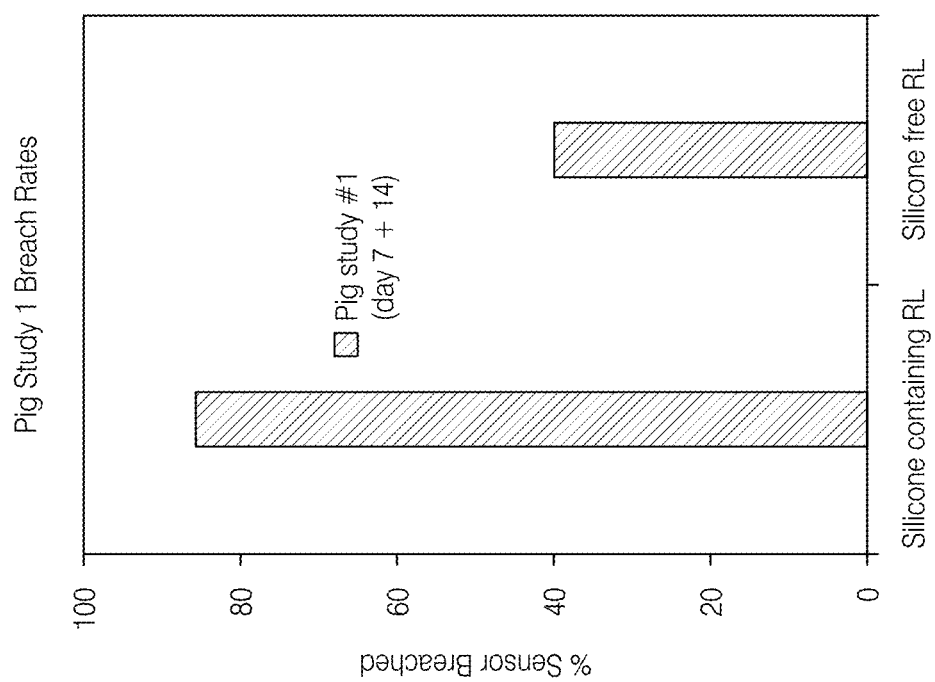
FIG. 45 shows the results from an in vivo sensor stability test (Pig model).
Figure 46:
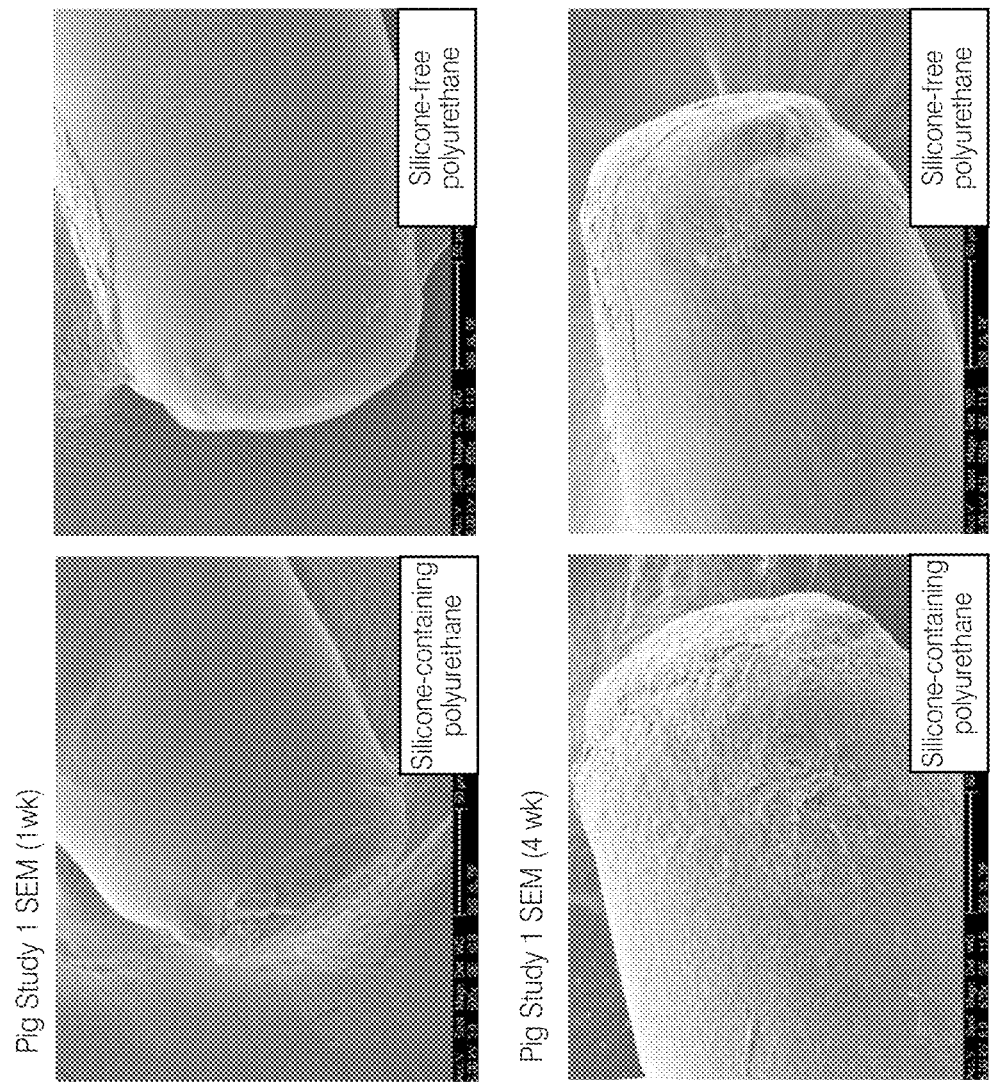
FIG. 46 shows images captured by a scanning electron microscope of sensors from the in vivo sensor stability test described in FIG. 45.

Sensors were prepared that contained a diffusion resistance layer comprising a blend of PVP and a polyurethane urea-polycarbonate block copolymer either with or without silicone. The sensitivity of the sensors were tested in an in vivo pig model. At day 7 and day 14 the sensors were removed and analyzed to determine the percent of breach. Data is shown in FIG. 45. In terms of resistance layer mechanical properties on sensor, in vivo stability test indicate the mechanical robust high $T_g$ polymer-based resistance layer has less breach rates.

Example 11

Figure 48:
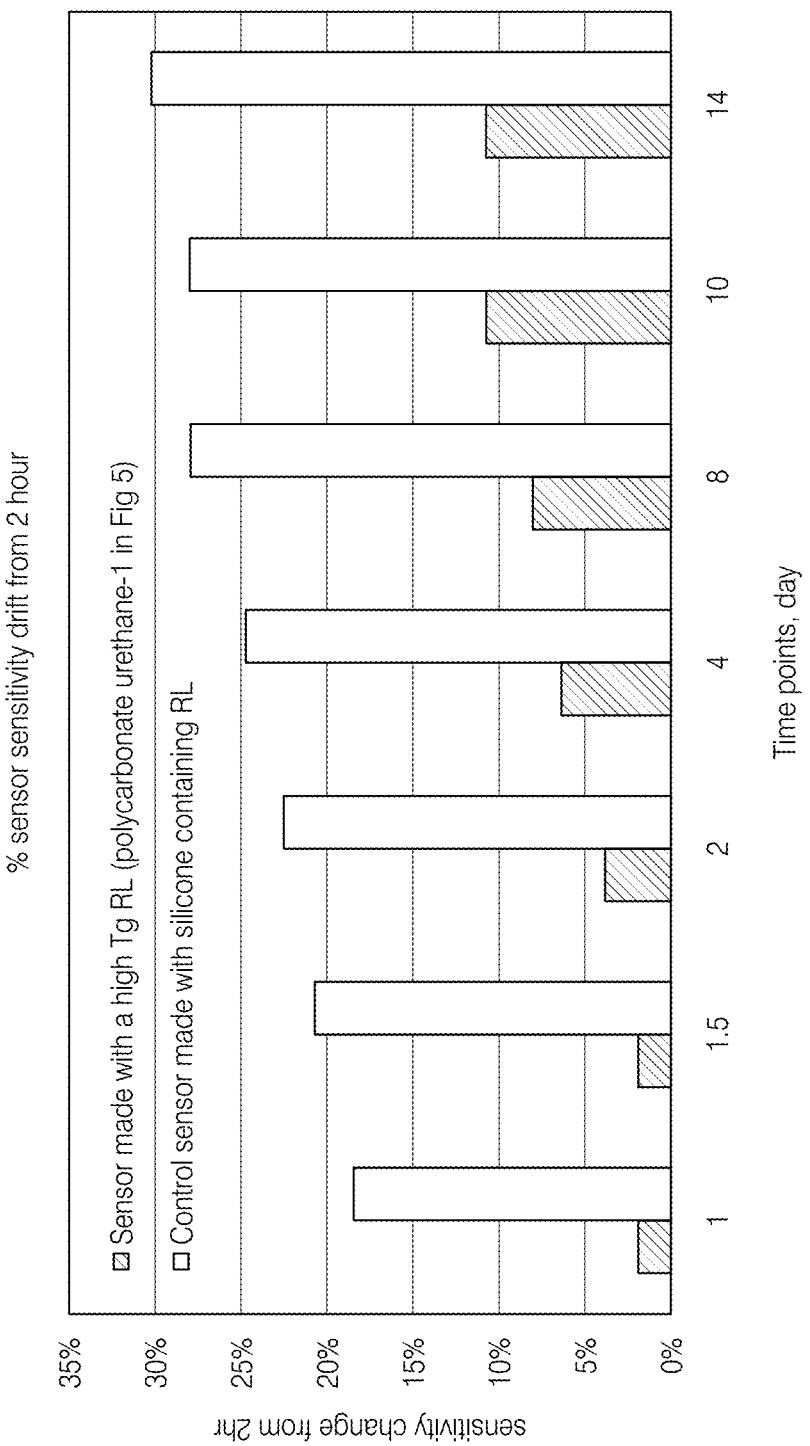
FIG. 48 is a graph showing drift testing of sensors constructed from a silicone free diffusion resistance (RL) membrane soaked in water before curing. The control represents sensors constructed with a silocne containing RL with a standard humidity cure.

A sensor was prepared with a diffusion resistance layer comprising a blend of PVP and a polyurethane urea-polycarbonate block copolymer without silicone. In one sample, the sensor was soaked in distilled water at 50° C. for various time intervals and then cured. In another sample, the sensor was cured without soaking. The results are shown in FIG. 48. The soak cure eliminated drift from calcheck. FIG. 48 is a comparison of sensor sensitivity drift between a control sensor prepared from a silicone containing diffusion resistance layer and a test sensor made with a high $T_g$ diffusion resistance layer, a polycarbonate urethane −1 as shown in FIG. 43. Sensors were exposed to a buffer solution with constant glucose concentration (300 mg/dL) and their sensitivity were measured after subtracting background signal and monitored over time up to 14 days. The sensitivity change over the 2 hr time point were calculated and plotted in FIG. 48. As can be seen, the sensor prepared from a high $T_g$ diffusion resistance layer experienced much lower magnitude of drift compared to the one prepared from silicone containing diffusion resistance layer.

Methods and devices that are suitable for use in conjunction with aspects of the preferred embodiments are disclosed in U.S. Pat. Nos. 4,757,022; 4,994,167; 6,001,067; 6,558,321; 6,702,857; 6,741,877; 6,862,465; 6,931,327; 7,074,307; 7,081,195; 7,108,778; 7,110,803; 7,134,999; 7,136,689; 7,192,450; 7,226,978; 7,276,029; 7,310,544; 7,364,592; 7,366,556; 7,379,765; 7,424,318; 7,460,898; 7,467,003; 7,471,972; 7,494,465; 7,497,827; 7,519,408; 7,583,990; 7,591,801; 7,599,726; 7,613,491; 7,615,007; 7,632,228; 7,637,868; 7,640,048; 7,651,596; 7,654,956; 7,657,297; 7,711,402; 7,713,574; 7,715,893; 7,761,130; 7,771,352; 7,774,145; 7,775,975; 7,778,680; 7,783,333; 7,792,562; 7,797,028; 7,826,981; 7,828,728; 7,831,287; 7,835,777; 7,857,760; 7,860,545; 7,875,293; 7,881,763; 7,885,697; 7,896,809; 7,899,511; 7,901,354; 7,905,833; 7,914,450; 7,917,186; 7,920,906; 7,925,321; 7,927,274; 7,933,639; 7,935,057; 7,946,984; 7,949,381; 7,955,261; 7,959,569; 7,970,448; 7,974,672; 7,976,492; 7,979,104; 7,986,986; 7,998,071; 8,000,901; 8,005,524; 8,005,525; 8,010,174; 8,027,708; 8,050,731; 8,052,601; 8,053,018; 8,060,173; 8,060,174; 8,064,977; 8,073,519; 8,073,520; 8,118,877; 8,128,562; 8,133,178; 8,150,488; 8,155,723; 8,160,669; 8,160,671; 8,167,801; 8,170,803; 8,195,265; 8,206,297; 8,216,139; 8,229,534; 8,229,535; 8,229,536; 8,231,531; 8,233,958; 8,233,959; 8,249,684; 8,251,906; 8,255,030; 8,255,032; 8,255,033; 8,257,259; 8,260,393; 8,265,725; 8,275,437; 8,275,438; 8,277,713; 8,280,475; 8,282,549; 8,282,550; 8,285,354; 8,287,453; 8,290,559; 8,290,560; 8,290,561; 8,290,562; 8,292,810; 8,298,142; 8,311,749; 8,313,434; 8,321,149; 8,332,008; 8,346,338; 8,364,229; 8,369,919; 8,374,667; 8,386,004; and 8,394,021.

Methods and devices that are suitable for use in conjunction with aspects of the preferred embodiments are disclosed in U.S. Patent Publication No. 2003-0032874-A1; U.S. Patent Publication No. 2005-0176136-A1; U.S. Patent Publication No. 2005-0182451-A1; U.S. Patent Publication No. 2005-0245799-A1; U.S. Patent Publication No. 2005-0033132-A1; U.S. Patent Publication No. 2005-0051427-A1; U.S. Patent Publication No. 2005-0056552-A1; U.S. Patent Publication No. 2005-0090607-A1; U.S. Patent Publication No. 2006-0015020-A1; U.S. Patent Publication No. 2006-0016700-A1; U.S. Patent Publication No. 2006-0020188-A1; U.S. Patent Publication No. 2006-0020190-A1; U.S. Patent Publication No. 2006-0020191-A1; U.S. Patent Publication No. 2006-0020192-A1; U.S. Patent Publication No. 2006-0036140-A1; U.S. Patent Publication No. 2006-0036143-A1; U.S. Patent Publication No. 2006-0040402-A1; U.S. Patent Publication No. 2006-0068208-A1; U.S. Patent Publication No. 2006-0142651-A1; U.S. Patent Publication No. 2006-0155180-A1; U.S. Patent Publication No. 2006-0198864-A1; U.S. Patent Publication No. 2006-0200020-A1; U.S. Patent Publication No. 2006-0200022-A1; U.S. Patent Publication No. 2006-0200970-A1; U.S. Patent Publication No. 2006-0204536-A1; U.S. Patent Publication No. 2006-0224108-A1; U.S. Patent Publication No. 2006-0235285-A1; U.S. Patent Publication No. 2006-0249381-A1; U.S. Patent Publication No. 2006-0252027-A1; U.S. Patent Publication No. 2006-0253012-A1; U.S. Patent Publication No. 2006-0257995-A1; U.S. Patent Publication No. 2006-0258761-A1; U.S. Patent Publication No. 2006-0263763-A1; U.S. Patent Publication No. 2006-0270922-A1; U.S. Patent Publication No. 2006-0270923-A1; U.S. Patent Publication No. 2007-0027370-A1; U.S. Patent Publication No. 2007-0032706-A1; U.S. Patent Publication No. 2007-0032718-A1; U.S. Patent Publication No. 2007-0045902-A1; U.S. Patent Publication No. 2007-0059196-A1; U.S. Patent Publication No. 2007-0066873-A1; U.S. Patent Publication No. 2007-0173709-A1; U.S. Patent Publication No. 2007-0173710-A1; U.S. Patent Publication No. 2007-0208245-A1; U.S. Patent Publication No. 2007-0208246-A1; U.S. Patent Publication No. 2007-0232879-A1; U.S. Patent Publication No. 2008-0045824-A1; U.S. Patent Publication No. 2008-0083617-A1; U.S. Patent Publication No. 2008-0086044-A1; U.S. Patent Publication No. 2008-0108942-A1; U.S. Patent Publication No. 2008-0119703-A1; U.S. Patent Publication No. 2008-0119704-A1; U.S. Patent Publication No. 2008-0119706-A1; U.S. Patent Publication No. 2008-0183061-A1; U.S. Patent Publication No. 2008-0183399-A1; U.S. Patent Publication No. 2008-0188731-A1; U.S. Patent Publication No. 2008-0189051-A1; U.S. Patent Publication No. 2008-0194938-A1; U.S. Patent Publication No. 2008-0197024-A1; U.S. Patent Publication No. 2008-0200788-A1; U.S. Patent Publication No. 2008-0200789-A1; U.S. Patent Publication No. 2008-0200791-A1; U.S. Patent Publication No. 2008-0214915-A1; U.S. Patent Publication No. 2008-0228054-A1; U.S. Patent Publication No. 2008-0242961-A1; U.S. Patent Publication No. 2008-0262469-A1; U.S. Patent Publication No. 2008-0275313-A1; U.S. Patent Publication No. 2008-0287765-A1; U.S. Patent Publication No. 2008-0306368-A1; U.S. Patent Publication No. 2008-0306434-A1; U.S. Patent Publication No. 2008-0306435-A1; U.S. Patent Publication No. 2008-0306444-A1; U.S. Patent Publication No. 2009-0018424-A1; U.S. Patent Publication No. 2009-0030294-A1; U.S. Patent Publication No. 2009-0036758-A1; U.S. Patent Publication No. 2009-0036763-A1; U.S. Patent Publication No. 2009-0043181-A1; U.S. Patent Publication No. 2009-0043182-A1; U.S. Patent Publication No. 2009-0043525-A1; U.S. Patent Publication No. 2009-0045055-A1; U.S. Patent Publication No. 2009-0062633-A1; U.S. Patent Publication No. 2009-0062635-A1; U.S. Patent Publication No. 2009-0076360-A1; U.S. Patent Publication No. 2009-0099436-A1; U.S. Patent Publication No. 2009-0124877-A1; U.S. Patent Publication No. 2009-0124879-A1; U.S. Patent Publication No. 2009-0124964-A1; U.S. Patent Publication No. 2009-0131769-A1; U.S. Patent Publication No. 2009-0131777-A1; U.S. Patent Publication No. 2009-0137886-A1; U.S. Patent Publication No. 2009-0137887-A1; U.S. Patent Publication No. 2009-0143659-A1; U.S. Patent Publication No. 2009-0143660-A1; U.S. Patent Publication No. 2009-0156919-A1; U.S. Patent Publication No. 2009-0163790-A1; U.S. Patent Publication No. 2009-0178459-A1; U.S. Patent Publication No. 2009-0192366-A1; U.S. Patent Publication No. 2009-0192380-A1; U.S. Patent Publication No. 2009-0192722-A1; U.S. Patent Publication No.

2009-0192724-A1; U.S. Patent Publication No. 2009-0192751-A1; U.S. Patent Publication No. 2009-0203981-A1; U.S. Patent Publication No. 2009-0216103-A1; U.S. Patent Publication No. 2009-0240120-A1; U.S. Patent Publication No. 2009-0240193-A1; U.S. Patent Publication No. 2009-0242399-A1; U.S. Patent Publication No. 2009-0242425-A1; U.S. Patent Publication No. 2009-0247855-A1; U.S. Patent Publication No. 2009-0247856-A1; U.S. Patent Publication No. 2009-0287074-A1; U.S. Patent Publication No. 2009-0299155-A1; U.S. Patent Publication No. 2009-0299156-A1; U.S. Patent Publication No. 2009-0299162-A1; U.S. Patent Publication No. 2010-0010331-A1; U.S. Patent Publication No. 2010-0010332-A1; U.S. Patent Publication No. 2010-0016687-A1; U.S. Patent Publication No. 2010-0016698-A1; U.S. Patent Publication No. 2010-0030484-A1; U.S. Patent Publication No. 2010-0331644 A1; U.S. Patent Publication No. 2010-0036215-A1; U.S. Patent Publication No. 2010-0036225-A1; U.S. Patent Publication No. 2010-0041971-A1; U.S. Patent Publication No. 2010-0045465-A1; U.S. Patent Publication No. 2010-0049024-A1; U.S. Patent Publication No. 2010-0076283-A1; U.S. Patent Publication No. 2010-0081908-A1; U.S. Patent Publication No. 2010-0081910-A1; U.S. Patent Publication No. 2010-0087724-A1; U.S. Patent Publication No. 2010-0096259-A1; U.S. Patent Publication No. 2010-0121169-A1; U.S. Patent Publication No. 2010-0161269-A1; U.S. Patent Publication No. 2010-0168540-A1; U.S. Patent Publication No. 2010-0168541-A1; U.S. Patent Publication No. 2010-0168542-A1; U.S. Patent Publication No. 2010-0168543-A1; U.S. Patent Publication No. 2010-0168544-A1; U.S. Patent Publication No. 2010-0168545-A1; U.S. Patent Publication No. 2010-0168546-A1; U.S. Patent Publication No. 2010-0168657-A1; U.S. Patent Publication No. 2010-0174157-A1; U.S. Patent Publication No. 2010-0174158-A1; U.S. Patent Publication No. 2010-0174163-A1; U.S. Patent Publication No. 2010-0174164-A1; U.S. Patent Publication No. 2010-0174165-A1; U.S. Patent Publication No. 2010-0174166-A1; U.S. Patent Publication No. 2010-0174167-A1; U.S. Patent Publication No. 2010-0179401-A1; U.S. Patent Publication No. 2010-0179402-A1; U.S. Patent Publication No. 2010-0179404-A1; U.S. Patent Publication No. 2010-0179408-A1; U.S. Patent Publication No. 2010-0179409-A1; U.S. Patent Publication No. 2010-0185065-A1; U.S. Patent Publication No. 2010-0185069-A1; U.S. Patent Publication No. 2010-0185070-A1; U.S. Patent Publication No. 2010-0185071-A1; U.S. Patent Publication No. 2010-0185075-A1; U.S. Patent Publication No. 2010-0191082-A1; U.S. Patent Publication No. 2010-0198035-A1; U.S. Patent Publication No. 2010-0198036-A1; U.S. Patent Publication No. 2010-0212583-A1; U.S. Patent Publication No. 2010-0217557-A1; U.S. Patent Publication No. 2010-0223013-A1; U.S. Patent Publication No. 2010-0223022-A1; U.S. Patent Publication No. 2010-0223023-A1; U.S. Patent Publication No. 2010-0228109-A1; U.S. Patent Publication No. 2010-0228497-A1; U.S. Patent Publication No. 2010-0240975-A1; U.S. Patent Publication No. 2010-0240976 C1; U.S. Patent Publication No. 2010-0261987-A1; U.S. Patent Publication No. 2010-0274107-A1; U.S. Patent Publication No. 2010-0280341-A1; U.S. Patent Publication No. 2010-0286496-A1; U.S. Patent Publication No. 2010-0298684-A1; U.S. Patent Publication No. 2010-0324403-A1; U.S. Patent Publication No. 2010-0331656-A1; U.S. Patent Publication No. 2010-0331657-A1; U.S. Patent Publication No. 2011-0004085-A1; U.S. Patent Publication No. 2011-0009727-A1; U.S. Patent Publication No. 2011-0024043-A1; U.S. Patent Publication No. 2011-0024307-A1; U.S. Patent Publication No. 2011-0027127-A1; U.S. Patent Publication No. 2011-0027453-A1; U.S. Patent Publication No. 2011-0027458-A1; U.S. Patent Publication No. 2011-0028815-A1; U.S. Patent Publication No. 2011-0028816-A1; U.S. Patent Publication No. 2011-0046467-A1; U.S. Patent Publication No. 2011-0077490-A1; U.S. Patent Publication No. 2011-0118579-A1; U.S. Patent Publication No. 2011-0124992-A1; U.S. Patent Publication No. 2011-0125410-A1; U.S. Patent Publication No. 2011-0130970-A1; U.S. Patent Publication No. 2011-0130971-A1; U.S. Patent Publication No. 2011-0130998-A1; U.S. Patent Publication No. 2011-0144465-A1; U.S. Patent Publication No. 2011-0178378-A1; U.S. Patent Publication No. 2011-0190614-A1; U.S. Patent Publication No. 2011-0201910-A1; U.S. Patent Publication No. 2011-0201911-A1; U.S. Patent Publication No. 2011-0218414-A1; U.S. Patent Publication No. 2011-0231140-A1; U.S. Patent Publication No. 2011-0231141-A1; U.S. Patent Publication No. 2011-0231142-A1; U.S. Patent Publication No. 2011-0253533-A1; U.S. Patent Publication No. 2011-0263958-A1; U.S. Patent Publication No. 2011-0270062-A1; U.S. Patent Publication No. 2011-0270158-A1; U.S. Patent Publication No. 2011-0275919-A1; U.S. Patent Publication No. 2011-0290645-A1; U.S. Patent Publication No. 2011-0313543-A1; U.S. Patent Publication No. 2011-0320130-A1; U.S. Patent Publication No. 2012-0035445-A1; U.S. Patent Publication No. 2012-0040101-A1; U.S. Patent Publication No. 2012-0046534-A1; U.S. Patent Publication No. 2012-0078071-A1; U.S. Patent Publication No. 2012-0108934-A1; U.S. Patent Publication No. 2012-0130214-A1; U.S. Patent Publication No. 2012-0172691-A1; U.S. Patent Publication No. 2012-0179014-A1; U.S. Patent Publication No. 2012-0186581-A1; U.S. Patent Publication No. 2012-0190953-A1; U.S. Patent Publication No. 2012-0191063-A1; U.S. Patent Publication No. 2012-0203467-A1; U.S. Patent Publication No. 2012-0209098-A1; U.S. Patent Publication No. 2012-0215086-A1; U.S. Patent Publication No. 2012-0215087-A1; U.S. Patent Publication No. 2012-0215201-A1; U.S. Patent Publication No. 2012-0215461-A1; U.S. Patent Publication No. 2012-0215462-A1; U.S. Patent Publication No. 2012-0215496-A1; U.S. Patent Publication No. 2012-0220979-A1; U.S. Patent Publication No. 2012-0226121-A1; U.S. Patent Publication No. 2012-0228134-A1; U.S. Patent Publication No. 2012-0238852-A1; U.S. Patent Publication No. 2012-0245448-A1; U.S. Patent Publication No. 2012-0245855-A1; U.S. Patent Publication No. 2012-0255875-A1; U.S. Patent Publication No. 2012-0258748-A1; U.S. Patent Publication No. 2012-0259191-A1; U.S. Patent Publication No. 2012-0260323-A1; U.S. Patent Publication No. 2012-0262298-A1; U.S. Patent Publication No. 2012-0265035-A1; U.S. Patent Publication No. 2012-0265036-A1; U.S. Patent Publication No. 2012-0265037-A1; U.S. Patent Publication No. 2012-0277562-A1; U.S. Patent Publication No. 2012-0277566-A1; U.S. Patent Publication No. 2012-0283541-A1; U.S. Patent Publication No. 2012-0283543-A1; U.S. Patent Publication No. 2012-0296311-A1; U.S. Patent Publication No. 2012-0302854-A1; U.S. Patent Publication No. 2012-0302855-A1; U.S. Patent Publication No. 2012-0323100-A1; U.S. Patent Publication No. 2013-0012798-A1; U.S. Patent Publication No. 2013-0030273-A1; U.S. Patent Publication No. 2013-0035575-A1; U.S. Patent Publication No. 2013-0035865-A1; U.S. Patent Publication No. 2013-0035871-A1; U.S. Patent Publication No. 2013-0053665-A1; U.S. Patent Publication No. 2013-0053666-A1; US. Patent Publication No. 2013-0060112-A1; US. Patent Publication No. 2013-0078912-A1; US. Patent Publication No. 2013-0076531-A1; US. Patent Publication No. 2013-0076532-A1; US. Patent Publication No. 2013-0131478-A1; US. Patent Publication No. 2013-150692-A1; U.S. Patent Publication No. 2014-0094671-A1; US. Patent Publication No. 2014-0005508-A1; US. Patent Publication No. 2014-0118166-A1; US. Patent Publication No. 2014-0118138-A1; US. Patent Publication No. 2014-0188402-A1; US. Patent Publication No. 2014-0182350-A1; and US. Patent Publication No. 2014-0275896-A1.

Methods and devices that are suitable for use in conjunction with aspects of the preferred embodiments are disclosed in U.S. application Ser. No. 09/447,227 filed on Nov. 22, 1999 and entitled "DEVICE AND METHOD FOR DETERMINING ANALYTE LEVELS," and U.S. application Ser. No. 13/461,625 filed on May 1, 2012 and entitled "DUAL ELECTRODE SYSTEM FOR A CONTINUOUS ANALYTE SENSOR."

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g. smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A device for monitoring an analyte concentration, the device comprising:
    a transcutaneous sensor configured to generate a signal associated with a concentration of an analyte;
    an enzyme layer; and
    a membrane located over both the transcutaneous sensor and the enzyme layer;
    wherein the membrane comprises a diffusion-resistance layer comprising a base polymer, the base polymer comprising silicone, wherein the silicone comprises less than 1 wt % of the base polymer, and the base polymer has a lowest glass transition temperature as measured using ASTM D3418 of greater than −50° C., and the base polymer has an ultimate tensile strength as measured by ASTM D1708 that is greater than 6000 psi.

2. The device of claim 1, wherein the lowest glass transition temperature of the base polymer is greater than 0° C.

3. The device of claim 1, wherein the lowest glass transition temperature of the base polymer is from 0° C. to 66° C.

4. The device of claim 1, wherein the lowest glass transition temperature of the base polymer is from 20° C. to 60° C.

5. The device of claim 1, wherein the lowest glass transition temperature of the base polymer is from 0° C. to 30° C.

6. The device of claim 1, wherein the lowest glass transition temperature of the base polymer is from 30° C. to 60° C.

7. The device of claim 1, wherein the base polymer has an ultimate tensile strength greater than 8250 psi.

8. The device of claim 1, wherein the base polymer is a segmented block copolymer.

9. The device of claim 1, wherein the base polymer comprises polyurethane and/or polyurea segments and one or more polycarbonate or polyester segments.

10. The device of claim 1, wherein the base polymer is a polyurethane copolymer chosen from a polycarbonate-urethane, polyether-urethane, and polyester-urethane.

11. The device of claim 1, wherein the base polymer comprises a polymer selected from the group consisting of epoxies, polystyrene, polyoxymethylene, polysiloxanes, polyethers, polyacrylics, polymethacrylic, polyesters, polycarbonates, polyamide, poly(ether ketone), and poly(ether imide).

12. The device of claim 1, wherein the diffusion-resistance layer further comprises a hydrophilic polymer.

13. The device of claim 12, wherein the hydrophilic polymer is selected from the group consisting of polyvinyl alcohol, polyethylene glycol, polyacrylamide, polyacetate, polyethylene oxide, polyethyleneamine, polyvinylpyrrolidone, polyoxazoline, and mixtures thereof.

14. The device of claim 12, wherein the hydrophilic polymer is blended with the base polymer.

15. The device of claim 12, wherein the hydrophilic polymer is covalently bonded to the base polymer.

16. The device of claim 12, wherein the base polymer or hydrophilic polymer comprises at least one crosslinker, wherein the at least one crosslinker comprises a polymer or an oligomer, the oligomer comprising polyfunctional isocyanate, polyfunctional aziridine, or polyfunctional carbodiimide.

17. The device of claim 1, wherein the diffusion-resistance layer comprises a blend of a polycarbonate-urethane base polymer and polyvinylpyrrolidone.

18. The device of claim 1, wherein the diffusion-resistance layer is from 0.01 μm to about 250 μm thick.

19. The device of claim 1, wherein the sensor has a drift of less than or equal to 10% over 10 days.

20. The device of claim 1, wherein the transcutaneous sensor comprises an electrode.

21. The device of claim 1, wherein the device is configured for continuous measurement of an analyte concentration.

22. The device of claim 1, wherein the analyte is glucose.

23. The device of claim 1, wherein the base polymer has a plurality of glass transition temperatures as measured using ASTM D3418.

* * * * *